(12) United States Patent
Leban et al.

(10) Patent No.: US 10,005,769 B2
(45) Date of Patent: Jun. 26, 2018

(54) 2,3-DIHYDROBENZOFURAN-5YL COMPOUNDS AS DYRK KINASE INHIBITORS

(71) Applicant: 4SC DISCOVERY GMBH, Planegg-Martinsried (DE)

(72) Inventors: Johann Leban, Vienna (AT); Mirko Zaja, Munich (DE)

(73) Assignee: 4SC AG, Planegg-Martinsried (DE)

( * ) Notice: Subject to any disclaimer, the term of this patent is extended or adjusted under 35 U.S.C. 154(b) by 0 days. days.

(21) Appl. No.: 14/899,335

(22) PCT Filed: Jun. 17, 2014

(86) PCT No.: PCT/EP2014/062774
§ 371 (c)(1),
(2) Date: Dec. 17, 2015

(87) PCT Pub. No.: WO2014/202638
PCT Pub. Date: Dec. 24, 2014

(65) Prior Publication Data
US 2016/0137637 A1    May 19, 2016

(30) Foreign Application Priority Data
Jun. 18, 2013  (EP) ..................... 13172577

(51) Int. Cl.
*C07D 417/14*  (2006.01)
(52) U.S. Cl.
CPC .................. *C07D 417/14* (2013.01)
(58) Field of Classification Search
CPC .................................................. C07D 417/14
See application file for complete search history.

(56) References Cited

U.S. PATENT DOCUMENTS

| | | | |
|---|---|---|---|
| 7,812,026 B2 | 10/2010 | Bauer et al. | |
| 9,206,142 B2 | 12/2015 | Shipps, Jr. et al. | |
| 2006/0199821 A1 | 9/2006 | Tester et al. | |
| 2009/0149474 A1 | 6/2009 | Bauer et al. | |
| 2012/0328691 A1 | 12/2012 | Shipps, Jr. et al. | |

FOREIGN PATENT DOCUMENTS

| | | | | |
|---|---|---|---|---|
| CA | 2706813 C | * | 6/2009 | ........... C07D 417/14 |
| WO | 2005033072 A2 | | 4/2005 | |
| WO | 2007073300 A1 | | 6/2007 | |
| WO | 2008054702 A1 | | 5/2008 | |

OTHER PUBLICATIONS

Chemical Abstracts Registry No. 1023591-58-3, indexed in the Registry file on STN CAS Online on May 29, 2008.*
International Search Report dated Jul. 25, 2014 issued in corresponding PCT/EP2014/062774 application (pp. 1-3).
X. Huang, et al., "Structure-based design and optimization of 2-aminothiazole-4-carboxamide as a new class of CHK1 inhibitors", Bioorganic & Medicinal Chemistry Letters, vol. 23, No. 9 (Mar. 2013) pp. 2590-2594.

* cited by examiner

*Primary Examiner* — Laura L. Stockton
(74) *Attorney, Agent, or Firm* — Millen, White, Zelano & Branigan, P.C.

(57) ABSTRACT

The present invention relates to compounds of below Formula (I), physiologically functional derivatives or salts thereof, where the groups $R^1$, $R^2$, $R^3$, $R^4$, $R^4$, $X^1$, and A, as well as the variables n, m and p are detailed further herein.

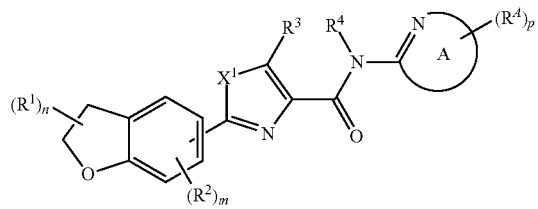

In another aspect, the present invention provides methods for their preparation, their medical use and pharmaceutical compositions comprising said compounds, physiologically functional derivatives, solvates or salts thereof.

39 Claims, 1 Drawing Sheet

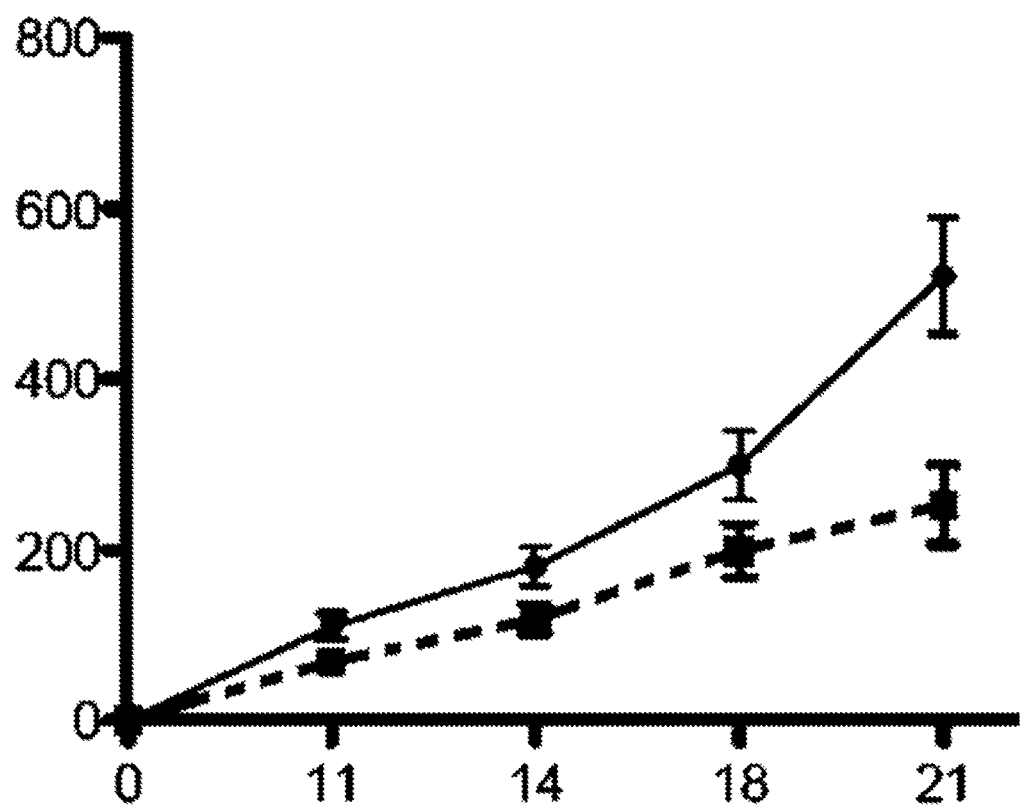

2,3-DIHYDROBENZOFURAN-5YL COMPOUNDS AS DYRK KINASE INHIBITORS

BACKGROUND OF THE INVENTION

The Dual-Specificity Tyrosine-Regulated Kinase 1B (DYRK1B, also referred to as Minibrain-Regulated Kinase MIRK) belongs to the DYRK family of serine/threonine kinases, which, based on sequence and structural homologies, can be divided into three subgroups: the YAK group with no members in the animal kingdom, the DYRK1 and the DYRK2 subgroup. The two DYRK1 subgroup members DYRK1A and DYRK1B share 85% identity at the amino acid level, though expression and functional characteristics are distinct (Aranda et al., FASEB J. 2011 February; 25(2): 449-462.).

The human DYRK1B gene encodes a 69 kDa protein with 629 amino acids in length. Alternative splicing and differential promoter engagement can yield two additional, slightly shorter DYRK1B isoforms with differential expression patterns, the shorter of which lacking kinase activity (Leder et al., Biochem J. 2003 Jun. 15; 372(Pt 3):881-888.).

The regulation of DYRK1B catalytic activity and function is not entirely understood. Given the extensive sequence similarity to DYRK1A, the intrinsic regulatory and catalytic properties of DYRK1B can—to a certain extent—be inferred from studies of DYRK1A regulation. DYRK family members are arginine-directed serine/threonine kinases, with DYRK1B phosphorylating either serine in the consensus substrate sequence SPSxxR (Friedman, J Cell Biochem. 2007 Oct. 1; 102(2):274-279; Himpel et al., J Biol Chem. 2000 Jan. 28; 275(4):2431-2438.). Activation of DYRK1B involves an intramolecular tyrosine (Y) auto-phosphorylation of the second tyrosine of an YxY motif in the conserved kinase domain and activation loop, respectively (Becker et al., FEBS J. 2011 January; 278(2):246-256; Himpel et al., J Biol Chem. 2000 Jan. 28; 275(4):2431-2438; Nolen at al., Mol Cell. 2004 Sep. 10; 15(5):661-675.). Notably, this Y-phosphorylation-dependent activation step occurs only during translation of DYRK kinases, resulting in activated DYRK proteins with serine/threonine kinase activity (Lochhead et al., Cell. 2005 Jun. 17; 121(6):925-936.). This implies that additional processes including protein-protein interactions, further post-translational modifications and/or subcellular localization control the response of DYRK kinases to extracellular signals. For instance, signaling via RAS/RAC/MKK3 is able to stimulate DYRK1B activity in certain cellular contexts such as in pancreatic cancer cells and interaction of DYRK1A with 14-3-3 proteins significantly enhances DYRK kinase activity (Deng et al., J Biol Chem. 2003 Oct. 17; 278(42):41347-41354; Jin et al., J Biol Chem. 2005 Dec. 23; 280(51):42097-42105; Jin et al., Cancer Res. 2007 Aug. 1; 67(15):7247-7255; Kim et al., Biochem Biophys Res Commun. 2004 Oct. 15; 323(2):499-504.).

During normal development DYRK1B expression is preferentially restricted to testes and muscle cells (Leder et al., Biochem J. 2003 Jun. 15; 372(Pt 3):881-888; Leder et al., Biochem Biophys Res Commun. 1999 Jan. 19; 254(2):474-479.). In muscle its expression is regulated by RHO and basic Helix-Loop-Helix transcription factors via binding to an E-box in the DYRK1B promoter (Deng et al., J Biol Chem. 2003 Oct. 17; 278(42):41347-41354; Friedman, J Cell Biochem. 2007 Oct. 1; 102(2):274-279.). Inhibition and overexpression studies suggest a pro-differentiation activity of DYRK1B in myoblast differentiation by enhancing the expression of myogenic transcription factors such as Mef2 (Deng et al., J Biol Chem. 2005 Feb. 11; 280(6):4894-4905.). This effect is mediated by DYRK1B-dependent phosphorylation of class II histone deacetylases (HDAC) thereby freeing Mef2 from complexes with inhibitory HDACs and allowing Mef2 to exert its pro-myogenic function (Deng et al., J Biol Chem. 2005 Feb. 11; 280(6):4894-4905.). In addition to its role in myoblast differentiation, DYRK1B also controls cell cycle arrest by phosphorylation-dependent destabilization of D-type cyclins and stabilization of cell cycle inhibitors including p27 and p21 (Deng et al., J Biol Chem. 2004 May 21; 279(21):22498-22504; Ewton et al., Mol Cancer Ther. 2011 November; 10(11):2104-2114; Mercer et al., J Biol Chem. 2005 Jul. 8; 280(27):25788-25801; Zou et al., J Biol Chem. 2004 Jun. 25; 279(26): 27790-27798.). Like DYRK1A, for which a larger number of substrate proteins has already been identified, DYRK1B can act as co-activator of the FOXO1a transcription factor, thereby regulating glucose-6-phosphatase expression (von Groote-Bidlingmaier et al., Biochem Biophys Res Commun. 2003 Jan. 17; 300(3):764-769.).

DYRK1B deficient mice do not display any evident developmental defects and survive several weeks post birth (Leder et al., Biochem J. 2003 Jun. 15; 372(Pt 3):881-888.). Details of the DYRK1B mutant phenotype remain to be reported. By contrast, DYRK1A deficiency in mice results in an embryonic lethal phenotype (Fotaki et al., Mol Cell Biol. 2002 September; 22(18):6636-6647.).

DYRK1B in Cancer

Several recent studies have implicated DYRK1B as a putative oncogenic factor in different cancer entities. DYRK1B localizes to the chromosomal region 19q13, which is frequently amplified in pancreatic and ovarian cancers (Friedman, J Cell Biochem. 2007 Oct. 1; 102(2): 274-279; Karhu et al., Genes Chromosomes Cancer. 2006 August; 45(8):721-730; Lee et al., Cancer Res. 2000 Jul. 1; 60(13):3631-3637.). Accordingly, DYRK1B is strongly expressed in a fraction of pancreatic and ovarian cancer cell lines (Friedman, J Cell Biochem. 2007 Oct. 1; 102(2):274-279; Hu and Friedman, Genes Cancer. 2010 Aug. 1; 1(8): 803-811.). Notably, in pancreatic cancer DYRK1B acts as survival effector kinase downstream of RAS-RAC1 to promote viability and clonal growth of cancer cells (Jin et al., Cancer Res. 2007 Aug. 1; 67(15):7247-7255.). In addition, several in vitro studies suggest that DYRK1B has pro-oncogenic function in colon cancer, osteosarcoma and rhabdomyosarcoma (RMS). RNA interference and overexpression studies demonstrated a pro-survival role of DYRK1B in colon cancer, osteosarcoma, RMS and pancreatic cancer (Deng et al., Cancer Res. 2009 Apr. 15; 69(8):3317-3324; Deng et al., Cancer Res. 2006 Apr. 15; 66(8):4149-4158; Friedman, Sarcoma. 2011; 2011:260757, doi:10.1155/2011/260757; Jin et al., Cancer Res. 2007 Aug. 1; 67(15):7247-7255; Mercer et al., Cancer Res. 2006 May 15; 66(10):5143-5150; Yang et al., Carcinogenesis. 2010 April; 31(4):552-558.). The pro-survival activity in sarcoma can—at least in part—be ascribed to the role of DYRK1B in promoting the inactivation of reactive oxygen species (ROS). DYRK1B is able to increase the expression of ROS detoxifying enzymes including superoxide dismutases 2 and 3 (Deng et al., Cancer Res. 2009 Apr. 15; 69(8):3317-3324; Hu and Friedman, Genes Cancer. 2010 Aug. 1; 1(8):803-811.). This may also explain the enhanced sensitivity of DYRK1B-depleted cancer cells to certain chemotherapeutic drugs such as cisplatin known to increase toxic ROS levels (Hu and Friedman, Genes Cancer. 2010 Aug. 1; 1(8):803-811.).

Hedgehog Signaling in Cancer Therapy

The Hedgehog (HH)/GLI signal transduction pathway is a key regulator of multiple developmental processes. Uncontrolled activation of HH/GLI signaling is a common feature of many human malignancies including cancers of the brain, skin, gastro-intestinal tract, prostate, breast lung, muscle and bone (reviewed in (Beachy et al., Nature. 2004 Sep. 23; 431(7007):402; Beachy et al., Nature. 2004 Nov. 18; 432(7015):324-331; Epstein, Nat Rev Cancer. 2008 October; 8(10):743-754; Kasper et al., J Clin Invest. 2012 Feb. 1; 122(2):455-463; Kasper et al., Eur J Cancer. 2006 March; 42(4):437-445; Merchant and Matsui, Clin Cancer Res. 2010 Jun. 15; 16(12):3130-3140; Ng and Curran, Nat Rev Cancer. 2011 May 26; 11(7):493-501; Ruiz i Altaba et al., Trends Cell Biol. 2007 September; 17(9):438-447; Ruiz i Altaba et al., Nat Rev Cancer. 2002 May; 2(5):361-372; Scales and de Sauvage, Trends Pharmacol Sci. 2009 June; 30(6):303-312; Teglund and Toftgard, Biochim Biophys Acta. 2010 April; 1805(2):181-208; Theunissen and de Sauvage, Cancer Res. 2009 Aug. 1; 69(15):6007-6010.).

Precise reversible regulation of Hedgehog signaling is a complex process and mandatory for proper normal development of both invertebrate and vertebrate organisms (for detailed reviews see (Huangfu and Anderson, Development. 2006 January; 133(1):3-14; Ingham and McMahon, Genes Dev. 2001 Dec. 1; 15(23):3059-3087; Teglund and Toftgard, Biochim Biophys Acta. 2010 April; 1805(2): 181-208.)).

In the absence of HH ligand, HH signaling is repressed by the activity of the HH receptor Patched (PTCH), a twelve-transmembrane domain protein whose intracellular localization is concentrated at the base of the primary cilium, a single antenna-like cell surface compartment that coordinates HH signal transduction. Unliganded PTCH prevents the translocation of the G-protein coupled receptor-like protein and essential pathway effector Smoothened into the primary cilium (Corbit et al., Nature. 2005 Oct. 13; 437 (7061):1018-1021; Rohatgi et al., Science. 2007 Jul. 20; 317(5836):372-376; Rohatgi and Scott, Nat Cell Biol. 2007 September; 9(9): 1005-1009.). This leads to protcolytic cleavage of the latent zinc finger transcription factors GLI3- and to some extent also of GLI2- into C-terminally truncated repressor forms ($GLI^R$). $GLI^R$ formation involves preceding and sequential phosphorylation by protein kinase A (PKA), glycogen synthase kinase 3-beta (GSK) and casein kinase I (CKI) (Price and Kalderon, Cell. 2002 Mar. 22; 108(6):823-835.) as well as a functional primary cilium (Smith and Rohatgi, Sci Signal. 2011 Jan. 11; 4(155):mr1; Wang et al., Cell. 2000 Feb. 18; 100(4):423-434; Wen et al., Mol Cell Biol. 2010 April; 30(8):1910-1922; Wong et al., Nat Med. 2009 September; 15(9):1055-1061.). Following processing, $GLI^R$ translocates to the nucleus to bind to HH target gene promoters and repress target gene expression (Aza-Blanc and Kornberg, Trends Genet. 1999 November; 15(11):458-462; Aza-Blanc et al., Cell. 1997 Jun. 27; 89(7):1043-1053.). GLI signals are also negatively regulated by proteasome-mediated degradation of GLI and by binding to Suppressor of Fused (SUFU), which sequesters GLI proteins in the cytoplasm and also contributes to GLI processing in the primary cilium (Humke et al., Genes Dev. 2010 Apr. 1; 24(7):670-682; Kogerman et al., Nat Cell Biol. 1999 September; 1(5):312-319.).

The therapeutic relevance of targeting HH/GLI signaling in human cancers with genetic, ligand-independent activation of HH/GLI signaling has recently been demonstrated for basal-cell carcinoma (BCC) and medulloblastoma. In both malignant entities, inhibition of the essential HH pathway effector Smoothened had a dramatic therapeutic benefit (Rudin et al., N Engl J Med. 2009 Sep. 17; 361(12):1173-1178; Skvara et al., J Invest Dermatol. 2011 August; 131 (8):1735-1744; Von Hoff et al., N Engl J Med. 2009 Sep. 17; 361(12):1164-1172.). Whether Smoothened antagonists will display therapeutic efficacy in HH ligand dependent cancers remains to be shown. Ongoing clinical trials with Smoothened antagonists from different pharmaceutical companies will eventually answer the question of the clinical efficacy of targeting Smoothened in Hedgehog associated malignancies (Aberger et al., Vitam Horm. 2012; 88:25-54; Lin and Matsui, Onco Targets Ther. 2012; 5:47-58; Ng and Curran, Nat Rev Cancer. 2011 May 26; 11(7):493-501; Scales and de Sauvage, Trends Pharmacol Sci. 2009 June; 30(6):303-312.). Clinical studies with small molecule Smoothened inhibitors to treat patients with metastatic colorectal cancer, ovarian cancer or pancreatic cancer failed to demonstrate therapeutic efficacy of Smoothened antagonists in combination with currents treatment regimens (Ng and Curran, Nat Rev Cancer. 2011 May 26; 11(7):493-501.).

One of the reasons for the lack of therapeutic efficacy of Smoothened inhibitors may be explained by Smoothened-independent activation of GLI transcription factors in different cancer entities such as pancreatic cancer, melanoma or Ewing's sarcoma. This non-canonical activation of GLI transcription factors can be induced by a variety of signals frequently hyperactive in malignant cells including TGF-b/SMAD, RAS-MEK/ERK, PI3K/AKT, EGFR signaling or the EWS-FLI1 oncogene (reviewed in (Aberger et al., Vitam Horm. 2012; 88:25-54; Mangelberger et al., Front Biosci. 2012 Jan. 1; 17:90-99; Stecca and Ruiz, J Mol Cell Biol. 2010 April; 2(2):84-95.).

Regulation of HH/GLI Signaling by DYRK Family Members

The first regulatory interactions between DYRK family members and the HH/GLI pathway came from studies of DYRK1A and its impact on the transcriptional activity of the GLI zinc finger transcription factors mediating the transcriptional output of HH pathway activation. Using reporter gene based assays, Mao et al. have shown that DYRK1A is able to enhance the activity of the GLI1 activator and stimulate HH target gene expression, respectively. DYRK1A can phosphorylate GLI1 in vitro and enhance the nuclear level of GLI1. Direct modification of GLI1 and enhanced nuclear localization in response to DYRK1A activity are likely to account for the enhanced expression of HH target genes (Mao et al., J Biol Chem. 2002 Sep. 20; 277(38):35156-35161.).

While DYRK1A enhances GLI activity, the class II DYRK family member DYRK2 acts as negative regulator of GLI activity. DYRK2 can directly phosphorylate GLI2 and GLI3 resulting in destabilization of GLI2/3 and enhanced proteasome-dependent degradation. Mutation of the DYRK2 substrate phosphorylation sites S384 and S1011 in GLI2 rendered GLI2 resistant to DYRK2 mediated inhibition of transcriptional activity and proteasomal degradation (Varjosalo et al., Cell. 2008 May 2; 133(3):537-548.).

Analysis of DYRK1B function in HH-unresponsive RAS mutant pancreatic cancer cells revealed another regulatory mechanism by which DYRK kinases can affect the activity of HH signaling. Lauth et al. (Nat Struct Mol Biol. 2010 June; 17(6):718-725) provide evidence that DYRK1B is involved in an autocrine-to-paracrine shift of HH signaling triggered by mutant RAS. This study suggests that oncogenic RAS signaling in pancreatic cancer cells increases HH ligand expression though at the same time it also prevents autocrine HH pathway activation (Lauth et al., Nat Struct Mol Biol. 2010 June; 17(6):718-725.). RAS signaling therefore contributes to paracrine HH signaling, with tumor cells representing the signal source and adjacent stroma cells the signal-receiving compartment (Yauch et al., Nature. 2008 Sep. 18; 455(7211):406-410.). Like RAS, expression of the RAS effector DYRK1B in HH activated mouse fibroblasts inhibited HH signaling, suggesting that DYRK1B can act downstream of RAS to prevent autocrine HH signaling. Further, RNAi knockdown of RAS and DYRK1B in RAS mutant pancreatic cancer cells both led to a GLI2-dependent increase in GLI1 mRNA expression (Lauth et al., Nat Struct Mol Biol. 2010 June; 17(6):718-725.). The detailed mechanisms of HH pathway inhibition by DYRK1B remain unknown.

Together, these reports show that DYRK2 and DYRK1B can have a repressive effect on HH/GLI signaling while DYRK1A functions as positive regulator of GLI transcriptional activity.

BRIEF SUMMARY OF THE INVENTION

The compounds of the present invention interact with DYRK kinase, suggesting their applicability in prevention and/or therapy of medical conditions wherein the function of Kinase plays a role.

In one aspect, the present invention provides compounds of below Formula (I), physiologically functional derivatives or salts thereof, where the groups $R^1$, $R^2$, $R^3$, $R^4$, $R^A$, $X^1$, and A, as well as the variables n, m and p are detailed further herein below.

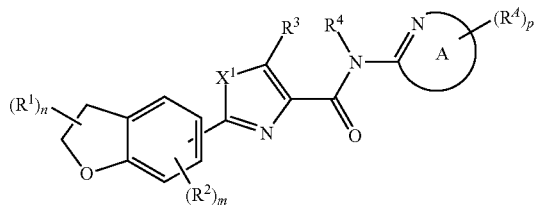

In another aspect, the present invention provides methods for preparation of compounds according to the present invention, physiologically functional derivatives, solvates or salts thereof, as detailed further herein below.

In another aspect, the present invention provides methods for the treatment or prevention of certain medical conditions, said methods comprising the administration of compounds according to the present invention, physiologically functional derivatives, solvates or salts thereof, to a subject in need thereof, as detailed further herein below.

In another aspect, the present invention provides the use of compounds according to the present invention, physiologically functional derivatives, solvates or salts thereof, in the manufacture of a medicament for the treatment or prevention of certain medical conditions, as detailed further herein below.

In another aspect, the present invention provides compounds according to the present invention, physiologically functional derivatives, solvates or salts thereof, for use in the treatment or prevention of certain medical conditions, as detailed further herein below.

In another aspect, the present invention provides pharmaceutical compositions comprising compounds according to the present invention, physiologically functional derivatives, solvates or salts thereof and one or more pharmaceutically acceptable excipients.

DESCRIPTION OF THE FIGURES

FIG. 1 shows the results of a xenograft assay with L3.6pl cancer cells in Foxn1nu/nu nude mice, administration of the compound of example 5 (dashed line) versus vehicle control (solid line). The x-axis reflects the time [in days], while the y-axis reflects the tumor volume [in mm$^3$].

DETAILED DESCRIPTION OF THE INVENTION

Certain embodiments of the present invention are enumerated in the following items:

1. A compound of formula (I) or a physiologically functional derivative, solvate or salt thereof,

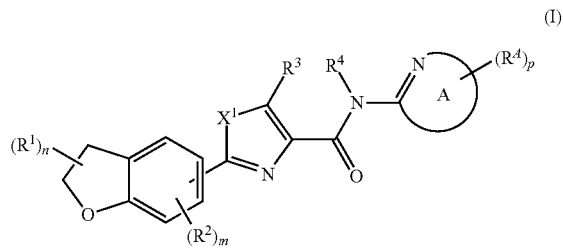

(I)

wherein the $X^1$-azol moiety is attached at the 5- or 6-position of the 2,3-dihydrobenzofuran mioety,
n is an integer from 0 to 2;
m is an integer from 0 to 3;
p is an integer from 0 to 4;
$R^1$ is independently selected from the group comprising H, halogen, alkyl, aralkyl, haloalkyl, haloalkoxy, OH, alkoxy, —CN, aryl, heteroaryl, cycloalkyl, heterocycloalkyl, —S—R', —SO—R', nitro, —NH$_2$, —N(R')$_2$, —NH(R'), —NHCO(R'), —CONH$_2$, —CONH(R'), —CO(R'), —COH, —COO(R'), —COOH, —SO$_2$NH$_2$, —SO$_2$NH(R'), —SO$_2$(R'), —NH—SO$_2$(R') and —NHCOOR';
$R^2$ is independently selected from the group comprising H, halogen, alkyl, aralkyl, haloalkyl, haloalkoxy, OH, alkoxy, —CN, aryl, heteroaryl, cycloalkyl, heterocycloalkyl, —S—R', —SO—R', nitro, —NH$_2$, —N(R')$_2$, —NH(R'), —NHCO(R'), —CONH$_2$, —CONH(R'), —CO(R'), —COH, —COO(R'), —COOH, —SO$_2$NH$_2$, —SO$_2$NH(R'), —SO$_2$(R'), —NH—SO$_2$(R') and —NHCOOR';
$R^3$ is independently selected from the group comprising H, halogen, alkyl, aralkyl, haloalkyl, haloalkoxy, OH, alkoxy, —CN, aryl, heteroaryl, cycloalkyl, heterocycloalkyl, —S—R', —SO—R', nitro, —NH$_2$, —N(R')$_2$, —NH(R'), —NHCO(R'), —CONH$_2$, —CONH(R'), —CO(R'), —COH, —COO(R'), —COOH, —SO$_2$NH$_2$, —SO$_2$NH(R'), —SO$_2$(R'), —NH—SO$_2$(R') and —NHCOOR';
$R^4$ is independently selected from the group comprising H, alkyl, aralkyl, haloalkyl, haloalkoxy, OH, alkoxy, aryl, heteroaryl, cycloalkyl, heterocycloalkyl, —CONH$_2$, —CONH(R'), —CO(R'), —COO(R'), and —SO$_2$(R');
$X^1$ is independently selected from the group comprising NR'', O or S;
R'' is independently selected from the group comprising H, alkyl, aralkyl, haloalkyl, haloalkoxy, OH, alkoxy, aryl, heteroaryl, cycloalkyl, heterocycloalkyl. —CONH$_2$, —CONH(R'), —CO(R'), —COO(R'), and —SO$_2$(R');

A is a monocyclic or bicyclic heteroaromatic ring system consisting of 5 to 10 ring atoms, at least one of which is an N atom, wherein optionally one to three further ring atoms are heteroatoms independently selected from the group comprising O, S and N and wherein the remaining ring atoms are carbon atoms;

R$^4$ is independently selected from the group comprising H, halogen, CN, NO$_2$, alkyl, haloalkyl, aryl, hetcroaryl, cycloalkyl, heterocycloalkyl, —OR', —CO—R', —COO—R', —CONH—R', —NHCO—R', —CON(R')$_2$, —NR'CO—R', —NR'—CONR', —NR'—COOR', —S—R', —SO—R', —SO$_2$—R', —NHSO$_2$—R', —SO$_2$NH—R', —O—CO—NHR', —O—CO—R', —R'—O—R', —R'—CO—R', —R'—NH—R', —R'—CONH—R', —R'—NHCO—R', —CONH-alkyl-O—R', —CONH-alkyl-R', —NHCO-alkyl-O—R', —NHCO-alkyl-R', —CO—R'-alkyl-R', —CO—R'-alkyl, —S-alkyl-R' and alkyl-R';

or in an alternative embodiment of item 1, R$^4$ is independently selected from the group comprising H, halogen, CN, NO$_2$, alkyl, haloalkyl, aryl, heteroaryl, cycloalkyl, heterocycloalkyl, —OR', —CO—R', —COO—R', —CONH—R', —NHCO—R', —CON(R')$_2$, —NR'CO—R', —NR'—CONR', —NR'—COOR', —S—R', —SO—R', —SO$_2$—R', —NHSO$_2$—R', —SO$_2$NH—R', —O—CO—NHR', —O—CO—R', —R'—O—R', —R'—CO—R', —R'—NH—R', —R'—CONH—R', —R'—NHCO—R', —CONH-alkyl-O—R', —CONH-alkyl-R', —NHCO-alkyl-O—R', —NHCO-alkyl-R', —CO—R'-alkyl-R', —CO—R'-alkyl, N(R')$_2$, —NHR', NH$_2$, —S—R', —S-alkyl-R' and alkyl-R';

R' is independently selected from the group comprising H, alkyl, haloalkyl, aryl, heteroaryl, cycloalkyl and heterocycloalkyl;

wherein any of the aforementioned alkyl, aryl, heteroaryl, cycloalkyl and heterocycloalkyl may independently be substituted with one or more, particularly one to three, more particularly one or two substituents R", wherein R" independently selected from the group comprising C$_{1-4}$-alkyl halogen, C$_{1-4}$-haloalkyl, OH, C$_{1-4}$-alkoxy, C$_{1-4}$-haloalkoxy, nitro, —NH$_2$, —N(C$_{1-4}$-alkyl)$_2$, —NH(C$_{1-4}$-alkyl), —NHCO(C$_{1-4}$-alkyl), —CONH$_2$, —CONH(C$_{1-4}$-alkyl), —CO(C$_{1-4}$-alkyl), —COH, —COO(C$_{1-4}$-alkyl), —COOH and —CN.

2. A compound according to item 1, wherein
R$^1$ is independently selected from the group comprising H, fluorine, chlorine, methyl, ethyl, isopropyl, trifluoromethyl, trifluoromethoxy, OH, methoxy, ethoxy, —CN, nitro, —NH$_2$, —N(methyl)$_2$, —NH-methyl, —NHCO-methyl, —CONH$_2$, —CONH-methyl, acetyl, —COO-methyl, and —COOH; and
R$^2$ is independently selected from the group comprising H, fluorine, chlorine, methyl, ethyl, isopropyl, trifluoromethyl, trifluoromethoxy, OH, methoxy, ethoxy, —CN, nitro, —NH$_2$, —N(methyl)$_2$, —NH-methyl, —NHCO-methyl, —CONH$_2$, —CONH-methyl, acetyl, —COO-methyl, and —COOH,
or a physiologically functional derivative, solvate or salt thereof.

3. A compound according to any of items 1 or 2, wherein n is 0 and m is 0, or a physiologically functional derivative, solvate or salt thereof.

4. A compound according to any of items 1 to 3, wherein R$^3$ is independently selected from the group comprising H, fluorine, chlorine, methyl, ethyl, isopropyl, trifluoromethyl, —OCF$_3$, OH, methoxy, ethoxy, —CN, nitro, —NH$_2$, —N(methyl)$_2$, —NH-methyl, —NHCO-methyl, —CONH$_2$, —CONH-methyl, acetyl, —COO-methyl, and —COOH, or a physiologically functional derivative, solvate or salt thereof.

5. A compound according to any of items 1 to 4, wherein R$^3$ is H, or a physiologically functional derivative, solvate or salt thereof.

6. A compound according to any of items 1 to 5, wherein R$^4$ is independently selected from the group comprising H, C$_{1-3}$-alkyl, C$_{1-4}$-haloalkyl, OH, —CONH$_2$, —CONH—C$_{1-3}$-alkyl, —CO—C$_{1-3}$-alkyl, and —COO—C$_{1-3}$-alkyl, or a physiologically functional derivative, solvate or salt thereof.

7. A compound according to any of items 1 to 6, wherein R$^4$ is H, or a physiologically functional derivative, solvate or salt thereof.

8. A compound according to any of items 1 to 7, wherein
A is a monocyclic heteroaromatic ring system consisting of 5 or 6 ring atoms, or a bicyclic heteroaromatic ring system consisting of 9 ring atoms, wherein at least one of the ring atoms is an N atom, wherein optionally one or two further ring atoms are N atoms and wherein the remaining ring atoms are carbon atoms,
or in an alternative embodiment of item 8, A is a monocyclic heteroaromatic ring system consisting of 5 or 6 ring atoms, or a bicyclic heteroaromatic ring system consisting of 9 ring atoms, wherein at least one of the ring atoms is an N atom, wherein optionally one or two further ring atoms are N atoms,
or one further ring atom is an O or S atom,
or one further ring atom is an N atom and one ring atom is an O or S atom,
and wherein the remaining ring atoms are carbon atoms;
wherein A is optionally substituted with one or two substituents R$^4$ selected from the group comprising H, CN, NO$_2$, halogen OH, alkoxy, haloalkyl, alkyl, haloalkoxy, —COOH, —COO-alkyl, aralkyl, aryl, —CO—N(alkyl)$_2$, —CONH-(alkyl), —CONH-alkyl-alkoxy, —CONH-cycloalkyl, —CONH-alkyl-heterocycloalkyl, —CO-heterocycloalkyl-alkyl-heterocycloalkyl, —CO-heterocycloalkyl, —SO$_2$-alkyl, —S-alkyl, and —S-aralkyl,
or a physiologically functional derivative, solvate or salt thereof,
or in an alternative embodiment of item 8, A is optionally substituted with one or two substituents R$^4$ selected from the group comprising H, CN, NO$_2$, NH$_2$, N(alkyl)$_2$, halogen OH, alkoxy, haloalkyl, alkyl, haloalkoxy, alkoxyalkyl, heterocycloalkyl, heterocycloalkyl-alkyl, -heterocycloalkyl-COO-alkyl, heteroaryl, —COOH, —COO-alkyl, aralkyl, aryl, -aryl-halogen, —CO—N(alkyl)$_2$, —CONH-(alkyl), —CONH-alkyl-alkoxy, —CONH-cycloalkyl, —CONH-alkyl-heterocycloalkyl, —CO-heterocycloalkyl-alkyl-heterocycloalkyl, —CO-heterocycloalkyl, —CO-heteroaryl, —CO-aryl, —CO-alkyl, —SO$_2$— alkyl, —S-alkyl, —S-alkyl-COO-alkyl, and —S-aralkyl.

9. A compound according to any of items 1 to 8, wherein
A is a monocyclic or bicyclic heteroaromatic ring system selected from the group comprising thiazole, oxazole, pyrazole, pyrrole, benzoxazole, benzothiazole, benzimidazole, imidazole, triazole, pyrazine, triazine, pyrimidine and pyridine, or in an alternative embodiment of item 9, A is a monocyclic or bicyclic heteroaromatic ring system selected from the group comprising thiazole, oxazole, pyrazole, pyrrole, benzoxazole, benzothiazole, benzimidazole, imidazole, triazole, pyrazine, triazine, pyrimidine, pyridine, thiadiazole, and oxadiazole, wherein A is optionally substituted with a substituent $R^A$ selected from the group comprising H, CN, F, Cl, OH, $C_{1-2}$-alkoxy, $CF_3$, $OCF_3$, —COOH, —COO—($C_{1-2}$-alkyl), benzyl, phenethyl, phenyl, —CO—N($C_{1-2}$-alkyl)$_2$, —CONH—($C_{1-2}$-alkyl), —CONH—($C_{1-2}$-alkyl)-O($C_{1-2}$-alkyl), —CONH—($C_{3-5}$-cycloalkyl), —CONH—($C_{1-2}$-alkyl-tetrahydrofuryl), —CO-piperazinyl-($C_{1-2}$-alkyl)-tetrahydrofuranyl, —CO-morholinyl, —CO-pyrrolidinyl, —CO-(methyl-piperazinyl)-, —SO$_2$($C_{1-2}$-alkyl), —S—($C_{1-4}$-alkyl), —S-benzyl, —S-(chlorophenylmethyl), and —S-phenethyl, or in an alternative embodiment of item 9, A is optionally substituted with a substituent $R^A$ selected from the group comprising H, CN, F, Cl, Br, OH, $C_{1-2}$-alkyl, $C_{1-2}$-alkoxy, $CF_3$, $OCF_3$, —COOH, —COO—($C_{1-2}$-alkyl), benzyl, phenethyl, phenyl, fluorophenyl, —CO—N($C_{1-2}$-alkyl)$_2$, —CONH—($C_{1-2}$-alkyl), —CONH—($C_{1-2}$-alkyl)-O($C_{1-2}$-alkyl), —CONH—($C_{3-5}$-cycloalkyl), —CONH—($C_{1-2}$-alkyl-tetrahydrofuryl), —CO-piperazinyl-($C_{1-2}$-alkyl)-tetrahydrofuranyl, —CO-morholinyl, —CO-pyrrolidinyl, —CO-(methyl-piperazinyl)-, —SO$_2$($C_{1-2}$-alkyl), —S—($C_{1-4}$-alkyl), —S-benzyl, —S-(chlorophenylmethyl), —S—phenethyl, —CO-thienyl, —CO-pyrrolyl, —CO-piperidinyl, —CO-piperidinyl-COO—($C_{1-2}$-alkyl), morpholinyl, $C_{1-2}$-alkylpiperazinyl, $C_{1-2}$-alkylthiazolyl, pyridyl, —CO-phenyl, —S—($C_{1-2}$-alkyl)-COO—($C_{1-2}$-alkyl), NH$_2$, N($C_{1-2}$-alkyl)$_2$, —CO—$C_{1-2}$-alkyl, —($C_{1-2}$-alkyl)-O($C_{1-2}$-alkyl)

and wherein, when A is benzoxazole, benzothiazole or benzimidazole, A may optionally further be substituted with a halogen atom, or in an alternative embodiment of item 9, when A is benzoxazole, benzothiazole or benzimidazole, A may optionally further be substituted with a halogen atom, and wherein, when A is thiazole, A may optionally further be substituted with a methyl group or a physiologically functional derivative, solvate or salt thereof.

10. A compound according to any of items 1 to 9, wherein the $X^1$-azol moiety is attached at the 5-position of the 2,3-dihydrobenzofuran mioety.

11. A compound according to item 1, wherein
the $X^1$-azol moiety is attached at the 5-position of the 2,3-dihydrobenzofuran mioety;
n is 0 or 1;
m is 0 or 1;
$X^1$ is independently selected from the group comprising NR″, O or S;
R″ is independently selected from the group comprising H, methyl, ethyl, OH, —CONH$_2$, —CONH-methyl, and —COO-methyl;
$R^1$ is independently selected from the group comprising H, fluorine, chlorine, methyl, ethyl, isopropyl, trifluoromethyl, trifluoromethoxy, OH, methoxy, ethoxy, —CN, nitro, —NH$_2$, —N(methyl)$_2$, —NH-methyl, —NHCO-methyl, —CONH$_2$, —CONH-methyl, acetyl, —COO-methyl, and —COOH;
$R^2$ is independently selected from the group comprising H, fluorine, chlorine, methyl, ethyl, isopropyl, trifluoromethyl, trifluoromethoxy, OH, methoxy, ethoxy, —CN, nitro, —NH$_2$, —N(methyl)$_2$, —NH-methyl, —NHCO-methyl, —CONH$_2$, —CONH-methyl, acetyl, —COO-methyl, and —COOH;
$R^3$ is independently selected from the group comprising H, fluorine, chlorine, methyl, ethyl, isopropyl, trifluoromethyl, trifluoromethoxy, OH, methoxy, ethoxy, —CN, nitro, —NH$_2$, —N(methyl)$_2$, —NH-methyl, —NHCO-methyl, —CONH$_2$, —CONH-methyl, acetyl, —COO-methyl, and —COOH;
$R^4$ is independently selected from the group comprising H, $C_{1-3}$-alkyl, $C_{1-4}$-haloalkyl, OH, —CONH$_2$, —CONH—$C_{1-3}$-alkyl, —CO—$C_{1-3}$-alkyl, and —COO—$C_{1-3}$-alkyl;
A is independently selected from the group comprising thiazole, oxazole, pyrazole, pyrrole, benzoxazole, benzothiazole, benzimidazole, imidazole, triazole, pyrazine, triazine, pyrimidine and pyridine;
or in an alternative embodiment of item 11, A is independently selected from the group comprising thiazole, oxazole, pyrazole, pyrrole, benzoxazole, benzothiazole, benzimidazole, imidazole, triazole, pyrazine, triazine, pyrimidine, pyridine, thiadiazole, and oxadiazole;
wherein A is optionally substituted with a substituent $R^A$ selected from the group comprising H, CN, F, Cl, OH, $C_{1-2}$-alkoxy, $CF_3$, $OCF_3$, —COOH, —COO—($C_{1-2}$-alkyl), benzyl, phenethyl, phenyl, —CO—N($C_{1-2}$-alkyl)$_2$, —CONH—($C_{1-2}$-alkyl), —CONH—($C_{1-2}$-alkyl)-O($C_{1-2}$-alkyl), —CONH—($C_{3-5}$-cycloalkyl), —CONH—($C_{1-2}$-alkyl-tetrahydrofuryl), —CO-piperazinyl-($C_{1-2}$-alkyl)-tetrahydrofuranyl, —CO-morholinyl, —CO-pyrrolidinyl, —CO-(methyl-piperazinyl)-, —SO$_2$($C_{1-2}$-alkyl), —S—($C_{1-4}$-alkyl), —S-benzyl, —S-(chlorophenylmethyl), and —S-phenethyl;

or in an alternative embodiment of item 11, A is optionally substituted with a substituent $R^A$ selected from the group comprising H, CN, F, Cl, Br, OH, $C_{1-2}$-alkyl, $C_{1-2}$-alkoxy, $CF_3$, $OCF_3$, —COOH, —COO—($C_{1-2}$-alkyl), benzyl, phenethyl, phenyl, fluorophenyl, —CO—N($C_{1-2}$-alkyl)$_2$, —CONH—($C_{1-2}$-alkyl), —CONH—($C_{1-2}$-alkyl)-O($C_{1-2}$-alkyl), —CONH—($C_{3-5}$-cycloalkyl), —CONH—($C_{1-2}$-alkyl-tetrahydrofuryl), —CO-piperazinyl-($C_{1-2}$-alkyl)-tetrahydrofuranyl, —CO-morholinyl, —CO-pyrrolidinyl, —CO-(methyl-piperazinyl)-, —SO$_2$($C_{1-2}$-alkyl), —S—($C_{1-4}$-alkyl), —S-benzyl, —S-(chlorophenylmethyl), —S—phenethyl, —CO-thienyl, —CO-pyrrolyl, —CO-piperidinyl, —CO-piperidinyl-COO—($C_{1-2}$-alkyl), morpholinyl, $C_{1-2}$-alkylpiperazinyl, $C_{1-2}$-alkylthiazolyl, pyridyl, —CO-phenyl, —S—($C_{1-2}$-alkyl)-COO—($C_{1-2}$-alkyl), NH$_2$, N($C_{1-2}$-alkyl)$_2$, —CO—$C_{1-2}$-alkyl, and —($C_{1-2}$-alkyl)-O($C_{1-2}$-alkyl);

and wherein, when A is benzoxazole, benzothiazole or benzimidazole, A may optionally further be substituted with a halogen atom, or in an alternative embodiment of item 11, when A is benzoxazole, benzothiazole or benzimidazole, A may optionally further be substituted with a halogen atom, and wherein, when A is thiazole, A may optionally further be substituted with a methyl group, or a physiologically functional derivative, solvate or salt thereof.

12. A compound according to item 1, wherein
the $X^1$-azol moiety is attached at the 5-position of the 2,3-dihydrobenzofuran mioety,
n is 0; m is 0; $X^1$ is S, $R^3$ is H; $R^4$ is H;

A is a monocyclic or bicyclic heteroaromatic ring system selected from the group comprising 1H-imidazol-2-yl, 1H-1,2,4-triazol-5-yl, 1H-benzo[d]imidazol-2-yl and pyridin-2-yl;

or in an alternative embodiment of item 12, A is a monocyclic or bicyclic heteroaromatic ring system selected from the group comprising 1H-imidazol-2-yl, 1H-1,2,4-triazol-5-yl, 1H-benzo[d]imidazol-2-yl, pyridin-2-yl, 1,3,4-thiadiazol-2-yl, 1H-pyrazol-3-yl, 1,3-thiazol-2-yl, and 1,2,4-thiadiazol-3-yl;

wherein A is optionally substituted with a substituent $R^A$ selected from the group comprising F, Cl, CN, —SO$_2$-Me, OMe, CF$_3$, —CO—N(Me)$_2$, —CO—N(Me)$_2$, 5-(4-((tetrahydrofuran-2-yl)methyl)piperazine-1-carbonyl, —COO-Et, morpholine-4-carbonyl, OCF$_3$, —COO-Me, OH, —CO—NHMe, —S-Me, pyrrolidin-1-carbonyl, —CO—NH—C$_2$H$_4$—OMe, —S-iPr, cyclopropylcarbamoyl, 4-methylpiperazine-1-carbonyl, —S-nPr, COOH, —S-benzyl, —S-(4-chlorobenzyl), —S-iBu, ((tetrahydrofuran-2-yl)methyl)carbamoyl, phenethyl and —S-phenethyl;

or in an alternative embodiment of item 12, A is optionally substituted with a substituent $R^A$ selected from the group comprising F, Cl, Br, CN, methyl, —SO$_2$-Me, OMe, CF$_3$, —CO—N(Me)$_2$, —CO—N(Me)$_2$, 5-(4-((tetrahydrofuran-2-yl)methyl)piperazine-1-carbonyl, —COO-Et, morpholine-4-carbonyl, OCF$_3$, —COO-Me, OH, —CO—NHMe, —S-Me, pyrrolidin-1-carbonyl, —CO—NH—C$_2$H$_4$—OMe, —S-iPr, cyclopropylcarbamoyl, 4-methylpiperazine-1-carbonyl, —S-nPr, COOH, —S-benzyl, —S-(4-chlorobenzyl), —S-iBu, ((tetrahydrofuran-2-yl)methyl)carbamoyl, phenethyl, —S-phenethyl, —CO-thien-2-yl, —CO-pyrrol-2-yl, —CO-piperidin-1-yl, —CO-(4ethoxycarbonyl-piperidin-1-yl), morpholin-4-yl, 4-methyl-piperazin-1-yl, 5-methyl-thiazol-2-yl, pyridin-4-yl, —CO-phenyl, —S—(CH$_2$)—COOMe, NH$_2$, —CO—C$_{1-2}$-alkyl, 3-fluorophenyl, acetyl, -methylthio, and methoxymethyl;

and wherein, when A is 1H-benzo[d]imidazol-2-yl, A may optionally further be substituted with a chlorine atom, or in an alternative embodiment of item 12, when A is 1H-benzo[d]imidazol-2-yl, A may optionally further be substituted with a chlorine atom, and when A is 1,3-thiazol-2-yl, A may optionally further be substituted with a methyl group, or a physiologically functional derivative, solvate or salt thereof.

13. A compound according to any of items 1 to 12, wherein said compound is selected from the group comprising the compounds 1 to 47, or in an alternative embodiment of item 13 compounds 1 to 82, as shown below in the example section, or a physiologically functional derivative, solvate or salt thereof.

14. A compound according to any of items 1 to 13, or a physiologically functional derivative, solvate or salt thereof for use in the treatment of a medical condition selected from the group comprising cancer of the breast, esophagus, gastrointestinal tract, gastro-intestinal stromal tumors, pancreas, prostate, biliary tract, bladder, basal cell carcinoma, medulloblastoma, rhabdomyosarcoma, glioma, small-cell lung cancer, oral squamous cell carcinoma, melanoma, colorectal cancer, non-small cell lung cancer, osteosarcoma, glioblastoma, chronic lymphacytic leukemia, chronic myeloid leukemia, multiple myeloma, acute myeloid leukemia, ovarian cancer, meningioma, and liver cancer.

15. A pharmaceutical composition comprising a compound according to any of items 1 to 13 or a physiologically functional derivative, solvate or salt thereof and one or more pharmaceutically acceptable excipients.

16. A method of treatment of a medical condition selected from the group comprising cancer of the breast, esophagus, gastrointestinal tract, gastro-intestinal stromal tumors, pancreas, prostate, biliary tract, bladder, basal cell carcinoma, medulloblastoma, rhabdomyosarcoma, glioma, small-cell lung cancer, oral squamous cell carcinoma, melanoma, colorectal cancer, non-small cell lung cancer, osteosarcoma, glioblastoma, chronic lymphacytic leukemia, chronic myeloid leukemia, multiple myeloma, acute myeloid leukemia, ovarian cancer, meningioma, and liver cancer, which comprises the administration of an effective amount of a compound according to any of items 1 to 13, or a physiologically functional derivative, solvate or salt thereof to a subject in need thereof.

17. Use of a compound according to any of items 1 to 13, or a physiologically functional derivative, solvate or salt thereof in the manufacture of a medicament for the treatment of a medical condition selected from the group comprising cancer of the breast, esophagus, gastrointestinal tract, gastro-intestinal stromal tumors, pancreas, prostate, biliary tract, bladder, basal cell carcinoma, medulloblastoma, rhabdomyosarcoma, glioma, small-cell lung cancer, oral squamous cell carcinoma, melanoma, colorectal cancer, non-small cell lung cancer, osteosarcoma, glioblastoma, chronic lymphacytic leukemia, chronic myeloid leukemia, multiple myeloma, acute myeloid leukemia, ovarian cancer, meningioma, and liver cancer.

In certain embodiments, n is an integer from 0 to 1, more particularly n is 0.

In certain embodiments, m is an integer from 0 to 2, more particularly 0 to 1, even more particularly 0.

In certain embodiments, p is an integer from 0 to 3, more particularly 0 to 2, even more particularly 0 to 1, yet even more particularly 1.

In certain embodiments, $R^1$ is independently selected from the group comprising H, halogen, $C_{1-4}$-alkyl, benzyl, $C_{1-4}$-haloalkyl, $C_{1-4}$-haloalkoxy, OH, $C_{1-4}$-alkoxy, —CN, phenyl, naphthyl, pyridyl, pyrrolyl, furanyl, thienyl, thiazolyl, oxazolyl, pyrazolyl, cyclopropyl, cyclobutyl, cyclopentyl, cyclohexyl, cycloheptyl, decalinyl, tetrahydrofuryl, tetrahydropyranyl, tetrahydrothienyl, piperidyl, piperazinyl, morpholinyl, pyrrolidinyl, —S—$C_{1-4}$alkyl, —SO—$C_{1-4}$alkyl, nitro, —NH$_2$, —N($C_{1-4}$alkyl)$_2$, —NH—$C_{1-4}$alkyl, —NHCO—$C_{1-4}$alkyl, —CONH$_2$, —CONH—$C_{1-4}$alkyl, —CO—$C_{1-4}$-alkyl, —COH, —COO—$C_{1-4}$alkyl, —COOH, —SO$_2$NH$_2$, —SO$_2$NH—$C_{1-4}$alkyl, —SO$_2$—$C_{1-4}$alkyl, —NH—SO$_2$—$C_{1-4}$alkyl and —NHCOO—$C_{1-4}$ alkyl.

In more particular embodiments, $R^1$ is independently selected from the group comprising H, halogen, $C_{1-4}$-alkyl, benzyl, $C_{1-4}$-haloalkyl, $C_{1-4}$-haloalkoxy, OH, $C_{1-4}$-alkoxy, —CN, phenyl, cyclopropyl, cyclobutyl, cyclopentyl, cyclohexyl, —S—$C_{1-4}$alkyl, —SO—$C_{1-4}$alkyl, nitro, —NH$_2$, —N($C_{1-4}$alkyl)$_2$, —NH—$C_{1-4}$alkyl, —NHCO—$C_{1-4}$alkyl, —CONH$_2$, —CONH—$C_{1-4}$alkyl, —CO—$C_{1-4}$alkyl, —COO—$C_{1-4}$alkyl, —COOH, —SO$_2$NH$_2$, —SO$_2$NH—$C_{1-4}$alkyl, —SO$_2$—$C_{1-4}$alkyl, —NH—SO$_2$—$C_{1-4}$alkyl and —NHCOO—$C_{1-4}$alkyl.

In even more particular embodiments, $R^1$ is independently selected from the group comprising H, halogen, $C_{1-4}$-alkyl, $C_{1-4}$-haloalkyl, $C_{1-4}$-haloalkoxy, OH, $C_{1-4}$-alkoxy, —CN, cyclopropyl, cyclobutyl, nitro, —NH$_2$, —N($C_{1-4}$alkyl)$_2$, —NH—$C_{1-4}$alkyl, —NHCO—$C_{1-4}$alkyl, —CONH$_2$, —CONH—$C_{1-4}$alkyl, —CO—$C_{1-4}$alkyl, —COO—$C_{1-4}$alkyl, and —COOH.

In yet even more particular embodiments, $R^1$ is independently selected from the group comprising H, halogen, $C_{1-4}$-alkyl, $C_{1-4}$-haloalkyl, $C_{1-4}$-haloalkoxy, OH, $C_{1-4}$-alkoxy, —CN, nitro, —$NH_2$, —$N(C_{1-2}$alkyl$)_2$, —NH—$C_{1-2}$alkyl, —NHCO—$C_{1-2}$alkyl, —$CONH_2$, —CONH—$C_{1-2}$alkyl, —CO—$C_{1-2}$alkyl, —COO—$C_{1-2}$alkyl, and —COOH.

In yet even more particular embodiments, $R^1$ is independently selected from the group comprising H, fluorine, chlorine, bromine, $C_{1-3}$alkyl, trifluoromethyl, difluoromethyl, trifluoromethoxy, OH, $C_{1-3}$-alkoxy, —CN, nitro, —$NH_2$, —$N(C_{1-2}$alkyl$)_2$, —NH—$C_{1-2}$alkyl, —NHCO—$C_{1-2}$alkyl, —$CONH_2$. —CONH—$C_{1-2}$alkyl, —CO—$C_{1-2}$alkyl, —COO—$C_{1-2}$alkyl, and —COOH. In yet even more particular embodiments. $R^1$ is independently selected from the group comprising H, fluorine, chlorine, methyl, ethyl, isopropyl, trifluoromethyl, trifluoromethoxy, OH, methoxy, ethoxy, —CN, nitro, —$NH_2$, —$N(methyl)_2$, —NH-methyl, —NHCO-methyl, —$CONH_2$, —CONH-methyl, acetyl, —COO-methyl, and —COOH.

In yet even more particular embodiments, $R^1$ is independently selected from the group comprising H, fluorine, chlorine, methyl, ethyl, isopropyl, trifluoromethyl, trifluoromethoxy, OH, and methoxy.

In yet even more particular embodiments, $R^1$ is independently selected from the group comprising H, fluorine, chlorine, methyl, trifluoromethyl, trifluoromethoxy, OH, and methoxy.

Most particularly, $R^1$ is independently H.

In certain embodiments, $R^2$ is independently selected from the group comprising H, halogen, $C_{1-4}$-alkyl, benzyl, $C_{1-4}$-haloalkyl, $C_{1-4}$-haloalkoxy, OH, $C_{1-4}$-alkoxy, —CN, phenyl, naphthyl, pyridyl, pyrrolyl, furanyl, thienyl, thiazolyl, oxazolyl, pyrazolyl, cyclopropyl, cyclobutyl, cyclopentyl, cyclohexyl, cycloheptyl, decalinyl, tetrahydrofuryl, tetrahydropyranyl, tetrahydrothienyl, piperidyl, piperazinyl, morpholinyl, pyrrolidinyl, —S—$C_{1-4}$alkyl, —SO—$C_{1-4}$alkyl, nitro, —$NH_2$, —$N(C_{1-4}$alkyl$)_2$, —NH—$C_{1-4}$alkyl, —NHCO—$C_{1-4}$alkyl, —$CONH_2$, —CONH—$C_{1-4}$alkyl, —CO—$C_{1-4}$alkyl, —COH, —COO—$C_{1-4}$alkyl, —COOH, —$SO_2NH_2$, —$SO_2NH$—$C_{1-4}$alkyl, —$SO_2$—$C_{1-4}$alkyl, —NH—$SO_2$—$C_{1-4}$alkyl and —NHCOO—$C_{1-4}$alkyl.

In more specific embodiments, $R^2$ is independently selected from the group comprising H, halogen, $C_{1-4}$-alkyl, benzyl, $C_{1-4}$-haloalkyl, $C_{1-4}$-haloalkoxy, OH, $C_{1-4}$-alkoxy, —CN, phenyl, cyclopropyl, cyclobutyl, cyclopentyl, cyclohexyl, —S—$C_{1-4}$alkyl, —SO—$C_{1-4}$alkyl, nitro, —$NH_2$, —$N(C_{1-4}$alkyl$)_2$, —NH—$C_{1-4}$alkyl, —NHCO—$C_{1-4}$alkyl, —$CONH_2$, —CONH—$C_{1-4}$alkyl, —CO—$C_{1-4}$alkyl, —COO—$C_{1-4}$alkyl, —COOH, —$SO_2NH_2$, —$SO_2NH$—$C_{1-4}$alkyl, —$SO_2$—$C_{1-4}$alkyl, —NH—$SO_2$—$C_{1-4}$alkyl and —NHCOO—$C_{1-4}$alkyl.

In even more particular embodiments, $R^2$ is independently selected from the group comprising H, halogen, $C_{1-4}$-alkyl, $C_{1-4}$-haloalkyl, $C_{1-4}$-haloalkoxy, OH, $C_{1-4}$-alkoxy, —CN, cyclopropyl, cyclobutyl, nitro, —$NH_2$, —$N(C_{1-4}$alkyl$)_2$, —NH—$C_{1-4}$alkyl, —NHCO—$C_{1-4}$alkyl, —$CONH_2$, —CONH—$C_{1-4}$alkyl, —CO—$C_{1-4}$alkyl, —COO—$C_{1-4}$alkyl, and —COOH.

In yet even more particular embodiments, $R^2$ is independently selected from the group comprising H, halogen, $C_{1-4}$-alkyl, $C_{1-4}$-haloalkyl, $C_{1-4}$-haloalkoxy, OH, $C_{1-4}$-alkoxy, —CN, nitro, —$NH_2$, —$N(C_{1-2}$alkyl$)_2$, —NH—$C_{1-2}$alkyl, —NHCO—$C_{1-2}$alkyl, —$CONH_2$, —CONH—$C_{1-2}$alkyl, —CO—$C_{1-2}$alkyl, —COO—$C_{1-2}$alkyl, and —COOH.

In yet even more particular embodiments, $R^2$ is independently selected from the group comprising H, fluorine, chlorine, bromine, $C_{1-3}$alkyl, trifluoromethyl, difluoromethyl, trifluoromethoxy, OH, $C_{1-3}$-alkoxy, —CN, nitro, —$NH_2$, —$N(C_{1-2}$alkyl$)_2$, —NH—$C_{1-2}$alkyl, —NHCO—$C_{1-2}$alkyl, —$CONH_2$, —CONH—$C_{1-2}$alkyl, —CO—$C_{1-2}$alkyl, —COO—$C_{1-2}$alkyl, and —COOH.

In yet even more particular embodiments, $R^2$ is independently selected from the group comprising H, fluorine, chlorine, methyl, ethyl, isopropyl, trifluoromethyl, trifluoromethoxy, OH, methoxy, ethoxy, —CN, nitro, —$NH_2$, —$N(methyl)_2$, —NH-methyl, —NHCO-methyl, —$CONH_2$, —CONH-methyl, acetyl, —COO-methyl, and —COOH.

In yet even more particular embodiments, $R^2$ is independently selected from the group comprising H, fluorine, chlorine, methyl, ethyl, isopropyl, trifluoromethyl, trifluoromethoxy, OH, and methoxy.

In yet even more particular embodiments, $R^2$ is independently selected from the group comprising H, fluorine, chlorine, methyl, trifluoromethyl, trifluoromethoxy, OH, and methoxy.

Most particularly, $R^2$ is independently H.

In certain embodiments, $R^3$ is independently selected from the group comprising H, halogen, $C_{1-4}$-alkyl, benzyl, $C_{1-4}$-haloalkyl, $C_{1-4}$-haloalkoxy, OH, $C_{1-4}$-alkoxy, —CN, phenyl, naphthyl, pyridyl, pyrrolyl, furanyl, thienyl, thiazolyl, oxazolyl, pyrazolyl, cyclopropyl, cyclobutyl, cyclopentyl, cyclohexyl, cycloheptyl, decalinyl, tetrahydrofuryl, tetrahydropyranyl, tetrahydrothienyl, piperidyl, piperazinyl, morpholinyl, pyrrolidinyl, —S—$C_{1-4}$alkyl, —SO—$C_{1-4}$alkyl, nitro, —$NH_2$, —$N(C_{1-4}$alkyl$)_2$, —NH—$C_{1-4}$alkyl, —NHCO—$C_{1-4}$alkyl, —$CONH_2$, —CONH—$C_{1-4}$alkyl, —CO—$C_{1-4}$alkyl, —COH, —COO—$C_{1-4}$alkyl, —COOH, —$SO_2NH_2$, —$SO_2NH$—$C_{1-4}$alkyl, —$SO_2$—$C_{1-4}$alkyl, —NH—$SO_2$—$C_{1-4}$alkyl and —NHCOO—$C_{1-4}$alkyl.

In more particular embodiments, $R^3$ is independently selected from the group comprising H, halogen, $C_{1-4}$-alkyl, benzyl, $C_{1-4}$-haloalkyl, $C_{1-4}$-haloalkoxy, OH, $C_{1-4}$-alkoxy, —CN, phenyl, cyclopropyl, cyclobutyl, cyclopentyl, cyclohexyl, —S—$C_{1-4}$alkyl, —SO—$Cl_4$alkyl, nitro, —$NH_2$, —$N(C_{1-4}$alkyl$)_2$, —NH—$C_{1-4}$alkyl, —NHCO—$C_{1-4}$alkyl, —$CONH_2$, —CONH—$C_{1-4}$alkyl, —CO—$C_{1-4}$alkyl, —COO—$C_{1-4}$alkyl, —COH. —$SO_2NH_2$, —$SO_2NH$—$C_{1-4}$alkyl, —$SO_2$—$C_{1-4}$alkyl, —NH—$SO_2$—$C_{1-4}$alkyl and —NHCOO—$C_{1-4}$alkyl.

In even more particular embodiments, $R^3$ is independently selected from the group comprising H, halogen, $C_{1-4}$-alkyl, $C_{1-4}$-haloalkyl, $C_{1-4}$-haloalkoxy, OH, $C_{1-4}$-alkoxy, —CN, cyclopropyl, cyclobutyl, nitro, —$NH_2$, —$N(C_{1-4}$alkyl$)_2$, —NH—$C_{1-4}$alkyl, —NHCO—$C_{1-4}$alkyl, —$CONH_2$, —CONH—$C_{1-4}$alkyl, —CO—$C_{1-4}$alkyl, —COO—$C_{1-4}$alkyl, and —COOH.

In yet even more particular embodiments, $R^3$ is independently selected from the group comprising H, halogen, $C_{1-4}$-alkyl, $C_{1-4}$-haloalkyl, $C_{1-4}$-haloalkoxy, OH, $C_{1-4}$-alkoxy, —CN, nitro, —$NH_2$, —$N(C_{1-2}$alkyl$)_2$, —NH—$C_{1-2}$alkyl, —NHCO—$C_{1-2}$alkyl, —$CONH_2$, —CONH—$C_{1-2}$alkyl, —CO—$C_{1-2}$alkyl, —COO—$C_{1-2}$alkyl, and —COOH.

In yet even more particular embodiments, $R^3$ is independently selected from the group comprising H, fluorine, chlorine, bromine, $C_{1-3}$alkyl, trifluoromethyl, difluoromethyl, trifluoromethoxy, OH, $C_{1-3}$-alkoxy, —CN, nitro, —NH$_2$, —N(C$_{1-2}$alkyl)$_2$, —NH—C$_{1-2}$alkyl, —NHCO—C$_{1-2}$alkyl, —CONH$_2$, —CONH—C$_{1-2}$alkyl, —CO—C$_{1-2}$alkyl, —COO—C$_{1-2}$alkyl, and —COOH.

In yet even more particular embodiments, R$^3$ is independently selected from the group comprising H, fluorine, chlorine, methyl, ethyl, isopropyl, trifluoromethyl, trifluoromethoxy, OH, methoxy, ethoxy, —CN, nitro, —NH$_2$, —N(methyl)$_2$, —NH-methyl, —NHCO-methyl, —CONH$_2$, —CONH-methyl, acetyl, —COO-methyl, and —COOH.

In yet even more particular embodiments, R$^3$ is independently selected from the group comprising H, fluorine, chlorine, methyl, ethyl, isopropyl, trifluoromethyl, trifluoromethoxy, OH, and methoxy.

In yet even more particular embodiments, R$^3$ is independently selected from the group comprising H, fluorine, chlorine, methyl, trifluoromethyl, trifluoromethoxy, OH, and methoxy.

Most particularly, R$^3$ is independently H.

In certain embodiments, R$^4$ is independently selected from the group comprising H, C$_{1-4}$-alkyl, benzyl, C$_{1-4}$-haloalkyl, C$_{1-4}$-haloalkoxy, OH, C$_{1-4}$-alkoxy, phenyl, naphthyl, pyridyl, pyrrolyl, furanyl, thienyl, thiazolyl, oxazolyl, pyrazolyl, cyclopropyl, cyclobutyl, cyclopentyl, cyclohexyl, cycloheptyl, decalinyl, tetrahydrofuryl, tetrahydropyranyl, tetrahydrothienyl, piperidyl, piperazinyl, morpholinyl, pyrrolidinyl, —CONH$_2$, —CONH—C$_{1-4}$-alkyl, —CO—C$_{1-4}$-alkyl, —COO—C$_{1-4}$-alkyl, and —SO$_2$—C$_{1-4}$-alkyl.

In more particular embodiments, R$^4$ is independently selected from the group comprising H, C$_{1-4}$-alkyl, benzyl, C$_{1-4}$-haloalkyl, C$_{1-4}$-haloalkoxy, OH, C$_{1-4}$-alkoxy, phenyl, —CONH$_2$, —CONH—C$_{1-4}$-alkyl, —CO—C$_{1-4}$-alkyl, —COO—C$_{1-4}$-alkyl, and —SO$_2$—C$_{1-4}$-alkyl.

In more particular embodiments, R$^4$ is independently selected from the group comprising H, C$_{1-3}$-alkyl, C$_{1-4}$-haloalkyl, OH, —CONH$_2$, —CONH—C$_{1-3}$-alkyl, —CO—C$_{1-3}$-alkyl, and —COO—C$_{1-3}$-alkyl.

In even more particular embodiments, R$^4$ is independently selected from the group comprising H, methyl, ethyl, OH, —CONH$_2$, —CONH-methyl, and —COO-methyl.

In yet even more particular embodiments, R$^4$ is independently selected from the group comprising H, and methyl.

Most particularly, R$^4$ is independently H.

In certain embodiments, X$^1$ is O or S. In more specific embodiments, X$^1$ is S.

In certain embodiments, R″ is independently selected from the group comprising H, C$_{1-4}$-alkyl, benzyl, C$_{1-4}$-haloalkyl, C$_{1-4}$-haloalkoxy, OH, C$_{1-4}$-alkoxy, phenyl, naphthyl, pyridyl, pyrrolyl, furanyl, thienyl, thiazolyl, oxazolyl, pyrazolyl, cyclopropyl, cyclobutyl, cyclopentyl, cyclohexyl, cycloheptyl, decalinyl, tetrahydrofuryl, tetrahydropyranyl, tetrahydrothienyl, piperidyl, piperazinyl, morpholinyl, pyrrolidinyl, —CONH$_2$, —CONH—C$_{1-4}$-alkyl, —CO—C$_{1-4}$-alkyl, —COO—C$_{1-4}$-alkyl, and —SO$_2$—C$_{1-4}$-alkyl.

In more particular embodiments, R″ is independently selected from the group comprising H, C$_{1-4}$-alkyl, benzyl, C$_{1-4}$-haloalkyl, C$_{1-4}$-haloalkoxy, OH, C$_{1-4}$-alkoxy, phenyl, —CONH$_2$, —CONH—C$_{1-4}$-alkyl, —CO—C$_{1-4}$-alkyl, —COO—C$_{1-4}$-alkyl, and —SO$_2$—C$_{1-4}$-alkyl.

In more particular embodiments, R″ is independently selected from the group comprising H, C$_{1-3}$-alkyl, C$_{1-4}$-haloalkyl, OH, —CONH$_2$, —CONH—C$_{1-3}$-alkyl, —CO—C$_{1-3}$-alkyl, and —COO—C$_{1-3}$-alkyl.

In even more particular embodiments, R″ is independently selected from the group comprising H, methyl, ethyl, OH, —CONH$_2$, —CONH-methyl, and —COO-methyl.

In yet even more particular embodiments, R″ is independently selected from the group comprising H, and methyl.

Most particularly, R″ is independently H.

In certain embodiments, A is a monocyclic or bicyclic heteroaromatic ring system consisting of 5 to 9 ring atoms, at least one of which is an N atom, wherein optionally one or two further ring atoms are heteroatoms independently selected from the group comprising O, S and N, particularly N, and wherein the remaining ring atoms are carbon atoms.

In more particular embodiments, A is a monocyclic heteroaromatic ring system consisting of 5 or 6 ring atoms, or a bicyclic heteroaromatic ring system consisting of 9 ring atoms, wherein at least one of the ring atoms is an N atom, wherein optionally one or two further ring atoms are heteroatoms independently selected from the group comprising O, S and N and wherein the remaining ring atoms are carbon atoms.

In other more particular embodiments, A is a 5-membered monocyclic heteroaromatic ring which is optionally fused to a phenyl ring, wherein at least one of the ring atoms is an N atom, wherein optionally one or two further ring atoms are N atoms and wherein the remaining ring atoms are carbon atoms.

In other more particular embodiments, A is a 5-membered monocyclic heteroaromatic ring which is optionally fused to a phenyl ring, wherein at least one of the ring atoms is an N atom, wherein optionally one further ring atom is an N atom and/or one further ring atom is an O or S atom, and wherein the remaining ring atoms are carbon atoms.

In even more particular embodiments, A is a monocyclic heteroaromatic ring system consisting of 5 or 6 ring atoms, or a bicyclic heteroaromatic ring system consisting of 9 ring atoms, wherein at least one of the ring atoms is an N atom, wherein optionally one or two further ring atoms are N atoms and wherein the remaining ring atoms are carbon atoms.

In other even more particular embodiments, A is a monocyclic heteroaromatic ring system consisting of 5 or 6 ring atoms, or a bicyclic heteroaromatic ring system consisting of 9 ring atoms, wherein at least one of the ring atoms is an N atom, wherein optionally one or two further ring atoms are N atoms,
or one further ring atom is an O or S atom,
or one further ring atom is an N atom and one ring atom is an O or S atom,
and wherein the remaining ring atoms are carbon atoms In other more particular embodiments, A is independently selected from the group comprising thiazole, oxazole, pyrazole, pyrrole, benzoxazole, benzothiazole, benzimidazole, imidazole, triazole, pyrazine, triazine, pyrimidine and pyridine, even more particularly thiazol-2-yl, oxazol-2-yl, pyrazol-2-yl, pyrrol-2-yl, benzoxazol-2-yl, benzothiazol-2-yl, benzimidazol-2-yl, imidazol-2-yl, triazol-5-yl, pyrazin-2-yl, triazin-2-yl, pyrimidin-2-yl and pyridin-2-yl.

In other more particular embodiments, A is independently selected from the group comprising thiazole, oxazole, pyrazole, pyrrole, benzoxazole, benzothiazole, benzimidazole, imidazole, triazole, pyrazine, triazine, pyrimidine, thiadiazole, oxadiazole, and pyridine, even more particularly thiazol-2-yl, oxazol-2-yl, pyrazol-2-yl, pyrrol-2-yl, benzoxazol-2-yl, benzothiazol-2-yl, benzimidazol-2-yl, imidazol-2-yl, triazol-5-yl, pyrazin-2-yl, triazin-2-yl, pyrimidin-2-yl, thiadiazol-2-yl, thiadiazol-3-yl, thiadiazol-5-yl, oxadiazol-2-yl, oxadiazol-3-yl, oxadiazol-5-yl, and pyridin-2-yl.

In yet even more particular embodiments, A is independently selected from the group comprising imidazolyl, triazolyl, benzoimidazol and pyridinyl, In other yet even more particular embodiments, A is independently selected from the group comprising imidazolyl, triazolyl, benzoimidazolyl, benzothiazolyl, thiadiazolyl, pyrazolyl, thiazolyl, oxazolyl, oxadiazolyl and pyridinyl.

In yet even more particular embodiments, A is independently selected from the group comprising 1H-imidazol-2-yl, 1H-1,2,4-triazol-5-yl, 1H-benzo[d]imidazol-2-yl and pyridin-2-yl.

In other yet even more particular embodiments, A is independently selected from the group comprising 1H-imidazol-2-yl, 1H-1,2,4-triazol-5-yl, 1H-benzo[d]imidazol-2-yl, pyridin-2-yl, 1,3,4-thiadiazol-2-yl, 1H-pyrazol-3-yl, 1,3-thiazol-2-yl, 1,2,4-thiadiazol-3-yl, 1,3,4-thiadiazol-2-yl, 1,2,4-thiadiazol-5-yl, 1,3-oxazol-2-yl and 1,2,4-oxadiazol-3-yl.

In yet even more particular embodiments, A is independently selected from the group comprising benzimidazol-2-yl and imidazol-2-yl.

In other yet even more particular embodiments, A is independently selected from the group comprising benzimidazol-2-yl, imidazol-2-yl, 1,3,4-thiadiazol-2-yl, 1H-pyrazol-3-yl, 1,3-thiazol-2-yl, and 1,2,4-thiadiazol-3-yl.

Most particularly, A is independently benzimidazol-2-yl.

In other embodiments, most particularly, A is independently independently selected from the group comprising benzimidazol-2-yl, 1,3,4-thiadiazol-2-yl, 1H-pyrazol-3-yl, and 1,3-thiazol-2-yl.

In all embodiments described herein, A may be substituted, where appropriate and chemically feasible, with 0 to 4, particularly, 0 to 2, more particularly 0 to 2, even more particularly 1 or 2 substituents $R^4$, wherein $R^4$ is independently selected as detailed in the embodiments as described herein. In certain particular embodiments, In certain particular embodiments, the thiazole, oxazole, pyrazole, pyrrole, or imidazole group A is particularly optionally substituted with one $R^4$ substituent in position 4, the triazole group A is optionally substituted with $R^4$ in position 3, the pyrazine, triazine, pyrimidine or pyridine group A is optionally substituted with $R^4$ in position 5, and the benzoxazole, benzothiazole, or benzimidazole group A is optionally substituted with $R^4$ in position 5 and/or 6, even more particularly optionally substituted with $R^4$ in position 5 and further optionally substituted in position 6 with a group selected from the group comprising halogen, methyl, ethyl, $CF_3$, CN, $NO_2$, COOH, OH, $NH_2$, $NMe_2$, and COOMe, more particularly selected from the group comprising halogen, methyl, $CF_3$, CN, and OH, even more particularly selected from the group comprising fluorine, chlorine, bromine, $CF_3$, CN and OH, yet even more particularly selected from the group comprising fluorine and chlorine, most particularly chlorine.

In other certain particular embodiments, the thiazole, oxazole, pyrazole, pyrrole, or imidazole group A is particularly optionally substituted with one $R^4$ substituent in position 4 or 5, the triazole group A is optionally substituted with $R^4$ in position 3, the pyrazine, triazine, pyrimidine or pyridine group A is optionally substituted with $R^4$ in position 5, and the benzoxazole, benzothiazole, or benzimidazole group A is optionally substituted with $R^4$ in position 5 and/or 6, or alternatively in position 1, and further optionally substituted in position 5 or 6 (whichever one is available) with a group selected from the group comprising halogen, methyl, ethyl, $CF_3$, CN, $NO_2$, COOH, OH, $NH_2$, $NMe_2$, and COOMe, more particularly selected from the group comprising halogen, methyl, $CF_3$, CN, and OH, even more particularly selected from the group comprising fluorine, chlorine, bromine, $CF_3$, CN and OH, yet even more particularly selected from the group comprising fluorine and chlorine, most particularly chlorine. For sake of completeness, it is mentioned that thiadiazole and oxadiazole groups are optionally substituted at the ring carbon atom available for binding.

In other more particular embodiments, A is a group of formula (Ia)

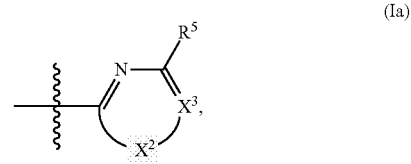

(Ia)

wherein
$X^2$ is a group selected from the group comprising N and ethenylene, which may optionally be substituted by one or two $R^4$; $X^3$ is an atom selected from the group comprising C and N which may optionally be substituted by $R^4$; $R^5$ is a substituent group selected from the groups as defined herein for $R^4$, or $R^5$, together with $X^3$ forms a monocyclic 5- or 6 membered aryl or heteroaryl ring, particularly a benzene ring, which may optionally be substituted by one or more $R^4$.

In other more particular embodiments, A is an aromatic group of formula (Ia)

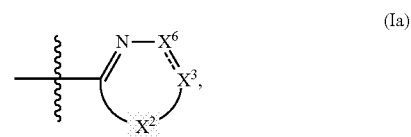

(Ia)

wherein
$X^2$ is selected from the group comprising N, S, O, NH, CH, $CR^4$ and ethenylene optionally substituted by one or two $R^4$, particularly selected from the group comprising N, S, O, NH, CH and $CR^4$; $X^3$ is selected from the group comprising N, S, NH, CH and $CR^4$; $X^6$ is selected from the group comprising N, S, O, NH, CH and $CR^5$, wherein $R^5$ is a substituent group selected from the groups as defined herein for $R^4$, or $R^5$, together with $X^3$ forms a monocyclic 5- or 6 membered aryl or heteroaryl ring, particularly a benzene ring, which may optionally be substituted by one or more $R^4$, particularly in positon 5 or 6 of a resulting benzazole derivative, wherein particularly said group A comprises not more than one atom selected from O and S and not more than three heteroatoms in total.

In yet other more particular embodiments, A is a group of formula (Ib)

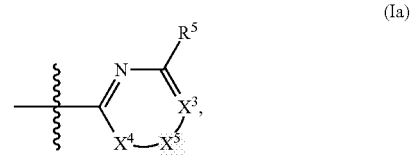

(Ia)

wherein
$X^4$ is selected from the group comprising CH and NH; $X^4$ is selected from the group comprising CH and a single bond; $X^3$ is an atom selected from the group comprising C and N which may optionally be substituted by $R^4$; $R^5$ is a substituent group selected from the groups as defined herein for $R^4$, or $R^5$, together with $X^3$ forms a monocyclic 5- or 6 membered aryl or heteroaryl ring, particularly a benzene ring, which may optionally be substituted by one or more $R^4$.

In yet other more particular embodiments, A is an aromatic group of formula (Ia)

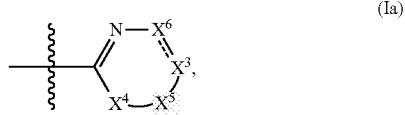
(Ia)

wherein
$X^4$ is selected from the group comprising N, S, O, NH, CH and $CR^4$; $X^5$ is selected from the group comprising CH and a single bond, particularly a single bond; $X^3$ is selected from the group comprising N, S, NH, CH and $CR^4$; $X^6$ is selected from the group comprising N, S, O, NH, CH and $CR^5$, wherein $R^5$ is a substituent group selected from the groups as defined herein for $R^4$, or $R^5$, together with $X^3$ forms a monocyclic 5- or 6 membered aryl or heteroaryl ring, particularly a benzene ring, which may optionally be substituted by one or more $R^4$, particularly in positon 5 or 6 of a resulting benzazole derivative, wherein particularly said group A comprises not more than one atom selected from O and S and not more than three heteroatoms in total.

For explanation, when $R^5$, together with $X^3$ forms a monocyclic 5- or 6 membered aryl or heteroaryl ring, particularly a benzene ring, which may optionally be substituted by one or more $R^4$, particularly in positon 5 or 6 of a resulting benzazole derivative, said positon 5 or 6 of a resulting benzazole derivative is as shown in the below structure:

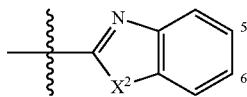

In certain embodiments, $R^4$ is independently selected from the group comprising H, CN, $NO_2$, halogen OH, alkoxy, haloalkyl, alkyl, haloalkoxy, —COOH, —COO-alkyl, aralkyl, aryl, —CO—N(alkyl)$_2$, —CONH-(alkyl), —CONH-alkyl-alkoxy, —CONH-cycloalkyl, —CONH-alkyl-heterocycloalkyl, —NHCO-(alkyl), —NHCO-alkyl-alkoxy, —NHCO-cycloalkyl, —NHCO-alkyl-heterocycloalkyl, —CO-heterocycloalkyl-alkyl-heterocycloalkyl, —CO-heterocycloalkyl, —SO$_2$— alkyl, —S-alkyl, —S-aralkyl, —CO-heteroaryl, heteroaryl, -heterocycloalkyl-alkoxycarbonyl, —CO-aryl, —S-alkyl-COO-alkyl, halophenyl, $NH_2$, NH(alkyl), N(alkyl), —CO-alkyl, and -alkyl-O-alkyl.

In certain embodiments, $R^4$ is independently selected from the group comprising H, CN, $NO_2$, halogen OH, alkoxy, haloalkyl, alkyl, haloalkoxy, —COOH, —COO-alkyl, aralkyl, aryl, —CO—N(alkyl)$_2$, —CONH-(alkyl), —CONH-alkyl-alkoxy, —CONH-cycloalkyl, —CONH-alkyl-heterocycloalkyl, —NHCO-(alkyl), —NHCO-alkyl-alkoxy, —NHCO-cycloalkyl, —NHCO-alkyl-heterocycloalkyl, —CO-heterocycloalkyl-alkyl-heterocycloalkyl, —CO-heterocycloalkyl, —SO$_2$-alkyl, —S-alkyl, and —S-aralkyl.

In further embodiments, $R^4$ is independently selected from the group comprising H, CN, $NO_2$, halogen OH, alkoxy, haloalkyl, alkyl, haloalkoxy, —COOH, —COO-alkyl, aralkyl, aryl, —CO—N(alkyl)$_2$, —CONH-(alkyl), —CONH-alkyl-alkoxy, —CONH-cycloalkyl, —CONH-alkyl-heterocycloalkyl, —CO-heterocycloalkyl-alkyl-heterocycloalkyl, —CO-heterocycloalkyl, —SO$_2$-alkyl, —S-alkyl, and —S-aralkyl.

In more particular embodiments, $R^4$ is independently selected from the group comprising H, CN, $NO_2$, halogen, OH, alkoxy, haloalkyl, alkyl, haloalkoxy, —COOH, —COO-alkyl, aralkyl, aryl, —CO—N(alkyl)$_2$, —CONH-(alkyl), —CONH-alkyl-alkoxy, —CONH-cycloalkyl, —CONH-alkyl-heterocycloalkyl, —CO-heterocycloalkyl-alkyl-heterocycloalkyl, —CO-heterocycloalkyl, —SO$_2$-alkyl, —S-alkyl, —S-aralkyl, —CO-heteroaryl, heteroaryl, -heterocycloalkyl-alkoxycarbonyl, —CO-aryl, —S-alkyl-COO-alkyl, halophenyl, $NH_2$, NH(alkyl), N(alkyl), —CO—alkyl, and -alkyl-O-alkyl.

In more particular embodiments, $R^4$ is independently selected from the group comprising H, CN, $NO_2$, halogen OH, alkoxy, haloalkyl, alkyl, haloalkoxy, —COOH, —COO-alkyl, aralkyl, aryl, —CO—N(alkyl)$_2$, —CONH-(alkyl), —CONH-alkyl-alkoxy, —CONH-cycloalkyl, —CONH-alkyl-heterocycloalkyl, —CO-heterocycloalkyl-alkyl-heterocycloalkyl, —CO-heterocycloalkyl, —SO$_2$-alkyl, —S-alkyl, and —S-aralkyl.

In even more particular embodiments, $R^4$ is independently selected from the group comprising H, CN, halogen, OH, $C_{1-4}$-alkoxy, $C_{1-4}$-alkyl, $C_{1-4}$-haloalkyl, $C_{1-4}$-haloalkoxy, —COOH, —COO—($C_{1-4}$-alkyl), benzyl, phenethyl, phenyl, —CO—N($C_{1-3}$-alkyl)$_2$, —CONH—($C_{1-3}$-alkyl), —CONH—($C_{1-3}$-alkyl)-O($C_{1-3}$-alkyl), —CONH—($C_{3-5}$-cycloalkyl), —CONH—($C_{1-3}$-alkyl)-($C_{5-6}$-heterocycloalkyl), —CO—($C_{5-6}$-heterocycloalkyl)-($C_{1-3}$-alkyl)-($C_{5-6}$-heterocycloalkyl), —CO—($C_{5-6}$-heterocycloalkyl), —SO$_2$($C_{1-4}$-alkyl), —S—($C_{1-4}$-alkyl), —S-benzyl, —S-(chlorophenylmethyl), —S-phenethyl, —CO—($C_{5-6}$-heteroaryl), $C_{5-6}$-heteroaryl, —$C_{5-6}$-heterocycloalkyl-($C_{1-4}$-alkoxycarbonyl), —CO-phenyl, —S—($C_{1-4}$-alkyl)-COO—($C_{1-4}$-alkyl), halophenyl, $NH_2$, NH($C_{1-4}$-alkyl), N($C_{1-4}$-alkyl)$_2$, —CO—($C_{1-4}$-alkyl), and —($C_{1-4}$-alkyl)-O—($C_{1-4}$-alkyl).

In even more particular embodiments, $R^4$ is independently selected from the group comprising H, CN, halogen OH, $C_{1-4}$-alkoxy, $C_{1-4}$-alkyl, $C_{1-4}$-haloalkyl, $C_{1-4}$-haloalkoxy, —COOH, —COO—($C_{1-4}$-alkyl), benzyl, phenethyl, phenyl, —CO—N($C_{1-3}$-alkyl)$_2$, —CONH—($C_{1-3}$-alkyl), —CONH—($C_{1-3}$-alkyl)-O($C_{1-3}$-alkyl), —CONH—($C_{3-5}$-cycloalkyl), —CONH—($C_{1-3}$-alkyl)-($C_{5-6}$-heterocycloalkyl), —CO—($C_{5-6}$-heterocycloalkyl)-($C_{1-3}$-alkyl)-($C_{5-6}$-heterocycloalkyl), —CO—($C_{5-6}$-heterocycloalkyl), —SO$_2$($C_{1-4}$-alkyl), —S—($C_{1-4}$-alkyl), —S-benzyl, —S-(chlorophenylmethyl), and —S-phenethyl.

In yet even more particular embodiments, $R^4$ is independently selected from the group comprising H, CN, F, Cl, OH, $C_{1-2}$-alkoxy, $CF_3$, $OCF_3$, —COOH, —COO—($C_{1-2}$-alkyl), benzyl, phenethyl, phenyl, —CO—N($C_{1-2}$-alkyl)$_2$, —CONH—($C_{1-2}$-alkyl), —CONH—($C_{1-2}$-alkyl)-O($C_{1-2}$-alkyl), —CONH—($C_{3-5}$-cycloalkyl), —CONH—($C_{1-2}$-alkyl-tetrahydrofuryl), —CO-piperazinyl-($C_{1-2}$-alkyl)-tetrahydrofuranyl, —CO-morpholinyl, —CO-pyrrolidinyl, —CO-(methyl-piperazinyl)-, —SO$_2$($C_{1-2}$-alkyl), —S—($C_{1-4}$-alkyl), —S-benzyl, —S-(chlorophenylmethyl), —S-phenethyl, —CO-thien-2-yl, —CO-pyrrol-2-yl, —CO-morpholin-4-yl, piperidin-1-yl-, 4-($C_{1-2}$-alkoxycarbonyl)-piperidin-1-yl, $C_{1-2}$-alkyl, $C_{1-2}$-alkoxycarbonyl, morpholin- 4-yl, 4-pyridyl, —CO-phenyl, —S—($C_{1-2}$-alkyl)-COO—($C_{1-2}$-alkyl), Br, 3-fluorophenyl, $NH_2$, —CO—($C_{1-2}$-alkyl), —S—($C_{1-2}$-alkyl), and —($C_{1-2}$-alkyl)-O—($C_{1-2}$-alkyl).

In yet even more particular embodiments, $R^A$ is independently selected from the group comprising H, CN, F, Cl, OH, $C_{1-2}$-alkoxy, $CF_3$, $OCF_3$, —COOH, —COO—($C_{1-2}$-alkyl), benzyl, phenethyl, phenyl, —CO—N($C_{1-2}$-alkyl)$_2$, —CONH—($C_{1-2}$-alkyl), —CONH—($C_{1-2}$-alkyl)-O($C_{1-2}$-alkyl), —CONH—($C_{3-5}$-cycloalkyl), —CONH—($C_{1-2}$-alkyl-tetrahydrofuryl), —CO-piperazinyl-($C_{1-2}$-alkyl)-tetrahydrofuranyl, —CO-morholinyl, —CO-pyrrolidinyl, —CO-(methyl-piperazinyl)-, —$SO_2$($C_{1-2}$-alkyl), —S—($C_{1-4}$-alkyl), —S-benzyl, —S-(chlorophenylmethyl), and —S-phenethyl.

In yet even more particular embodiments, $R^A$ is independently selected from the group comprising H, CN, F, Cl, —$SO_2$Me, —OMe, $CF_3$, —CO—$NMe_2$, —CO-piperazine-1,4-yl-$CH_2$-tetrahydrofurane-2-yl, —COO-Et, —CO-morholine-1-yl, 3-methoxyphenyl, $OCF_3$, —COOMe, OH, —CONH-Me, —SMe, —CO-pyrrolidine-1-yl, —CONH—$CH_2$—$CH_2$—OMe, —S-iPr, —CONH— cyclopropyl, —CO-(4-methyl-piperazine-1-yl)-, —S-nPr, —COOH, —S-benzyl, —S-(4-chlorophenylmethyl), —S-iBu, —CONH—$CH_2$-tetrahydrofurane-2-yl, phenethyl, —S-phenethyl, —CO-thien-2-yl, —CO-pyrrol-2-yl, —CO-morpholin-4-yl, piperidin-1-yl-, 4-ethoxycarbonyl-piperidin-1-yl, methyl, ethoxycarbonyl, morpholin-4-yl, 4-pyridyl, —CO-phenyl, —S—$CH_2$—COO-Et, Br, 3-fluorophenyl, $NH_2$, acetyl, —S-Me, and —$CH_2$—OMe.

In yet even more particular embodiments, $R^A$ is independently selected from the group comprising H, CN, F, Cl, —$SO_2$Me, —OMe, $CF_3$, —CO—$NMe_2$, —CO-piperazine-1,4-yl-$CH_2$-tetrahydrofurane-2-yl, —COO-Et, —CO-morholine-1-yl, 3-methoxyphenyl, $OCF_3$, —COOMe, OH, —CONH-Me, —SMe, —CO-pyrrolidine-1-yl, —CONH—$CH_2$—$CH_2$—OMe, —S-iPr, —CONH— cyclopropyl, —CO-(4-methyl-piperazine-1-yl)-, —S-nPr, —COOH, —S-benzyl, —S-(4-chlorophenylmethyl), —S-iBu, —CONH—$CH_2$-tetrahydrofurane-2-yl, phenethyl, and —S-phenethyl.

In other particular embodiments, $R^A$ is independently selected from the group comprising H, —$SO_2$($C_{1-4}$-alkyl), —CO—N($C_{1-4}$-alkyl)$_2$, —CO—NH($C_{1-4}$-alkyl), —CO—$NH_2$, —CO—($C_{5-6}$-heterocycloalkyl)-$C_{1-4}$-alkyl-($C_{5-6}$-heterocycloalkyl), —COO—($C_{1-4}$-alkyl), —CO—($C_{5-6}$-heterocycloalkyl), —CONH—$C_{1-4}$-alkyl-O($C_{1-4}$-alkyl), —CONH—$C_{1-4}$-alkyl-($C_{5-6}$-heteroaryl), halogen, $C_{1-4}$-haloalkyl, 3-($C_{1-4}$-alkoxy)-aryl, $C_{1-4}$-haloalkoxy, —CONH—($C_{1-4}$-alkyl), —CONH—($C_{3-5}$-cycloalkyl), —($C_{5-6}$-heterocycloalkyl)-($C_{1-4}$-alkyl), $C_{5-6}$-heteroaryl, and —CO—($C_{1-4}$-alkyl)-($C_{5-6}$-heterocycloalkyl), —CO—($C_{5-6}$-heteroaryl), —CO—($C_{5-6}$-heterocycloalkyl), —($C_{5-6}$-heterocycloalkyl)-($C_{1-4}$-alkoxycarbonyl), $C_{1-4}$-alkyl, $C_{1-4}$-alkoxycarbonyl, —CO-phenyl, —S—($C_{1-4}$-alkylene)-COO—($C_{1-4}$-alkyl), and $C_{1-4}$-alkoxy.

In other particular embodiments, $R^A$ is independently selected from the group comprising H, —$SO_2$($C_{1-4}$-alkyl), —CO—N($C_{1-4}$-alkyl)$_2$, —CO—NH($C_{1-4}$-alkyl), —CO—$NH_2$, —CO—($C_{5-6}$-heterocycloalkyl)-$C_{1-4}$-alkyl-($C_{5-6}$-heterocycloalkyl), —COO—($C_{1-4}$-alkyl), —CO—($C_{5-6}$-heterocycloalkyl), —CONH—$C_{1-4}$-alkyl-O($C_{1-4}$-alkyl), —CONH—$C_{1-4}$-alkyl-($C_{5-6}$-heteroaryl), halogen, $C_{1-4}$-haloalkyl, 3-($C_{1-4}$-alkoxy)-aryl, $C_{1-4}$-haloalkoxy, —CONH—($C_{1-4}$-alkyl), —CONH—($C_{3-5}$-cycloalkyl), ($C_{5-6}$-heterocycloalkyl)-($C_{1-4}$-alkyl), $C_{5-6}$-heteroaryl, and —CO—($C_{1-4}$-alkyl)-($C_{5-6}$-heterocycloalkyl).

In other more particular embodiments, $R^A$ is independently selected from the group comprising H, —$SO_2$($C_{1-4}$-alkyl), —CO—N($C_{1-4}$-alkyl)$_2$, —CO-piperazine-1,4-yl-$C_{1-4}$-alkyl-tetrahydrofurane-2-yl, —COO—($C_{1-4}$-alkyl), —CO-morholine-1-yl, —CO-pyrrolidine-1-yl, —CONH—$C_{1-4}$-alkyl-O($C_{1-4}$-alkyl), —CONH—$C_{1-4}$-alkyl-tetrahydrofurane-2-yl, halogen, $C_{1-4}$-haloalkyl, 3-($C_{1-4}$-alkoxy)-phenyl, $C_{1-4}$-haloalkoxy, —CONH—($C_{1-4}$-alkyl), —CONH—($C_{3-5}$-cycloalkyl), 4-($C_{1-4}$-alkyl)-piperazine-1-yl, 3-pyridyl, 2-furanyl, —CO-(4-[$C_{1-4}$-alkyl]-piperazine-1-yl), —CO-thien-2-yl, —CO-pyrrol-2-yl, —CO-morpholin-4-yl, piperidin-1-yl-, 4-$C_{1-4}$-alkoxycarbonyl-piperidin-1-yl, $C_{1-4}$-alkyl, $C_{1-4}$-alkoxycarbonyl, morpholin-4-yl, 4-pyridyl, —CO-phenyl, —S—($C_{1-4}$-alkylene)-COO—($C_{1-4}$-alkyl), and $C_{1-4}$-alkoxy.

In other more particular embodiments, $R^A$ is independently selected from the group comprising H, —$SO_2$($C_{1-4}$-alkyl), —CO—N($C_{1-4}$-alkyl)$_2$, —CO-piperazine-1,4-yl-$C_{1-4}$-alkyl-tetrahydrofurane-2-yl, —COO—($C_{1-4}$-alkyl), —CO-morholine-1-yl, —CO-pyrrolidine-1-yl, CONH—$C_{1-4}$-alkyl-O($C_{1-4}$-alkyl), —CONH—$C_{1-4}$-alkyl-tetrahydrofurane-2-yl, halogen, $C_{1-4}$-haloalkyl, 3-($C_{1-4}$-alkoxy)-phenyl, $C_{1-4}$-haloalkoxy, —CONH—($C_{1-4}$-alkyl), —CONH—($C_{3-5}$-cycloalkyl), 4-($C_{1-4}$-alkyl)-piperazine-1-yl, 3-pyridyl, 2-furanyl and —CO-(4-[$C_{1-4}$-alkyl]-piperazine-1-yl).

In other even more particular embodiments, $R^A$ is independently selected from the group comprising H, —$SO_2$($C_{1-2}$-alkyl), —CO—N($C_{1-2}$-alkyl)$_2$, —CO-piperazine-1,4-yl-$C_{1-2}$-alkyl-tetrahydrofurane-2-yl, —COO—($C_{1-2}$-alkyl), —CO-morholine-1-yl, —CO-pyrrolidine-1-yl, —CONH—$C_{1-2}$-alkyl-O($C_{1-2}$-alkyl), —CONH—$C_{1-2}$-alkyl-tetrahydrofurane-2-yl, halogen, $C_{1-2}$-haloalkyl, 3-($C_{1-2}$-alkoxy)-phenyl, $C_{1-4}$-haloalkoxy, —CONH—($C_{1-4}$-alkyl), —CONH—($C_{3-5}$-cycloalkyl), 4-($C_{1-4}$-alkyl)-piperazine-1-yl, 3-pyridyl, 2-furanyl, —CO-(4-[$C_{1-4}$-alkyl]-piperazine-1-yl), —CO-thien-2-yl, —CO-pyrrol-2-yl, —CO-morpholin-4-yl, piperidin-1-yl-, 4-$C_{1-2}$-alkoxycarbonyl-piperidin-1-yl, $C_{1-2}$-alkyl, $C_{1-2}$-alkoxycarbonyl, morpholin-4-yl, 4-pyridyl, —CO-phenyl, —S—($C_{1-2}$-alkylene)-COO—($C_{1-2}$-alkyl), and $C_{1-2}$-alkoxy.

In other even more particular embodiments, $R^A$ is independently selected from the group comprising H, —$SO_2$($C_{1-2}$-alkyl), —CO—N($C_{1-2}$-alkyl)$_2$, —CO-piperazine-1,4-yl-$C_{1-2}$-alkyl-tetrahydrofurane-2-yl, —COO—($C_{1-2}$-alkyl), —CO-morholine-1-yl, —CO-pyrrolidine-1-yl, CONH—$C_{1-2}$-alkyl-O($C_{1-2}$-alkyl), —CONH—$C_{1-2}$-alkyl-tetrahydrofurane-2-yl, halogen, $C_{1-2}$-haloalkyl, 3-($C_{1-2}$-alkoxy)-phenyl, $C_{1-4}$-haloalkoxy, —CONH—($C_{1-4}$-alkyl), —CONH—($C_{3-5}$-cycloalkyl), 4-($C_{1-4}$-alkyl)-piperazine-1-yl, 3-pyridyl, 2-furanyl and —CO-(4-[$C_{1-4}$-alkyl]-piperazine-1-yl).

In other yet even more particular embodiments, $R^A$ is independently selected from the group comprising —$SO_2$Me, —CO—$NMe_2$, —CO-piperazine-1,4-yl-$CH_2$-tetrahydrofurane-2-yl, —COO-Et, —CO-morholine-1-yl, —CO-pyrrolidine-1-yl, —CONH—($CH_2$)$_2$—OMe, —CONH—$CH_2$-tetrahydrofurane-2-yl, Cl, $CF_3$, H, 3-methoxyphenyl, $OCF_3$, —CONH-Me, —CONH— cyclopropyl, 4-methyl-piperazine-1-yl, 3-pyridyl, 2-furanyl, —CO-(4-ethyl-piperazine-1-yl), —CO-thien-2-yl, —CO-pyrrol-2-yl, —CO-morpholin-4-yl, piperidin-1-yl-, 4-ethoxycarbonyl-piperidin-1-yl, methyl, ethoxycarbonyl, morpholin-4-yl, 4-pyridyl, —CO-phenyl, —S—$CH_2$—COO-Et, and methoxy.

In other yet even more particular embodiments, $R^A$ is independently selected from the group comprising —$SO_2$Me, —CO—$NMe_2$, —CO-piperazine-1,4-yl-$CH_2$-tetrahydrofurane-2-yl, —COO-Et, —CO-morholine-1-yl, —CO-pyrrolidine-1-yl, —CONH—($CH_2$)$_2$—OMe, —CONH—$CH_2$-tetrahydrofurane-2-yl, Cl, $CF_3$, H, 3-methoxyphenyl, $OCF_3$, —CONH-Me, —CONH— cyclopropyl, 4-methyl-piperazine-1-yl, 3-pyridyl, 2-furanyl and —CO-(4-ethyl-piperazine-1-yl).

In other particular embodiments, $R^A$ is independently selected from the group comprising —$SO_2$($C_{1-4}$-alkyl), —CO—N($C_{1-4}$-alkyl)$_2$, —CO—NH($C_{1-4}$-alkyl), —CO—$NH_2$, —CO—($C_{5-6}$-heterocycloalkyl)-$C_{1-4}$-alkyl-($C_{5-6}$-heterocycloalkyl), —COO—($C_{1-4}$-alkyl), —CO—($C_{5-6}$-heterocycloalkyl), —CONH—$C_{1-4}$-alkyl-O($C_{1-4}$-alkyl), —CONH—$C_{1-4}$-alkyl-($C_{5-6}$-heteroaryl), H, —CO—($C_{5-6}$-heteroaryl), —($C_{5-6}$-heterocycloalkyl), $C_{1-4}$-alkyloxycarbonyl-substituted $C_{5-6}$-heterocycloalkyl, and $C_{1-4}$-alkyl.

In other particular embodiments, $R^A$ is independently selected from the group comprising —$SO_2$($C_{1-4}$-alkyl), —CO—N($C_{1-4}$-alkyl)$_2$, —CO—NH($C_{1-4}$-alkyl), —CO—$NH_2$, —CO—($C_{5-6}$-heterocycloalkyl)-$C_{1-4}$-alkyl-($C_{5-6}$-heterocycloalkyl), —COO—($C_{1-4}$-alkyl), —CO—($C_{5-6}$-heterocycloalkyl), —CONH—$C_{1-4}$-alkyl-O($C_{1-4}$-alkyl), and —CONH—$C_{1-4}$-alkyl-($C_{5-6}$-heteroaryl).

In other more particular embodiments, $R^A$ is independently selected from the group comprising —$SO_2$($C_{1-4}$-alkyl), —CO—N($C_{1-4}$-alkyl)$_2$, —CO-piperazine-1,4-yl-$C_{1-4}$-alkyl-tetrahydrofurane-2-yl, —COO—($C_{1-4}$-alkyl), —CO-morholine-1-yl, —CO-pyrrolidine-1-yl, —CONH—$C_{1-4}$-alkyl-O($C_{1-4}$-alkyl), —CONH—$C_{1-4}$-alkyl-tetrahydrofurane-2-yl, H, —CO-thien-2-yl, —CO-pyrrol-2-yl, —CO-morpholin-4-yl, piperidin-1-yl-4-$C_{1-4}$-alkyloxycarbonyl-piperidin-1-yl, and $C_{1-4}$-alkyl.

In other more particular embodiments, $R^A$ is independently selected from the group comprising —$SO_2$($C_{1-4}$-alkyl), —CO—N($C_{1-4}$-alkyl)$_2$, —CO-piperazine-1,4-yl-$C_{1-4}$-alkyl-tetrahydrofurane-2-yl, —COO—($C_{1-4}$-alkyl), —CO-morholine-1-yl, —CO-pyrrolidine-1-yl, CONH—$C_{1-4}$-alkyl-O($C_{1-4}$-alkyl), and —CONH—$C_{1-4}$-alkyl-tetrahydrofurane-2-yl.

In other even more particular embodiments, $R^A$ is independently selected from the group comprising —$SO_2$($C_{1-2}$-alkyl), —CO—N($C_{1-2}$-alkyl)$_2$, —CO-piperazine-1,4-yl-$C_{1-2}$-alkyl-tetrahydrofurane-2-yl, —COO—($C_{1-2}$-alkyl), —CO-morholine-1-yl, —CO-pyrrolidine-1-yl, CONH—$C_{1-2}$-alkyl-O($C_{1-2}$-alkyl), —CONH—$C_{1-2}$-alkyl-tetrahydrofurane-2-yl, H, —CO-thien-2-yl, —CO-pyrrol-2-yl, —CO-morpholin-4-yl, piperidin-1-yl-4-$C_{1-2}$-alkyloxycarbonyl-piperidin-1-yl, and $C_{1-2}$-alkyl.

In other even more particular embodiments, $R^A$ is independently selected from the group comprising —$SO_2$($C_{1-2}$-alkyl), —CO—N($C_{1-2}$-alkyl)$_2$, —CO-piperazine-1,4-yl-$C_{1-2}$-alkyl-tetrahydrofurane-2-yl, —COO—($C_{1-2}$-alkyl), —CO-morholine-1-yl, —CO-pyrrolidine-1-yl, —CONH—$C_{1-2}$-alkyl-O($C_{1-2}$-alkyl), and —CONH—$C_{1-2}$-alkyl-tetrahydrofurane-2-yl.

In other yet even more particular embodiments, $R^A$ is independently selected from the group comprising —$SO_2$Me, —CO—$NMe_2$, —CO-piperazine-1,4-yl-$CH_2$-tetrahydrofurane-2-yl, —COO-Et, —CO-morholine-1-yl, —CO-pyrrolidine-1-yl, —CONH—($CH_2$)$_2$—OMe, —CONH—$CH_2$-tetrahydrofurane-2-yl, H, —CO-thien-2-yl, —CO-pyrrol-2-yl, —CO-morpholin-4-yl, piperidin-1-yl-4-ethoxycarbonyl-piperidin-1-yl, and methyl.

In other yet even more particular embodiments, $R^A$ is independently selected from the group comprising —$SO_2$Me, —CO—$NMe_2$, —CO-piperazine-1,4-yl-$CH_2$-tetrahydrofurane-2-yl, —COO-Et, —CO-morholine-1-yl, —CO-pyrrolidine-1-yl, —CONH—($CH_2$)$_2$—OMe, and —CONH—$CH_2$-tetrahydrofurane-2-yl.

In certain embodiments, R' is independently selected from the group comprising H, $C_{1-6}$-alkyl, $C_{1-6}$-haloalkyl, phenyl, naphthyl, $C_{5-6}$-heteroaryl, $C_{3-7}$-cycloalkyl and $C_{4-7}$-heterocycloalkyl.

In certain embodiments, R' is independently selected from the group comprising H, $C_{1-6}$-alkyl, $C_{1-6}$-haloalkyl, phenyl, naphthyl, $C_{5-6}$-heteroaryl, $C_{3-7}$-cycloalkyl and $C_{4-7}$-heterocycloalkyl.

In more particular embodiments, R' is independently selected from the group comprising H, $C_{1-4}$-alkyl, $C_{1-4}$-haloalkyl, phenyl, $C_{5-6}$-heteroaryl comprising 1 to 3 heteroatoms independently selected from the group comprising N, O and S, $C_{3-7}$-cycloalkyl and $C_{4-7}$-heterocycloalkyl comprising 1 or 2 heteroatoms independently selected from the group comprising N, O and S.

In even more particular embodiments, R' is independently selected from the group comprising H, $C_{1-4}$-alkyl, $C_{1-3}$-haloalkyl, phenyl, $C_{5-6}$-heteroaryl comprising 1 or 2 heteroatoms independently selected from the group comprising N, O and S, $C_{3-6}$-cycloalkyl and $C_{5-6}$-heterocycloalkyl comprising 1 or 2 heteroatoms independently selected from the group comprising N, O and S.

In even more particular embodiments, R' is independently selected from the group comprising H, methyl, ethyl, i-propyl, n-propyl, i-butyl, n-butyl, t-butyl, $CF_3$, phenyl, pyridine, pyrimidine, pyrrol, furane, thiphene, oxazol, pyrazol, imidazol, isothiazol, isoxazol, thiazol, oxazol, $C_{3-6}$-cycloalkyl, thiomorpholine, morpholine, piperidine, piperazine, tetrahydrofurane, tetrahydropyrane, pyrrolidine, pyrroline, dihydrofurane, dihydrothiphene, tetrahydrothiphene, dihydropyrane, pyrazoline, pyrazolidine, imidazoline, imidazolidine, isothiazoline, isothiazolidine, isoxazoline, isoxazolidine, thiazoline, thiazolidine, oxazoline, oxazoline, and oxazolidine.

In yet even more particular embodiments, R' is independently selected from the group comprising H, methyl, ethyl, n-propyl, i-propyl, n-butyl, i-butyl, tetrahydrofurane, tetrahydrothiphene, phenyl, pyrrolidine, piperazine, piperidine, morpholine, cyclopropyl, cyclobutyl, cyclopentyl, $CF_3$, thienyl, pyrrol and piperidine.

In yet even more particular embodiments, R' is independently selected from the group comprising H, methyl, ethyl, n-propyl, i-propyl, n-butyl, i-butyl, tetrahydrofurane, tetrahydrothiphene, phenyl, pyrrolidine, piperazine, piperidine, morpholine, cyclopropyl, cyclobutyl, cyclopentyl, and $CF_3$.

In yet even more particular embodiments, R' is independently selected from the group comprising H, methyl, ethyl, n-propyl, i-propyl, i-butyl, tetrahydrofurane, phenyl, pyrrolidine, piperazine, morpholine, cyclopropyl, $CF_3$, thienyl, pyrrole and piperidine.

In yet even more particular embodiments, R' is independently selected from the group comprising H, methyl, ethyl, n-propyl, i-propyl, i-butyl, tetrahydrofurane, phenyl, pyrrolidine, piperazine, morpholine, cyclopropyl, and $CF_3$.

Any of the aforementioned alkyl, aryl, heteroaryl, cycloalkyl and heterocycloalkyl, including any particular or otherwise further specified embodiments thereof (e.g. for alkyl: $C_{1-6}$-alkyl, isopropyl, methyl etc.), may independently be substituted with one or more, particularly one to three, more particularly one or two substituents R", wherein R" is independently selected from the group comprising $C_{1-4}$-alkyl, halogen, $C_{1-4}$-haloalkyl, OH, $C_{1-4}$-alkoxy, $C_{1-4}$-haloalkoxy, —$NO_2$, —CN, —$NH_2$, —N($C_{1-4}$-alkyl)$_2$, —NH($C_{1-4}$-alkyl), —NHCO($C_{1-4}$-alkyl), —$CONH_2$, —CONH($C_{1-4}$-alkyl), —CO($C_{1-4}$-alkyl), —COH, —COO($C_{1-4}$-alkyl), —COOH and —CN.

In certain embodiments, R" is independently selected from the group comprising H, $C_{1-3}$-alkyl, chlorine, fluorine, bromine, $C_{1-3}$-haloalkyl, OH, $C_{1-3}$-alkoxy, $C_{1-3}$-haloalkoxy, —$NH_2$, —$N(C_{1-3}$-alkyl$)_2$, —$NH(C_{1-3}$-alkyl), —NHCO($C_{1-3}$-alkyl), —$CONH_2$, —$CONH(C_{1-3}$-alkyl), —$CO(C_{1-3}$-alkyl), —COH, —$COO(C_{1-3}$-alkyl), —COOH and —CN.

In more particular embodiments, R" is independently selected from the group comprising $C_{1-3}$-alkyl, chlorine, fluorine, bromine, $C_{1-3}$, OH, OMe, OEt, $OCF_3$, —$NH_2$, —$N(Me)_2$, —$N(Et)_2$, —NH-Me, —NH-Et, —NH-iPr, —NHCO-Me, —$CONH_2$, —CONH-Me, —CONH-Et, —CONH-iPr, acetyl, —COO-Me, —COO-Et, —COOH and —CN.

In even more particular embodiments, R" is independently selected from the group comprising methyl, chlorine, fluorine, $CF_3$, OH, OMe, $OCF_3$, —$NH_2$, —$N(Me)_2$, —$N(Et)_2$, —NHCO-Me, acetyl, —COO-Me, —COOH and —COOEt.

In even more particular embodiments, R" is independently selected from the group comprising methyl, chlorine, fluorine, $CF_3$, OH, OMe, $OCF_3$, —$NH_2$, —$N(Me)_2$, —$N(Et)_2$, —NHCO-Me, acetyl, —COO-Me, and —COOH.

In yet even more particular embodiments, R" is independently selected from the group comprising chlorine, fluorine, $CF_3$, OH, OMe, $OCF_3$, —$NH_2$, —$N(Me)_2$, —NHCO-Me, acetyl, —COO-Me, —COOH, —COOEt and methyl.

In yet even more particular embodiments, R" is independently selected from the group comprising chlorine, fluorine, $CF_3$, OH, OMe, $OCF_3$, —$NH_2$, —$N(Me)_2$, —NHCO-Me, acetyl, —COO-Me, and —COOH.

In yet even more particular embodiments, R" is independently selected from the group comprising H, chlorine, fluorine, $CF_3$, OH, OMe, $OCF_3$, —$NH_2$, —$N(Me)_2$, —COOEt and methyl.

In yet even more particular embodiments, R" is independently selected from the group comprising chlorine, fluorine, $CF_3$, OH, OMe, $OCF_3$, —$NH_2$, and —$N(Me)_2$.

Particularly, the substituent R" is not further substituted.

In a specific embodiment, the compounds of the present invention are selected from the group comprising compounds 1 to 48 as described herein in the example section.

In a specific embodiment, the compounds of the present invention are selected from the group comprising compounds 1 to 82 as described herein in the example section.

In a specific embodiment, the compounds of the present invention are selected from the group comprising compounds 1, 2, 3, 4, 5, 6, 7, 8, 9, 10, 11, 14, 17, 18, 19, 21, 22, 23, 24, 25, 26, 27, 28, 29, 30, 31, 34, 35, 37, 38, 39, 40, 41, 42, 44, 45, 46, 47, and 48 to 71 as described herein in the example section.

In a more specific embodiment, the compounds of the present invention are selected from the group comprising compounds 1, 2, 3, 4, 6, 7, 8, 9, 10, 14, 17, 18, 19, 21, 22, 23, 24, 25, 27, 28, 30, 34, 35, 38, 39, 40, 41, 42, 45, 46 47, and 48 to 65 as described herein in the example section.

In an even more specific embodiment, the compounds of the present invention are selected from the group comprising compounds 1, 3, 6, 7, 8, 9, 10, 19, 22, 23, 25, 30, 35, 38, 42, 45 47 and 48 to 51 as described herein in the example section.

In another specific embodiment, the compounds of the present invention are selected from the group comprising compounds 1, 2, 3, 5, 6, 7, 8, 9, 10, 11, 12, 13, 14, 15, 16, 18, 19, 20, 21, 22, 23, 24, 25, 30, 31, 33, 34, 35, 36, 37, 38, 39, 40, 41, 45, 46 and 47 as described herein in the example section.

In another more specific embodiment, the compounds of the present invention are selected from the group comprising compounds 1, 2, 3, 5, 6, 7, 8, 9, 10, 11, 12, 13, 14, 19, 22, 23, 25, 35, 41, 45, 46 and 47 as described herein in the example section.

In another even more specific embodiment, the compounds of the present invention are selected from the group comprising compounds 3, 7, 8, 9, 10, 22, 23 and 35 as described herein in the example section.

In another yet even more specific embodiment, the compounds of the present invention are selected from the group comprising compounds 11, 42, 45, 46, 47, 50, 54, 55 and 62 as described herein in the example section.

In a specific embodiment, the compounds of the present invention are selected from the group comprising compounds 1, 2, 3, 5, 6, 7, 8, 9, 10, 11, 14, 17, 18, 19, 21, 22, 23, 24, 25, 26, 27, 28, 29, 30, 31, 34, 35, 37, 38, 39, 40, 41, 42, 44, 45, 46, and 47 as described herein in the example section.

In a more specific embodiment, the compounds of the present invention are selected from the group comprising compounds 1, 2, 3, 6, 7, 8, 9, 10, 14, 17, 18, 19, 21, 22, 23, 24, 25, 27, 28, 30, 34, 35, 38, 39, 40, 41, 42, 45, 46 and 47 as described herein in the example section.

In an even more specific embodiment, the compounds of the present invention are selected from the group comprising compounds 1, 3, 6, 7, 8, 9, 10, 19, 22, 23, 25, 30, 35, 38, 42, 45 and 47 as described herein in the example section.

In another specific embodiment, the compounds of the present invention are selected from the group comprising compounds 1, 2, 3, 5, 6, 7, 8, 9, 10, 11, 12, 13, 14, 15, 16, 18, 19, 20, 21, 22, 23, 24, 25, 30, 31, 33, 34, 35, 36, 37, 38, 39, 40, 41, 45, 46 and 47 as described herein in the example section.

In another more specific embodiment, the compounds of the present invention are selected from the group comprising compounds 1, 2, 3, 5, 6, 7, 8, 9, 10, 11, 12, 13, 14, 19, 22, 23, 25, 35, 41, 45, 46 and 47 as described herein in the example section.

In another even more specific embodiment, the compounds of the present invention are selected from the group comprising compounds 3, 7, 8, 9, 10, 22, 23 and 35 as described herein in the example section.

As used herein, a "ring atom" represents an atom which is part of the cyclic structure of a ring or ring system, wherein this definition does not include hydrogen atoms or substituents bound to the ring or ring system. For example, a pyridine group comprises 6 ring atoms, i.e. one N atom and five C atoms;

The following definitions are meant to further define certain terms used in the context of the present invention. If a particular term used herein is not specifically defined, the term should not be considered to be indefinite. Rather, such terms are to be construed in accordance with their meaning as regularly understood by the skilled artisan in the field of art to which the invention is directed, particularly in the field of organic chemistry, pharmaceutical sciences and medicine.

In the context of the present invention, and for reasons of legibility, chemical group names such as "alkyl", "aryl", "phenyl", "heteroaryl", "cycloalkyl", "heterocyclyl", etc., depending on the respective particular context, are meant to include terminal groups and connecting groups which are often referred to as " . . . ene" groups, such as for example "alkylene", "arylene", etc. Moreover, in the context of the present invention, the suffix "-yl" is in many cases omitted, which is not to be understood to delimit chemical names comprising said suffix from chemical names not comprising said suffix; for example "furyl", "furanyl" and "furane" are meant to be used interchangeably.

As used herein, the term "X¹-azol moiety" refers to the below chemical entity, which is part of formular (I) according to the present invention:

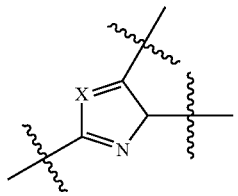

As used herein, an alkyl group particularly encompasses alkanyl, alkenyl, alkynyl, wherein alkanyl means a completely saturated hydrocarbon chain, alkenyl means a hydrocarbon chain comprising at least one carbon-carbon double bond, alkynyl means a hydrocarbon chain comprising at least one carbon-carbon triple bond (including a hydrocarbon chain comprising one or more carbon-carbon double bonds and at least one carbon-carbon triple bond). In the context of the present invention, an alkanyl group, if not stated otherwise, particularly denotes a linear or branched $C_1$-$C_6$-alkanyl, more particularly a linear or branched $C_1$-$C_5$-alkanyl, even more particularly a linear or branched $C_1$-$C_4$-alkanyl; an alkenyl group, if not stated otherwise, particularly denotes a linear or branched $C_2$-$C_6$-alkenyl, more particularly a linear or branched $C_2$-$C_4$-alkenyl, even more particularly ethenyl; and an alkynyl group, if not stated otherwise, particularly denotes a linear or branched $C_2$-$C_6$-alkynyl group, more particularly a linear or branched $C_2$-$C_4$-alkynyl, even more particularly ethynyl. In certain particular embodiments the alkyl group is selected from the group comprising methyl, ethyl, n-propyl, isopropyl, n-butyl, isobutyl, sec-butyl, tert-butyl, pentyl, hexyl, ethenyl, ethynyl, propen-1-yl, propen-2-yl, propen-3-yl, —C≡C—CH₃, and —CH₂—C≡CH. The alkyl, alkanyl, alkenyl, and alkynyl groups as defined above, including the groups enumerated as examples and particular or otherwise further defined embodiments thereof, are optionally substituted by one or more substituents R".

As used herein, the term "aryl" particularly denotes an aromatic mono- or polycyclic hydrocarbon ring system, which may optionally be fused to one or more cycloalkyl or heterocycloalkyl rings, and wherein the total number of ring atoms in the aryl group is 6 to 14, particularly 6 to 10, more particularly 6. The point of attachment of said aryl group to the central moiety may be located on the aromatic mono- or polycyclic hydrocarbon ring system or on the optionally fused cycloalkyl or heterocycloalkyl ring. Examples of the aryl group are phenyl, naphthyl, indenyl, azulenyl, fluorenyl, 1,2-dihydronaphthyl, 1,2,3,4-tetrahydronaphthyl, 2,3-dihydroindenyl, 1,5-dihydro-s-indacenyl, 1,6-dihydro-as-indacenyl, 1H-cyclopenta[a]naphthyl and 1H-cyclopenta[b]naphthyl, phenalenyl, phenanthrenyl, anthracenyl, 1,6-dihydropentalenyl, 1,6a-dihydropentalenyl, 1,2,3,4-tetrahydroanthracenyl, 1,2,3,4-tetrahydrophenanthrenyl, 2,3-dihydro-1H-cyclopenta[a]naphthalenyl, 2,3-dihydro-1H-cyclopenta[b]naphthalenyl, 2,3-dihydro-1H-phenalenyl, 2,3-dihydrobenzo[b]thiophenyl-1,1-dioxide, 1,2,3,4-tetrahydroisoquinolinyl, 1,2,3,4-tetrahydroquinolinyl, 2,3-dihydrobenzo[b][1,4]dioxinyl, 2,3-dihydrobenzo[b]thiophenyl, 2,3-dihydrobenzofuranyl, benzo[d][1,3]dioxolyl, chromanyl, indazolinyl and indolinyl. In particular embodiments, the aryl group is phenyl, 2,3-dihydrobenzo[b][1,4]dioxinyl, 2,3-dihydrobenzofuranyl or benzo[d][1,3]dioxolyl, more particularly phenyl. The aryl groups as defined above, including the groups enumerated as examples and particular or otherwise further defined embodiments thereof, are optionally substituted by one or more substituents R".

As used herein, the term "halophenyl" particularly denotes a phenyl group substituted with one or more halogen atoms, particularly with one halogen atom.

As used herein, the term "heteroaryl" particularly denotes an aromatic mono- or polycyclic hydrocarbon ring system wherein one or more carbon atoms are replaced by heteroatoms independently selected from the group comprising O, N and S, wherein the aromatic mono- or polycyclic hydrocarbon ring system may optionally be fused to one or more cycloalkyl or heterocycloalkyl rings, and wherein the total number of ring atoms in the heteroaryl group is 5 to 14, particularly 5 to 10, more particularly 5 or 6. The point of attachment of said heteroaryl group to the central moiety may be located on the mono- or polycyclic aromatic hydrocarbon ring system or on the optionally fused cycloalkyl or heterocycloalkyl ring. Examples of the heteroaryl group are furan-2-yl, furan-3-yl, thiophen-2-yl, thiophen-3-yl, thiazol-4-yl, pyrazol-3-yl, pyrazol-4-yl, oxazol-4-yl, oxazol-5-yl, isoxazol-4-yl, isoxazol-5-yl, pyrazin-2-yl, pyridin-2-yl, pyridin-3-yl, pyridin-4-yl, pyrrol-2-yl, 1,2,3-thiadiazol-5-yl, 1,2,4-thiadiazol-3-yl, benzothiophen-3-yl, 1,2,3-triazol-4-yl, 1,2,4-triazol-5-yl, quinolin-2-yl, thiazol-2-yl, thiazol-5-yl, isothiazol-3-yl, isothiazol-4-yl, isothiazol-5-yl, oxazol-2-yl, isoxazol-3-yl, 1,2,4-oxadiazol-3-yl, 1,2,4-oxadiazol-5-yl, 1,2,5-oxadiazol-3-yl, 1,2,5-oxadiazol-4-yl, 1,2,3-oxadiazol-4-yl, 1,2,3-oxadiazol-5-yl, 1,3,4-oxadiazol-2-yl, 1,2,4-thiadiazol-5-yl, 1,2,5-thiadiazol-3-yl, 1,2,5-thiadiazol-4-yl, 1,3,4-thiadiazol-2-yl, 1,2,3-thiadiazol-4-yl, pyrrol-1-yl, pyrrol-3-yl, pyrazol-1-yl, purin-2-yl, purin-6-yl, purin-8-yl, purin-9-yl, pyrimidin-2-yl, pyrimidin-4-yl, pyrimidin-5-yl, pyrimidin-6-yl, imidazol-1-yl, imidazol-2-yl, imidazol-4-yl, 1,2,3-triazol-5-yl, 1,2,4-triazol-3-yl, furan-2-yl, benzo[b]furanyl, quinolinyl, isoquinolinyl, indol-2-yl, indol-3-yl, isoindol-1-yl, isoindol-3-yl, indol-2-yl,indol-3-yl, purin-2-yl. In particular embodiments, the heteroaryl group is selected from the group comprising furan-2-yl, thiophen-3-yl, pyrimidin-2-yl, or pyrimidin-6-yl, and pyridine-4-yl. In other particular embodiments, the heteroaryl group is selected from the group comprising furan-2-yl, thiophen-3-yl, pyrimidin-2-yl, pyrimidin-6-yl, pyridine-4-yl, 1H-imidazol-2-yl, 1H-1,2,4-triazol-5-yl, 1H-benzo[d]imidazol-2-yl, pyridin-2-yl, 1H-imidazol-2-yl, 1,3,4-thiadiazol-2-yl, 1H-pyrazol-3-yl, 1,3-thiazol-2-yl, 1,2,4-thiadiazol-3-yl, 1,3,4-thiadiazol-2-yl, 1,2,4-thiadiazol-5-yl, 1,3-oxazol-2-yl and 1,2,4-oxadiazol-3-yl.

The heteroaryl groups as defined above, including the groups enumerated as examples and particular or otherwise further defined embodiments thereof, are optionally substituted by one or more substituents R".

As used herein, the term "cycloalkyl" particularly denotes a non-aromatic, mono- or polycyclic completely saturated or partially unsaturated hydrocarbon ring system. Said cycloalkyl is particularly mono- or bicyclic, more particularly monocyclic. Said cycloalkyl is particularly completely saturated. Said cycloalkyl particularly comprises 3 to 10 carbon atoms, more particularly 3 to 7, even more particularly 3 to 6 carbon atoms. Even more particularly, said cycloalkyl is selected from the group comprising cyclopropyl, cyclobutyl, cyclopentyl, cyclohexyl, cycloheptyl, 1-norbornyl, 2-norbornyl, 7-norbornyl, 1-adamantyl, and 2-adamantyl, yet even more particularly said cycloalkyl is cyclohexyl. The cycloalkyl groups as defined above, including the groups enumerated as examples and particular or otherwise further defined embodiments thereof, are optionally substituted by one or more substituents R', and 0, 1 or 2, particularly 0 or 1, more particularly 0 of the ring carbon atoms are attached to an oxygen atom via a double bond to form a carbonyl group.

As used herein, the term "heterocycloalkyl" particularly denotes a non-aromatic mono- or polycyclic completely saturated or partially unsaturated hydrocarbon ring system, wherein one or more, particularly 1 to 3, more particularly 1 or 2 of the ring carbon atoms are replaced by a heteroatom independently selected from N, O, or S. Said heterocycloalkyl is particularly mono- or bicyclic, more particularly monocyclic. Said heterocycloalkyl is particularly completely saturated. Said heterocycloalkyl particularly is a 5- to 10-membered mono- or polycyclic ring system, more particularly 5- to 7-membered monocyclic ring system, even more particularly 5- or 6-membered monocyclic ring system. Even more particularly said heterocycloalkyl is selected from the group comprising morpholinyl, piperidinyl, pyrrolidinyl, and piperazinyl. The heterocycloalkyl group as defined above, including the groups enumerated as examples and particular or otherwise further defined embodiments thereof, are optionally substituted by one or more substituents R' as described herein, and 0, 1 or 2, particularly 0 or 1, more particularly 0 of the ring carbon atoms are attached to an oxygen atom via a double bond to form a carbonyl group.

As used herein, the term "halo" or "halogen" particularly independently denotes fluorine, chlorine, bromine or iodine, more particularly bromine, chlorine or fluorine, even more particularly chlorine or fluorine.

As used herein, the term "haloalkyl" denotes an alkyl group wherein one or more, particularly at least half, more particularly all of the hydrogen atoms on the hydrocarbon chain are replaced by halogen atoms. The haloalkyl group is particularly selected from the group comprising —C($R^{10}$)$_3$, —CH$_2$—C($R^{10}$)$_3$, —C($R^{10}$)$_2$—CH$_3$, —C($R^{10}$)$_2$—C($R^{10}$)$_3$, —C($R^{10}$)$_2$—CH($R^{10}$)$_2$, —CH$_2$—CH($R^{10}$)$_2$, —CH($R^{10}$)—C($R^{10}$)$_3$, —CH($R^{10}$)—CH$_3$, and —C$_2$H$_4$—C($R^{10}$)$_3$, more particularly —C($R^{10}$)$_3$, wherein $R^{10}$ represents halogen, particularly F. More particular haloalkyl groups are —CF$_3$, —CH$_2$CF$_3$, and CF$_2$Cl.

As used herein, the term "alkoxy" denotes an O-alkyl group, the alkyl group being defined as defined above. The alkoxy group is particularly selected from the group comprising methoxy and ethoxy.

As used herein, the term "alkylthio" denotes an —S-alkyl group, the alkyl group being as defined above.

As used herein, the term "haloalkoxy" denotes an O-haloalkyl group, haloalkyl group being defined as defined above. The haloalkoxy group is particularly selected from the group comprising —OC($R^{10}$)$_3$, —OCR$^{10}$($R^{10'}$)$_2$, —OCH$_2$—C($R^{10}$)$_3$, and —OC$_2$H$_4$—C($R^{10}$)$_3$, wherein $R^{10}$, $R^{10'}$ represent F, Cl, Br or I, particularly F.

As used herein, the term "alkylamino" denotes a NH-alkyl or N-dialkyl group, the alkyl group being as defined above.

As used herein, the term "arylalkyl" or "aralkyl" particularly denotes a linear or branched C$_1$-C$_6$-alkyl, more particularly C$_{1-4}$-alkyl, even more particularly C$_{1-2}$-alkyl, yet even more particularly methyl, wherein "alkyl" is as defined herein, substituted with at least one, particularly exactly one, aryl group as defined herein. Exemplary arylalkyl groups include styryl, benzyl, phenylethyl, particularly the arylalkyl group is styryl or benzyl, particularly optionally substituted at its phenyl part as defined above for the aryl group.

Where chemically feasible from the viewpoint of molecule stability and/or chemical valence rules, a nitrogen heteroatom as defined herein, e.g. in the context of "heteroaryl" and "heterocycle", may include the N-oxide.

Where chemically feasible from the viewpoint of molecule stability under physiological conditions and/or chemical valence rules, the definition of a sulfur heteroatom as defined herein, e.g. in the context of "heteroaryl" and "heterocycle", may include the sulfur oxide and/or the sulfur dioxide, respectively.

For sake of completeness, it is mentioned that "morpholine-4-carbonyl" is a group —CO-morpholine-4-yl.

As used herein the term "substituted with" or, "substituted by" means that one or more hydrogen atoms connected to a carbon atom or heteroatom of a chemical group or entity are exchanged with a substituent group, respectively; e.g. substituted aryl comprises 4-hydroxyphenyl, wherein the H-atom in the 4-position of the phenyl group is exchanged with a hydroxyl group. Said hydrogen atom(s) to be replaced may be attached to a carbon atom or heteroatom, and may be expressly shown in a specific formula, such as for example in an —NH— group, or may not expressly be shown but intrinsically be present, such as for example in the typical "chain" notation which is commonly used to symbolize e.g. hydrocarbons. The skilled person will readily understand that particularly such substituents or substituent patterns are excluded, which lead to compounds which are not stable and/or not accessible via the synthesis methods known in the art.

Unless specified otherwise, references to the compounds according to the present invention include the pharmaceutically acceptable derivatives, solvates or salts thereof as described herein, as well as to salts or solvates of said pharmaceutically acceptable derivatives and solvates of said salts.

As used herein, the term "pharmaceutically acceptable derivative" of a compound according to the present invention is for instance a prodrug of said compound, wherein at least one of the following groups are derivatized as specified in the following: A carboxylic acid group is derivatized into an ester, a hydroxyl group is derivatized into an ester, a carboxylic acid is derivatized into an amide, an amine is derivatized into an amide, a hydroxyl group is derivatized into a phosphate ester.

As used herein, the term "tautomer" used in reference to the compounds according to the present invention, in particular includes tautomers that typically form with respect to substituted benzimidazole groups. As an illustration two tautomeric forms of an exemplary substituted benzimidazole moiety, as is present in the compounds according to the present invention, are shown:

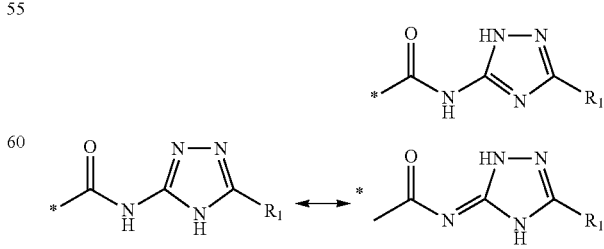

The compounds according to the present invention are to be understood to comprise all tautomeric forms thereof, even if not expressly shown in the formulae described herein, including formula (I). Throughout this specification, whenever a chemical formula, generic or otherwise, discloses a compound having a 1H-benzimidazole moiety that is unsubstituted at the 1 position, as shown on the left-hand side of the above exemplary illustration, said chemical formula it is to be understood to implicitly also relate to compounds wherein the benzimidazole moiety is tautomerized to form the structure as shown on the right-hand side of the above exemplary illustration.

The compounds of formula (I) as defined herein are to be understood to encompass, where applicable, all stereoisomers of said compounds, unless specified otherwise. The term "stereoisomer" as used herein refers to a compound with at least one stereogenic centre, which may be R- or S-configured, as defined by the according IUPAC rules, and encompasses enantiomers and diastereomers as commonly understood by the skilled person. It has to be understood, that in compounds with more than one stereogenic centre, each of the individual stereogenic centres may independently from each other be R- or S-configured. The term "stereoisomer" as used herein also refers to salts of the compounds herein described with optically active acids or bases.

In the present invention, the salts of the compounds according to the present invention are in particular embodiments pharmaceutically acceptable salts of the compounds according to the present invention. Pharmaceutically acceptable salts are such salts which are usually considered by the skilled person to be suitable for medical applications, e.g. because they are not harmful to subjects which may be treated with said salts, or which give rise to side effects which are tolerable within the respective treatment. Usually, said pharmaceutically acceptable salts are such salts which are considered as acceptable by the regulatory authorities, such as the US Food and Drug Administration (FDA), the European Medicines Agency (EMA), or the Japanese Ministry of Health, Labor and Welfare Pharmaceuticals and Medical Devices Agency (PMDA). However, the present invention in principle also encompasses salts of the compounds according to the present invention which are as such not pharmaceutically acceptable, e.g. as intermediates in the production of the compounds according to the present invention or physiologically functional derivatives thereof, or as intermediates in the production pharmacologically acceptable salts of the compounds according to the present invention or physiologically functional derivatives thereof.

In each case, the skilled person can readily determine whether a certain compound according to the present invention or pharmaceutically acceptable derivative thereof can form a salt, i.e. whether said compound according to the present invention or pharmaceutically acceptable derivative or solvate thereof has a group which may carry a positive or negative charge, such as e.g. an amino group, a carboxylic acid group, etc.

As used herein, a "solvate" is a complex formed in the crystalline state between one or more compounds according to the present invention (or pharmaceutically acceptable derivative or salt thereof) and one or more solvent molecules. In certain embodiments, such solvates are 1:2, 2:1 or 1:1, more particularly 1:1 stoichiometric complexes. Furthermore, in certain embodiments, complexes, such solvates are formed with a solvent selected from the group comprising water, methanol, ethanol or propanol, particularly water, methanol or ethanol, more particularly water (the latter is typically also known under the term "hydrate").

As used herein, the term "room temperature", "rt" or "r.t." relates to a temperature of about 25° C., unless specified otherwise.

As used herein, the term "stable" particularly relates to a compound in which the chemical structure is not altered when the compound is stored at a temperature from about −80° C. to about +40° C., more particularly from about −80° C. to +25° C. in the absence of light, moisture or other chemically reactive conditions for at least one week, more particularly at least one month, even more particularly at least six months, yet even more particularly, at least one year, and/or a compound which under IUPAC standard conditions and in the absence of light, moisture or other chemically reactive conditions maintains its structural integrity long enough to be useful for therapeutic or prophylactic administration to a patient, i.e. at least one week. Stable in this context mean that under the aforementioned conditions and time periods and compared with the the timepoint 0, i.e. when it was produced, the amount of impurities has increased by less than 2%, particularly less than 1% more particularly less thatn 0.5%, which can e.g. be determined by analytic HPLC or LC-MS, or the like. Compounds which are not stable as described above are usually to be considered not encompassed by the present invention. In particular, such compounds which at IUPAC standard conditions spontaneously decompose within a period of less than one day are regarded as not being stable compounds. The skilled person will readily recognize, based on his general knowledge in his field of expertise, which compounds and which substitution patterns result in stable compounds.

As used herein, the term "treatment" includes complete or partial healing of a disease, prevention of a disease, alleviation of a disease or stop of progression of a given disease.

As used herein, the term "medicament" includes the compounds of formula (I) as described herein, pharmacologically acceptable salts or physiologically functional derivatives thereof, which are to be administered to a subject in pure form, as well as compositions comprising at least one compound according to the present invention, a pharmacologically acceptable salt or physiologically functional derivative thereof, which is suitable for administration to a subject. The compounds according to the present invention and their pharmacologically acceptable salts and physiologically functional derivatives can be administered to animals, particularly to mammals, and in particular to humans as therapeutics per se, as mixtures with one another or particularly in the form of pharmaceutical preparations or compositions which allow enteral (e.g. oral) or parenteral administration and which comprise as active constituent a therapeutically effective amount of at least one compound according to the present invention, or a salt or physiologically functional derivative thereof, in addition to e.g. one or more components selected from the group comprising customary adjuvants, pharmaceutically innocuous excipients, carriers, buffers, diluents, and/or other customary pharmaceutical auxiliaries.

The pharmaceutical compositions, medical uses and methods of treatment according to the present invention may comprise the application or inclusion of more than one compound according to the present invention.

Pharmaceutical compositions comprising a compound according to the present invention, or a pharmaceutically acceptable salt or physiologically functional derivative may optionally comprise one or more further therapeutically active substances which are not compounds of formula (I) according to the present invention. As used herein, the term "therapeutically active substance" specifies a substance which upon administration can induce a medical effect in a subject. Said medical effect may include the medical effect described herein for the compounds of formula (1) of the present invention, but may also, in the case of therapeutically active substances which are to be co-administered with the compounds according to the present invention, include other medical effects, such as e.g. analgesic, antiinflammatory, anticmetic.

The term "pharmaceutically acceptable" is well known to the skilled person and usually means that the respective entity is not harmful to the subject to which the entity or the composition comprising the entity is administered, that said entity is stable and that said entity is chemically compatible (i.e. non-reactive) with other ingredients of the respective pharmaceutical composition.

Medicaments and pharmaceutical compositions according to the present invention, comprising at least one compound according to the present invention or a pharmacologically acceptable salt or a physiologically functional derivative thereof include those suitable for oral, rectal, bronchial, nasal, topical, buccal, sub-lingual, vaginal or parenteral (including transdermal, subcutaneous, intramuscular, intrapulmonary, intravascular, intracranial, intraperitoneal, intravenous, intraarterial, intracerebral, intraocular injection or infusion) administration, or those in a form suitable for administration by inhalation or insufflation, including powders and liquid aerosol administration, or by controlled release (e.g. sustained release, pH-controlled release, delayed, release, repeat action release, prolonged release, extended release) systems. Suitable examples of controlled release systems include semipermeable matrices of solid hydrophobic polymers containing the compound of the invention, which matrices may be in form of shaped articles, e.g. films or microcapsules or colloidal drug carriers, e.g. polymeric nanoparticles, or controlled release solid dosage forms, e.g. core tablets or multi-layer tablets.

The production of medicaments or pharmaceutical compositions comprising the compounds according to the present invention and their application can be performed according to methods which are well-known to the medical practitioner.

Pharmaceutically acceptable carriers used in the preparation of a pharmaceutical composition or medicament comprising a compound according to the present invention, a pharmacologically acceptable salt or physiologically functional derivative thereof, can be either solid or liquid. Solid form pharmaceutical compositions comprising a compound according to the present invention, a pharmacologically acceptable salt or physiologically functional derivative thereof, include powders, tablets, pills, capsules, sachets, suppositories, and dispersible granules. A solid carrier may comprise one or more components, which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component. In tablets, the active component is mixed with the carrier having the necessary binding capacity in suitable proportions and compacted in the shape and size desired. The tableting mixture can be granulated, sieved and compressed or direct compressed. Suitable carriers are magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, sachets and lozenges are included. Tablets, powders, capsules, pills, sachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into conveniently sized moulds, allowed to cool, and thereby to solidify. Compositions suitable for vaginal administration may be presented as peccaries, tampons, creams, gels, pastes, foams or sprays containing in addition to the active ingredient such carriers as are known in the art to be appropriate. Liquid preparations include solutions, suspensions, and emulsions, for example, water or water-propylene glycol solutions. For example, parenteral injection liquid preparations can be formulated as solutions in aqueous polyethylene glycol solution.

The compounds according to the present invention may be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilizing and/or dispersing agents. Alternatively, the active ingredient may be in powder form, obtained by aseptic isolation of sterile solid or by lyophilization from solution, for re-constitution with a suitable vehicle, e.g. sterile, pyrogen-free water, before use.

Aqueous solutions suitable for oral administration can be prepared by dissolving the active component in water and adding for example suitable colorants, flavours, stabilizing and thickening agents, as desired. Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations, which are intended to be converted, shortly before administration, to liquid form preparations for oral administration. Such liquid forms include solutions, suspensions, and emulsions. These preparations may contain, in addition to the active component, for example colorants, flavours, stabilizers, buffers, artificial and natural sweeteners, dispersants, thickeners, solubilizing agents, and the like.

In an particular embodiment of the present invention the medicament is applied topically, e.g. in the form of transdermal therapeutic systems (e.g. patches) or topical formulations (e.g. liposomes, cremes, ointment, lotion, gels, dispersion, suspension, spray, solution, foam, powder). This may be suitable to reduce possible side effects and, where appropriate, limit the necessary treatment to those areas affected.

Particularly the medicament may comprise carrier materials or excipients, including but not limited to a lipophilic phase (as for example Vaseline, paraffines, triglycerides, waxes, polyalcylsiloxanes), oils (olive oil, peanut oil, castor oil, triglyceride oil), emulsifier (as for example lecithin, phosphatidylglyceroles, alkyl alcohols, sodium lauryl sulphate, polysorbates, Cholesterol, sorbitan fatty acid ester, polyoxyethylene fatty acid glycerol and -ester, poloxamers), preservatives (for instance benzalkonium chloride, chlorobutanol, parabene or thiomersal), flavouring agents, buffer substances (for example salts of acetic acid, citric acid, boric acid, phosphoric acid, tartric acid, trometamole or trolamine), solvents (for instance polyethylenglycols, glycerol, ethanol, isopropanol or propylene glycol) or solubilizers, agents for achieving a depot effect, salts for modifying the osmotic pressure, carrier materials for patches (for instance polypropylene, ethylene-vinylacetate-copolymer, polyacrylates, silicone) or antioxidants (for example ascorbate, tocopherol, butylhydroxyanisole, gallic acid esters or butylhydroxytoluol).

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatine and glycerine or sucrose and acacia; and mouthwashes comprising the active ingredient in a suitable liquid carrier.

Solutions or suspensions may be applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant such as a chlorofluorocarbon (CFC), for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the medicament may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form, for example in capsules or cartridges of, e.g., gelatine, or blister packs from which the powder may be administered by means of an inhaler.

In compositions for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations in certain embodiments are in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, sachet, or lozenge itself, or it can be the appropriate number of any of these in packaged form. Tablets or capsules for oral administration and liquids for intravenous administration and continuous infusion are particular compositions.

Further details on techniques for formulation and administration may be found in the 21$^{st}$ edition of Remington's Pharmaceutical Sciences (Maack Publishing Co. Easton, Pa.).

The compounds of the present invention may be used in combination with radiation therapy, or in combination with radiation therapy and other active compounds, already known for the treatment of the medical conditions disclosed herein, whereby a favourable additive or amplifying effect is noticed.

To prepare the pharmaceutical preparations, pharmaceutically inert inorganic or organic excipients can be used. To prepare pills, tablets, coated tablets and hard gelatine capsules, for example, lactose, cornstarch or derivatives thereof, talc, stearic acid or its salts, etc. can be used. Excipients for soft gelatine capsules and suppositories are, for example, fats, waxes, semi-solid and liquid polyols, natural or hardened oils etc. Suitable excipients for the production of solutions and syrups are, for example, water, sucrose, invert sugar, glucose, polyols etc. Suitable excipients for the production of injection solutions are, for example, water, alcohols, glycerol, polyols or vegetable oils.

The dose can vary within wide limits and is to be suited to the individual conditions in each individual case. For the above uses the appropriate dosage will vary depending on the mode of administration, the particular condition to be treated and the effect desired. In general, however, satisfactory results are achieved at dosage rates of about 1 to 100 mg/kg animal body weight particularly 1 to 50 mg/kg. Suitable dosage rates for larger mammals, for example humans, are of the order of from about 10 mg to 3 g/day, conveniently administered once, in divided doses 2 to 4 times a day, or in sustained release form.

The compounds according to the present invention can be used for modulating cell proliferation. Accordingly, diseases that may be treated using the compounds according to the present invention include hyperproliferative diseases, such diseases related to benign cell growth or malignant cell growth.

Furthermore, the present invention relates to a method of treatment or prevention of the medical conditions specified herein, which comprises the administration of an effective amount of a compound according to the present invention, or a physiologically functional derivative, solvate or salt thereof to a subject in need thereof.

Furthermore, the present invention relates to the use of a compound according to the present invention, or a physiologically functional derivative, solvate or salt thereof in the treatment or prevention of the medical conditions specified herein.

More particularly, the compounds according to the present invention, solvates salts or physiologically functional derivatives thereof can be used for treating cancer.

In certain embodiments of the present invention, said cancer is selected from the group comprising cancer of the breast, esophagus, gastrointestinal tract, gastro-intestinal stromal tumors, pancreas, prostate, biliary tract, bladder, basal cell carcinoma, medulloblastoma, rhabdomyosarcoma, glioma, small-cell lung cancer, oral squamous cell carcinoma, melanoma, colorectal cancer, non-small cell lung cancer, osteosarcoma, glioblastoma, chronic lymphacytic leukemia, chronic myeloid leukemia, multiple myeloma, acute myeloid leukemia, ovarian cancer, meningioma, and liver cancer, more particularly pancreas cancer. In said cancer types, activation of the Hedgehog pathway and/or GLI1 expression may be independent of the G protein-coupled receptor Smoothened. For further reference, see the introductory section of this specification and the reference documents cited herein.

In particular embodiments of the present invention, in said cancer, the hedgehog signaling pathway is activated.

In particular embodiments of the present invention, in cells of said cancer, the hedgehog signaling pathway is activated.

In further particular embodiments of the present invention, said cancer does not respond to Smoothened inhibitor therapy.

In further particular embodiments of the present invention, cells of said cancer do not respond to Smoothened inhibitor therapy.

In further particular embodiments of the present invention, in said cancer the activation of the hedgehog signaling pathway is independent of signaling by the G protein-coupled receptor Smoothened.

In further particular embodiments of the present invention, in cells of said cancer the activation of the hedgehog signaling pathway is independent of signaling by the G protein-coupled receptor Smoothened.

In further particular embodiments of the present invention, in said cancer the G protein-coupled receptor Smoothened is not responsive to inhibition by Smoothened inhibitors.

In further particular embodiments of the present invention, in cells of said cancer the G protein-coupled receptor Smoothened is not responsive to inhibition by Smoothened inhibitors.

In the context of the present invention, said cancer or cells of said cancer being not responsive to Smoothened inhibitor therapy includes both the case that the activation of the hedgehog signaling pathway is independent of signaling by the G protein-coupled receptor Smoothened, and that the G protein-coupled receptor Smoothened is not responsive to inhibition by Smoothened inhibitors.

In the present invention patients wherein in said cancer, or in cells of said cancer, the hedgehog signaling pathway is activated are in short referred to as "Hedgehog dependent patients", and patients wherein in said cancer, or in the cells of said cancer, the hedgehog signaling pathway is not activated are in short referred to as "Hedgehog independent patients". In the present invention, patients e.g. can be stratified into Hedgehog dependent patients and Hedgehog independent patients by a procedure comprising the steps of
1) providing a sample from said patient, wherein said sample comprises cancer cells from said patient.
2) optionally subjecting said sample to a work-up step.
3) adding a labeled antibody which specifically binds to at least one protein playing a role in the hedgehog signaling pathway,
or
    adding a first antibody which specifically binds to at least one protein playing a role in the hedgehog signaling pathway, and subsequently adding a second antibody which specifically binds to said first antibody, and wherein said second antibody is a labeled antibody,
4) washing said sample after step 3.
5) determining whether said labeled antibody is detectable in said sample after step 4).
6) if in step 5) said marker moiety is detectable, classifying said patient as Hedgehog dependent patient, and if in step 5) said marker moiety is not detectable, classifying said patient as Hedgehog independent patient.

Antibodies used in the present invention are typically monoclonal antibodies.

The label in said labeled antibody can be selected from any label typically used as antibody label in the field of biochemistry, cellular biology, immunochemistry, etc., for a label selected from the group comprising a fluorescence label, a dye, a FRET label, a radioactive label. moiety, or an enzymatically active moiety. Said enzymatically active moiety can process a reaction which in turn results in the release of a detectable substance, e.g. a dye.

In the above method of stratifying patients into Hedgehog dependent patients and Hedgehog independent patients, the work-up step is e.g. in particular embodiments selected from the group comprising preservation, embedding, slicing and staining. Preservation can be performed by cryopreservation or fixation by e.g. formaldehyde or ethanol. Embedding the tumor material prepares it for slicing. Staining can be performed with direct or indirect methods. For further information and examples see DOI: 10.1354/vp42-4-405 J. A. Ramos-Vara, Technical Aspects of Immunohistochemistry, (2005) 42: 405 Vet Pathol.

In the context of the present invention, the expression "said labeled antibody is detectable" means that by the state of the art measurement methods used for detecting said label, no signal relating to said label is detectable, and/or said signal is not significant in relation to the background noise generated by said measurement method.

In the above method to stratify patients into Hedgehog dependent patients and Hedgehog independent patients, washing step 4 is to remove unbound and/or unspecifically bound antibodies from step 3. In particular embodiments, said washing step comprises washing with a buffer, e.g. a PBS buffer, and optionally a serum protein, e.g. BSA. Washing step 4 can be repeated as necessary to obtain a suitable signal/noise ratio, e.g. 2 or more, 3 or more. 4 or more times.

In certain embodiments of the above method to stratify patients into Hedgehog dependent cancer patients and Hedgehog independent cancer patients, background signal by unspecific binding of antibodies is excluded by an isotype control. This control can be utilized when working with monoclonal primary antibodies. A comparative sample treated as above is incubated with antibody diluent, supplemented with a non-immune immunoglobulin of the same isotype (for example, $IgG_1$, $IgG2_A$, $IgG2_B$, IgM) and concentration as the aforementioned antibody. The sample is then incubated with the labeled antibody and detection reagents. These steps will help ensure that what appears to be specific staining was not caused by non-specific interactions of immunoglobulin molecules with the sample. Examples and a further description of this method can be found in "Tissue Microarrays—Methods in Molecular Biology Volume 664, 2010, pp 1.13-126. Immunohistochemical Analysis of Tissue Microarrays: Ronald Simon. Martina Mirlacher, and Guido Sauter".

In the context of the present invention the G protein-coupled receptor Smoothened is interchangeably abbreviated as "Smoothened" and "Smo".

In the context of the present invention the expression "the activation of the hedgehog signaling pathway" in particular refers to the activation of expression of primary target genes of the Hedgehog signaling pathway, including GLI, HHIP, Ptch, more particularly of GLI expression via the hedgehog pathway. Typically, GLI expression is triggered via binding of hedgehog to the Smo/Ptch (Smoothened/Patched) complex and thereupon GLI expression via signalling by Smo.

In the context of the present invention, the "activation of the hedgehog signaling pathway is independent of signaling by the G protein-coupled receptor Smoothened" as used in the present invention refers to the ability of certain cancers to activate the expression of primary target proteins of the Hedgehog signaling pathway, more particularly of GLI expression independent of signaling via Smo. Instead, in these cases GLI expression is activated by alternate routes, which are independent of the hedgehog signaling pathway as described above.

Known Smoothened inhibitors are for example LDE225 (by Novartis), LEQ506 (by Novartis). Vismodegib (GDC-0449). IPI-926 (by Infinity Pharmaceuticals), BMS-833923 (XL139) (by Bristol Myers Squibb: Exelixis), or PF-04449913 (by Pfizer), N-[3-(1H-Benzimridazol-2-yl)-4-chlorophenyl]-3,4,5-triethoxybenzamide (SANT-2), SANT19, SANT74, aSANT75, (3β,23β)-17,23-Epoxy-3-hydroxyveratraman-11-one (11-ketocyclopamine/Jervine), Cur61414 (by Curis), IPI 269609 (by Infinity), MRT 10, and for example cyclopamine (for further information and further Smoothened inhibitors, see e.g. Peukert S., Miller-Moslin K., ChemMedChem Volume 5, Issue 4, pages 500-512, Apr. 6, 2010).

In the present invention, patients e.g. can be stratified into patients wherein said cancer, or cells of said cancer, do not respond to Smoothened inhibitor therapy, and patients wherein in said cancer, or in the cells of said cancer, respond to Smoothened inhibitor therapy, based on their medical history, i.e. if at a previous point said cancer did not respond or ceased to respond to (wherein said response encompasses the amelioration or stabilization of one or more of the following: Disease state, symptom severity, tumor volume, tumor aggressiveness, propensity to form metastases, tumor malignancy, tumor invasiveness and patient's overall physical state), to Smoothened inhibitor therapy. Alternatively, said stratification can be done by a procedure comprising the steps of 1) providing a sample from said patient, wherein said sample comprises cancer cells from said patient,
2) preparing two or more cell cultures from said sample,
3) incubating said cell cultures to increase the number of cells in order to obtain in each cell culture a cell number which is sufficient to provide at least 1 μg total RNA,
4) adding a Smo-inhibitor to all but one of said cell cultures,
5) adding a Smoothened agonist to said cell cultures,
6) incubating said cell cultures.
7) determining the level of GLI expression in said cell cultures,
8) comparing the level of GLI expression in said cell cultures to which a Smoothened inhibitor has been added to said sample which no Smoothened inhibitor has been added,
9) if the expression of GLI in at least one of said cell cultures to which a Smoothened inhibitor has been added is lower than the expression of GLI in said sample which no Smoothened inhibitor has been added, classifying said patient as patient wherein said cancer, or the cells of said cancer, respond to Smoothened inhibitor therapy, and otherwise classifying said patient as patient wherein said cancer, or cells of said cancer, do not respond to Smoothened inhibitor therapy.

In the above method,
in step 2, cell cultures usually comprise at least a growth medium typically used in the field of cell biology;
in step 3 in particular embodiments, said cell number is at least 500.000, more particularly at least 1,000,000, even more particularly at least 1,500,000 cells:
in step 4 a Smoothened inhibitor is in particular embodiments added in an amount known to usually at least partially inhibit cellular Smo activity; in the particular embodiments where a Smoothened inhibitor is added to more than one cell culture, a concentration gradient can be prepared by adding different amounts of Smoothened inhibitor to each cell culture; in step 4 the Smoothened inhibitor is in particular embodiments a small molecule, more particularly a Smoothened inhibitor as described herein, even more particularly a compound of the present invention,
in step 5 in particular embodiments the Smoothened agonist is added to each cell culture in the same amount with respect to the cell number (i.e. more agonist for a higher cell number) in said cell culture, and in an amount known to usually at least partially activate GLI expression: said amount can for instance be determined in one or more comparative cell cultures comprising cancer cells of the same or similar tissue from a subject which is known to be a as patient wherein said cancer, or the cells of said cancer, respond to Smoothened inhibitor therapy;
in step 6 in particular embodiments said cell cultures are incubated for at least 24 h, 36 h, or 48 h. in this way the cells can express GLI upon the addition of the Smoothened agonist (and in the case that said cancer cells respond to Smoothened inhibitor therapy, allows said cancer cells to degrade GLI):
in steps 7 the level of GLI expression can e.g. be determined with the qPCR and/or Western blot methods described herein;
in step 9, in particular embodiments, to classify said patient as patient wherein said cancer, or the cells of said cancer, respond to Smoothened inhibitor therapy, the difference in the level of GLI expression between said at least one of said cell cultures to which a Smoothened inhibitor has been added and said sample which no Smoothened inhibitor has been added is statistically significantly, e.g. at least 20%, particularly at least 40%, more particularly at least 60%, even more particularly at least 75%, yet even more particularly at least 90%.

Patients can be stratified into patients having cancer wherein in said cancer or in cells of said cancer the activation of the hedgehog signaling pathway is independent of signaling by the G protein-coupled receptor Smoothened and patients having cancer wherein in said cancer or in cells of said cancer the activation of the hedgehog signaling pathway is dependent of signaling by the C protein-coupled receptor Smoothened with common methods. For example, the specific genetic subtype of cancer can be determined and compared with a database. If in said specific genetic subtype of cancer activation of the hedgehog signaling pathway is known to be independent of signaling by the G protein-coupled receptor Smoothened, e.g. in the scientific literature, and in a particular example in the scientific literature cited herein, said patient is classified as Smo independent cancer patient. If in said specific genetic subtype of cancer activation of the hedgehog signaling pathway is known to be dependent of signaling by the G protein-coupled receptor Smoothened. e.g. in the scientific literature, and in a particular example in the, said patient is classified as Smo dependent cancer patient.

Patients can further be stratified into patients having cancer wherein in said cancer or in cells of said cancer the activation of the hedgehog signaling pathway is independent of signaling by the G protein-coupled receptor Smoothened and patients having cancer wherein in said cancer or in cells of said cancer the activation of the hedgehog signaling pathway is dependent of signaling by the G protein-coupled receptor Smoothened by a method comprising the steps of
1) providing a sample from said patient, wherein said sample comprises cancer cells from said patient,
2) preparing a cell culture from said sample,
3) incubating said cell culture to increase the number of cells in order to obtain a cell number which is sufficient to provide at least 1 µg total RNA,
4) adding a Smo-inhibitor to said cell culture,
5) incubating said cell cultures,
6) determining the level of GLI expression in said cell cultures,
7) if GLI expression is detectable in said cell culture, classifying said patient as patient having cancer wherein in said cancer or in cells of said cancer the activation of the hedgehog signaling pathway is independent of signaling by the G protein-coupled receptor Smoothened, and if GLI expression is not detectable in said cell culture, if GLI expression is detectable in said cell culture, classifying said patient as patient having cancer wherein in said cancer or in cells of said cancer the activation of the hedgehog signaling pathway is dependent of signaling by the G protein-coupled receptor Smoothened.

In the above method,
in step 2, cell cultures usually comprise at least a growth medium typically used in the field of cell biology;
in step 3 in particular embodiments, said cell number is at least 500,000, more particularly at least 1,000,000, even more particularly at least 1,500,000 cells;
in step 4 a Smoothened inhibitor is in particular embodiments added in an amount known to usually at least partially inhibit cellular Smo activity; in the particular embodiments where a Smoothened inhibitor is added to more than one cell culture, a concentration gradient can be prepared by adding different amounts of Smoothened inhibitor to each cell culture; in this case, the Smoothened inhibitor can also be and RNA molecule inhibiting the expression of Smo, e.g. siRNA or shRNA, particularly an RNA molecule which specifically and/or selectively binds to the gene encoding for Smo and prevents transcription of said gene (this is typically also known as a Smo knockdown);
in step 4 the Smoothened inhibitor is in particular embodiments a small molecule, more particularly a Smoothened inhibitor as described herein, even more particularly a compound of the present invention,
in step 5 in particular embodiments in particular embodiments said cell cultures are incubated for at least 12 h, 24 h, or 36 h, in this way the cells can express GLI;
in step 6 the level of GLI expression can e.g. be determined with the qPCR and/or Western blot methods described herein;
in step 7, in particular embodiments, detectable means that by the state of the art measurement methods used for detecting said label, no signal relating to GLI expression is detectable, and/or said signal is not significant in relation to the background noise generated by said measurement method.

In the context of the present invention "the G protein-coupled receptor Smoothened is not responsive to inhibition by Smoothened inhibitors" means that Smoothened activity is not inhibited by Smoothened inhibitors. Usually, in these cases cancer cells show at least one mutation in a gene encoding for Smoothened, particularly The D473H mutation which results in an amino acid substitution at position 473 in Smoothened, from an aspartic acid (D) to a histidine (H). Said mutation typically leads to an alteration of the Smoothened receptor which prevents binding of Smoothened inhibitors, in particular of known Smoothened inhibitors which target wild type Smoothened. Said mutation may originate from the patient's innate chromosomal setup, i.e. a hereditary trait, or may be acquired at a later point, e.g. by a spontaneous mutation of cancer cell DNA, which is then selected and passed on to further cancer cell generations as a response to therapy with Smoothened inhibitors. Patients can accordingly be classified as patients having cancer wherein in said cancer or in cells of said cancer the activation of the hedgehog signaling pathway is independent of signaling by the G protein-coupled receptor Smoothened by analyzing the genes encoding for Smo in cells from said patient's cancer for the presence of a mutation as described above, which can e.g. be done by the qPCR methods as described herein.

Patients having cancer wherein in said cancer or in cells of said cancer the activation of the hedgehog signaling pathway is dependent of signaling by the G protein-coupled receptor Smoothened can further be stratified into patients having cancer wherein the G protein-coupled receptor Smoothened is not responsive to inhibition by Smo inhibitors and patients having cancer wherein the G protein-coupled receptor Smoothened is not responsive to inhibition by Smo inhibitors by the method described above for stratifying into patients wherein said cancer, or cells of said cancer, do not respond to Smoothened inhibitor therapy, and patients wherein in said cancer, or in the cells of said cancer, respond to Smoothened inhibitor therapy.

In the context of the present invention, said sample from said patient comprising cancer cells from said patient is for instance a biopsy of said patient's cancer.

As used herein, the term "DYRK1B" means an enzyme from the family of serine/threonine kinases, more particularly a member of the Minibrain/DYRK family of kinases which is specified by the UniProt/Swiss-Prot ID Q9Y463; or as Refseq proteins: NP_004705.1, NP_006474.1 and NP_006475.1, and/or an expression product of a gene encoding for DYRK1B as defined herein below. As used herein, the term "DYRK1B" in certain embodiments also includes variants of DYRK1B, such as isoforms, homologs and mutants of DYRK1B, which share at least 95% sequence homology, more particularly at least 97% sequence homology, even more particularly at least 99% sequence homology with DYRK1B as defined above, and in the case of proteins and/or gene expression products in certain embodiments have essentially the same enzymatic activity profile, i.e. process essentially the same substrates as DYRK1B as defined above, wherein however the enzymatic activity of said variants of DYRK1B may differ (i.e. be higher or lower than) from DYRK1B as defined above by up to two orders of magnitude, particularly up to one order of magnitude, more particularly up to a factor of 2. A particular variant of DYRK1B which is comprised by the present invention is Mirk, which typically is located in skeletal muscle tissue, whereas DYRK1B typically is located in brain tissue.

In the context of the present invention said at least one protein playing a role in the hedgehog signaling pathway can e.g. be selected from the group comprising Patched, GLI, Smoothened. HHIP, Hedgehog and SUFU.

In the context of the present invention, the term "GLI" refers to members of the GLI protein family, such as GLI1, GLI2, GLI3 in particular embodiments and, unless specified otherwise particularly to GLI1.

In general, and unless specified otherwise, the proteins, genes and/or gene expression products as defined herein in certain embodiments also include variants of said proteins, genes and gene expression products, such as isoforms, homologs and mutants thereof, which share at least 95% sequence homology, more particularly at least 97% sequence homology, even more particularly at least 99% sequence homology with, the proteins, genes and/or gene expression products as defined herein, and in the case of proteins and/or gene expression products in certain embodiments have essentially the same enzymatic activity as, the proteins and/or gene expression products as defined herein, wherein however the enzymatic activity of said variants may differ (i.e. be higher or lower than) from the proteins, and/or gene expression products as defined herein by up to two orders of magnitude, particularly up to one order of magnitude, more particularly up to a factor of 2.

As used herein, the term "DYRK1B inhibitor" or "compound which inhibits the activity of DYRK1B" means a compound which is capable of inhibiting the enzymatic activity of DYRK1B in vitro and/or in vivo e.g. in a patient in need thereof, particularly with an inhibitory concentration $IC_{50}$ of 50 mM or lower, more particularly with an inhibitory concentration $IC_{50}$ of 20 mM or lower, even more particularly with an inhibitory concentration $IC_{50}$ of 5 mM or lower, yet even more particularly with an inhibitory concentration $IC_{50}$ of 1 mM or lower, e.g. in the kinase assay described herein. The chemical nature of the DYRK1B inhibitor is not particularly limited and can for example be selected from the group comprising synthetic compounds, naturally occurring compounds, peptides, proteins, antibodies, and small molecules.

In certain embodiments of the present invention, said DYRK1B inhibitor is selective and/or specific for DYRK1B. In certain embodiments of the present invention, said DYRK1B inhibitor is non-selective and/or non-specific for DYRK1B. It is apparent that non-selectivity and/or non-specificity is acceptable, as long as no intolerable side-effect occurs due to the non-selectivity and/or non-specificity of the DYRK1B inhibitor. In this context, "intolerable side-effect" means an effect of the addition or administration of the DYRK1B inhibitor which is different from the inhibition of DYRK1B, e.g. the inhibition of one or more further enzymes, and which conflicts with the objective to be achieved by the addition or administration of the DYRK1B inhibitor to such a degree that no acceptable results may be achieved. Examples are for instance a pharmaceutical side effect which would prevent the use of the DYRK1B inhibitor for therapeutic purposes, such as high toxicity, cancerogenity or the like. As one example of tolerable non-selectivity and/or non-specificity, the DYRK1B inhibitor may inhibit DYRK1A in addition to DYRK1B. DYRK1A function is largely dispensable in GLI-driven cancer cells. Off-target effects of DYRK1B inhibitors will not be critical as inhibition of DYRK1A—if at all—will enhance the GLI-antagonizing effect of DYRK1B inhibition in cancer cells. This effect is for instance credible in view of the results shown in Mao et al., J. Biol. Chem. 2002, 277, 38, 35156-35161, in particular FIGS. 4 and 6.

As used herein, the expression that in a cancer or cells in a cancer the "hedgehog signaling pathway is independent of signaling by the G protein-coupled receptor Smoothened" means that the proliferation of a certain cancer entity is independent of the G protein-coupled receptor Smoothened and thus not affected. or at least not substantially affected, by inhibition of the (G protein-coupled receptor Smoothened. Accordingly, patients suffering from such cancer cannot be treated and do not benefit by therapeutic approaches which are directed to inhibition of the G protein-coupled receptor Smoothened.

As used herein, the term "hedgehog signaling pathway" means a cellular signaling pathway comprising an interaction with a protein of the family known as hedgehog proteins, such as e.g. the proteins commonly known as "sonic hedgehog" (UniProtKB/Swiss-Prot: Q15465), "indian hedgehog" (UniProtKB/Swiss-Prot: Q14623) and "desert hedgehog" (UniProtKB/Swiss-Prot: 043323) (Ingham and McMahon, 2001).

As used herein, the term "treating" or "treatment" encompasses the amelioration or stabilization of one or more of the following: Disease state, symptom severity, tumor volume, tumor aggressiveness, propensity to form metastases, tumor malignancy, tumor invasiveness and patient's overall physical state.

As used herein, the term "therapeutically effective amount" means an amount, e.g. of a compound, which upon administration to a patient in need thereof results in a therapeutic effect on the disease to be treated. Such therapeutic effects, e.g. in cancer therapy, may comprise an effect on diseased tissue or cells including changes in tumor size, metabolic activity, cell viability, blood supply of the tumor. i.e. angiogenesis, composition of the tumor. e.g. relationship of cells comprising the tumor e.g. tumor cells, immune cells, tibroblasts and endothelial cells: and an effect on the patient's medical state including improvements in clinical status, health status, progression or stabilization of disease, increased time of progression free survival, cure of disease, enhanced overall survival, delay of disease progression and alleviation of symptoms. Such effects usually do not occur immediately after administration of a compound and may be delayed, e.g. by hours, days, weeks or months, depending e.g. on the specific patient, type of disease and overall situation under which the therapy is administered.

As used herein, the term "sample" in principle comprises samples from natural sources, such as a sample obtainable from a mammal, and artificial samples, which are obtainable by admixing several ingredients, wherein said ingredients may or may not be derived from natural sources, and may e.g. comprise ingredients selected from the group comprising synthetic and/or natural proteins, peptides, oligo- or polynucleic acids, etc. In certain embodiments, samples are from natural sources, which include bodily fluids and/or tissue samples, such as bodily fluid and/or a tissue sample obtainable from mammals. Said samples from natural sources can be used in the present invention with or without further processing after being obtained from their source, e.g. a mammal. Such processing can for instance comprise separation, fractionation, dilution, dispersion, mechanical treatment such as sonification, or grinding, concentration, removal of certain components of said sample, or addition of compounds, such as salts, buffers, detergents, etc.

As used herein, the term "bodily fluid" or "body fluid" specifies a fluid or part of a fluid originating from the body of a patient, including fluids that are excreted or secreted from the body of the patient, including but not limited to blood, including peripheral blood, serum, plasma, urine, interstitial fluid, liquor, aqueous humour and vitreous humour, bile, breast milk, cerebrospinal fluid, endolymph, perilymph, ejaculate, gastric juice, mucus, peritoneal fluid, pleural fluid, saliva, sweat, tears and vaginal secretion, particularly peripheral blood, serum, plasma and urine. Said bodily fluid itself may or may not comprise diseased and/or non-diseased cells.

As used herein, the term "tissue sample" specifies a non-fluid material or solid originating from the body of a patient. Tissue samples include, but are not limited to samples of bone material, bone marrow, skin, hair follicle, mucosa, brain, cartilage, muscles, lung, kidney, stomach, intestines, bladder and liver. Said tissue sample itself may or may not comprise diseased cells, and may for instance be a sample taken from a diseased region of a patient's body, such as a biopsy of a tumor. In certain embodiments the tissue sample is selected from skin, hair follicle or oral mucosa.

In the embodiments of the present invention, the sample is obtained from the patient by any method and/or means commonly known to the skilled person in the field of medicine, e.g. in certain embodiments blood sample taking by venipuncture.

As used herein, the term "peripheral blood" specifies blood obtained from the circulation remote from the heart. i.e. the blood in the systemic circulation, as for example blood from acral areas.

As used herein, the term "whole blood" specifies unmodified blood comprising cells and fluid, as obtained from the donor of said blood, such as a patient.

As used herein, the term "patient" specifies a subject which is suspected of having a disease or disorder, in certain embodiments having a medical condition, which may require treatment. In certain embodiments of the present invention, the patient is a cancer patient, i.e. a subject suffering from cancer. The patient may have received prior treatment for the disease in question, e.g. in the case of a cancer patient by radiation or chemotherapy, or the patient's disease may be untreated prior to the application of the embodiments of the present invention to said patient.

As used herein, the term "gene encoding for DYRK1B" means a gene identified by the NCBI reference sequence (Refseq mRNAs NM_004714.1. NM_006483.1. NM_006484.1, or the Ensemble transcripts ENST00000323039(uc002omj.2) ENST00000348817 (uc002omi.2) ENST00000430012(uc002omk.2 uc002oml.2))

As used herein, the term "inhibited on the DNA level and/or on the RNA level" means that the intracellular level of the protein of interest, in the case of the present invention DYRK1B, is diminished by inhibiting the expression of the gene encoding for the protein of interest. This can be achieved either by an inhibition on the DNA level, i.e. by inhibiting transcription of the gene encoding for the protein of interest, or by an inhibition on the RNA level, i.e. by inhibiting translation of an RNA transcribed from the gene encoding for the protein of interest. The methods by which inhibition on the DNA level and/or on the RNA level can be achieved are well known to the skilled person and any such well known method which is suitable for the purposes of the present invention. e.g. for therapeutic use in a patient suffering from cancer, or for in vitro use such as in an assay, can be applied in the embodiments of the present invention.

In the context of the present invention, a mammal is in certain embodiments a human.

As used herein, the terms "inhibit DYRK1B", "inhibition of DYRK1B" and "DYRK1B inhibition" are used interchangeably and mean that the enzymatic activity of DYRK1B is diminished, which results in a diminished turnover rate with respect to the conversion of DYRK1B substrates by DYRK1B, which can particularly be determined by measuring a reduction in the level of GLI expression by the methods described herein, e.g. the qPCR or Western Blot methods described herein. Said reduction in the level of GLI expression is in particular embodiments at least 50%, more particularly at least 70%, even more particularly at least 80%, yet even more particularly at least 90%.

As used herein, the term "formation of resistance of cancer cells against chemotherapeutic agents" means that over the course of a treatment with a chemotherapeutic agent, the treated cancer cells develop a resistance against said chemotherapeutic agent, i.e. become non-responsive to said chemotherapeutic agent. The result of resistance against said chemotherapeutic agent is that the cancer cells will proliferate, irrespective of continued therapy with said chemotherapeutic agent. Usually, such resistance against a chemotherapeutic agent is not reversible, and usually, in such cases of resistance against a chemotherapeutic agent, therapy has to be changed to a different treatment regimen. e.g. encompassing the administration of a different chemotherapeutic agent, radiotherapy, or the like.

In the embodiments of the present invention, in particular wherein a DYRK1B inhibitor is administered in an amount which is effective to inhibit DYRK1B said DYRK1B inhibitor is administered in an amount which is effective to inhibit DYRK1B by for example by at least 50%, more particularly at least 75%, even more particularly at least 90%, inhibition of DYRK1B can be determined in vitro by a DYRK1B kinase assay and ex vivo by measuring the expression level of a primary target gene of the hedgehog signaling pathway, e.g. GLI, particularly in a sample obtained from a patient; this can be done by the methods described herein.

In further particular embodiments of the present invention, the compounds inhibit the hedgehog signaling pathway, which can be determined by measuring the expression level of a primary target gene of the hedgehog signaling pathway, e.g. GLI, particularly in a sample obtained from a patient; this can be done by the methods described herein. e.g. qPCR or Western Blot.

In further particular embodiments of the present invention, the compounds inhibit the cellular expression of GLI, particularly GLI1.

In further particular embodiments of the present invention, the compounds inhibit the hedgehog signaling pathway-mediated cellular expression of GLI, particularly GLI1.

Furthermore, particular cancer types of certain embodiments of the present invention are listed in the following; reference documents with further information are indicated in parentheses:

esophagus/GI (Wang. Y., et al. (2012). Canc. cell 21(3) 374-387. doi: 10.1016/j.ccr.2011.12.028);
gastrointestinal (Berman, D. M., et al. (2003). Nature, 425 (6960). 846-851. doi: 10.1038/nature01972);
gastrointestinal stromal tumors (Pelezar, P. et al. (2013). Gastroenterology. 144(1), 134-144.e6. doi: 10.1053/j.gastro.2012.09.061);
pancreas (Nolan-Stevaux. O. et al. (2009). Genes & Development. 23(1). 24-36. doi:10.1101/gad. 1753809, Feldmann, G., et al. (2007). Cancer Research, 67(5), 2187-2196. doi:10.1158/0008-5472.CAN-06-3281; Karhu, R. et al. (2006) Genes, chromosomes & cancer 45, 721-730; Merchant. A. A., and Matsui, W. (2010) Clin. Canc. Res. 16, 3130-3140);
prostate (Karhadkar. S S et al. (2004). Nature, 431(7009). 707-712. doi:10.1038/nature02962;
Sánchez, P., et al. (2004). PNAS, 101(34). 12561-12566. doi:10.1073/pnas.0404956101); biliary tract (Berman. D M et al. (2003). Nature. 425(6960), 846-851. doi: 10.1038/nature01972);

bladder/urogenital (Fei, D L et al. Cancer Res. 2012 Sep. 1; 72(17):4449-58);
basal cell carcinoma/skin (Hahn, H., et al. (1996). Cell, 85(6). 841-851);
medulloblastoma/brain (Goodrich, L. V., et al. (1997). Science, 277(5329). 1109-1113);
rhabdomyosarcoma (Ecke, I. et al. (2008). Molecular carcinogenesis, 47(5), 361-372. doi:10.1002/mc.20394; Deng, X. et al. (2006) Cancer research 66, 4149-4158; Friedman, E. (2011) Sarcoma 2011, 260757, doi:10.1155/2011/260757; Jin. K. et al. (2007) Cancer research 67, 7247-7255; Mercer. S. E. et al. (2006) Cancer research 66, 5143-5150; Yang et al., Carcinogenesis. 2010 April; 31 (4):552-558):
glioma/brain (Clement, V., et al. (2007). Current biology: CB, 17(2). 165-172. doi: 10.1016/j.cub.2006.11.033);
small-cell lung cancer/lung (Watkins. D. N. et al. (2003). Nature. 422(6929), 313-317. doi:10.1038/nature01493; Park K S, et al. Nat Med. 2011 Oct. 9; 17(11):1504-8. doi: 10.1038/nm.2473.);
oral squamous cell carcinoma (Yan M, et al. Oral Oncol. 2011 June; 47(6):504-9. doi: 10.1016/j.oraloncology.2011.03.027. Epub 2011 May 4);
melanoma/skin (Stecca B et al. (2007) PNAS 104(14) 5895-5900 doi:10.1073/pnas.0700776104);
colorectal cancer/GI (Varnat, F., et al. (2009). EMBO molecular medicine, 1(6-7). 338-351. doi:10.1002/emmm.200900039; Deng. X. et al. (2006) Cancer research 66, 4149-4158; Friedman, E. (2011) Sarcoma 2011, 260757, doi:10.1155/2011/260757; Jin. K. et al. (2007) Cancer research 67, 7247-7255; Mercer. S. E. et al. (2006) Cancer research 66, 5143-5150; Yang et al., Carcinogenesis. 2010 April; 31 (4):552-558);
non-small cell lung cancer/lung (Yuan. Z., et al. (2007). Oncogene. 26(7). 1046-1055. doi:10.1038/sj.onc.1209860);
osteosarcoma/bone (Bove, J. V. M. G., et al. (2010). Nature Reviews Cancer, 10(7), 481-488. doi:10.1038/nrc2869; Ho, L., et al. (2009). Cancer cell, 16(2), 126-136. doi: 10.1016/j.ccr.2009.05.013; Friedman. E. (2011) Sarcoma 2011, 260757, doi:10.1155/2011/260757; Jin, K. et al. (2007) Cancer research 67, 7247-7255; Mercer, S. E. et al. (2006) Cancer research 66. 5143-5150; Yang et al., Carcinogenesis. 2010 April; 31(4):552-558):
glioblastoma/brain (Clement, V., et al. (2007). Current biology: CB, 17(2), 165-172. doi:10.1016/j.cub.2006.11.033);
chronic lymphacytic leukemia/blood (Desch, P., et al. (2010). Oncogene, 1-11. doi: 10.1038/onc.2010.243);
chronic myeloid leukemia/blood (Dierks, C., et al. (2008). Cancer cell. 14(3), 238-249. doi: 10.1016/j.ccr.2008.08.003);
multiple mycloma/blood (Peacock C D. et al. PNAS 2007 Mar. 6:104(10):4048-53);
ovarian cancer/urogenital (McCann C K. et al. PLoS One. 2011:6(11):e28077. doi: 10.1371/joumal.pone.0028077. Epub 2011 Nov. 29; Friedman, E. (2007) Journal of cellular biochemistry 102, 274-279, 2007; Karhu et al., Genes Chromosomes Cancer. 2006 August; 45(8):721-730);
meningioma/brain (Clark, V. E. et al., Science, 2013 Jan. 24, Epub ahead of print. PMID (PubMed-ID) 23348505—as supplied by publisher: Aavikko M. et al., Am J Hum Genet. 2012 Sep. 7, 91(3), 520-526):
liver/GI (Arzumanyan A. et al. Cancer Res. 2012 Nov. 15:72(22):5912-20);
liver (Huang, S., et al. (2006). Carcinogenesis, 27(7). 1334-1340. doi: 10.1093/carcin/bgi378).

It is apparent that the embodiments of the present invention as described herein may be combined to form further particular embodiments of the present invention.

EXAMPLES

Synthesis Examples

Synthesis of Final Compounds

Unless otherwise specified, starting materials, reagents and solvents were commercially available and were used without further purification.

N-(5-Cyano-1H-benzo[d]imidazol-2-yl)-2-(2,3-dihydrobenzofuran-5-yl)thiazole-4-carboxamide (1)

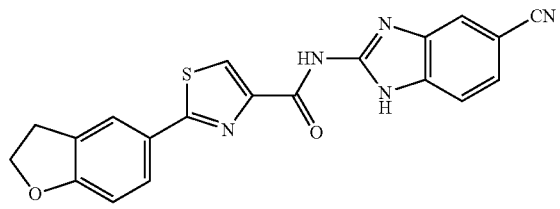 [SMILES: N#Cc1ccc2[nH]c(NC(=O)c3csc(-c4ccc5c(c4)CCO5)n3)nc2c1]

To a solution of 2-(2,3-dihydro-1-benzofuran-5-yl)-1,3-thiazole-4-carboxylic acid (123 mg, 0.50 mmol) in 2 ml N,N-dimethylformamide, were added 2-amino-1H-benzo[d]imidazole-5-carbonitrile (130 mg, 0.54 mmol), 2-(1H-benzotriazole-1-yl)-1,1,3,3-tetramethyluronium hexafluorophosphate (HBTU) (188 mg, 0.5 mmol), 4-dimethylaminopyridine (6 mg, 0.05 mmol) and N,N-diisopropylethylamine (0.22 ml, 1.24 mmol). The reaction mixture was stirred overnight at room temperature. It was poured into ice water. The formed precipitate was filtered off and dried. The product was obtained as a light yellow solid (154 mg, 0.40 mmol, 79% yield). $^1$H NMR (400 MHz, DMSO-$d_6$) δ ppm 3.29 (t, J=8.75 Hz, 2H), 4.65 (t, J=8.75 Hz, 2H), 6.91 (d, J=8.34 Hz, 1H), 7.54 (dd, J=8.25 Hz, J=1.32 Hz, 1H), 7.67 (d, J=8.28 Hz, 1H), 7.92 (d, J=1.92 Hz, 1H), 7.95 (bs, 1H), 8.13 (bs, 1H), 8.58 (s, 1H), 11.84 (bs, 1H), 12.69 (bs, 1H). LC/MS [M+H]$^+$: 387.8

N-(5-Chloro-6-fluoro-1H-benzo[d]imidazol-2-yl)-2-(2,3-dihydrobenzofuran-5-yl)thiazole-4-carboxamide (2)

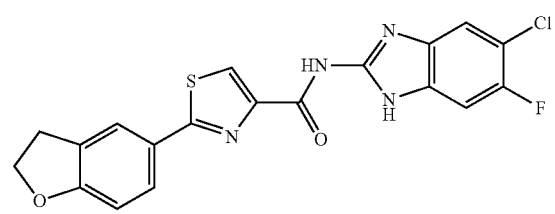

To a solution of 2-(2,3-dihydro-1-benzofuran-5-yl)-1,3-thiazole-4-carboxylic acid (150 mg, 0.61 mmol) in 4 ml N,N-dimethylformamide was added 5-chloro-6-fluoro-1H-benzo[d]imidazol-2-amine (124 mg, 0.67 mmol). Then 2-(1H-benzotriazole-1-yl)-1,1,3,3-tetramethyluronium hexafluorophosphate (HBTU) (230 mg, 0.61 mmol), 4-dimethylaminopyridine (7 mg, 0.06 mmol) and N,N-diisopropylethylamine (0.26 ml, 1.52 mmol) were added. The reaction mixture was stirred overnight at room temperature. It was poured into ice water. The formed precipitate was filtered off and dried to obtain a white solid. The crude product was purified by preparative TLC (PLC silica gel 60 F$_{254}$, 1 mm, DCM:MeOH 9:1). The product was obtained as a white solid (4 mg, 0.01 mmol, 2% yield). $^1$H NMR (400 MHz, DMSO-d$_6$) δ ppm 3.22-3.36 (m, 2H), 4.64 (t, J=8.75 Hz, 2H), 6.91 (d, J=8.34 Hz, 1H), 7.49 (d, J=9.75 Hz, 1H), 7.65 (d, J=6.87 Hz, 1H), 7.92 (dd, J=8.37 Hz, J=1.83 Hz, 1H), 8.11 (bs, 1H), 8.56 (s, 1H), 11.71 (bs, 1H), 12.49 (bs, 1H). LC/MS [M+H]$^+$: 414.7

2-(2,3-Dihydrobenzofuran-5-yl)-N-(5-(methylsulfonyl)-1H-benzo[d]imidazol-2-yl)thiazole-4-carboxamide (3)

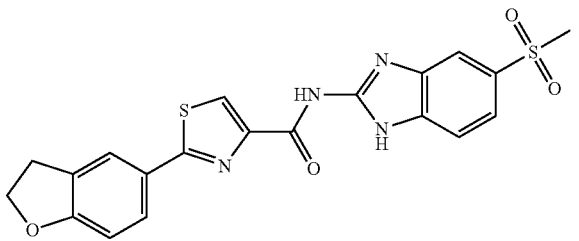 [SMILES: CS(=O)(=O)c1ccc2[nH]c(NC(=O)c3csc(-c4ccc5c(c4)CCO5)n3)nc2c1]

To a solution of 2-(2,3-dihydro-1-benzofuran-5-yl)-1,3-thiazole-4-carboxylic acid (142 mg, 0.58 mmol) in 3 ml N,N-dimethylformamide, were added 5-(methylsulfonyl)-1H-benzo[d]imidazol-2-amine (134 mg, 0.63 mmol), 2-(1H-benzotriazole-1-yl)-1,1,3,3-tetramethyluronium hexafluorophosphate (HBTU) (218 mg, 0.58 mmol), 4-dimethylaminopyridine (7 mg, 0.06 mmol) and N,N-diisopropylethylamine (0.25 ml, 1.44 mmol). The reaction mixture was stirred overnight at room temperature. It was poured into ice water and extracted with EtOAc and DCM. The organic extracts were combined, dried over MgSO$_4$, filtered and concentrated under reduced pressure. The residue was washed with MeOH and diisopropylether. The product was obtained as a pale yellow solid (142 mg, 0.32 mmol, 51% yield). $^1$H NMR (400 MHz, DMSO-d$_6$) δ ppm 3.19 (s, 1H), 3.24-3.41 (m, 2H), 7.49 (d, J=9.75 Hz, 1H), 7.65 (d, J=6.87 Hz, 1H), 4.65 (t, J=8.67 Hz, 2H), 6.91 (d, J=8.31 Hz, 1H), 7.71 (bs, 2H), 7.93 (d, J=8.19 Hz, 1H), 8.05 (bs, 1H), 8.13 (bs, 1H), 8.58 (s, 1H), 11.98 (bs, 1H), 12.64 (bs, 1H). LC/MS [M+H]$^+$: 440.7

2-(2,3-Dihydrobenzofuran-5-yl)-N-(5-methoxy-1H-benzo[d]imidazol-2-yl)thiazole-4-carboxamide (4)

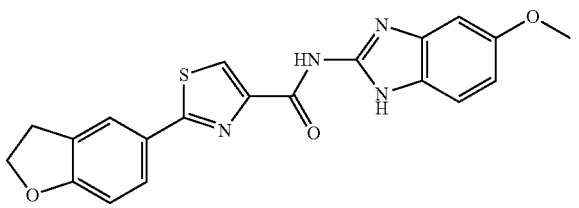 [SMILES: COc1ccc2[nH]c(NC(=O)c3csc(-c4ccc5c(c4)CCO5)n3)nc2c1]

To a solution of 2-(2,3-dihydro-1-benzofuran-5-yl)-1,3-thiazole-4-carboxylic acid (200 mg, 0.81 mmol) in 5 ml N,N-dimethylformamide was added 5-methoxy-1H-benzo[d]imidazol-2-amine hydrobromide (310 mg, 0.89 mmol). Then 2-(1H-benzotriazole-1-yl)-1,1,3,3-tetramethyluronium hexafluorophosphate (HBTU) (307 mg, 0.81 mmol), 4-dimethylaminopyridine (10 mg, 0.08 mmol) and N,N-diisopropylethylamine (0.35 ml, 2.0 mmol) were added. The reaction mixture was stirred overnight at room temperature. It was poured into ice water, a precipitate was obtained. The crude product was purified by preparative TLC (PLC silica gel 60 F254, 1 mm, DCM:MeOH 9:1). The crude product was purified by preparative HPLC. The product was obtained as a rose solid (8 mg, 0.02 mmol, 3% yield). $^1$H NMR (400 MHz, DMSO-d$_6$) δ ppm 3.29 (t, J=8.66 Hz, 2H), 3.78 (s, 3H), 4.64 (t, J=8.75 Hz, 2H), 6.79 (dd, J=8.70 Hz, J=2.43 Hz, 1H), 6.91 (d, J=8.34 Hz, 1H), 7.07 (d, J=2.31 Hz, 1H), 7.40 (d, J=8.67 Hz, 1H), 7.90 (dd, J=8.34 Hz, J=1.95 Hz, 1H), 8.08 (bs, 1H), 8.51 (s, 1H), 11.94 (bs, 2H). LC/MS [M+H]$^+$: 392.8

2-(2,3-Dihydrobenzofuran-5-yl)-N-(5-(trifluoromethyl)-1H-benzo[d]imidazol-2-yl)thiazole-4-carboxamide (5)

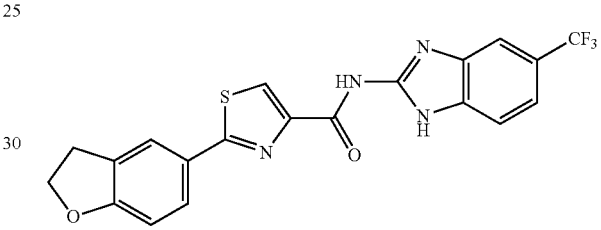

To a solution of 2-(2,3-dihydro-1-benzofuran-5-yl)-1,3-thiazole-4-carboxylic acid (1.00 g. 4.04 mmol) in 20 ml N,N-dimethylformamide, were added 5-(trifluoromethyl)-1H-benzo[d]imidazol-2-amine (895 mg, 4.45 mmol), 2-(1H-benzotriazole-1-yl)-1,1,3,3-tetramethyluronium hexafluorophosphate (HBTU) (1.53 g, 4.04 mmol), 4-dimethylaminopyridine (49 mg, 0.40 mmol) and N,N-diisopropylethylamine (1.76 ml, 10.11 mmol). The reaction mixture was stirred over weekend at room temperature. It was poured into ice water. The formed precipitate was dried and purified by flash column chromatography (DCM/MeOH 95:5 to 0:100). The crude product was suspended in Et$_2$O, filtered and dried. The product was obtained as a white solid (1.07 g, 2.49 mmol, 62% yield). $^1$H NMR (400 MHz, DMSO-d$_6$) δ ppm 3.16-3.30 (m, 2H), 4.57 (t, J=8.75 Hz, 2H), 7.40 (dd, J=8.46 Hz, J=1.44 Hz, 1H), 7.62 (d, J=8.34 Hz, 1H), 7.77 (bs, 1H), 7.85 (dd, J=8.33 Hz, J=1.91 Hz, 1H), 8.04 (bs, 1H), 8.50 (s, 1H), 11.81 (bs, 1H), 12.51 (bs, 1H). LC/MS [M+H]$^+$: 431.0

N-(5-Chloro-1H-benzo[d]imidazol-2-yl)-2-(2,3-dihydrobenzofuran-5-yl)thiazole-4-carboxamide (6)

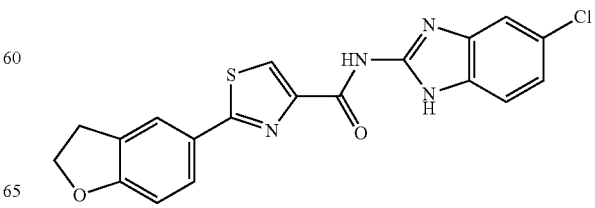

To a solution of 2-(2,3-dihydro-1-benzofuran-5-yl)-1,3-thiazole-4-carboxylic acid (100 mg, 0.40 mmol) in 4 ml N,N-dimethylformamide, was added 5-chloro-1H-benzo[d]imidazol-2-amine hydrobromide (75 mg, 0.44 mmol). Then 2-(1H-benzotriazole-1-yl)-1,1,3,3-tetramethyluronium hexafluorophosphate (HBTU) (153 mg, 0.40 mmol), 4-dimethylaminopyridine (5 mg, 0.04 mmol) and N,N-diisopropylethylamine (0.18 ml, 1.01 mmol) were added. The reaction mixture was stirred overnight at room temperature. It was poured into ice water. The formed precipitate was filtered off and dried to obtain a yellow solid. The crude product was washed with acetone, methanol and EtOAc. The solid was filtered off and dried. The product was obtained as a beige solid (55 mg, 0.14 mmol, 34% yield). $^1$H NMR (400 MHz, DMSO-$d_6$) δ ppm 3.13-3.47 (m, 2H), 4.64 (t, J=8.76 Hz, 2H), 6.90 (d, J=8.34 Hz, 1H), 7.16 (dd, J=8.46 Hz, J=1.92 Hz, 1H), 7.50 (d, J=8.58 Hz, 1H), 7.53 (bs, 1H), 7.91 (d, J=8.31 Hz, 1H), 8.10 (bs, 1H), 8.54 (s, 1H), 11.66 (bs, 1H), 12.41 (bs, 1H). LC/MS [M+H]$^+$: 396.8

2-(2,3-Dihydrobenzofuran-5-yl)-N-(5-(dimethylcarbamoyl)-1H-benzo[d]imidazol-2-yl)thiazole-4-carboxamide (7)

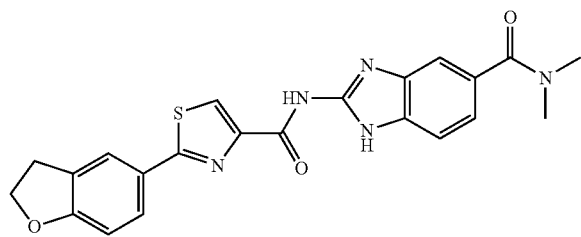 [SMILES: CN(C)C(=O)c1ccc2[nH]c(NC(=O)c3csc(-c4ccc5c(c4)CCO5)n3)nc2c1]

To a solution of 2-(2,3-dihydro-1-benzofuran-5-yl)-1,3-thiazole-4-carboxylic acid (319 mg, 1.29 mmol) in 6 ml N,N-dimethylformamide, were added 2-amino-N,N-dimethyl-1H-benzo[d]imidazole-5-carboxamide (290 mg, 1.42 mmol), 2-(1H-benzotriazole-1-yl)-1,1,3,3-tetramethyluronium hexafluorophosphate (HBTU) (490 mg, 1.29 mmol), 4-dimethylaminopyridine (16 mg, 0.13 mmol) and N,N-diisopropylethylamine (0.56 ml, 3.23 mmol). The reaction mixture was stirred overnight at room temperature. It was poured into ice water. The formed precipitate was filtered off, washed with MeOH and diisopropylether and dried. The product was obtained as a white solid (170 mg, 0.39 mmol, 30% yield) and was sent for biological evaluation. $^1$H NMR (400 MHz, DMSO-$d_6$) δ ppm 2.98 (s, 6H), 3.11-3.53 (m, 2H), 4.64 (t, J=8.61 Hz, 2H), 6.90 (d, J=8.31 Hz, 1H), 7.20 (d, J=7.62 Hz, 1H), 7.52 (d, J=8.43 Hz, 1H), 7.55 (bs, 1H), 7.91 (d, J=7.98 Hz, 1H), 8.10 (bs, 1H), 8.54 (s, 1H), 11.984 (bs, 2H). LC/MS [M+H]$^+$: 433.8

2-(2,3-Dihydrobenzofuran-5-yl)-N-(5-(4-((tetrahydrofuran-2-yl)methyl)piperazine-1-carbonyl)-1H-benzo[d]imidazol-2-yl)thiazole-4-carboxamide (8)

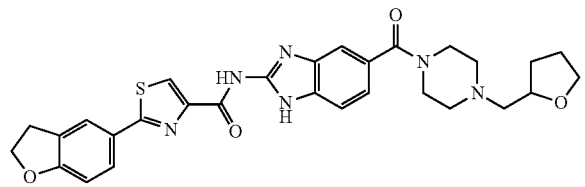 [SMILES: O=C(Nc1nc2cc(C(=O)N3CCN(CC4CCCO4)CC3)ccc2[nH]1)c1csc(-c2ccc3c(c2)CCO3)n1]

To a solution of 2-(2,3-dihydro-1-benzofuran-5-yl)-1,3-thiazole-4-carboxylic acid (135 mg, 0.55 mmol) in 3 ml N,N-dimethylformamide, were added (2-amino-1H-benzo[d]imidazol-5-yl)(4-((tetrahydrofuran-2-yl)methyl)piperazin-1-yl)methanone hydrobromide (I-50) (198 mg, 0.60 mmol), 2-(1H-benzotriazole-1-yl)-1,1,3,3-tetramethyluronium hexafluorophosphate (HBTU) (207 mg, 0.55 mmol), 4-dimethylaminopyridine (7 mg, 0.05 mmol) and N,N-diisopropylethylamine (0.24 ml, 1.37 mmol). The reaction mixture was stirred overnight at room temperature. It was poured into ice water and extracted with EtOAc. The organic extracts were dried over MgSO$_4$, filtered and concentrated under reduced pressure. The residue was washed with MeOH and diisopropylether and dried. The crude product was purified by preparative TLC (DCM/MeOH 90:10). The crude product was suspended in Et$_2$O, filtered and dried. The product was obtained as a light yellow solid (65 mg, 0.12 mmol, 21% yield). $^1$H NMR (400 MHz, DMSO-$d_6$) δ ppm 3.28-3.40 (m, 3H), 1.37-1.57 (m, 1H), 1.67-186 (m, 2H), 1.87-2.00 (m, 1H), 2.31-2.47 (m, 3H), 3.40-3.66 (m, 8H), 3.68-3.79 (m, 2H), 3.88-4.00 (m, 1H), 4.65 (t, J=8.76 Hz, 2H), 6.91 (d, J=8.34 Hz, 1H), 7.18 (dd, J=8.19 Hz, J=1.50 Hz, 1H), 7.48-7.60 (m, 2H), 7.92 (dd, J=8.34 Hz, J=1.95 Hz, 1H), 8.11 (bs, 1H), 8.54 (s, 1H), 11.67 (bs, 1H), 12.43 (bs, 1H). LC/MS [M+H]$^+$: 558.8

Ethyl 2-(2-(2,3-dihydrobenzofuran-5-yl)thiazole-4-carboxamido)-1H-benzo[d]imidazole-5-carboxylate (9)

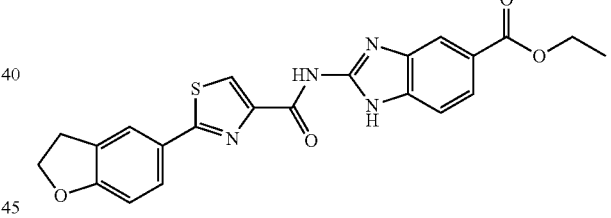

2-(2,3-Dihydrobenzofuran-5-yl)thiazole-4-carboxylic acid (80 mg, 0.32 mmol), ethyl 2-amino-1H-benzo[d]imidazole-5-carboxylate (66 mg, 0.32 mmol), 2-(1H-benzo[1,2,3]triazol-1-yl)-1,1,3,3-tetramethyluronium hexafluorophosphate (HBTU) (123 mg, 0.32 mmol) and N,N-dimethylpyridin-4-amine (4 mg, 0.03 mmol) were suspended in 1 ml N,N-dimethylformamide. N,N'diisopropylethylamine (0.13 ml, 0.81 mmol) was added and the reaction mixture was stirred at 60° C. for 18 h. It was poured into ice water and extracted with EtOAc. The organic extracts were dried over MgSO$_4$, filtered and concentrated under reduced pressure. The residue was purified by preparative HPLC. The product was obtained as a light yellow solid (6 mg, 0.01 mmol, 4% yield). $^1$H NMR (400 MHz, DMSO-$d_6$) δ ppm 1.35 (t, J=7.11 Hz, 3H), 3.20-3.36 (m, 2H), 4.33 (q, J=7.11 Hz, 2H), 4.65 (t, J=8.76 Hz, 2H), 6.91 (d, J=8.34 Hz, 1H), 7.51-7.63 (m, 1H), 7.81 (dd, J=8.40 Hz, J=1.62 Hz, 1H), 7.93 (dd, J=8.34 Hz, J=1.98 Hz, 1H), 8.04-8.23 (m, 2H), 8.57 (s, 1H), 11.74 (bs, 1H), 12.58 (bs, 1H). LC/MS [M+H]$^+$: 434.9

2-(2,3-Dihydrobenzofuran-5-yl)-N-(5-(morpholine-4-carbonyl)-1H-benzo[d]imidazol-2-yl)thiazole-4-carboxamide (10)

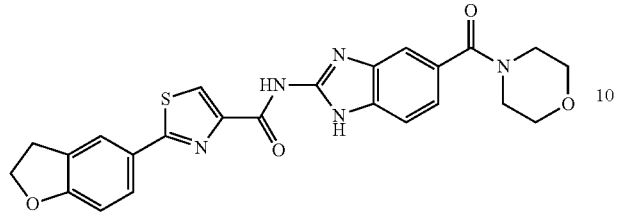

To a solution of 2-(2,3-dihydro-1-benzofuran-5-yl)-1,3-thiazole-4-carboxylic acid (142 mg, 0.58 mmol) in 3 ml N,N-dimethylformamide, were added (2-amino-1H-benzo[d]imidazol-5-yl)(morpholino)methanone (156 mg, 0.63 mmol), 2-(1H-benzotriazole-1-yl)-1,1,3,3-tetramethyluronium hexafluorophosphate (HBTU) (218 mg, 0.58 mmol), 4-dimethylaminopyridine (7 mg, 0.06 mmol) and N,N-diisopropylethylamine (0.25 ml, 1.44 mmol). The reaction mixture was stirred overnight at room temperature. It was poured into ice water and extracted with EtOAc and DCM. The organic extracts were combined, dried over MgSO$_4$, filtered and concentrated under reduced pressure. The residue was washed with MeOH and diisopropylether. The product was obtained as a pale yellow solid (108 mg, 0.23 mmol, 36% yield). $^1$H NMR (400 MHz, DMSO-d$_6$) δ ppm 3.15-3.44 (m, 2H), 3.53 (bs, 4H), 3.61 (bs, 4H), 4.64 (t, J=8.58 Hz, 2H), 6.91 (d, J=8.28 Hz, 1H), 7.21 (d, J=7.71 Hz, 1H), 7.45-7.64 (m, 2H), 7.92 (d, J=8.52 Hz, 1H), 8.11 (bs, 1H), 8.54 (s, 1H), 11.66 (bs, 1H), 12.44 (bs, 1H). LC/MS [M+H]$^+$: 475.8

2-(2,3-Dihydrobenzofuran-5-yl)-N-(1H-imidazol-2-yl)thiazole-4-carboxamide (11)

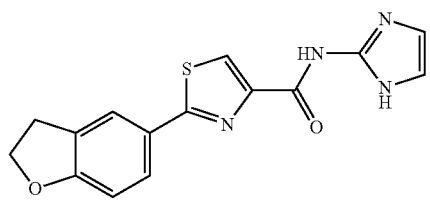

To a solution of 2-(2,3-dihydro-1-benzofuran-5-yl)-1,3-thiazole-4-carboxylic acid (150 mg, 0.61 mmol) in 2 ml N,N-dimethylformamide, were added 1H-Imidazol-2-ylamine (88 mg, 0.67 mmol), 2-(1H-benzotriazole-1-yl)-1,1,3,3-tetramethyluronium hexafluorophosphate (HBTU) (230 mg, 0.61 mmol), 4-dimethylaminopyridine (7 mg, 0.06 mmol) and N,N-diisopropylethylamine (0.26 ml, 1.52 mmol). The reaction mixture was stirred overnight at room temperature. It was poured into ice water. The precipitate was filtered off, washed with MeOH and diisopropylether. The crude product was purified by preparative TLC (DCM/MeOH 90:10). The product was obtained as a light yellow solid (40 mg, 0.13 mmol, 21% yield). $^1$H NMR (400 MHz, DMSO-d$_6$) δ ppm 3.22-3.36 (m, 2H), 4.63 (t, J=8.76 Hz, 2H), 6.84 (bs, 2H), 6.89 (d, J=8.37 Hz, 1H), 7.88 (dd, J=8.34 Hz, J=1.53 Hz, 1H), 8.06 (bs, 1H), 8.40 (s, 1H), 11.48 (bs, 2H). LC/MS [M+H]$^+$: 312.8

2-(2,3-Dihydrobenzofuran-5-yl)-N-(4-(trifluoromethyl)-1H-benzo[d]imidazol-2-yl)thiazole-4-carboxamide (12)

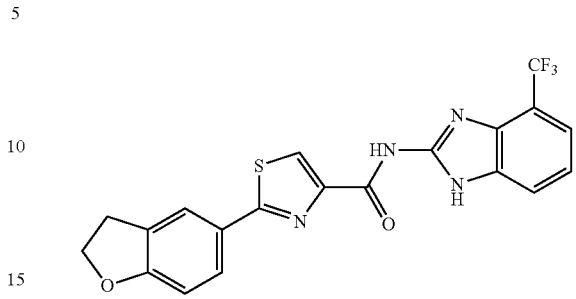

To a solution of 2-(2,3-dihydro-1-benzofuran-5-yl)-1,3-thiazole-4-carboxylic acid (104 mg, 0.42 mmol) in 2.5 ml N,N-dimethylformamide was added 7-(trifluoromethyl)-1H-benzo[d]imidazol-2-amine (130 mg, 0.46 mmol). Then 2-(1H-benzotriazole-1-yl)-1,1,3,3-tetramethyluronium hexafluorophosphate (HBTU) (159 mg, 0.42 mmol), 4-dimethylaminopyridine (5 mg, 0.04 mmol) and N,N-diisopropylethylamine (0.17 ml, 1.00 mmol) were added. The reaction mixture was stirred over weekend at room temperature. It was poured into ice water. The precipitate was filtered off, washed with MeOH and diisopropylether. The product was obtained as a white solid (135 mg, 0.31 mmol, 75% yield). $^1$H NMR (400 MHz, DMSO-d$_6$) δ ppm 3.21-3.39 (m, 2H), 4.65 (t, J=8.73 Hz, 2H), 6.91 (d, J=8.34 Hz, 1H), 7.28 (t, J=7.85 Hz, 2H), 7.48 (d, J=7.62 Hz, 1H), 7.84 (d, J=7.95 Hz, 1H), 7.94 (dd, J=8.29 Hz, J=1.90 Hz, 1H), 8.15 (bs, 1H), 8.59 (s, 1H), 11.89 (bs, 1H), 12.70 (bs, 1H). LC/MS [M+H]$^+$: 430.7

2-(2,3-Dihydrobenzofuran-5-yl)-N-(4-(3-methoxyphenyl)-1H-imidazol-2-yl)thiazole-4-carboxamide (13)

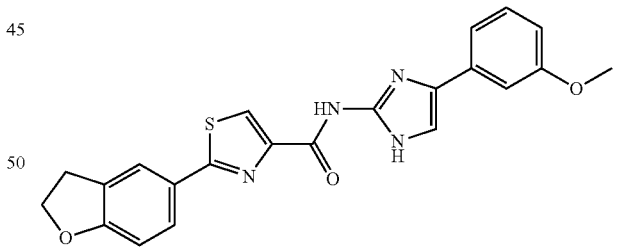

A mixture of (2-amino-4-(3-methoxyphenyl)-1H-imidazol-1-yl)(2-(2,3-dihydrobenzofuran-5-yl)thiazol-4-yl)methanone (I-48) (206 mg, 0.49 mmol), 10 ml xylene and 1 ml N,N-dimethylformamide was refluxed for 4 h. All volatiles were removed under reduced pressure. The residual solid was washed with diisopropylether. The product was obtained as a light yellow solid (144 mg, 0.34 mmol, 70% yield). $^1$H NMR (400 MHz, DMSO-d$_6$) δ ppm 3.18-3.44 (m, 2H), 3.79 (s, 3H), 4.64 (t, J=8.70 Hz, 2H), 6.76 (d, J=6.30 Hz, 1H), 6.90 (d, J=8.16 Hz, 1H), 7.15-7.49 (m, 4H), 7.91 (d, J=7.95 Hz, 1H), 8.11 (bs, 1H), 8.44 (s, 1H), 11.20 (bs, 1H), 11.95 (bs, 1H). LC/MS [M+H]$^+$: 418.8

2-(2,3-Dihydrobenzofuran-5-yl)-N-(6-(trifluoromethoxy)-1H-benzo[d]imidazol-2-yl)thiazole-4-carboxamide (14)

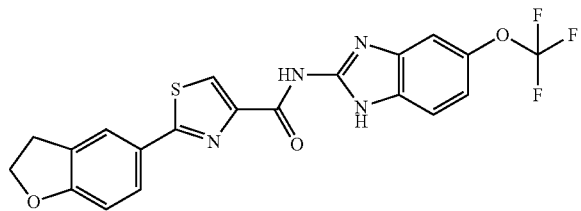 [SMILES: O=C(Nc1nc2cc(OC(F)(F)F)ccc2[nH]1)c1csc(-c2ccc3c(c2)CCO3)n1]

To a solution of 2-(2,3-dihydro-1-benzofuran-5-yl)-1,3-thiazole-4-carboxylic acid (122 mg, 0.50 mmol) in 2 ml N,N-dimethylformamide, were added 6-(trifluoromethoxy)-1H-benzo[d]imidazol-2-amine (162 mg, 0.54 mmol), 2-(1H-benzotriazole-1-yl)-1,1,3,3-tetramethyluronium hexafluorophosphate (HBTU) (188 mg, 0.50 mmol), 4-dimethylaminopyridine (6 mg, 0.05 mmol) and N,N-diisopropylethylamine (0.22 ml, 1.24 mmol). The reaction mixture was stirred overnight at room temperature. It was poured into ice water. The formed precipitate was filtered off, washed with Et$_2$O and dried. The product was obtained as a light yellow solid (86 mg, 0.19 mmol, 39% yield). $^1$H NMR (400 MHz, DMSO-d$_6$) δ ppm 3.15-3.51 (m, 2H), 4.65 (t, J=8.34 Hz, 2H), 6.91 (d, J=7.80 Hz, 1H), 7.13 (d, J=7.32 Hz, 1H), 7.48 (s, 1H), 7.59 (d, J=7.32 Hz, 1H), 7.93 (d, J=7.53 Hz, 1H), 8.11 (bs, 1H), 8.56 (s, 1H), 11.70 (bs, 1H), 12.50 (bs, 1H). LC/MS [M+H]$^+$: 446.8

Methyl 5-(2-(2,3-dihydrobenzofuran-5-yl)thiazole-4-carboxamido)-1H-1,2,4-triazole-3-carboxylate (15)

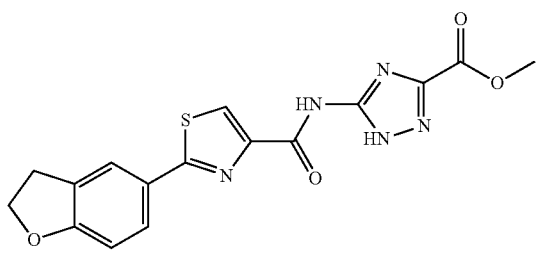 [SMILES: COC(=O)c1n[nH]c(NC(=O)c2csc(-c3ccc4c(c3)CCO4)n2)n1]

To a solution of 2-(2,3-dihydro-1-benzofuran-5-yl)-1,3-thiazole-4-carboxylic acid (100 mg, 0.40 mmol) in 5 ml N,N-dimethylformamide was added 5-Amino-1H-[1,2,4]-triazole-3-carboxylic acid methyl ester (58 mg, 0.40 mmol). Then 2-(1H-benzotriazole-1-yl)-1,1,3,3-tetramethyluronium hexafluorophosphate (HBTU) (153 mg, 0.40 mmol), 4-dimethylaminopyridine (5 mg, 0.04 mmol) and N,N-diisopropylethylamine (0.18 ml, 2.02 mmol) were added. The reaction mixture was stirred at 65° C. for 18 h. Additional N,N-diisopropylethylamine (0.18 ml, 1.01 mmol) and 2-(1H-benzotriazole-1-yl)-1,1,3,3-tetramethyluronium hexafluorophosphate (HBTU) (153 mg, 0.40 mmol) were added and the reaction mixture was stirred at 65° C. for further 3 h. The mixture was diluted with water and extracted with EtOAc. The organic layer was washed with an aqueous 5% citric acid solution and an aqueous 5% NaHCO$_3$ solution. The organic layer was dried over MgSO$_4$ and concentrated in vacuo. The product was obtained as a white solid (1.5 mg, 0.004 mmol, 1% yield). $^1$H NMR (400 MHz, DMSO-d$_6$) δ ppm 3.20-3.36 (m, 2H), 3.89 (s, 3H), 4.64 (t, J=8.75 Hz, 2H), 6.90 (d, J=8.34 Hz, 1H), 7.92 (dd, J=8.34 Hz, J=1.74 Hz, 1H), 8.12 (bs, 1H), 8.53 (s, 1H), 11.98 (bs, 1H), 14.26 (bs, 1H). LC/MS [M+H]$^+$: 372.0

2-(2,3-Dihydrobenzofuran-5-yl)-N-(3-hydroxypyridin-2-yl)thiazole-4-carboxamide (16)

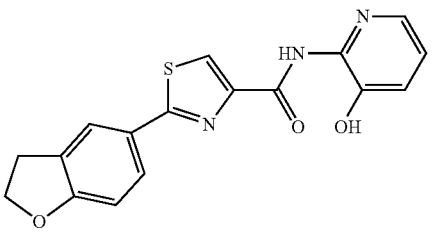 [SMILES: O=C(Nc1ncccc1O)c1csc(-c2ccc3c(c2)CCO3)n1]

To a solution of 2-(2,3-dihydro-1-benzofuran-5-yl)-1,3-thiazole-4-carboxylic acid (100 mg, 0.4 mmol) in 3 ml N,N-dimethylformamide, was added 2-amino-3-hydroxypyridine (49 mg, 0.44 mmol). Then 2-(1H-benzotriazole-1-yl)-1,1,3,3-tetramethyluronium hexafluorophosphate (HBTU) (153 mg, 0.4 mmol), 4-dimethylaminopyridine (5 mg, 0.04 mmol) and N,N-diisopropylethylamine (0.17 ml, 1.00 mmol) were added. The reaction mixture was stirred over weekend at room temperature. It was poured into ice water. The precipitate was washed with diisopropylether and dried. The product was obtained as a yellow solid (57 mg, 0.17 mmol, 42% yield). $^1$H NMR (400 MHz, DMSO-d$_6$) δ ppm 3.19-3.43 (m, 2H), 4.64 (t, J=8.73 Hz, 2H), 6.92 (d, J=8.31 Hz, 1H), 7.17 (dd, J=4.63 Hz, J=7.96 Hz, 1H), 7.33 (d, J=7.95 Hz, 1H), 7.85 (d, J=8.31 Hz, 1H), 7.95 (d, J=4.44 Hz, 1H), 7.99 (bs, 1H), 8.41 (s, 1H), 10.20 (bs, 1H), 10.31 (bs, 1H). LC/MS [M+H]$^+$: 340.0

2-(2,3-Dihydrobenzofuran-5-yl)-N-(pyridin-2-yl)thiazole-4-carboxamide (17)

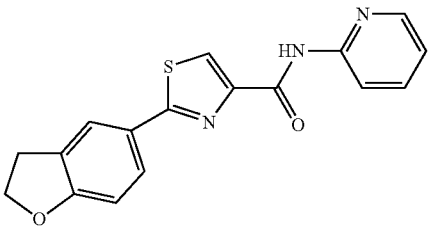 [SMILES: O=C(Nc1ccccn1)c1csc(-c2ccc3c(c2)CCO3)n1]

To a solution of 2-(2,3-dihydro-1-benzofuran-5-yl)-1,3-thiazole-4-carboxylic acid (100 mg, 0.40 mmol) in 5 ml N,N-dimethylformamide was added 2-aminopyridine (42 mg, 0.44 mmol). Then 2-(1H-benzotriazole-1-yl)-1,1,3,3-tetramethyluronium hexafluorophosphate (HBTU) (153 mg, 0.40 mmol), 4-dimethylaminopyridine (5 mg, 0.04 mmol) and N,N-diisopropylethylamine (0.18 ml, 1.01 mmol) were added. The reaction mixture was stirred overnight at room temperature. The mixture was poured into ice water and the resulting precipitate was filtered off. The crude product was purified by preparative TLC (PLC silica gel 60 F254, 1 mm, eluent DCM:MeOH 98:2). The product was obtained as a white solid (24 mg, 0.07 mmol, 18% yield). $^1$H NMR (400 MHz, DMSO-d$_6$) δ ppm 3.24-3.34 (m, 2H), 4.64 (t, J=8.76 Hz, 2H), 6.91 (d, J=8.34 Hz, 1H), 7.21 (ddd, J=7.59 Hz, J=4.87 Hz, J=1.02 Hz, 1H), 7.82-7.93 (m, 2H), 8.01 (d, J=1.53 Hz, 1H), 8.23 (dt, J=8.31 Hz, J=0.90 Hz, 1H), 8.40 (ddd, J=4.96 Hz, J=1.89 Hz, J=0.90 Hz, 1H), 8.47 (s, 1H), 10.04 (bs, 1H). LC/MS [M+H]$^+$: 324.0

N-(4-Cyanopyridin-2-yl)-2-(2,3-dihydrobenzofuran-5-yl)thiazole-4-carboxamide (18)

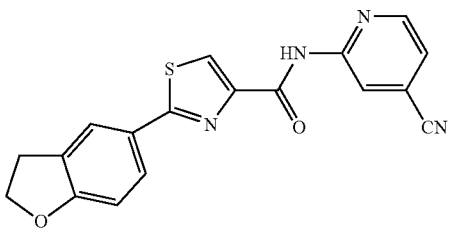 [SMILES: N#Cc1ccnc(NC(=O)c2csc(-c3ccc4c(c3)CCO4)n2)c1]

To a solution of 2-(2,3-dihydro-1-benzofuran-5-yl)-1,3-thiazole-4-carboxylic acid (100 mg, 0.40 mmol) in 4 ml N,N-dimethylformamide was added 2-Amino-4-cyanopyridine (53 mg, 0.44 mmol). Then 2-(1H-benzotriazole-1-yl)-1,1,3,3-tetramethyluronium hexafluoro-phosphate (HBTU) (153 mg, 0.40 mmol), 4-dimethylaminopyridine (5 mg, 0.04 mmol) and N,N-diisopropylethylamine (0.18 ml, 1.01 mmol) were added. The reaction mixture was stirred overnight at room temperature. Additional 4-dimethylaminopyridine (5 mg, 0.04 mmol) was added and the mixture was stirred at room temperature for 5 days. Additional N,N-diisopropylethylamine (0.18 ml, 1.01 mmol) and 2-(1H-benzotriazole-1-yl)-1,1,3,3-tetramethyluronium hexafluorophosphate (HBTU) (77 mg, 0.20 mmol) were added and the mixture was stirred at room temperature for 18 h. The mixture was diluted with EtOAc and the hiphasic mixture was separated. The organic layer was washed three times with an aqueous 5% NaHCO$_3$ solution. The organic layer was dried over MgSO$_4$ and concentrated in vacuo. The crude product was purified by preparative TLC (PLC silica gel 60 F$_{254}$, 2 mm, eluent: DCM:MeOH 95:5). The product was obtained as a white solid (1 mg, 0.003 mmol, 1% yield). $^1$H NMR (400 MHz, DMSO-d$_6$) δ ppm 3.25-3.34 (m, 2H), 4.64 (t, J=8.78 Hz, 2H), 6.91 (d, J=8.28 Hz, 1H), 7.66 (dd, J=5.04 Hz, J=1.41 Hz, 1H), 7.87 (dd, J=8.34 Hz, J=2.01 Hz, 1H), 8.04 (d, J=1.53 Hz, 1H), 8.51 (dd, J=1.35 Hz, J=0.93 Hz, 1H), 8.53 (s, 1H), 8.67 (dd, J=5.06 Hz, J=0.90 Hz, 1H), 10.49 (bs, 1H). LC/MS [M+H]$^+$: 349.0

2-(2,3-Dihydrobenzofuran-5-yl)-N-(3-(methylcarbamoyl)-1H-1,2,4-triazol-5-yl)thiazole-4-carboxamide (19)

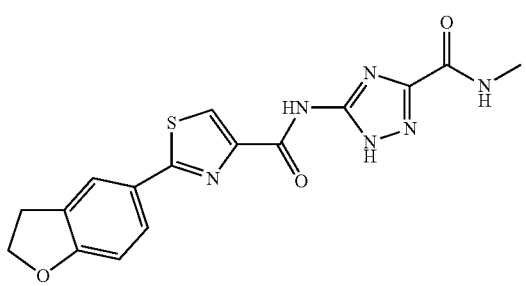 [SMILES: CNC(=O)c1n[nH]c(NC(=O)c2csc(-c3ccc4c(c3)CCO4)n2)n1]

To a solution of 2-(2,3-dihydro-1-benzofuran-5-yl)-1,3-thiazole-4-carboxylic acid (100 mg, 0.40 mmol) in 5 mil N,N-dimethylformamide was added 3,5-diamino-1,2,4-triazole (40 mg, 0.40 mmol). Then 2-(1H-benzotriazole-1l-yl)-1,1,3,3-tetramethyluronium hexafluorophosphate (HBTU) (153 mg, 0.40 mmol), 4-dimethylaminopyridine (5 mg, 0.04 mmol) and N,N-diisopropylethylamine (0.18 ml, 1.01 mmol) were added. The reaction mixture was stirred at 65° C. for 6 h. The mixture was poured into ice water, no precipitate was obtained. The mixture was diluted with EtOAc and the organic layer was washed three times with an aqueous 5% NaHCO$_3$ solution, an aqueous 5% citric acid solution and water. The organic layer was dried over MgSO$_4$ and concentrated in vacuo. The crude product was purified by preparative TLC (PLC silica gel 60 F254, 1 mm, DCM:MeOH 9:1). The product was obtained as a light yellow solid (4 mg, 0.01 mmol, 3% yield). $^1$H NMR (400 MHz, DMSO-d$_6$) δ ppm 2.78 (d, J=4.74 Hz, 3H), 3.09-3.45 (m, 2H), 4.64 (t, J=8.76 Hz, 2H), 6.90 (d, J=8.34 Hz, 1H), 7.90 (dd, J=8.34 Hz, J=1.83 Hz, 1H), 8.07 (s, 1H), 8.35 (bs, 1H), 8.47 (s, 1H). LC/MS [M+H]$^+$: 371.1

Ethyl 5-(2-(2,3-dihydrobenzofuran-5-yl)thiazole-4-carboxamido)-4H-1,2,4-triazole-3-carboxylate (20)

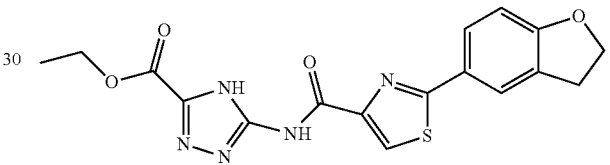

Method A. To a suspension of 2-(2,3-dihydro-1-benzofuran-5-yl)-1,3-thiazole-4-carboxylic acid (381 mg, 1.54 mmol) and ethyl 5-amino-1,2,4-triazole-3-carboxylate (219 mg, 1.54 mmol) in 5.4 ml dry pyridine at boiling 2-(1H-benzotriazole-1-yl)-1,1,3,3-tetramethyluronium hexafluorophosphate (HBTU) (643 mg, 1.70 mmol) was added in portions while solid dissolves gradually; clear solution forms 5 minutes after all 2-(1H-benzotriazole-1-yl)-1,1,3,3-tetramethyluronium hexafluorophosphate (HBTU) was added. The solution war kept at stirring at 80° C. during 15 h. Pyridine was evaporated to dryness, residue was washed with water, an aqueous NaHCO$_3$ solution, water, diluted aqueous AcOH and again water. The residue was dissolved in hot N,N-dimethylformamide, filtered, filtrate was evaporated to dryness, the residue was treated with boiling ethanol, cooled and filtered off. The procedure was repeated twice after which the residue was washed with ether and dried to give (339 mg, 0.88 mmol, 57%) pure product. $^1$H NMR (400 MHz, DMSO-d$_6$) δ ppm 14.16 (s, 1H, NH), 11.95 (s, 1H, NH), 8.46 (s, 1H, CH-thiazole), 8.08 (s, 1H, CH—Ar), 7.88 (d, J=8.2 Hz, 1H, CH—Ar), 6.84 (d, J=8.3 Hz, 1H, CH—Ar), 4.65 (t, J=8.7 Hz, 2H, OCH$_2$CH$_2$), 4.34 (q, J=7.0 Hz, 2H, OCH$_2$CH$_3$), 3.30 (t, J=8.7 Hz, 1H, OCH$_2$CH$_2$), 1.37 (t, J=7.1 Hz, 3H, OCH$_2$CH$_3$). LC/MS [M+H]$^+$: 386.0

Method B. Solution of 2-(2,3-dihydro-1-benzofuran-5-yl)-1,3-thiazole-4-carboxylic acid (174 mg, 0.70 mmol) in 10 ml SOCl$_2$ was refluxed for 2 h and evaporated to dryness. To the residue (yellow powder), ethyl 5-amino-4H-1,2,4-triazole-3-carboxylate was added (100 mg, 0.64 mmol). To a mixture, 4 ml pyridine was added at cooling with ice water bath. New precipitate formed gradually. The suspension was refluxed for 10 min while precipitate dissolved completely. The solution was refluxed for further 1 h. The reaction mixture was evaporated to dryness, the residue was washed with water, an aqueous NaHCO$_3$ solution, water, diluted aqueous AcOH and again water. The residue was dissolved in hot N,N-dimethylformamide, filtered, the filtrate was evaporated to dryness, the residue was treated with boiling ethanol, cooled, filtered off, washed with some ether and dried to give (168 mg, 0.44 mmol, 68% yield) as a grey powder. $^1$H NMR (400 MHz, DMSO-d$_6$) δ ppm 14.16 (s, 1H, NH), 11.95 (s, 1H, NH), 8.46 (s, 1H, CH-thiazole), 8.08 (s, 1H, CH—Ar), 7.88 (d, J=8.2 Hz, 1H, CH—Ar), 6.84 (d, J=8.3 Hz, 1H, CH—Ar), 4.65 (t, J=8.7 Hz, 2H, OCH$_2$CH$_2$), 4.34 (q, J=7.0 Hz, 2H, OCH$_2$CH$_3$), 3.30 (t, J=8.7 Hz, 1H, OCH$_2$CH$_2$), 1.37 (t, J=7.1 Hz, 3H, OCH$_2$CH$_3$). LC/MS [M+H]$^+$: 386.0

2-(2,3-Dihydrobenzofuran-5-yl)-N-(5-(methylthio)-4H-1,2,4-triazol-3-yl)thiazole-4-carboxamide (21)

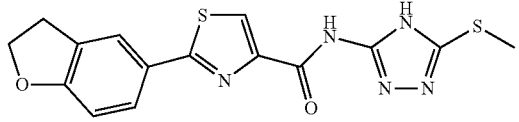 [SMILES: CSc1nnc(NC(=O)c2csc(-c3ccc4c(c3)CCO4)n2)[nH]1]

Suspension of 2-(2,3-dihydro-1-benzofuran-5-yl)-1,3-thiazole-4-carboxylic acid (247 mg, 1.00 mmol) in 10 ml thionyl chloride was refluxed 1 h during which the acid dissolved gradually followed by formation of new precipitate. Excess thionyl chloride was evaporated to dryness, to a residue 3-(methylthio)-1,2,4-triazol-5-amine (130 mg, 1.00 mmol) was added. To a mixture, 4 ml dry pyridine was added. The reaction mixture was refluxed for 1 h. The reaction mixture was evaporated to dryness, the residue was washed with water, an aqueous NaHCO$_3$ solution, water, diluted aqueous AcOH and again water. The residue was dissolved in hot N,N-dimethylformamide, filtered, the filtrate was evaporated to dryness, the residue was treated with boiling ethanol, cooled and filtered off, washed with ether and dried to give (131 mg, 0.36 mmol, 36% yield) pure product. $^1$H NMR (400 MHz, DMSO-d$_6$) δ ppm 13.34 (s, 1H, NH), 11.33 (s, 1H, NH), 8.38 (s, 1H, CH-arom), 8.04 (s, 1H, CH-arom), 7.85 (d, J=8.2 Hz, 1H, CH-arom), 6.81 (d, J=8.3 Hz, 1H, CH-arom), 4.65 (t, J=8.7 Hz, 2H, CH$_2$CH$_2$), 3.31 (t, J=8.7 Hz, 2H, CH$_2$CH$_2$), 2.55 (s, 3H, SMe). LC/MS [M+H]$^+$: 360.0

2-(2,3-Dihydrobenzofuran-5-yl)-N-(5-(pyrrolidine-1-carbonyl)-1H-benzo[d]imidazol-2-yl)thiazole-4-carboxamide (22)

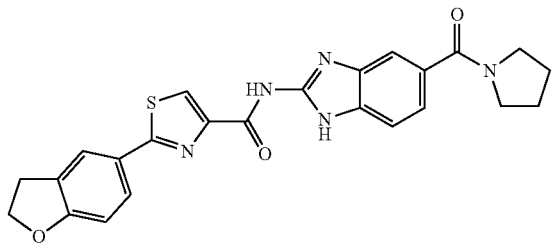 [SMILES: O=C(Nc1nc2cc(C(=O)N3CCCC3)ccc2[nH]1)c1csc(-c2ccc3c(c2)CCO3)n1]

A mixture of (3,4-dinitrophenyl)(pyrrolidin-1-yl)methanone (120 mg, 0.45 mmol), 10 ml ethanol and Pd/C catalyst (0.05 g, 10% Pd) was stirred in an autoclave under hydrogen pressure 10 kg/cm$^2$ and room temperature for 3 h. The catalyst was filtered off and cyanogen bromide (80 mg, 0.75 mmol) was added to the filtrate. After stirring at room temperature for 1 day the solvent was evaporated in vacuo and to the residue were added 10 ml dichloromethane and 2-(2,3-dihydro-1-benzofuran-5-yl)-1,3-thiazole-4-carboxylic acid (106 mg, 0.4 mmol), 2-(1H-benzotriazole-1-yl)-1,1,3,3-tetramethyluronium hexafluorophosphate (HBTU) (208 mg, 0.55 mmol) and diisopropylether (0.2 ml, 1.15 mmol). The mixture was stirred at room temperature for 1 day, the solvent was evaporated to dryness in vacuo and an aqueous 5% Na$_2$CO$_3$ solution (10 ml) was added to the residue. In 1 h the residue solidified, the precipitate was filtered off and crystallized from ethanol to give the product as white crystals (65 mg, 0.14 mmol, 35% yield). M.p.=245-250° C. $^1$H NMR (400 MHz, DMSO-d$_6$) δ ppm 1.85 (d, J=19.56 Hz, 4H) 3.18-3.32 (m, 3H) 3.40-3.60 (m, 5H) 4.64 (t, J=8.51 Hz, 2H) 6.90 (d, J=8.41 Hz, 1H) 7.33 (d, J=8.22 Hz, 1H) 7.51 (d, J=7.83 Hz, 1H) 7.67 (bs, 1H) 7.91 (d, J=8.22 Hz, 1H) 8.10 (bs, 1H) 8.55 (s, 1H) 12.36 (bs, 1H). LC/MS [M+H]$^+$: 460.0

2-(2,3-Dihydrobenzofuran-5-yl)-N-(5-((2-methoxyethyl)carbamoyl)-1H-benzo[d]imidazol-2-yl)thiazole-4-carboxamide (23)

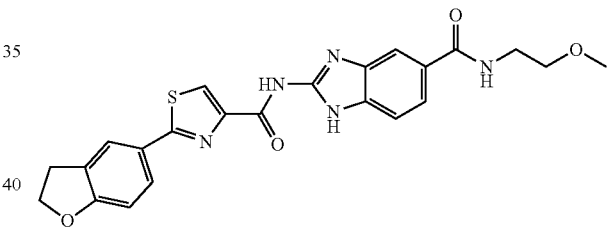

A mixture of N-(2-methoxyethyl)-3,4-dinitrobenzamide (I-52) (121 mg, 0.45 mmol), 10 ml ethanol and Pd/C catalyst (0.05 g, 10% Pd) was stirred in an autoclave under hydrogen pressure 10 kg/cm$^2$ and room temperature for 3 h. The catalyst was filtered off and cyanogen bromide (80 mg, 0.75 mmol) was added to the filtrate. After stirring at room temperature for 1 day the solvent was evaporated in vacuum and to the residue were added 10 ml dichloromethane and 2-(2,3-dihydro-1-benzofuran-5-yl)-1,3-thiazole-4-carboxylic acid (106 mg, 0.4 mmol), 2-(1H-benzotriazole-1-yl)-1,1,3,3-tetramethyluronium hexafluorophosphate (HBTU) (208 mg, 0.55 mmol) and diisopropylether (0.2 ml, 1.15 mmol). The mixture was stirred for 1 day at room temperature, the solvent was evaporated to dryness in vacuo and an aqueous 5% Na$_2$CO$_3$ solution (10 ml) was added to the residue. In 1 h the residue solidified, the precipitate was filtered off and crystallized from ethanol to give the product as white crystals (75 mg, 0.16 mmol, 40% yield). M.p.=185-190° C. $^1$H NMR (400 MHz, DMSO-d$_6$) δ ppm 3.13 (bs, 4H) 3.32 (bs, 4H) 3.48 (bs, 4H) 4.64 (t, J=7.40 Hz, 2H) 6.82 (d, J=7.53 Hz, 1H) 7.49 (bs, 1H) 7.65 (d, J=7.53 Hz, 1H) 7.76-7.93 (m, 1H) 7.93-8.14 (m, 2H) 8.25 (bs, 1H) 8.42 (bs, 1H) 11.40 (bs, 1H) 12.38 (bs, 1H). LC/MS [M+H]$^+$: 463.9

2-(2,3-Dihydrobenzofuran-5-yl)-N-(3-(isopropyl-thio)-1H-1,2,4-triazol-5-yl)thiazole-4-carboxamide (24)

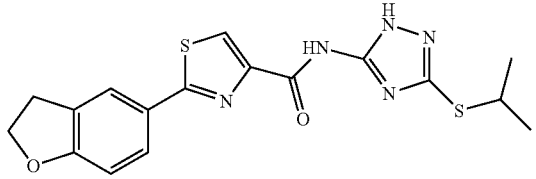 [SMILES: CC(C)Sc1n[nH]c(NC(=O)c2csc(-c3ccc4c(c3)CCO4)n2)n1]

To a mixture of 2-(2,3-dihydro-1-benzofuran-5-yl)-1,3-thiazole-4-carbonyl chloride (202 mg, 0.76 mmol) and 3-(isopropylthio)-1H-1,2,4-triazol-5-amine (120 mg, 0.76 mmol) 3 ml of dry hot pyridine was added. The solution was heated at reflux for 3 h, pyridine was evaporated and the residue was diluted with an aqueous $Na_2CO_3$ solution. The resulting precipitate was filtered off and purified by flash chromatography (EtOAc) to give the product as a light yellow solid (80 mg, 0.21 mmol, 27% yield). $^1$H NMR (400 MHz, DMSO-$d_6$) δ ppm 1.35 (6H, d, 2CH$_3$), 3.29 (2H, t, CH$_2$CH2O), 3.69 (1H, m, SCH), 4.64 (2H, t, OCH$_2$), 6.90 (1H, d, CH-arom.), 7.91 (1H, d, CH-arom.), 8.10 (1H, s, CH-arom.), 8.49 (1H, s, CH-thiazol), 11.70 (1H, bs, NH), 13.70 (1H, bs, NH). LC/MS [M+H]$^+$: 388.0

N-(3-(Cyclopropylcarbamoyl)-1H-1,2,4-triazol-5-yl)-2-(2,3-dihydrobenzofuran-5-yl)thiazole-4-carboxamide (25)

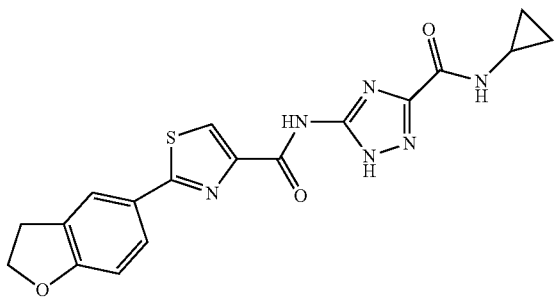 [SMILES: O=C(Nc1nc(C(=O)NC2CC2)n[nH]1)c1csc(-c2ccc3c(c2)CCO3)n1]

To a mixture of 2-(2,3-dihydro-1-benzofuran-5-yl)-1,3-thiazole-4-carboxylic acid (74 mg, 0.30 mmol), 1H-1,2,4-triazol-5-amine (50 mg, 0.30 mmol) and 2-(1H-benzotriazole-1-yl)-1,1,3,3-tetramethyluronium hexafluorophosphate (HBTU) (120 mg, 0.32 mmol) under stirring and heating at 110° C. 2 ml of dry pyridine were added. The mixture was heated at 110° C. for 5 h, pyridine was evaporated, and the residue was diluted with an aqueous $Na_2CO_3$ solution. The resulting precipitate was filtered off, dried and washed with EtOAc and hexane. The product was obtained as a light yellow solid (80 mg, 0.20 mmol, 67% yield). $^1$H NMR (400 MHz, DMSO-$d_6$) δ ppm 0.64-0.69 (4H, m, 2CH$_2$), 2.85 (1H, m, CH), 3.28 (2H, t, CH$_2$CH$_2$O), 4.64 (2H, t, OCH$_2$), 6.90 (1H, d, CH-arom.), 7.90 (1H, d, CH-arom.), 8.08 (1H, s, CH-arom.), 8.46 (1H, s, NH), 8.48 (1H, s, CH-thiazol), 11.70 (1H, s, NH), 13.70 (1H, s, NH). LC/MS [M+H]$^+$: 397.0

2-(2,3-Dihydrobenzofuran-5-yl)-N-(5-(morpholine-4-carbonyl)-4H-1,2,4-triazol-3-yl)thiazole-4-carboxamide (26)

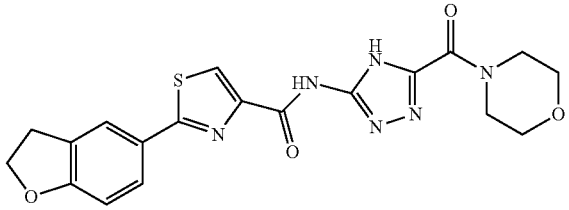 [SMILES: O=C(Nc1nnc(C(=O)N2CCOCC2)[nH]1)c1csc(-c2ccc3c(c2)CCO3)n1]

A solution of ethyl 5-({[2-(2,3-dihydro-1-benzofuran-5-yl)-1,3-thiazol-4-yl]carbonyl}amino)-1,2,4-triazole-3-carboxylate (35 mg, 0.10 mmol) in 2 ml morpholine was refluxed for 1 h. Excess morpholine was evaporated, the residue was crystallized from ethanol to give pure product as a light yellow powder (23 mg, 0.05 mmol, 54% yield). $^1$H NMR (400 MHz, DMSO+D$_3$CC(=O)OD) δ ppm 8.52 (s, 1H, CH-arom.), 8.10 (s, 1H, CH-arom.), 7.92 (d, J=7.8 Hz, 1H, CH-arom.), 6.90 (d, J=8.3 Hz, 1H, CH-het.), 4.64 (t, J=8.6 Hz, 1H, CH$_2$CH$_2$), 3.87 (s, 2H, CH$_2$-morph.), 3.65 (m, 6H, CH$_2$-morph.), 3.28 (t, J=8.6 Hz, 1H, CH$_2$CH$_2$). LC/MS [M+H]$^+$: 427.0

2-(2,3-Dihydrobenzofuran-5-yl)-N-(5-(4-methylpiperazine-1-carbonyl)-4H-1,2,4-triazol-3-yl)thiazole-4-carboxamide (27)

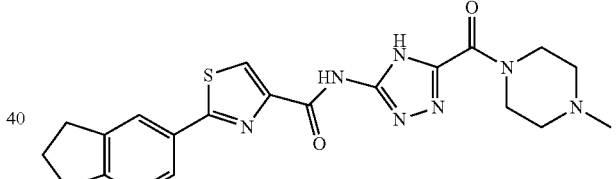

Method A. A solution of ethyl 5-({[2-(2,3-dihydro-1-benzofuran-5-yl)-1,3-thiazol-4-yl]carbonyl}amino)-1,2,4-triazole-3-carboxylate (56 mg, 0.16 mmol) in 3.4 ml 1-methylpiperazine was refluxed for 85 min. Solution attained reddish color. All volatiles were evaporated, the residue was treated subsequently with boiling hexane and water. The residue was collected with ethanol, solvent was evaporated, the residue was crystallized from EtOAc-hexane to give the product as light yellow needles (17 mg, 0.04 mmol, 24% yield). $^1$H NMR (400 MHz, DMSO-$d_6$) δ ppm 8.50 (s, 1H, CH-arom.), 8.10 (s, 1H, CH-arom.), 7.95-7.87 (m, 1H, CH-arom.), 6.90 (d, J=8.4 Hz, 1H, CH-het.), 4.64 (t, J=8.7 Hz, 2H, CH$_2$CH$_2$), 3.79 (s, 2H, CH$_2$-piperaz.), 3.65 (s, 2H, CH$_2$-piperaz.), 3.28 (t, J=8.8 Hz, 2H, CH$_2$CH$_2$), 2.35 (d, J=13.7 Hz, 4H, CH$_2$-piperaz.), 2.21 (s, 3H, CH$_3$). LC/MS [M+H]$^+$: 440.0

Method B. To a suspension of 5-({[2-(2,3-dihydro-1-benzofuran-5-yl)-1,3-thiazol-4-yl]carbonyl}amino)-1,2,4-triazole-3-carboxylic acid (51 mg, 0.14 mmol) in 2.7 ml absolute dioxane 2-(1H-benzotriazole-1-yl)-1,1,3,3-tetramethyluronium hexafluorophosphate (HBTU) (126 mg, 0.33 mmol) was added. After that N-methylpiperazine (182 mg, 1.82 mmol) were added. The precipitate dissolved partially at warming and stirring. The reaction mixture was warmed to boiling until the precipitate dissolved completely. After that the solution was left stirring at room temperature for 2 days. Dioxane was evaporated, the residue was dissolved in water and filtered off. The filtrate was neutralized with AcOH which lead to a precipitate formation. The precipitate was filtered off and dried. The precipitate was then collected with hot N,N-dimethylformamide, N,N-dimethylformamide was evaporated to dryness, the residue was crystallized from EtOH to give the product as a light brown powder (37 mg, 0.08 mmol, 60% yield). $^1$H NMR (400 MHz, DMSO-$d_6$) δ ppm 8.50 (s, 1H, CH-arom.), 8.10 (s, 1H, CH-arom.), 7.95-7.87 (m, 1H, CH-arom.), 6.90 (d, J=8.4 Hz, 1H, CH-het.), 4.64 (t, J=8.7 Hz, 2H, CH$_2$CH$_2$), 3.79 (s, 2H, CH$_2$-piperaz.), 3.65 (s, 2H, CH$_2$-piperaz.), 3.28 (t, J=8.8 Hz, 2H, CH$_2$CH$_2$), 2.35 (d, J=13.7 Hz, 4H, CH$_2$-piperaz.), 2.21 (s, 3H, CH$_3$). LC/MS [M+H]$^+$: 440.0

2-(2,3-Dihydrobenzofuran-5-yl)-N-(5-(pyrrolidine-1-carbonyl)-4H-1,2,4-triazol-3-yl)thiazole-4-carboxamide (28)

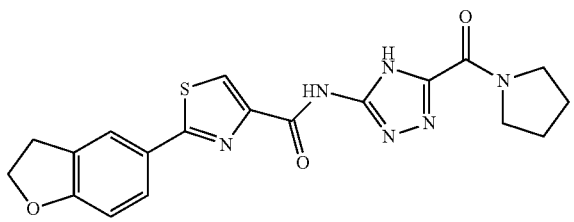 [SMILES: O=C(Nc1nnc(C(=O)N2CCCC2)[nH]1)c1csc(-c2ccc3c(c2)CCO3)n1]

A solution of ethyl ethyl 5-({[2-(2,3-dihydro-1-benzofuran-5-yl)-1,3-thiazol-4-yl]carbonyl}amino)-1,2,4-triazole-3-carboxylate (22 mg, 0.06 mmol) in 2.3 ml piperidine was refluxed for 70 min. All volatiles were evaporated in vacuo, the residue was treated subsequently with boiling hexane and water. The residue was crystallized from EtOH to give of pure product as light yellow powder (10 mg, 0.02 mmol, 41% yield). $^1$H NMR (400 MHz, DMSO-$d_6$) δ ppm 12.28 (bs, 1H, NH), 10.39 (bs, 1H, NH), 8.23 (s, 1H, CH-arom.), 7.86 (s, 1H, CH-arom.), 7.71 (d, J=7.9 Hz, 1H, CH-arom.), 6.86 (d, J=8.2 Hz, 1H, CH-het.), 4.68 (t, J=8.6 Hz, 1H, CH$_2$CH$_2$), 3.72 (t, J=6.6 Hz, 1H, CH$_2$CH$_2$), 3.97 (bs, 2H, CH$_2$-piperid.), 3.32 (t, J=8.6 Hz, 2H, CH$_2$-piperid.), 2.05-1.87 (m, 4H, CH$_2$-piperid.). LC/MS [M+H]$^+$: 411.0

2-(2,3-Dihydrobenzofuran-5-yl)-N-(5-(dimethylcarbamoyl)-4H-1,2,4-triazol-3-yl)thiazole-4-carboxamide (29)

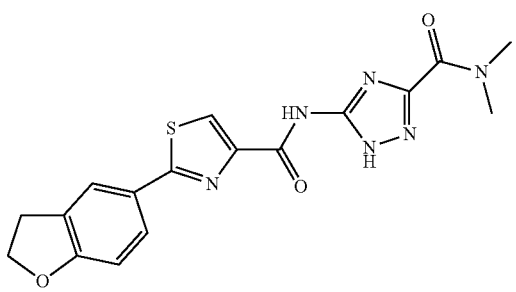 [SMILES: CN(C)C(=O)c1n[nH]c(NC(=O)c2csc(-c3ccc4c(c3)CCO4)n2)n1]

To a suspension of 5-amino-N,N-dimethyl-1,2,4-triazole-3-carboxamide hydrochloride (77 mg, 0.40 mmol) and 2-(2,3-dihydro-1-benzofuran-5-yl)-1,3-thiazole-4-carboxylic acid (99 mg, 0.40 mmol) in 2.6 ml dry pyridine (166 mg, 0.44 mmol) 2-(1H-benzotriazole-1-yl)-1,1,3,3-tetramethyluronium hexafluorophosphate (HBTU) was added. The suspension was refluxed for 5 h. Pyridine was evaporated and the residue was treated subsequently with water, a saturated aqueous NaHCO$_3$ solution, water, aqueous AcOH and water again. The residue was dissolved in hot N,N-dimethylformamide and filtered. The filtrate was concentrated under reduced pressure. The residue was crystallized from ethanol to give the product as grayish powder (52 mg, 0.14 mmol, 34% yield). $^1$H NMR (400 MHz, DMSO-$d_6$) δ ppm 13.99 (s, 1H, NH), 11.89 (s, 1H, NH), 8.50 (s, 1H), 8.10 (s, 1H, CH-arom.), 7.91 (d, J=8.3 Hz, 1H, CH-arom.), 6.90 (d, J=8.3 Hz, 1H, CH-arom.), 4.64 (t, J=8.7 Hz, 2H, CH$_2$CH$_2$), 3.34 (s, 3H, NCH$_3$), 3.28 (t, J=8.7 Hz, 2H, CH$_2$CH$_2$), 3.02 (s, 3H, NCH$_3$). LC/MS [M+H]$^+$: 385.0

2-(2,3-Dihydrobenzofuran-5-yl)-N-(3-(propylthio)-1H-1,2,4-triazol-5-yl)thiazole-4-carboxamide (30)

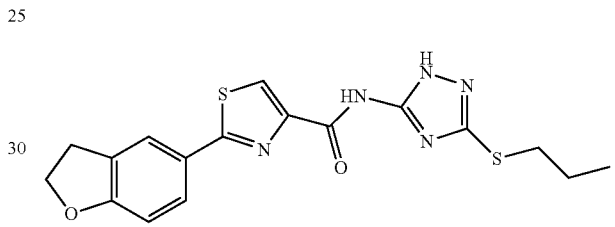

To a mixture of 2-(2,3-dihydro-1-benzofuran-5-yl)-1,3-thiazole-4-carbonyl chloride (125 mg, 0.47 mmol) and 3-(propylthio)-1H-1,2,4-triazol-5-amine (70 mg, 0.44 mmol) 3 ml of dry pyridine was added. The solution was heated at reflux for 2 h, pyridine was evaporated and the residue was diluted with aqueous Na$_2$CO$_3$. The resulting precipitate was filtered off and washed with ethanol to give the product as a light yellow solid (35 mg, 0.09 mmol, 21% yield). $^1$H NMR (400 MHz, DMSO-$d_6$) δ ppm 0.98 (3H, t, CH$_3$), 1.69 (2H, m, CH$_2$), 3.06 (2H, m, SCH$_2$), 3.29 (2H, t, CH$_2$CH$_2$O), 4.64 (2H, t, OCH$_2$), 6.90 (1H, d, CH-arom.), 7.90 (1H, d, CH-arom.), 8.10 (1H, s, CH-arom.), 8.49 (1H, s, CH-thiazol), 11.70 (1H, bs, NH), 13.60 (1H, bs, NH). LC/MS [M+H]$^+$: 388.0

5-(2-(2,3-Dihydrobenzofuran-5-yl)thiazole-4-carboxamido)-4H-1,2,4-triazole-3-carboxylic acid (31)

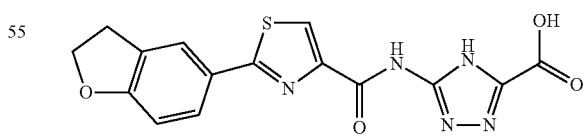

To suspension of ethyl 5-({[2-(2,3-dihydro-1-benzofuran-5-yl)-1,3-thiazol-4-yl]carbonyl}amino)-1,2,4-triazole-3-carboxylate (20) (99 mg, 0.26 mmol) in 3.48 ml water NaOH was added (53 mg, 1.33 mmol). The reaction mixture was stirred at room temperature while the solid dissolved almost immediately. After several minutes, new white amorphous precipitate formed. The suspension was stirred at room temperature for 1 day after which 6 drops conc. HCl were added, to give pH-2. Bulky white precipitate formed. The precipitate was centrifuged with water twice, than with ethanol and ether to give the product as white powder. (76 mg, 0.21 mmol, 82% yield). $^1$H NMR (400 MHz, DMSO-$d_6$) δ ppm 14.17 (bs, 1H), 13.22 (bs, 1H, OH). 11.99 (bs, 1H, NH). 8.52 (s, 1H, CH-arom.), 8.12 (s, 1H. CH-arom.), 7.92 (d, J=8.3 Hz, 1H, CH-arom.), 6.90 (d, J=8.3 Hz, 1H, CH-arom.), 4.64 (t, J=8.7 Hz, 2H, CH$_2$CH$_2$), 3.28 (t, J=8.7 Hz, 2H, CH$_2$CH$_2$). LC/MS [M+H]$^+$: 358.0

N-(3-(Benzylthio)-1H-1,2,4-triazol-5-yl)-2-(2,3-dihydrobenzofuran-5-yl)thiazole-4-carboxamide (32)

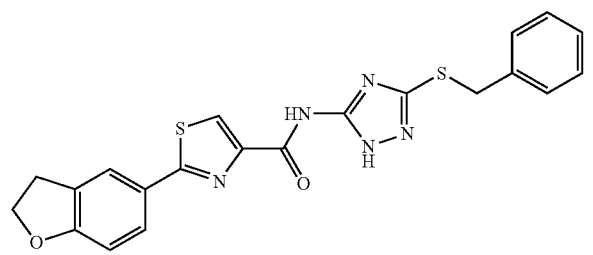

To a mixture of 2-(2,3-dihydro-1-benzofuran-5-yl)-1,3-thiazole-4-carboxylic acid (60 mg, 0.24 mmol), 3-(benzylthio)-1H-1,2,4-triazol-5-amine (50 mg, 0.24 mmol) and 2-(1H-benzotriazole-1-yl)-1,1,3,3-tetramethyluronium hexafluorophosphate (HBTU) (120 mg, 0.32 mmol) under stirring and heating at 110° C. 2 ml of dry pyridine were added. The mixture was heated at 110° C. for 5 h, pyridine was evaporated, and the residue was diluted with a saturated aqueous Na$_2$CO$_3$ solution. The resulting precipitate was filtered off, dried and washed with EtOAc and hexane. The product was obtained as a light yellow solid (72 mg, 0.17 mmol, 69% yield). $^1$H NMR (400 MHz, DMSO-$d_6$) δ ppm 3.28 (2H, t, CH$_2$CH$_2$O), 4.36 (2H, s, CH$_2$), 4.64 (2H, t, OCH$_2$), 6.90 (1H, d, CH-arom.), 7.23-7.42 (5H, m, CH-arom.), 7.91 (1H, d, CH-arom.), 8.11 (1H, s, CH-arom.), 8.50 (1H, s, CH-thiazol), 11.70 (1H, bs, NH), 13.70 (1H, bs, NH). LC/MS [M+H]$^+$: 436.0

N-(3-((4-Chlorobenzyl)thio)-1H-1,2,4-triazol-5-yl)-2-(2,3-dihydrobenzofuran-5-yl)thiazole-4-carboxamide (33)

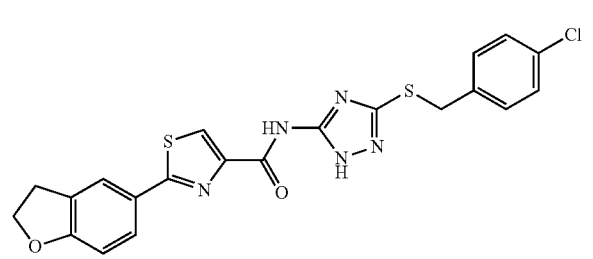 [SMILES: O=C(Nc1nc(SCc2ccc(Cl)cc2)n[nH]1)c1csc(-c2ccc3c(c2)CCO3)n1]

To a mixture of 2-(2,3-dihydro-1-benzofuran-5-yl)-1,3-thiazole-4-carboxylic acid (51 mg, 0.21 mmol), 3-((4-chlorobenzyl)thio)-1H-1,2,4-triazol-5-amine (50 mg, 0.21 mmol) and 2-(1H-benzotriazole-1-yl)-1,1,3,3-tetramethyluronium hexafluorophosphate (HBTU) (120 mg, 0.32 mmol) under stirring and heating at 110° C. 2 ml of dry pyridine were added. The mixture was heated at 110° C. for 5 h, pyridine was evaporated, and the residue was diluted with a saturated aqueous Na$_2$CO$_3$ solution. The resulting precipitate was filtered off, dried and washed with EtOAc and hexane. The product was obtained as a light yellow solid (62 mg, 0.13 mmol, 63% yield). $^1$H NMR (400 MHz, DMSO-$d_6$) δ ppm 3.28 (2H, t, CH$_2$CH$_2$O), 3.35 (2H, s, CH$_2$), 4.64 (2H, t, OCH$_2$), 6.90 (1H, d, CH-arom.), 7.37+7.43 (4H, AB-syst., CH-arom.), 7.91 (1H, d, CH-arom.), 8.11 (1H, s, CH-arom.), 8.49 (1H, s, CH-thiazol), 11.70 (1H, bs, NH), 13.70 (1H, bs, NH). LC/MS [M+H]$^+$: 469.9

2-(2,3-Dihydrobenzofuran-5-yl)-N-(3-(isobutylthio)-1H-1,2,4-triazol-5-yl)thiazole-4-carboxamide (34)

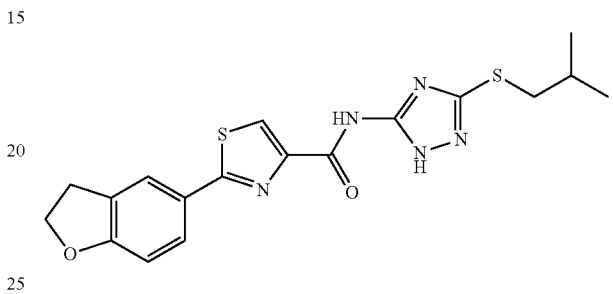

To a mixture of 2-(2,3-dihydro-1-benzofuran-5-yl)-1,3-thiazole-4-carboxylic acid (72 mg, 0.29 mmol), 3-(isobutylthio)-1H-1,2,4-triazol-5-amine (50 mg, 0.29 mmol) and 2-(1H-benzotriazole-1-yl)-1,1,3,3-tetramethyluronium hexafluorophosphate (HBTU) (120 mg, 0.32 mmol) under stirring and heating at 110° C. 2 ml of dry pyridine were added. The mixture was heated at 110° C. for 5 h, pyridine was evaporated, and the residue was diluted with a saturated aqueous Na$_2$CO$_3$ solution. The resulting precipitate was filtered off, dried and crystallized from EtOAc:hexane. The product was obtained as a light yellow solid (65 mg, 0.16 mmol, 56% yield). $^1$H NMR (400 MHz, DMSO-$d_6$) δ ppm 0.99 (6H, d, 2CH$_3$), 1.91 (1H, m, CH), 2.99 (2H, d, CH$_2$), 3.28 (2H, t, CH$_2$CH$_2$O), 4.64 (2H, t, OCH$_2$), 6.90 (1H, d, CH-arom.), 7.91 (1H, d, CH-arom.), 8.10 (1H, s, CH-arom.), 8.48 (1H, s, CH-thiazol), 11.70 (1H, bs, NH), 13.70 (1H, bs, NH). LC/MS [M+H]$^+$: 402.0

2-(2,3-Dihydrobenzofuran-5-yl)-N-(5-(((tetrahydrofuran-2-yl)methyl)carbamoyl)-1H-benzo[d]imidazol-2-yl)thiazole-4-carboxamide (35)

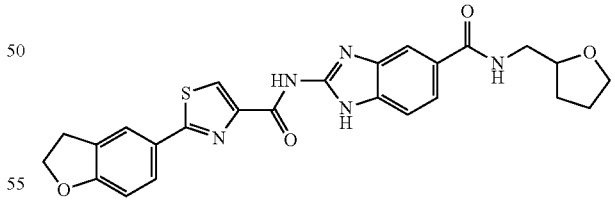

A mixture of 3,4-dinitro-N-((tetrahydrofuran-2-yl)methyl)benzamide (I-51) (132 mg, 0.45 mmol), 10 ml ethanol and Pd/C catalyst (0.05 g, 10% Pd) was stirred in an autoclave under hydrogen pressure 10 kg/cm$^2$ and room temperature for 3 h. The catalyst was filtered off and cyanogen bromide (80 mg, 0.75 mmol) was added to the filtrate. After stirring at room temperature for 1 day the solvent was evaporated in vacuo and to the residue were added 10 ml dichloromethane and 2-(2,3-dihydro-1-benzofuran-5-yl)-1,3-thiazole-4-carboxylic acid (106 mg, 0.43 mmol), 2-(1H-benzotriazole-1-yl)-1,1,3,3-tetramethyluronium hexafluorophosphate HBTU (208 mg, 0.55 mmol) and diisopropylether (0.2 ml, 1.15 mmol). The reaction mixture was stirred for 1 day at room temperature, the solvent was evaporated in vacuo and and 10 ml of an aqueous 5% $Na_2CO_3$ solution were added to the residue. In 1 h the residue solidified, the precipitate was filtered off and crystallized from ethanol to give the product as white crystals (88 mg, 0.18 mmol, 45% yield). M.p.=185-190° C. $^1$H NMR (400 MHz, DMSO-$d_6$) δ ppm 1.57-1.74 (m, 1H) 1.75-2.05 (m, 3H) 3.21-3.41 (m, 4H) 3.66 (q, J=7.11 Hz, 1H) 3.83 (q, J=7.03 Hz, 1H) 3.93-4.06 (m, 1H) 4.64 (t, J=8.66 Hz, 2H) 6.82 (d, J=8.28 Hz, 1H) 7.48 (d, J=7.53 Hz, 1H) 7.57-7.72 (m, 1H) 7.84 (d, J=7.78 Hz, 1H) 8.01 (d, J=6.52 Hz, 2H) 8.11-8.28 (m, 1H) 8.42 (s, 1H) 11.38 (bs, 1H) 12.35 (bs, 1H). LC/MS [M+H]$^+$: 490.0

2-(2,3-Dihydrobenzofuran-5-yl)-N-(3-phenethyl-1H-1,2,4-triazol-5-yl)thiazole-4-carboxamide (36)

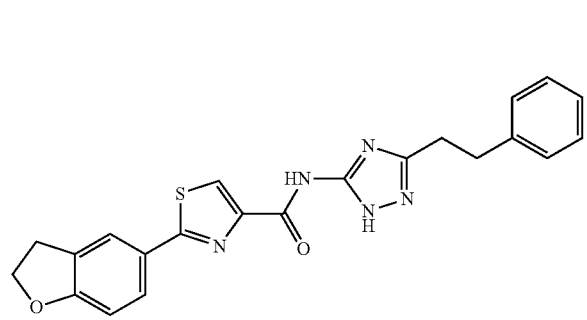 [SMILES: O=C(Nc1nc(CCc2ccccc2)n[nH]1)c1csc(-c2ccc3c(c2)CCO3)n1]

To a mixture of 2-(2,3-dihydro-1-benzofuran-5-yl)-1,3-thiazole-4-carboxylic acid (66 mg, 0.26 mmol), 1H-1,2,4-triazol-5-amine (50 mg, 0.26 mmol) and 2-(1H-benzotriazole-1-yl)-1,1,3,3-tetramethyluronium hexafluorophosphate (HBTU) (120 mg, 0.32 mmol) under stirring and heating at 110° C. 2 ml of dry pyridine were added. The mixture was heated at 110° C. for 5 h, pyridine was evaporated, and the residue was diluted with a saturated aqueous $Na_2CO_3$ solution. The resulting precipitate was filtered off, dried and crystallized from EtOAc:hexane. The product was obtained as a light yellow solid (49 mg, 0.12 mmol, 44% yield). $^1$H NMR (400 MHz, DMSO-$d_6$, $CCl_4$) δ ppm 2.92 (2H, m, $CH_2$), 3.03 (2H, t, $CH_2$), 3.30 (2H, t, $\underline{CH_2}CH_2O$), 4.64 (2H, t, $OCH_2$), 6.81 (1H, d, CH-arom.), 7.14-7.26 (5H, m, CH-arom.), 7.83 (1H, d, CH-arom.), 8.02 (1H, s, CH-arom.), 8.34 (1H, s, CH-thiazol), 11.30 (1H, bs, NH), 13.10 (1H, bs, NH). LC/MS [M+H]$^+$: 418.0

2-(2,3-Dihydrobenzofuran-5-yl)-N-(3-(phenethylthio)-1H-1,2,4-triazol-5-yl)thiazole-4-carboxamide (37)

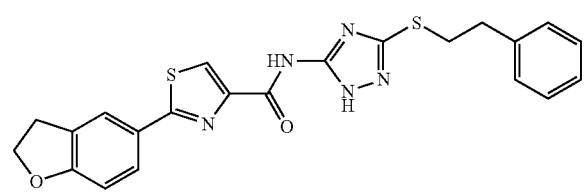 [SMILES: O=C(Nc1nc(SCCc2ccccc2)n[nH]1)c1csc(-c2ccc3c(c2)CCO3)n1]

To a mixture of 2-(2,3-dihydro-1-benzofuran-5-yl)-1,3-thiazole-4-carboxylic acid (56 mg, 0.23 mmol), 3-(phenethylthio)-1H-1,2,4-triazol-5-amine (50 mg, 0.23 mmol) and 2-(1H-benzotriazole-1-yl)-1,1,3,3-tetramethyluronium hexafluorophosphate (HBTU) (120 mg, 0.32 mmol) under stirring and heating at 110° C. 2 ml of dry pyridine were added. The mixture was heated at 110° C. for 5 h, pyridine was evaporated, and the residue was diluted with a saturated aqueous $Na_2CO_3$ solution. The resulting precipitate was filtered off, dried and washed with EtOAc and hexane. The product was obtained as a light yellow solid (70 mg, 0.16 mmol, 69% yield). $^1$H NMR (400 MHz, DMSO-$d_6$) δ ppm 2.99 (2H, t, $CH_2$), 3.28 (2H, t, $\underline{CH_2}CH_2O$), 3.32 (2H, t, $CH_2$), 4.64 (2H, t, $OCH_2$), 6.90 (1H, d, CH-arom.), 7.21 . . . 7.33 (5H, m, CH-arom.), 7.91 (1H, d, CH-arom.), 8.11 (1H, s, CH-arom.), 8.51 (1H, s, CH-thiazol), 11.74 (1H, s, NH), 13.67 (1H, s, NH). LC/MS [M+H]$^+$: 449.9

N-(3-((Cyanomethyl)thio)-1H-1,2,4-triazol-5-yl)-2-(2,3-dihydrobenzofuran-5-yl)thiazole-4-carboxamide (38)

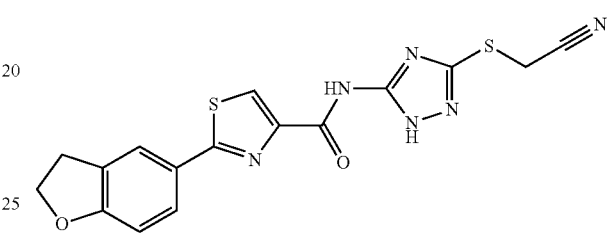

To a mixture of 2-(2,3-dihydro-1-benzofuran-5-yl)-1,3-thiazole-4-carboxylic acid (80 mg, 0.32 mmol), 1H-1,2,4-triazol-5-amine (50 mg, 0.32 mmol) and 2-(1H-benzotriazole-1-yl)-1,1,3,3-tetramethyluronium hexafluorophosphate (HBTU) (120 mg, 0.32 mmol) under stirring and heating at 110° C. 2 ml of dry pyridine were added. The mixture was heated at 110° C. for 5 h, pyridine was evaporated, and the residue was diluted with an aqueous $Na_2CO_3$ solution. The resulting precipitate was filtered off, dried and washed with EtOAc and hexane. The product was obtained as light yellow solid (42 mg, 0.11 mmol, 34% yield). $^1$H NMR (400 MHz, DMSO-$d_6$) δ ppm 3.28 (2H, t, $\underline{CH_2}CH_2O$), 4.23 (2H, s, $CH_2$), 4.64 (2H, t, $OCH_2$), 6.90 (1H, d, CH-arom.), 7.91 (1H, d, CH-arom.), 8.11 (1H, s, CH-arom.), 8.53 (1H, s, CH-thiazol), 11.80 (1H, bs, NH), 13.90 (1H, bs, NH). LC/MS [M+H]$^+$: 384.9

N-(3-(Allylthio)-1H-1,2,4-triazol-5-yl)-2-(2,3-dihydrobenzofuran-5-yl)thiazole-4-carboxamide (39)

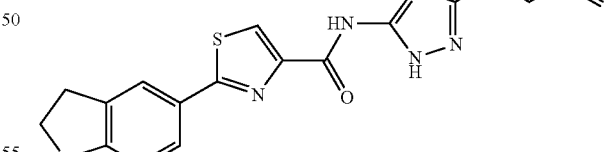

To a mixture of 2-(2,3-dihydro-1-benzofuran-5-yl)-1,3-thiazole-4-carboxylic acid (80 mg, 0.32 mmol), 1H-1,2,4-triazol-5-amine (50 mg, 0.32 mmol) and 2-(1H-benzotriazole-1-yl)-1,1,3,3-tetramethyluronium hexafluorophosphate (HBTU) (120 mg, 0.32 mmol) under stirring and heating at 110° C. 2 ml of dry pyridine were added. The mixture was heated at 110° C. for 5 h, pyridine was evaporated, and the residue was diluted with an aqueous $Na_2CO_3$ solution. The resulting precipitate was filtered off, dried and washed with EtOAc and hexane. The product was obtained as a light yellow solid (65 mg, 0.17 mmol, yield 53% yield). $^1$H NMR (400 MHz, DMSO-d$_6$) δ ppm 3.28 (2H, t, CH$_2$CH$_2$O), 3.76 (2H, d, CH$_2$), 4.64 (2H, t, OCH$_2$), 5.09 (1H, d, CH), 5.26 (1H, d, CH), 5.96 (1H, m, CH), 6.90 (1H, d, CH-arom.), 7.91 (1H, d, CH-arom.), 8.11 (1H, s, CH-arom.), 8.49 (1H, s, CH-thiazol), 11.70 (1H, bs, NH), 13.70 (1H, bs, NH). LC/MS [M+H]$^+$: 385.9

2-(2,3-Dihydrobenzofuran-5-yl)-N-(6-(morpholinomethyl)benzo[d]thiazol-2-yl)thiazole-4-carboxamide (40)

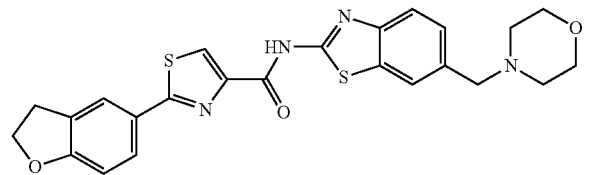 [SMILES: O=C(Nc1nc2ccc(CN3CCOCC3)cc2s1)c1csc(-c2ccc3c(c2)CCO3)n1]

To a solution of 2-(2,3-dihydro-1-benzofuran-5-yl)-1,3-thiazole-4-carboxylic acid (100 mg, 0.40 mmol) in 5 ml N,N-dimethylformamide, was added 6-(morpholinomethyl)benzo[d]thiazol-2-amine (101 mg, 0.40 mmol). Then 2-(1H-benzotriazole-1-yl)-1,1,3,3-tetramethyluronium hexafluorophosphate (HBTU) (153 mg, 0.40 mmol), 4-dimethylaminopyridine (4.9 mg, 0.04 mmol) and N,N-diisopropylethylamine (0.18 ml, 1.01 mmol) were added. The reaction mixture was stirred overnight at room temperature. The mixture was poured into ice water. The resulting precipitate was filtered off, dried and purified by preparative TLC (PLC silica gel 60 F254, 1 mm, PE:EtOAc:MeOH 4:6:1). The main spot was isolated, concentrated in vacuo and dried. The product was obtained as a baige solid (12 mg, 0.03 mmol, 6% yield). $^1$H NMR (400 MHz, DMSO-d$_6$) δ ppm 2.39 (bs, 4H), 3.22-3.35 (m, 2H), 3.59 (bs, 6H), 4.65 (t, J=8.76 Hz, 2H), 6.91 (d, J=8.34 Hz, 1H), 7.43 (dd, J=8.28 Hz, J=1.47 Hz, 1H), 7.75 (d, J=8.28 Hz, 1H), 7.90-7.99 (m, 2H), 8.14 (bs, 1H), 8.59 (s, 1H), 12.48 (bs, 1H). LC/MS [M+H]$^+$: 479.0

2-(2,3-Dihydrobenzofuran-5-yl)-N-(6-(4-methylpiperazin-1-yl)benzo[d]thiazol-2-yl)thiazole-4-carboxamide (41)

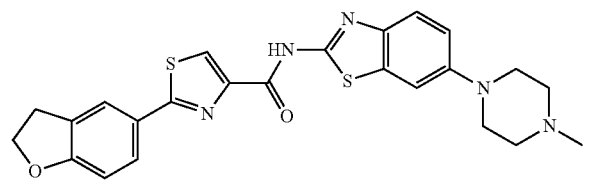 [SMILES: CN1CCN(c2ccc3nc(NC(=O)c4csc(-c5ccc6c(c5)CCO6)n4)sc3c2)CC1]

To a solution of 2-(2,3-dihydro-1-benzofuran-5-yl)-1,3-thiazole-4-carboxylic acid (100 mg, 0.40 mmol) in 5 ml N,N-dimethylformamide, was added 6-(4-Methyl-piperazin-1-yl)-benzothiazol-2-ylamine (100 mg, 0.40 mmol). Then 2-(1H-benzotriazole-1-yl)-1,1,3,3-tetramethyluronium hexafluorophosphate (HBTU) (153 mg, 0.40 mmol), 4-dimethylaminopyridine (4.9 mg, 0.04 mmol) and N,N-diisopropylethylamine (0.18 ml, 1.01 mmol) were added. The reaction mixture was stirred overnight at room temperature. The mixture was poured into ice water. The mixture was diluted with EtOAc and the biphasic mixture was separated. The organic layer was washed with an aqueous 5% NaHCO$_3$ solution, an aqueous 5% citric acid solution and water. The organic layer was dried over MgSO$_4$ and concentrated in vacuo. The crude yellow oil was purified by preparative TLC (PLC silica gel 60 F$_{254}$, 2 mm, eluent: DCM:MeOH 9:1). The crude yellow solid was purified again by preparative TLC (PLC silica gel 60 F$_{254}$, 1 mm, DCM:MeOH 9:1). The product was obtained as a yellow solid (14 mg, 0.03 mmol, 7% yield). $^1$H NMR (400 MHz, DMSO-d$_6$) δ ppm 2.24 (s, 3H), 2.43-2.55 (m, 4H), 3.08-3.23 (m, 4H), 3.23-3.45 (m, 2H), 4.65 (t, J=8.76 Hz, 2H), 6.90 (d, J=8.34 Hz, 1H), 7.15 (dd, J=8.98 Hz, J=2.44 Hz, 1H), 7.51 (d, J=2.37 Hz, 1H), 7.63 (d, J=8.91 Hz, 1H), 7.92 (dd, J=8.34 Hz, J=1.95 Hz, 1H), 8.12 (bs, 1H), 8.55 (s, 1H), 12.26 (bs, 1H). LC/MS [M+H]$^+$: 477.9

2-(2,3-Dihydrobenzofuran-5-yl)-N-(3-(pyridin-4-yl)-1H-1,2,4-triazol-5-yl)thiazole-4-carboxamide (42)

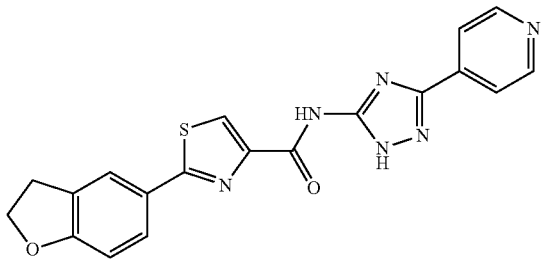 [SMILES: O=C(Nc1nc(-c2ccncc2)n[nH]1)c1csc(-c2ccc3c(c2)CCO3)n1]

To a mixture of 2-(2,3-dihydro-1-benzofuran-5-yl)-1,3-thiazole-4-carboxylic acid (77 mg, 0.31 mmol), 1H-1,2,4-triazol-5-amine (50 mg, 0.31 mmol) and 2-(1H-benzotriazole-1-yl)-1,1,3,3-tetramethyluronium hexafluorophosphate (HBTU) (120 mg, 0.32 mmol) under stirring and heating at 110° C. 2 ml of dry pyridine were added. The mixture was heated at 110° C. for 5 h, pyridine was evaporated, and the residue was diluted with an aqueous Na$_2$CO$_3$ solution. The resulting precipitate was filtered off, dissolved in hot N,N-dimethylformamide, settled by addition of EtOAc and hexane, filtered off and dried. The product was obtained as a light yellow solid (75 mg, 0.19 mmol, 62% yield). $^1$H NMR (400 MHz, DMSO-d$_6$, CCl$_4$) δ ppm 3.31 (2H, t, CH$_2$CH$_2$O), 4.65 (2H, t, OCH$_2$), 6.83 (1H, d, CH-arom.), 7.87 (1H, d, CH-arom.), 7.90 (2H, m, CH-pyr.), 8.07 (1H, s, CH-arom.), 8.44 (1H, s, CH-thiazol), 8.62 (2H, m, CH-pyr.), 11.68 (1H, bs, NH), 13.87 (1H, bs, NH). LC/MS [M+H]$^+$: 391.0

2-(2,3-Dihydrobenzofuran-5-yl)-N-(3-(methylsulfonyl)-1H-1,2,4-triazol-5-yl)thiazole-4-carboxamide (43)

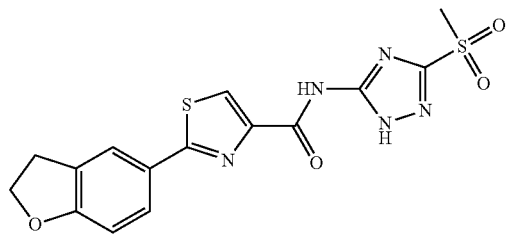 [SMILES: CS(=O)(=O)c1n[nH]c(NC(=O)c2csc(-c3ccc4c(c3)CCO4)n2)n1]

To a mixture of 2-(2,3-dihydro-1-benzofuran-5-yl)-1,3-thiazole-4-carboxylic acid (76 mg, 0.31 mmol), 1H-1,2,4-triazol-5-amine (50 mg, 0.31 mmol) and 2-(1H-benzotriazole-1-yl)-1,1,3,3-tetramethyluronium hexafluorophosphate (HBTU) (120 mg, 0.32 mmol) under stirring and heating at 110° C. 2 ml of dry pyridine were added. The mixture was heated at 110° C. for 5 h, pyridine was evaporated, and the residue was diluted with an aqueous Na$_2$CO$_3$ solution. The resulting precipitate was filtered off, dissolved in hot N,N-dimethylformamide, settled by addition of EtOAc and hexane, filtered off and dried. The product was obtained as a light yellow solid (60 mg, 0.15 mmol, 49% yield). $^1$H NMR (400 MHz, DMSO-d$_6$, CCl$_4$) δ ppm 3.28 (3H, s, CH$_3$), 3.30 (2H, t, CH$_2$CH$_2$O), 4.64 (2H, t, OCH$_2$), 6.82 (1H, d, CH-arom.), 7.87 (1H, d, CH-arom.), 8.07 (1H, s, CH-arom.), 8.44 (1H, bs, CH-thiazol), 12.03 (1H, bs, NH), 14.45 (1H, bs, NH). LC/MS [M+H]$^+$: 391.9

2-(2,3-Dihydrobenzofuran-5-yl)-N-(3-methyl-1H-1,2,4-triazol-5-yl)thiazole-4-carboxamide (44)

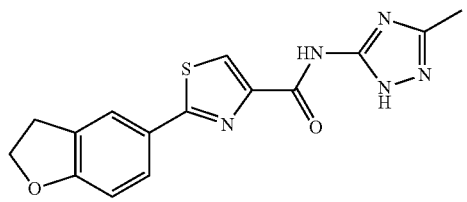 [SMILES: Cc1n[nH]c(NC(=O)c2csc(-c3ccc4c(c3)CCO4)n2)n1]

To a mixture of 2-(2,3-dihydro-1-benzofuran-5-yl)-1,3-thiazole-4-carboxylic acid (126 mg, 0.51 mmol), 1H-1,2,4-triazol-5-amine (50 mg, 0.51 mmol) and 2-(1H-benzotriazole-1-yl)-1,1,3,3-tetramethyluronium hexafluorophosphate (HBTU) (120 mg, 0.32 mmol) under stirring and heating at 110° C. 2 ml of dry pyridine were added. The mixture was heated at 110° C. for 5 h, pyridine was evaporated, and the residue was diluted with an aqueous Na$_2$CO$_3$ solution. The resulting precipitate was filtered off, dissolved in hot N,N-dimethylformamide, settled by addition of EtOAc and hexane, filtered off and dried. The product was obtained as a light yellow solid (82 mg, 0.25 mmol, 49% yield). $^1$H NMR (400 MHz, DMSO-d$_6$, CCl$_4$) δ ppm 2.29 (3H, bs, CH$_3$), 3.30 (2H, t, CH$_2$CH$_2$O), 4.64 (2H, t, OCH$_2$), 6.80 (1H, d, CH-arom.), 7.82 (1H, d, CH-arom.), 8.00 (1H, s, CH-arom.), 8.31 (1H, bs, CH-thiazol), 11.20 (1H, bs, NH), 12.95 (1H, bs, NH). LC/MS [M+H]$^+$: 328.0

2-(2,3-Dihydrobenzofuran-5-yl)-N-(3-(pyridin-3-yl)-1H-1,2,4-triazol-5-yl)thiazole-4-carboxamide (45)

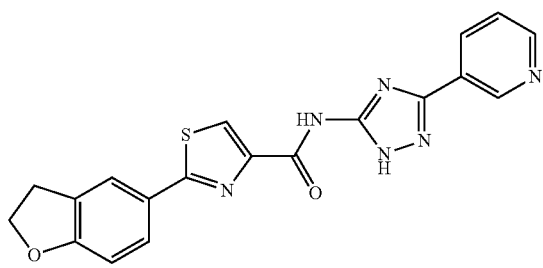 [SMILES: O=C(Nc1nc(-c2cccnc2)n[nH]1)c1csc(-c2ccc3c(c2)CCO3)n1]

To a mixture of 2-(2,3-dihydro-1-benzofuran-5-yl)-1,3-thiazole-4-carboxylic acid (77 mg, 0.31 mmol), 1H-1,2,4-triazol-5-amine (50 mg, 0.31 mmol) and 2-(1H-benzotriazole-1-yl)-1,1,3,3-tetramethyluronium hexafluorophosphate (HBTU) (120 mg, 0.32 mmol) under stirring and heating at 110° C. 2 ml of dry pyridine were added. The mixture was heated at 110° C. for 5 h, pyridine was evaporated, and the residue was diluted with an aqueous Na$_2$CO$_3$ solution. The resulting precipitate was filtered off, dissolved in hot N,N-dimethylformamide, settled by addition of EtOAc and hexane, filtered off and dried. The product was obtained as a light yellow solid (78 mg, 0.20 mmol, 64% yield). $^1$H NMR (400 MHz, DMSO-d$_6$, CCl$_4$) δ ppm 3.31 (2H, t, CH$_2$CH$_2$O), 4.65 (2H, t, OCH$_2$), 6.84 (1H, d, CH-arom.), 7.45 (1H, m, CH-pyr.), 7.88 (1H, d, CH-arom.), 8.08 (1H, s, CH-arom.), 8.30 (1H, d, CH-pyr.), 8.45 (1H, s, CH-thiazol), 8.57 (1H, m, CH-pyr.), 9.17 (1H, s, CH-pyr.), 11.68 (1H, bs, NH), 13.76 (1H, bs, NH). LC/MS [M+H]$^+$: 391.0

2-(2,3-Dihydrobenzofuran-5-yl)-N-(3-(furan-2-yl)-1H-1,2,4-triazol-5-yl)thiazole-4-carboxamide (46)

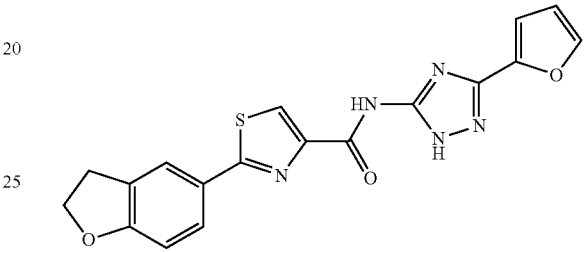

To a mixture of 2-(2,3-dihydro-1-benzofuran-5-yl)-1,3-thiazole-4-carboxylic acid (82 mg, 0.33 mmol), 1H-1,2,4-triazol-5-amine (50 mg, 0.33 mmol) and 2-(1H-benzotriazole-1-yl)-1,1,3,3-tetramethyluronium hexafluorophosphate (HBTU) (120 mg, 0.32 mmol) under stirring and heating at 110° C. 2 ml of dry pyridine were added. The mixture was heated at 110° C. for 5 h, pyridine was evaporated, and the residue was diluted with an aqueous Na$_2$CO$_3$ solution.

The resulting precipitate was filtered off, dissolved in hot N,N-dimethylformamide, settled by addition of EtOAc and hexane, filtered off and dried. The product was obtained as a light yellow solid (85 mg, 0.22 mmol, 70% yield). $^1$H NMR (400 MHz, DMSO-d$_6$, CCl$_4$) δ ppm 3.31 (2H, t, CH$_2$CH$_2$O), 4.64 (2H, t, OCH$_2$), 6.53 (1H, s, CH-furyl), 6.80 (1H, d, CH-arom.), 6.83 (1H, s, CH-furyl), 7.63 (1H, s, CH-furyl), 7.85 (1H, d, CH-arom.), 8.05 (1H, s, CH-arom.), 8.38 (1H, s, CH-thiazol), 11.51 (1H, bs, NH), 13.52 (1H, bs, NH); MSHR: LC/MS [M+H]$^+$: 380.0

2-(2,3-Dihydrobenzofuran-5-yl)-N-(5-(4-ethylpiperazine-1-carbonyl)-1H-benzo[d]imidazol-2-yl)thiazole-4-carboxamide (47)

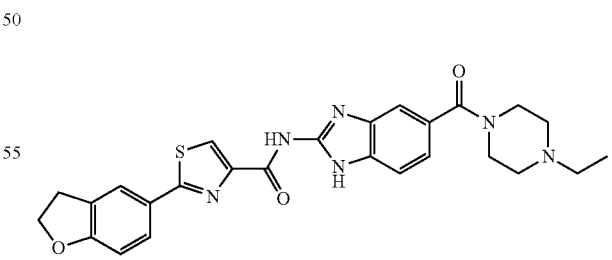

A mixture of 2-(2,3-dihydro-1-benzofuran-5-yl)-1,3-thiazole-4-carboxylic acid (160 mg, 0.6 mmol), (2-amino-1H-benzimidazol-5-yl)(4-ethylpiperazin-1-yl)methanone hydrobromide (I-54) (248 mg, 0.7 mmol), 2-(1H-benzotriazole-1-yl)-1,1,3,3-tetramethyluronium hexafluorophosphate (HBTU) (312 mg, 0.82 mmol), diisopropylether (0.3 ml, 1.82 mmol) and 10 ml DCM was stirred at room temperature for 1 day. The solvent was evaporated in vacuum and 20 ml of an aqueous 10% Na$_2$CO$_3$ solution were added to the residue. The resin formed. The supernatant was poured out; the resin was washed with water, dissolved in 5 ml chloroform and separated on the column with silica gel (0.040-0.100 mm). Eluent: chloroform:ethanol=5:1. The fraction with R$_f$=0.55 was collected, the solvent evaporated and the residue crystallized from minimal amount of ethanol to give the product as a yellowish solid (87 mg, 0.17 mmol, 29% yield). M.p.=238-240° C. $^1$H NMR (400 MHz, DMSO-d$_6$) δ ppm 1.05 (t, J=6.53 Hz, 4H) 2.39 (bs, 7H) 3.09 (bs, 2H) 3.29 (t, J=8.16 Hz, 3H) 3.37-3.67 (m, 5H) 4.63 (t, J=8.41 Hz, 3H) 6.81 (d, J=8.28 Hz, 1H) 7.11 (d, J=7.78 Hz, 1H) 7.50 (bs, 2H) 7.83 (d, J=7.78 Hz, 1H) 8.01 (bs, 1H) 8.43 (s, 1H) 11.97 (bs, 1H). LC/MS [M+H]$^+$: 503.0

2-(2,3-Dihydro-1-benzofuran-5-yl)-N-[5-(thiophene-2-carbonyl)-1H-1,3-benzodiazol-2-yl]-1,3-thiazole-4-carboxamide (48)

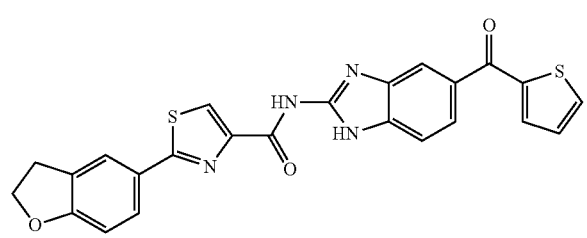 [SMILES: O=C(Nc1nc2cc(C(=O)c3cccs3)ccc2[nH]1)c1csc(-c2ccc3c(c2)CCO3)n1]

To a solution of 2-(2,3-dihydro-1-benzofuran-5-yl)-1,3-thiazole-4-carboxylic acid (111 mg, 0.45 mmol) in 5 ml N,N-dimethylformamide were added (2-Amino-1H-benzoimidazol-5-yl)-thiophen-3-yl-methanonehydrobromide (160 mg, 0.49 mmol), 2-(1H-benzotriazole-1-yl)-1,1,3,3-tetramethyluroniumhexafluorophosphate (HBTU) (170 mg, 0.45 mmol), 4-(dimethylamino)-pyridine (5.5 mg, 0.04 mmol) and N,N-diisopropylethyl amine (0.2 ml, 1.12 mmol). The reaction mixture was stirred at room temperature for 18 h, and then poured into ice water. The formed precipitate was filtered off and dried. The crude product was washed with diisopropyl ether and MeOH. The product was obtained as a yellow solid (102 mg, 0.22 mmol, 48% yield). $^1$H NMR (400 MHz, DMSO-d$_6$) δ ppm 3.20-3.40 (m, 2H), 4.65 (t, J=8.2 Hz, 2H), 6.91 (d, J=8.3 Hz, 1H), 7.24-7.39 (m, 1H), 7.59-7.87 (m, 3H), 7.93 (d, J=8.5 Hz, 1H), 8.02-8.21 (m, 3H), 8.58 (s, 1H), 11.86 (bs, 1H), 12.55 (bs, 1H). LC/MS [M+H]$^+$: 472.8.

2-(2,3-Dihydro-1-benzofuran-5-yl)-N-[5-(H-pyrrole-2-carbonyl)-1H-1,3-benzodiazol-2-yl]-1,3-thiazole-4-carboxamide (49)

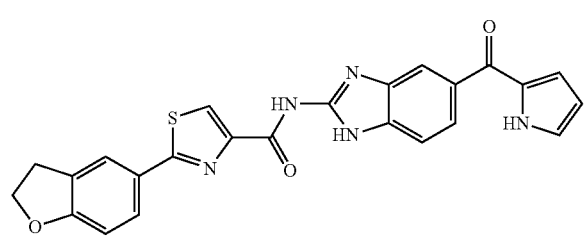 [SMILES: O=C(Nc1nc2cc(C(=O)c3ccc[nH]3)ccc2[nH]1)c1csc(-c2ccc3c(c2)CCO3)n1]

To a solution of 2-(2,3-dihydro-1-benzofuran-5-yl)-1,3-thiazole-4-carboxylic acid (171 mg, 0.69 mmol) in 5 ml N,N-dimethylformamide, were added (2-amino-1H-benzo[d]imidazol-5-yl) (1H-pyrrol-2-yl)methanone hydrobromide (234 mg, 0.76 mmol), 2-(1H-benzotriazole-1-yl)-1,1,3,3-tetramethyluroniumhexafluorophosphate (HBTU) (262 mg, 0.69 mmol), 4-(dimethylamino)-pyridine (8.5 mg, 0.07 mmol) and N,N-diisopropylethylamine (0.3 ml, 1.73 mmol). The reaction mixture was stirred at room temperature for 18 h, and then poured into ice water. The formed white precipitate was filtered off and dried. The crude product was washed with diisopropyl ether and MeOH. The product was obtained as a light brown solid (236 mg, 0.52 mmol, 75% yield). $^1$H NMR (400 MHz, DMSO-d$_6$) δ ppm 3.10-3.50 (m, 2H), 4.64 (bt, 2H), 6.29 (s, 1H), 6.71-7.07 (m, 2H), 7.19 (s, 1H), 7.46-7.82 (m, 2H), 7.82-8.27 (m, 3H), 8.56 (s, 1H), 11.81 (bs. 1H), 11.95 (s, 1H), 12.49 (bs, 1H). LC/MS [M+H]$^+$: 455.8.

N-(1H-1,3-Benzodiazol-2-yl)-2-(2,3-dihydro-1-benzofuran-5-yl)-1,3-thiazole-4-carboxamide (50)

To a solution of 2-(2,3-dihydro-1-benzofuran-5-yl)-1,3-thiazole-4-carboxylic acid (179 mg, 0.72 mmol) in 4 ml N,N-dimethylformamide, were added 2-aminobenzimidazole (106 mg, 0.8 mmol), 2-(1H-benzotriazole-1-yl)-1,1,3,3-tetramethyluroniumhexafluorophosphate (HBTU) (275 mg, 0.72 mmol), 4-dimethylaminopyridine 8.8 mg, 0.07 mmol) and N,N-diisopropylethylamine (0.32 ml, 1.81 mmol). The reaction mixture was stirred at room temperature for 18 h, and then poured into ice water. The formed white precipitate was filtered off and dried. The crude product was washed with MeOH and diisopropyl ether and dried. The product was obtained as a white solid (183 mg, 0.5 mmol, 70% yield). $^1$H NMR (400 MHz, DMSO-d$_6$) δ ppm 3.15-3.50 (m, 2H), 4.64 (t, J=8.3 Hz, 2H), 6.91 (d, J=8.0 Hz, 1H), 7.14 (bs, 2H), 7.50 (bs, 2H), 7.91 (d, J=7.68 Hz, 1H), 8.10 (s, 1H), 8.51 (s, 1H), 11.92 (bs, 2H). LC/MS [M+H]$^+$: 362.9.

2-(2,3-Dihydro-1-benzofuran-5-yl)-N-[6-(morpholine-4-carbonyl)-1,3-benzothiazol-2-yl]-1,3-thiazole-4-carboxamide (51)

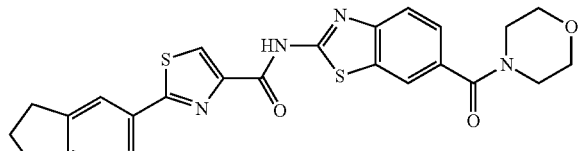

To a stirred suspension of 2-({[2-(2,3-dihydro-1-benzofuran-5-yl)-1,3-thiazol-4-yl]carbonyl}amino)-1,3-benzothiazole-6-carboxylic acid (230 mg, 0.54 mmol) and HBTU (309 mg, 0.82 mmol) in 3.6 ml absolute dioxane, morpholine (238 mg, 3.26 mmol) was added. The reaction mixture was stirred at room temperature for 24 h, the precipitate was filtered off and washed with dioxane. Filtrate was evaporated to dryness, residue was treated with water which led to an oily residue which solidified on treating with diluted HCl. The product was filtered off, washed with water and crystallized from EtOH. The precipitate was dissolved in chloroform and subjected to flash column chromatography on silica gel, eluent chloroform followed by EtOAc. Fractions containing the product were combined, the solvent was evaporated to dryness and the residue was crystallized from a mixture of chloroform and EtOH to give pure product as light beige powder (60 mg, 0.12 mmol, 23% yield). $^1$H NMR (400 MHz, CDCl$_3$) δ ppm 3.33 (t, J=8.7 Hz, 3H), 3.75 (bs, 8H), 4.70 (t, J=8.8 Hz, 2H), 6.87 (d, J=8.3 Hz, 1H), 7.51 (dd, J=8.3, 1.6 Hz, 1H), 7.74 (dd, J=8.3, 1.9 Hz, 1H), 7.85 (d, J=8.3 Hz, 1H), 7.88 (d, J=1.3 Hz, 1H), 7.98 (d, J=1.3 Hz, 1H), 8.25 (s, 1H), 10.78 (s, 1H). M.p.: 258-260° C. (decomposition). LC/MS [M+H]$^+$: 492.8.

2-(2,3-Dihydro-1-benzofuran-5-yl)-N-[5-(piperidin-1-yl)-1,3,4-thiadiazol-2-yl]-1,3-thiazole-4-carboxamide (52)

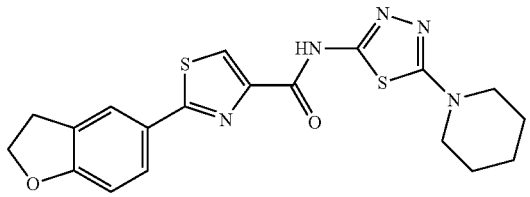 [SMILES: O=C(Nc1nnc(N2CCCCC2)s1)c1csc(-c2ccc3c(c2)CCO3)n1]

To a stirred suspension of 2-(2,3-dihydro-1-benzofuran-5-yl)-1,3-thiazole-4-carboxylic acid (235 mg, 0.95 mmol), 5-piperidin-1-yl-1,3,4-thiadiazol-2-amine (88 mg 1.05 mmol) and HBTU (541 mg, 1.43 mmol) in 2.2 ml absolute dioxane DIPEA (346 mg, 2.68 mmol) was added. The suspension was stirred at room temperature for 20 h, filtered, washed with some dioxane and Et$_2$O. The residue was crystallized from a mixture of DMF and EtOH, and washed with some cold EtOH, Et$_2$O and dried. The product was obtained as a pale pink powder (69 mg, 0.17 mmol, 18% yield). $^1$H NMR (400 MHz, DMSO-d$_6$) δ ppm 12.20 (s, 1 H), 8.47 (s, 1H), 8.09 (d, J=1.4 Hz, 1H), 7.89 (dd, J=8.3, 2.0 Hz, 1H), 6.88 (d, J=8.3 Hz, 1H), 4.63 (t, J=8.8 Hz, 2H), 3.42 (d, J=5.1 Hz, 4H), 3.27 (t, J=8.8 Hz, 2H), 1.60 (s, 6H). M.p.: 208-210° C. (decomposition). LC/MS [M+H]$^+$: 413.9.

Ethyl 1-{5-[2-(2,3-dihydro-1-benzofuran-5-yl)-1,3-thiazole-4-amido]-1,3,4-thiadiazol-2-yl}piperidine-4-carboxylate (53)

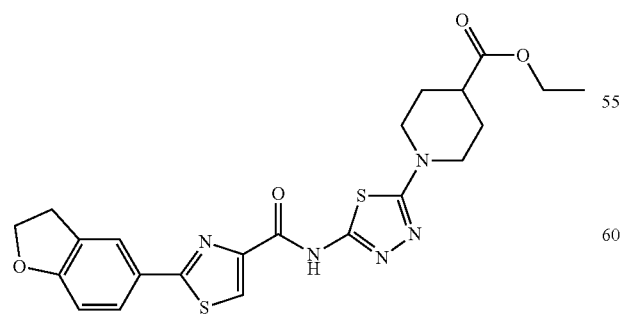

To a mixture of 2-(2,3-dihydro-1-benzofuran-5-yl)-1,3-thiazole-4-carboxylic acid (80 mg, 0.32 mmol), ethyl 1-(5-amino-1,3,4-thiadiazol-2-yl)piperidine-4-carboxylate (83 mg, 0.32 mmol) and HBTU (120 mg, 0.32 mmol) under stirring and heating at 100° C. 1 ml of dry pyridine was added. The mixture was stirred at 100° C. for 5 h, pyridine was evaporated, and the residue was diluted with an aqueous Na$_2$CO$_3$ solution. The resulting precipitate was filtered off and purified by flash column chromatography on silica gel (EtOAc as eluent). The product was obtained as a light yellow solid (112 mg, 0.23 mmol, yield 72% yield). $^1$H NMR (DMSO-d$_6$, CCl$_4$) δ ppm 1.24 (t, J=7.2 Hz, 3H), 1.73 (m, 2H), 1.98 (m, 2H), 2.59 (m, 1H), 3.18 (m, 2H), 3.30 (t, J=8.6 Hz, 2H), 3.85 (m, 2H), 4.10 (q, J=7.2 Hz, 2H), 4.64 (t, J=8.6 Hz, 2H), 6.81 (d, J=8.4 Hz, 1H), 7.85 (dd, J=8.4, 2.0 Hz, 1H), 8.05 (d, J=2.0 Hz, 1H.), 8.17 (s, 1H), 11.94 (bs, 1H). M.p.: 186-188° C. LC/MS [M+H]$^+$: 485.9.

2-(2,3-Dihydro-1-benzofuran-5-yl)-N-(1-methyl-1H-1,3-benzodiazol-2-yl)-1,3-thiazole-4-carboxamide (54)

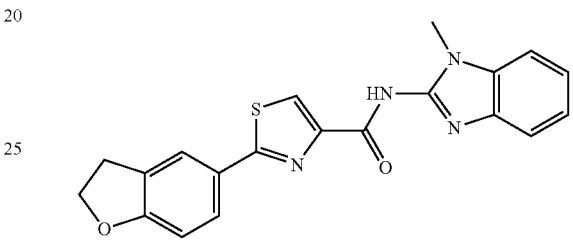

To a solution of 2-(2,3-dihydro-1-benzofuran-5-yl)-1,3-thiazole-4-carboxylic acid (171 mg, 0.69 mmol) in 4 ml N,N-dimethylformamide, were added 2-amino-1-methyl-benzimidazole (112 mg, 0.76 mmol), 2-(1H-benzotriazole-1-yl)-1,1,3,3-tetramethyluroniumhexafluoro-phosphate (HBTU) 262 mg, 0.69 mmol), 4-(dimethylamino)pyridine (8.5 mg, 0.07 mmol) and N,N-diisopropylethylamine (0.3 ml, 1.73 mmol). The reaction mixture was stirred at room temperature for 18 h, and then poured into ice water. The formed white precipitate was filtered off and dried. The crude product was washed with MeOH and diisopropyl ether and dried. The product was obtained as a white solid (212 mg, 0.56 mmol, 82% yield). $^1$H NMR (400 MHz, DMSO-d$_6$) δ ppm 3.13-3.49 (m, 2H), 3.71 (s, 3H), 4.63 (t, J=8.3 Hz, 2H), 6.90 (d, J=8.0 Hz, 1H), 7.08-7.36 (m, 2H), 7.36-7.68 (m, 2H), 7.68-8.04 (m, 2H), 8.39 (s, 1H), 12.56 (bs, 1H). LC/MS [M+H]$^+$: 376.9.

Ethyl 3-[2-(2,3-dihydro-1-benzofuran-5-yl)-1,3-thiazole-4-amido]-1H-pyrazole-4-carboxylate (55)

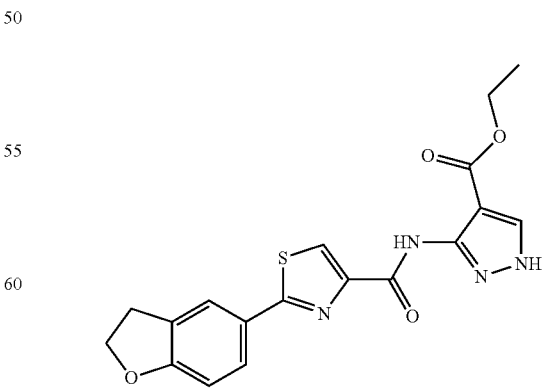

The mixture of ethyl 3-amino-1H-pyrazole-4-carboxylate (62 mg, 0.40 mmol), 2-(2,3-dihydro-1-benzofuran-5-yl)-1, 3-thiazole-4-carboxylic acid (106 mg, 0.43 mmol), HBTU (205 mg, 0.54 mmol) and 1 ml dry pyridine was stirred at 100° C. for 2 h. After cooling, 5 ml ethanol was added to the reaction mixture and the suspension was stirred for 0.5 h. The precipitate was filtered off, suspended in 20 ml ethanol and refluxed for 10 min. After cooling, the precipitate was filtered off, washed with ethanol and dried on air. The product was obtained as a white solid (85 mg, 0.22 mmol, 55% yield). $^1$H NMR (400 MHz, DMSO-d$_6$+CD$_3$COOD) δ ppm 1.38 (t, J=7.0 Hz, 3H) 3.31 (t, J=8.7 Hz, 2H) 4.35 (q, J=7.2 Hz, 2H) 4.65 (t, J=8.7 Hz, 2H) 6.86 (d, J=8.3 Hz, 1H) 7.75-7.84 (m, 2H) 7.87 (s, 1H) 8.39 (d, J=1.3 Hz, 1H) 10.96 (s, 1H). M.p.: 230-233° C. LC/MS [M+H]$^+$: 384.8.

2-(2,3-Dihydro-1-benzofuran-5-yl)-N-[5-(morpholin-4-yl)-1,3,4-thiadiazol-2-yl]-1,3-thiazole-4-carboxamide (56)

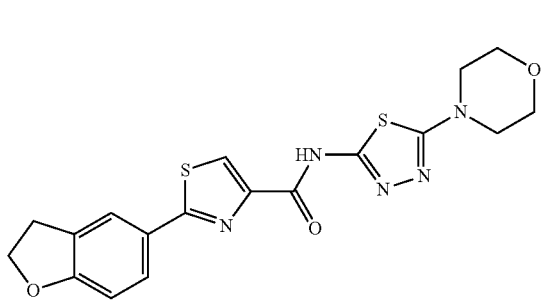 [SMILES: O=C(Nc1nnc(N2CCOCC2)s1)c1csc(-c2ccc3c(c2)CCO3)n1]

To a mixture of 2-(2,3-dihydro-1-benzofuran-5-yl)-1,3-thiazole-4-carboxylic acid (80 mg, 0.32 mmol), 5-morpholin-4-yl-1,3,4-thiadiazol-2-amine (62 mg, 0.32 mmol) and HBTU (120 mg, 0.32 mmol) under stirring and heating at 100° C., 1 ml of dry pyridine was added. The mixture was heated at 100° C. for 4 h, pyridine was evaporated, and the residue was diluted with an aqueous Na$_2$CO$_3$ solution. The resulting precipitate was filtered off, washed with hot EtOAc and hexane, filtered off and dried. The product was obtained as a light yellow solid (115 mg, 0.28 mmol, 86% yield). $^1$H NMR (DMSO-d6, CCl$_4$) δ ppm 3.30 (t, J=8.6 Hz, 2H), 3.43 (m, 4H), 3.76 (m, 4H), 4.64 (t, J=8.6 Hz, 2H), 6.81 (d, J=8.4 Hz, 1H), 7.86 (dd, J=8.2, 1.8 Hz, 1H), 8.05 (s, 1H), 8.38 (s, 1H), 12.02 (bs, 1H). M.p.: 213-215° C. LC/MS [M+H]$^+$: 415.9.

2-(2,3-Dihydro-1-benzofuran-5-yl)-N-[5-(4-methylpiperazin-1-yl)-1,3,4-thiadiazol-2-yl]-1,3-thiazole-4-carboxamide (57)

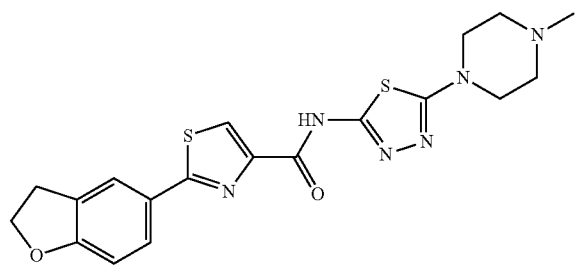 [SMILES: CN1CCN(c2nnc(NC(=O)c3csc(-c4ccc5c(c4)CCO5)n3)s2)CC1]

To a mixture of 2-(2,3-dihydro-1-benzofuran-5-yl)-1,3-thiazole-4-carboxylic acid (80 mg, 0.32 mmol). 5-(4-methylpiperazin-1-yl)-1,3,4-thiadiazol-2-amine (64 mg, 0.32 mmol) and HBTU (120 mg, 0.32 mmol) under stirring and heating at 100° C., 1 ml of dry pyridine was added. The mixture was heated at 100° C. for 5 h, pyridine was evaporated, and the residue was diluted with an aqueous Na$_2$CO$_3$ solution. The resulting precipitate was filtered off, washed with hot EtOAc and hexane, filtered off and dried. The product was obtained as a pale yellow solid (97 mg, 0.23 mmol, 71% yield). $^1$H NMR (DMSO-d$_6$, CCl$_4$) δ ppm 2.26 (s, 3H), 2.49 (m, 4H), 3.30 (t, J=8.6 Hz, 2H), 3.43 (m, 4H), 4.64 (t, J=8.6 Hz, 2H), 6.81 (d, J=8.4 Hz, 1H), 7.83 (d, J=8.2 Hz, 1H), 8.02 (s, 1H), 8.31 (s, 1H), 12.00 (bs, 1H). M.p.: 230-232° C. LC/MS [M+H]$^+$: 428.8.

2-(2,3-Dihydro-1-benzofuran-5-yl)-N-(5-methyl-1,3-thiazol-2-yl)-1,3-thiazole-4-carboxamide (58)

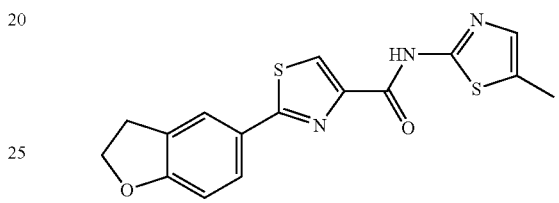

To a mixture of 2-(2,3-dihydro-1-benzofuran-5-yl)-1,3-thiazole-4-carboxylic acid (80 mg, 0.32 mmol), 5-methylthiazol-2-amine (37 mg, 0.32 mmol) and HBTU (120 mg, 0.32 mmol) under stirring and heating at 90° C., 1 ml of dry pyridine was added. The mixture was heated at 90° C. for 4.5 h, pyridine was evaporated, and the residue was diluted with an aqueous Na$_2$CO$_3$ solution. The resulting precipitate was filtered off and purified by flash column chromatography on silica gel (CHCl$_3$ as eluent). The product was obtained as a white solid (94 mg, 0.27 mmol, 86% yield). $^1$H NMR (DMSO-d$_6$, CCl$_4$) δ ppm 2.42 (s, 3H), 3.30 (t, J=8.6 Hz, 2H), 4.64 (t, J=8.6 Hz, 2H), 6.81 (d, J=8.4 Hz, 1H), 7.14 (s, 1H), 7.83 (dd, J=8.4, 2.0 Hz, 1H), 8.01 (d, J=1.2 Hz, 1H), 8.38 (s, 1H), 11.61 (bs, 1H). M.p.: 230-232° C. LC/MS [M+H]$^+$: 343.8.

2-(2,3-Dihydro-1-benzofuran-5-yl)-N-[5-(pyridin-4-yl)-1,3,4-thiadiazol-2-yl]-1,3-thiazole-4-carboxamide (59)

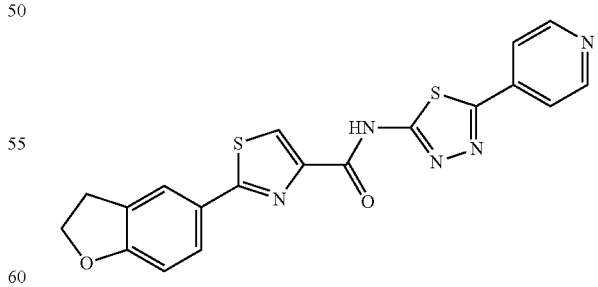

To a stirred suspension of 2-(2,3-dihydro-1-benzofuran-5-yl)-1,3-thiazole-4-carboxylic acid (77 mg, 0.31 mmol), 5-pyridin-4-yl-1,3,4-thiadiazol-2-amine (61 mg 0.34 mmol) and HBTU (177 mg, 0.47 mmol) in 2.3 ml dry CH$_2$Cl$_2$, DIPEA (128 mg, 0.99 mmol) was added. The suspension was stirred at room temperature for 24 h, the precipitate was filtered off, washed with some CH$_2$Cl$_2$, Et$_2$O, diluted AcOH, then with water and dried. The precipitate was crystallized from a mixture of DMF and EtOH to give the product as a pale yellow powder (118 mg, 0.29 mmol, 93% yield). $^1$H NMR (400 MHz, DMSO-d$_6$) δ ppm 12.93 (s, 1H), 8.71 (d, J=6.0 Hz, 2H), 8.52 (s, 1H), 8.08 (s, 1H), 7.91 (d, J=1.6 Hz, 1H), 7.88 (s, 1H), 6.84 (d, J=8.3 Hz, 2H), 4.65 (t, J=8.8 Hz, 2H), 3.32 (t, J=8.7 Hz, 2H). M.p.: 177-180° C. LC/MS [M+H]$^+$: 407.8.

N-(5-Benzoyl-1H-1,3-benzodiazol-2-yl)-2-(2,3-dihydro-1-benzofuran-5-yl)-1,3-thiazole-4-carboxamide (60)

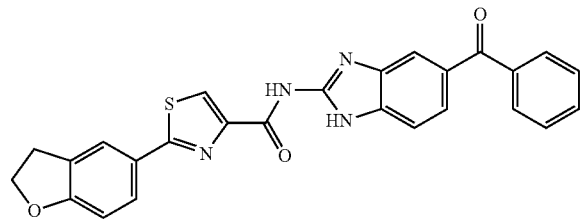 [SMILES: O=C(c1ccccc1)c1ccc2[nH]c(NC(=O)c3csc(-c4ccc5c(c4)CCO5)n3)nc2c1]

To a solution of 2-(2,3-dihydro-1-benzofuran-5-yl)-1,3-thiazole-4-carboxylic acid (104 mg, 0.42 mmol) in 5 ml N,N-dimethylformamide, were added (2-amino-1H-benzo[d]imidazol-5-yl)(phenyl)methanone hydrobromide (147 mg, 0.46 mmol), 2-(1H-benzotriazole-1-yl)-1,1,3,3-tetramethyluroniumhexafluorophosphate (HBTU) (160 mg, 0.42 mmol), 4-(dimethylamino)-pyridine (5.1 mg, 0.04 mmol) and N,N-diisopropylethyl amine (0.18 ml, 1.05 mmol). The reaction mixture was stirred at room temperature for 18 h, and then poured into ice water. The formed precipitate was filtered off and dried. The crude product was washed with diisopropyl ether and MeOH. The product was obtained as a white solid (119 mg, 0.26 mmol, 61% yield). $^1$H NMR (400 MHz, DMSO-d$_6$) δ ppm 3.15-3.51 (m, 2H), 4.65 (bs, 2H), 6.92 (bs, 1H), 7.44-8.25 (m, 10H), 8.57 (s, 1H), 11.87 (bs, 1H), 12.57 (bs, 1H). LC/MS [M+H]$^+$: 466.8.

Ethyl 2-({5-[2-(2,3-dihydro-1-benzofuran-5-yl)-1,3-thiazole-4-amido]-1H-1,2,4-triazol-3-yl}sulfanyl)acetate (61)

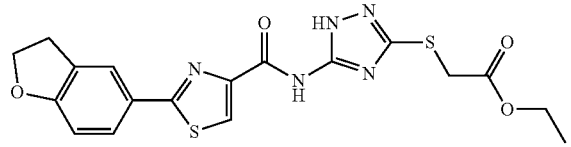 [SMILES: CCOC(=O)CSc1n[nH]c(NC(=O)c2csc(-c3ccc4c(c3)CCO4)n2)n1]

To a mixture of 2-(2,3-dihydro-1-benzofuran-5-yl)-1,3-thiazole-4-carbonyl chloride (144 mg, 0.54 mmol) and 1H-1,2,4-triazol-5-amine (100 mg, 0.49 mmol) 2 ml of dry hot pyridine was added. The solution was heated at reflux for 3 h, pyridine was evaporated and the residue was diluted with an aqueous Na$_2$CO$_3$ solution. The resulting precipitate was filtered off and dried. The crude product was purified by flash column chromatography on silica gel (EtOAc:CH$_2$Cl$_2$ 1:1). The product was obtained as a light yellow solid (40 mg, 0.09 mmol, 19% yield). $^1$H NMR (DMSO-d$_6$) δ ppm 1.19 (t, J=7.2 Hz, 3H), 3.28 (t, J=8.8 Hz, 2H), 4.01 (s, 2H), 4.11 (q, J=7.2 Hz, 2H), 4.64 (t, J=8.8 Hz, 2H), 6.90 (d, J=8.4 Hz, 1H), 7.91 (d, J=8.4 Hz, 1H), 8.10 (s, 1H), 8.50 (s, 1H), 11.70 (bs, 1H), 13.70 (bs, 1H). LC/MS [M+H]$^+$: 431.8.

2-(2,3-Dihydro-1-benzofuran-5-yl)-N-(1H-pyrazol-3-yl)-1,3-thiazole-4-carboxamide (62)

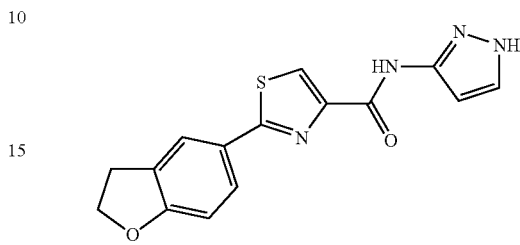

The mixture of 1H-pyrazol-3-amine (50 mg, 0.61 mmol), 2-(2,3-dihydro-1-benzofuran-5-yl)-1,3-thiazole-4-carboxylic acid (106 mg, 0.40 mmol), HBTU (205 mg, 0.54 mmol) and 1 ml dry pyridine was stirred at 100° C. for 2 h. After cooling 10 ml water was added to the reaction mixture and the suspension was stirred for 0.5 h. The precipitate was filtered off and crystallized from a minimal amount of ethanol (1 ml). The product was obtained as a light yellow solid (54 mg, 0.17 mmol, 43% yield). $^1$H NMR (400 MHz, DMSO-d$_6$) δ ppm 3.30 (t, J=8.7 Hz, 2H) 4.64 (t, J=8.8 Hz, 2H) 6.64 (bs, 1H) 6.82 (d, J=8.3 Hz, 1H) 7.52 (bs, 1H) 7.80 (dd, J=8.3, 1.51 Hz, 1H) 7.94 (s, 1H) 8.21 (s, 1H) 9.91 (bs, 1H) 12.37 (bs, 1H). M.p.: 200-203° C. LC/MS [M+H]$^+$: 312.9.

2-(2,3-Dihydro-1-benzofuran-5-yl)-N-(1H-1,2,4-triazol-3-yl)-1,3-thiazole-4-carboxamide (63)

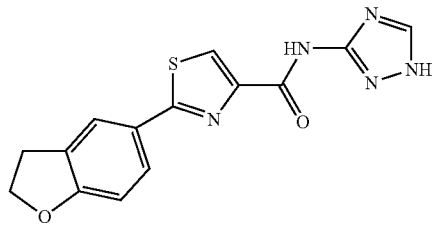 [SMILES: O=C(Nc1nc[nH]n1)c1csc(-c2ccc3c(c2)CCO3)n1]

To a stirred suspension of 2-(2,3-dihydro-1-benzofuran-5-yl)-1,3-thiazole-4-carboxylic acid (100 mg, 0.40 mmol), 1H-1,2,4-triazol-3-amine (34 mg 0.41 mmol) and HBTU (230 mg, 0.61 mmol) in 1.8 ml dry pyridine, DIPEA (131 mg, 1.01 mmol) was added. The suspension was refluxed under stirring for 2 h and all volatiles were evaporated to dryness at reduced pressure. The residue was washed subsequently with water, an aqueous Na$_2$CO$_3$ solution, water, diluted HCl, water again, and then dried. The crude product was crystallized from DMF. The product was obtained as a light yellow solid (71 mg, 0.23 mmol, 57% yield). $^1$H NMR (400 MHz, acetic acid) δ ppm 9.07 (s, 1H), 9.01 (s, 1H), 8.06 (s, 1H), 8.00 (d, J=8.5 Hz, 1H), 7.10 (d, J=8.6 Hz, 1H), 4.87 (t, J=8.7 Hz, 2H), 3.42 (t, J=8.7 Hz, 2H). M.p.: >307° C. LC/MS [M+H]$^+$: 313.9.

2-(2,3-Dihydro-1-benzofuran-5-yl)-N-(5-methoxy-1,2,4-thiadiazol-3-yl)-1,3-thiazole-4-carboxamide (64)

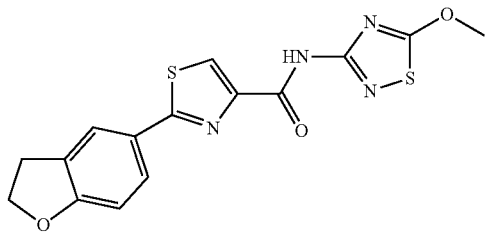 [SMILES: COc1nc(NC(=O)c2csc(-c3ccc4c(c3)CCO4)n2)ns1]

The mixture of 5-methoxy-1,2,4-thiadiazol-3-amine (59 mg, 0.45 mmol), 2-(2,3-dihydro-1-benzofuran-5-yl)-1,3-thiazole-4-carboxylic acid (106 mg, 0.43 mmol), HBTU (205 mg, 0.54 mmol), DIPEA (0.15 ml, 0.87 mmol) and 5 ml dry DCM was stirred at room temperature for 18 h. Subsequently, the solvent was evaporated to dryness, 5 ml of an 5% aqueous Na$_2$CO$_3$ solution were added to the residue and the suspension was stirred for 1 h. The supernatant was poured off from the resulting resin. The resin was dissolved in 3 ml chloroform and subjected to flash column chromatography on silica gel (0.040-0.100 mm) using chloroform as eluent. The fractions containing product were collected. The product was obtained as a light yellow solid (54 mg, 0.15 mmol, 38% yield). $^1$H NMR (400 MHz, DMSO-d$_6$) δ ppm 3.29 (t, J=8.8 Hz, 2H) 4.20 (s, 3H) 4.63 (t, J=8.8 Hz, 2H) 6.85 (d, J=8.3 Hz, 1H) 7.83 (dd, J=8.3, 1.76 Hz, 1H) 7.98 (s, 1H) 8.37 (s, 1H) 10.60 (s, 1H). M.p.: 133-136° C. LC/MS [M+H]$^+$: 360.8.

2-(2,3-Dihydro-1-benzofuran-5-yl)-N-(1,3-thiazol-2-yl)-1,3-thiazole-4-carboxamide (65)

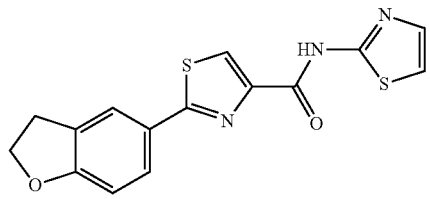

To a solution of 2-(2,3-dihydro-1-benzofuran-5-yl)-1,3-thiazole-4-carboxylic acid (110 mg, 0.44 mmol) in 2 ml N,N-dimethylformamide, were added 2-aminothiazole (49 mg, 0.49 mmol), 2-(1H-benzotriazole-1-yl)-1,1,3,3-tetramethyluroniumhexafluorophosphate (HBTU) (169 mg, 0.44 mmol), 4-(dimethylamino)pyridine (5.4 mg, 0.04 mmol) and N,N-diisopropylethyl amine (0.19 ml, 1.11 mmol). The reaction mixture was stirred at room temperature for 18 h, and then poured into ice water. The formed precipitate was filtered off. The crude product was purified by flash column chromatography on silica gel (eluent: DCM 100%). The crude product was suspended in diisopropyl ether, filtered off and dried. The product was obtained as a white solid (67 mg, 0.2 mmol, 46% yield). $^1$H NMR (400 MHz, DMSO-d$_6$) δ ppm 3.20-3.36 (m, 2H), 4.63 (t, J=8.8 Hz, 2H), 6.90 (d, J=8.3 Hz, 1H), 7.32 (d, J=3.5 Hz, 1H), 7.58 (d, J=3.5 Hz, 1H), 7.91 (dd, J=8.3, 1.9 Hz, 1H), 8.10 (bs, 1H), 8.51 (s, 1H), 12.21 (bs, 1H). LC/MS [M+H]$^+$: 329.8.

2-(2,3-Dihydro-1-benzofuran-5-yl)-N-(5-methyl-1H-pyrazol-3-yl)-1,3-thiazole-4-carboxamide (66)

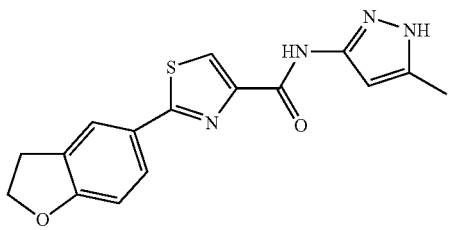 [SMILES: Cc1cc(NC(=O)c2csc(-c3ccc4c(c3)CCO4)n2)n[nH]1]

To a mixture of 2-(2,3-dihydro-1-benzofuran-5-yl)-1,3-thiazole-4-carboxylic acid (80 mg, 0.32 mmol), 5-methyl-1H-pyrazol-3-amine (31 mg, 0.32 mmol) and HBTU (120 mg, 0.32 mmol) under stirring and heating at 90° C., 1 ml of dry pyridine was added. The mixture was heated at 90° C. for 5 h, pyridine was evaporated, and the residue was diluted with an aqueous Na$_2$CO$_3$ solution. The resulting precipitate was filtered off and purified by flash column chromatography on silica gel (EtOAc:CHCl$_3$ 1:1). The product was obtained as a white solid (56 mg, 0.17 mmol, 54% yield). $^1$H NMR (DMSO-d$_6$, CCl$_4$) δ ppm 2.27 (s, 3H), 3.30 (t, J=8.8 Hz, 2H), 4.63 (t, J=8.6 Hz, 2H), 6.39 (s, 1H), 6.81 (d, J=8.4 Hz, 1H), 7.79 (dd, J=8.6 1.2 Hz, 1H), 7.94 (s, 1H), 8.19 (s, 1H), 9.76 (bs, 1H), 12.03 (bs, 1H). M.p.: 210-212° C. LC/MS [M+H]$^+$: 326.9.

N-(5-Bromo-1,3,4-thiadiazol-2-yl)-2-(2,3-dihydro-1-benzofuran-5-yl)-1,3-thiazole-4-carboxamide (67)

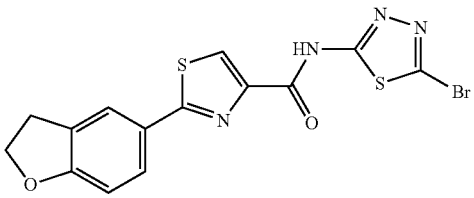 [SMILES: O=C(Nc1nnc(Br)s1)c1csc(-c2ccc3c(c2)CCO3)n1]

To a stirred suspension of 2-(2,3-dihydro-1-benzofuran-5-yl)-1,3-thiazole-4-carboxylic acid (116 mg, 0.47 mmol), 5-bromo-1,3,4-thiadiazol-2-amine (92 mg 0.52 mmol) and HBTU (266 mg, 0.70 mmol) in 1.9 ml absolute dioxane, DIPEA (151 mg, 1.17 mmol) was added. The suspension was stirred at room temperature for 20 h, filtered, washed with some EtOH and Et$_2$O, dried, washed with water and dried again. The product was obtained as a pale yellow powder (70 mg, 0.17 mmol, 36% yield). $^1$H NMR (400 MHz, DMSO-d$_6$) δ ppm 3.31 (t, J=8.7 Hz, 2H), 4.65 (t, J=8.8 Hz, 2H), 6.83 (d, J=8.3 Hz, 1H), 7.88 (dd, J=8.3, 1.9 Hz, 1H), 8.07 (d, J=1.3 Hz, 1H), 8.51 (s, 1H), 13.06 (s, 1H). M.p.: 142-144° C. LC/MS [M+H]$^+$: 408.9.

2-(2,3-Dihydro-1-benzofuran-5-yl)-N-[3-(3-fluorophenyl)-1H-1,2,4-triazol-5-yl]-1,3-thiazole-4-carboxamide (68)

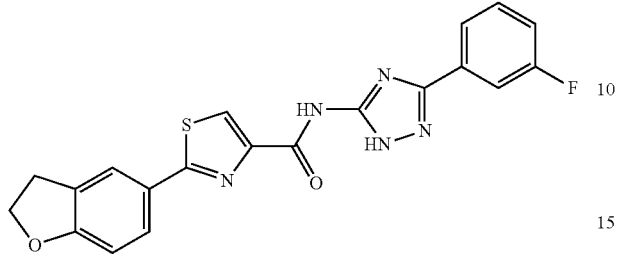

To a mixture of 2-(2,3-dihydro-1-benzofuran-5-yl)-1,3-thiazole-4-carboxylic acid (70 mg, 0.28 mmol), 1H-1,2,4-triazol-5-amine (50 mg, 0.28 mmol) and HBTU (120 mg, 0.32 mmol) under stirring and heating at 110° C., 2 ml of dry pyridine was added. The mixture was heated at 110° C. for 5 h, pyridine was evaporated, and the residue was diluted with an aqueous $Na_2CO_3$ solution. The resulting precipitate was filtered off, dissolved in hot DMF, settled by addition of EtOAc and hexane, filtered off and dried. The product was obtained as a light yellow solid (67 mg, 0.16 mmol, 59% yield). $^1$H NMR (DMSO-$d_6$, $CCl_4$) δ ppm 3.31 (t, J=8.8 Hz, 2H), 4.65 (t, J=8.8 Hz, 2H), 6.83 (d, J=8.0 Hz, 1H), 7.14 (m, 1H), 7.46 (m, 1H), 7.71 (d, J=10.4 Hz, 1H), 7.84-7.90 (m, 2H), 8.06 (s, 1H), 8.42 (s, 1H), 11.55 (bs, 1H), 13.66 (bs, 1H). LC/MS [M+H]$^+$: 407.8.

2-(2,3-Dihydro-1-benzofuran-5-yl)-N-(3-methyl-1,2,4-thiadiazol-5-yl)-1,3-thiazole-4-carboxamide (69)

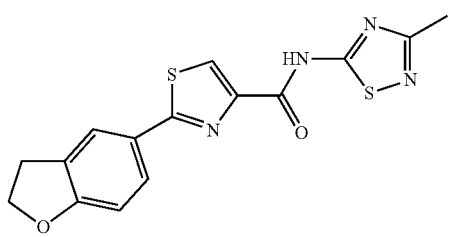 [SMILES: Cc1nsc(NC(=O)c2csc(-c3ccc4c(c3)CCO4)n2)n1]

The mixture of 3-methyl-1,2,4-thiadiazol-5-amine (50 mg, 0.43 mmol), 2-(2,3-dihydro-1-benzofuran-5-yl)-1,3-thiazole-4-carboxylic acid (106 mg, 0.40 mmol), HBTU (205 mg, 0.54 mmol), DIPEA (0.15 ml, 0.87 mmol) and 5 ml dry DCM was stirred at room temperature for 18 h. Subsequently, the solvent was evaporated to dryness, 5 ml ethanol was added to the residue and the suspension was refluxed for 15 min. After cooling, the precipitate was filtered off, washed with ethanol and dried on air. The product was obtained as a pale yellow solid (99 mg, 0.29 mmol, 72% yield). $^1$H NMR (400 MHz, DMSO-$d_6$) δ ppm 2.52 (s, 3H) 3.30 (t, J=8.66 Hz, 2H) 4.64 (t, J=8.7 Hz, 2H) 6.81 (d, J=8.3 Hz, 1H) 7.86 (dd, J=8.3, 1.76 Hz, 1H) 8.05 (s, 1H) 8.50 (s, 1H) 12.92 (s, 1H). M.p.: 208-210° C. LC/MS [M+H]$^+$: 344.8.

N-(5-Amino-1,2,4-thiadiazol-3-yl)-2-(2,3-dihydro-1-benzofuran-5-yl)-1,3-thiazole-4-carboxamide (70)

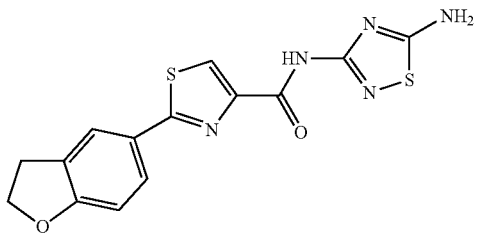 [SMILES: Nc1nc(NC(=O)c2csc(-c3ccc4c(c3)CCO4)n2)ns1]

The mixture of 1,2,4-thiadiazole-3,5-diamine (96 mg, 0.80 mmol), 2-(2,3-dihydro-1-benzofuran-5-yl)-1,3-thiazole-4-carboxylic acid (106 mg, 0.40 mmol), HBTU (205 mg, 0.54 mmol), DIPEA (0.15 ml, 0.87 mmol) and 5 ml dry DCM was stirred at room temperature for 18 h. The precipitate was filtered off, washed by DCM and suspended in ethanol (20 ml). The suspension was refluxed for 15 min. After cooling the precipitate was filtered off and the filtrate was evaporated in vacuum to 5 ml volume. After staying for 2 hours in the refrigerator (approx. 4° C.) the residue of pure product was filtered off, washed with ethanol and dried on air. The product was obtained as a white solid (60 mg, 0.17 mmol, 43% yield). $^1$H NMR (400 MHz, DMSO-$d_6$) δ ppm 3.30 (t, J=8.8 Hz, 2H) 4.64 (t, J=8.8 Hz, 2H) 6.82 (d, J=8.3 Hz, 1H) 7.77 (dd, J=8.3, 1.76 Hz, 1H) 7.85-7.98 (m, 3H) 8.27 (s, 1H) 9.97 (s, 1H). M.p.: 245-248° C. LC/MS [M+H]$^+$: 345.8.

2-(2,3-Dihydro-1-benzofuran-5-yl)-N-(1,3,4-thiadiazol-2-yl)-1,3-thiazole-4-carboxamide (71)

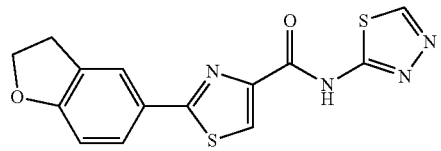 [SMILES: O=C(Nc1nncs1)c1csc(-c2ccc3c(c2)CCO3)n1]

To a mixture of 2-(2,3-dihydro-1-benzofuran-5-yl)-1,3-thiazole-4-carboxylic acid (80 mg, 0.32 mmol), 1,3,4-thiadiazol-2-amine (33 mg, 0.32 mmol) and HBTU (120 mg, 0.32 mmol) under stirring and heating at 100° C., 1 ml of dry pyridine was added. The mixture was heated at 100° C. for 5 h, pyridine was evaporated, and the residue was diluted with an aqueous $Na_2CO_3$ solution. The resulting precipitate was filtered off, washed with hot EtOAc and hexane, filtered off and dried. The product was obtained as a pale yellow solid (87 mg, 0.26 mmol, 82% yield). $^1$H NMR (DMSO-$d_6$, $CCl_4$) δ ppm 3.31 (t, J=8.6 Hz, 2H), 4.64 (t, J=8.6 Hz, 2H), 6.82 (d, J=8.8 Hz, 1H), 7.87 (d, J=8.8 Hz, 1H), 8.07 (s, 1H), 8.47 (s, 1H), 9.11 (s, 1H), 12.57 (bs, 1H). M.p.: 214° C. LC/MS [M+H]$^+$: 330.8.

2-(2,3-Dihydro-1-benzofuran-5-yl)-N-(4-methyl-1,3-thiazol-2-yl)-1,3-thiazole-4-carboxamide (72)

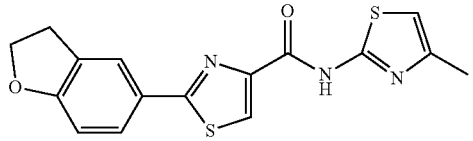 [SMILES: Cc1csc(NC(=O)c2csc(-c3ccc4c(c3)CCO4)n2)n1]

To a mixture of 2-(2,3-dihydro-1-benzofuran-5-yl)-1,3-thiazole-4-carboxylic acid (80 mg, 0.32 mmol), 4-methyl-thiazol-2-amine hydrochloride (49 mg, 0.32 mmol) and HBTU (120 mg, 0.32 mmol) under stirring and heating at 100° C., 1 ml of dry pyridine was added. The mixture was heated at 100° C. for 5 h, pyridine was evaporated, and the residue was diluted with an aqueous $Na_2CO_3$ solution. The resulting precipitate was filtered off and purified by flash column chromatography on silica gel (EtOAc as eluent). The product was obtained as a pale yellow solid (60 mg, 0.17 mmol, 55% yield). $^1$H NMR (DMSO-$d_6$, $CCl_4$) δ ppm 2.34 (s, 3H), 3.30 (t, J=8.6 Hz, 2H), 4.64 (t, J=8.6 Hz, 2H), 6.70 (s, 1H), 6.81 (d, J=8.6 Hz, 1H), 7.84 (dd, J=8.6, 2.0 Hz, 1H), 8.03 (d, J=1.2 Hz, 1H), 8.38 (s, 1H), 11.74 (bs, 1H). M.p.: 136-138° C. LC/MS $[M+H]^+$: 343.8.

2-(2,3-Dihydro-1-benzofuran-5-yl)-N-(1,2,4-thiadiazol-5-yl)-1,3-thiazole-4-carboxamide (73)

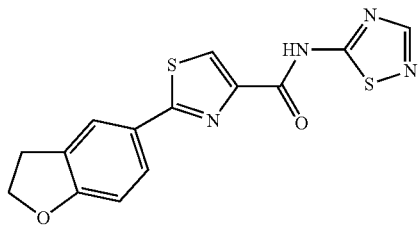 [SMILES: O=C(Nc1ncns1)c1csc(-c2ccc3c(c2)CCO3)n1]

To a stirred suspension of 2-(2,3-dihydro-1-benzofuran-5-yl)-1,3-thiazole-4-carboxylic acid (100 mg, 0.41 mmol), 1,2,4-thiadiazol-5-amine (41 mg 0.41 mmol) and HBTU (230 mg, 0.61 mmol) in 2.7 ml dry $CH_2Cl_2$, DIPEA (131 mg, 1.01 mmol) was added. The suspension was stirred at room temperature for 2 days and filtered, washed with some $CH_2Cl_2$. The precipitate on the filter was washed subsequently with water, an aqueous $Na_2CO_3$ solution, water, diluted HCl, water again and then dried. The crude product was crystallized from a mixture of DMF and EtOH to give the product as a pale yellow solid (102 mg, 0.31 mmol, 75% yield). $^1$H NMR (400 MHz, DMSO-$d_6$) δ ppm 13.31 (s, 1H), 8.63 (s, 1H), 8.52 (s, 1H), 8.09 (s, 1H), 7.91 (dd, J=8.3, 1.6 Hz, 1H), 6.88 (d, J=8.3 Hz, 1H), 4.65 (t, J=8.7 Hz, 2H), 3.30 (t, J=8.7 Hz, 2H). M.p.: 274-276° C. (without decomposition). LC/MS $[M+H]^+$: 330.8.

2-(2,3-Dihydro-1-benzofuran-5-yl)-N-(dimethyl-1,3-thiazol-2-yl)-1,3-thiazole-4-carboxamide (74)

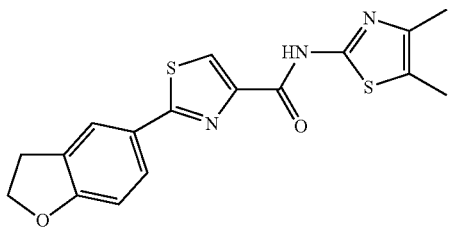 [SMILES: Cc1nc(NC(=O)c2csc(-c3ccc4c(c3)CCO4)n2)sc1C]

To a mixture of 2-(2,3-dihydro-1-benzofuran-5-yl)-1,3-thiazole-4-carboxylic acid (80 mg, 0.32 mmol), 4,5-dimethylthiazol-2-amine (41 mg, 0.32 mmol) and HBTU (120 mg, 0.32 mmol) under stirring and heating at 90° C. 1 ml of dry pyridine was added. The mixture was heated at 90° C. for 4.5 h, pyridine was evaporated, and the residue was diluted with an aqueous $Na_2CO_3$ solution. The resulting precipitate was filtered off and purified by flash column chromatography on silica gel ($CHCl_3$ as solvent). The product was obtained as a white solid (93 mg, 0.26 mmol, 81% yield). $^1$H NMR (DMSO-$d_6$, $CCl_4$) δ ppm 2.22 (s, 3H), 2.30 (s, 3H), 3.29 (t, J=8.6 Hz, 2H), 4.64 (t, J=8.6 Hz, 2H), 6.80 (d, J=8.4 Hz, 1H), 7.82 (dd, J=8.4, 1.6 Hz, 1H), 8.01 (d, J=1.2 Hz, 1H), 8.35 (s, 1H), 11.48 (bs, 1H). M.p.: 194° C. LC/MS $[M+H]^+$: 357.8.

N-(1,3-Benzothiazol-2-yl)-2-(2,3-dihydro-1-benzofuran-5-yl)-1,3-thiazole-4-carboxamide (75)

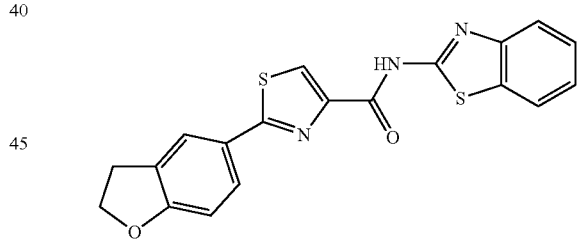

The mixture of 1,3-benzothiazol-2-amine (60 mg, 0.40 mmol), 2-(2,3-dihydro-1-benzofuran-5-yl)-1,3-thiazole-4-carboxylic acid (106 mg, 0.40 mmol), HBTU (205 mg, 0.54 mmol), DIPEA (0.15 ml, 0.87 mmol) and 5 ml dry DCM was stirred at room temperature for 18 h. Subsequently, the solvent was evaporated to dryness. The residue was suspended in a mixture of 10 ml water and 0.2 ml triethylamine and stirred at room temperature for 1 day. The precipitate was filtered off, washed with water and crystallized (with filtration from insoluble part) from 20 ml ethanol. The product was obtained as a pale yellow solid (74 mg, 0.20 mmol, 50% yield). $^1$H NMR (400 MHz, DMSO-$d_6$) δ ppm 3.31 (t, J=8.7 Hz, 2H) 4.64 (t, J=8.7 Hz, 2H) 6.82 (d, J=8.3 Hz, 1H) 7.25-7.35 (m, 1H) 7.37-7.47 (m, 1H) 7.76 (d, J=8.0 Hz, 1H) 7.86 (dd, J=8.4, 1.9 Hz, 1H) 7.92 (d, J=7.3 Hz, 1H) 8.05 (s, 1H) 8.48 (s, 1H) 12.06 (bs, 1H). M.p.: 212-214° C. LC/MS $[M+H]^+$: 379.8.

87

N-(4-Acetyl-1,3-thiazol-2-yl)-2-(2,3-dihydro-1-benzofuran-5-yl)-1,3-thiazole-4-carboxamide (76)

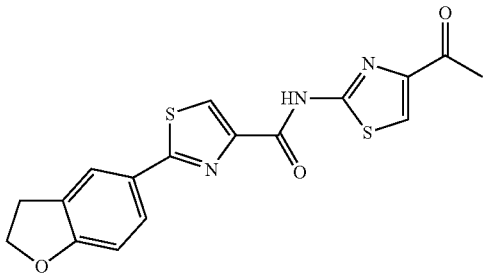 [SMILES: CC(=O)c1csc(NC(=O)c2csc(-c3ccc4c(c3)CCO4)n2)n1]

The mixture of 1-(2-amino-1,3-thiazol-4-yl)ethanone (57 mg, 0.40 mmol), 2-(2,3-dihydro-1-benzofuran-5-yl)-1,3-thiazole-4-carboxylic acid (106 mg, 0.40 mmol), HBTU (205 mg, 0.54 mmol), DIPEA (0.15 ml, 0.87 mmol) and 5 ml dry DCM was stirred at room temperature for 18 h. Subsequently, the solvent was evaporated to dryness, 5 ml ethanol was added to the residue and the suspension was stirred at room temperature for 1 day. The precipitate was filtered off, washed with ethanol and dried on air. The product was obtained as a pale yellow solid (102 mg, 0.27 mmol, 69% yield). $^{1}$H NMR (400 MHz, DMSO-d$_{6}$) δ ppm 2.56 (s, 3H) 3.30 (t, J=8.7 Hz, 2H) 4.64 (t, J=8.7 Hz, 2H) 6.84 (d, J=8.0 Hz, 1H) 7.88 (d, J=8.3 Hz, 1H) 7.99-8.18 (m, 2H) 8.49 (bs, 1H) 12.38 (d, J=14.6 Hz, 1H). M.p.: 223-227° C. LC/MS [M+H]$^{+}$: 371.8.

2-(2,3-Dihydro-1-benzofuran-5-yl)-N-[5-(methylsulfanyl)-1,2,4-thiadiazol-3-yl]-1,3-thiazole-4-carboxamide (77)

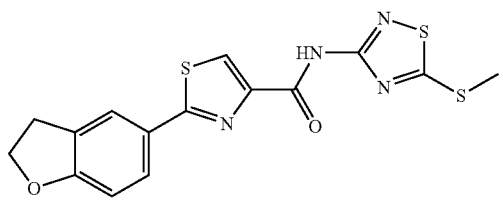 [SMILES: CSc1nc(NC(=O)c2csc(-c3ccc4c(c3)CCO4)n2)ns1]

The mixture of 5-(methylsulfanyl)-1,2,4-thiadiazol-3-amine (49 mg, 0.40 mmol), 2-(2,3-dihydro-1-benzofuran-5-yl)-1,3-thiazole-4-carboxylic acid (106 mg, 0.40 mmol), HBTU (205 mg, 0.54 mmol) and 1 ml dry pyridine was stirred at 100° C. for 2 h. After cooling 10 ml water were added to the reaction mixture and a resin formed. The supernatant was poured off; the resin was dissolved in 3 ml chloroform and purified by flash column chromatography on silica gel (0.040-0.100 mm) using chloroform as eluent. The fractions containing compound were collected. Subsequently, the solvent was evaporated in vacuum and the residue was crystallized from 3 ml ethanol. The product was obtained as a white solid (75 mg, 0.20 mmol, 50% yield). $^{1}$H NMR (400 MHz, DMSO-d$_{6}$) δ ppm 2.79 (s, 3H) 3.30 (t, J=8.7 Hz, 2H) 4.64 (t, J=8.7 Hz, 2H) 6.82 (d, J=8.3 Hz, 1H) 7.81 (dd, J=8.3, 2.0 Hz, 1H) 7.92-8.01 (m, 1H) 8.34 (s, 1H) 10.67 (s, 1H). M.p.: 105-107° C. LC/MS [M+H]$^{+}$: 376.7.

88

Ethyl 2-[2-(2,3-dihydro-1-benzofuran-5-yl)-1,3-thiazole-4-amido]-1,3-thiazole-4-carboxylate (78)

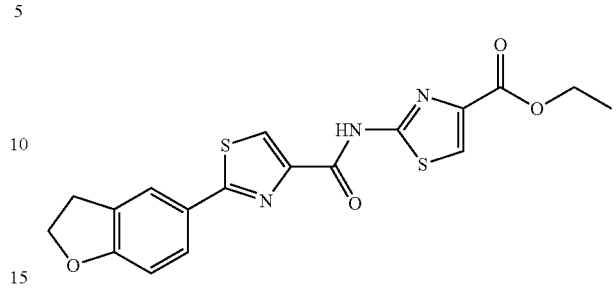

The mixture of ethyl 2-amino-1,3-thiazole-4-carboxylate (344 mg, 2.0 mmol), 2-(2,3-dihydro-1-benzofuran-5-yl)-1,3-thiazole-4-carboxylic acid (530 mg, 2.0 mmol), HBTU (1.03 g, 2.7 mmol), 0.75 ml DIPEA and 25 ml dry DCM was stirred at room temperature for 18 h. Subsequently, the solvent was evaporated to dryness, 50 ml of an 10% aqueous Na$_{2}$CO$_{3}$ solution was added to the residue and the mixture was stirred for 2-3 h until the resinous residue solidified. The precipitate was filtered off and refluxed in 30 ml ethanol for 30 min. After cooling the precipitate was filtered off, washed with ethanol and dried on air. The product was obtained as a pale yellow solid (450 mg. 1.12 mmol, 56% yield). $^{1}$H NMR (400 MHz, DMSO-d$_{6}$) δ ppm 1.37 (t, J=7.0 Hz, 3H), 3.30 (t, J=8.7 Hz, 2H), 4.31 (q, J=7.2 Hz, 2H), 4.64 (t, J=8.8 Hz, 2H), 6.80 (d, J=8.3 Hz, 1H), 7.85 (dd, J=8.3, 1.5 Hz, 1H), 7.94 (s, 1H), 8.05 (s, 1H), 8.42 (s, 1H), 12.46 (s, 1H). M.p.: 183-185° C. LC/MS [M+H]$^{+}$: 401.8.

2-(2,3-Dihydro-1-benzofuran-5-yl)-N-(1,3-oxazol-2-yl)-1,3-thiazole-4-carboxamide (79)

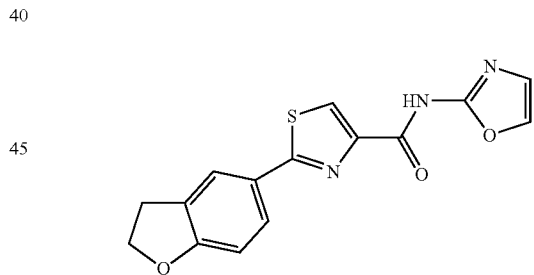

To a stirred suspension of 2-(2,3-dihydro-1-benzofuran-5-yl)-1,3-thiazole-4-carboxylic acid (100 mg, 0.41 mmol), 1,3-oxazol-2-amine (34 mg, 0.41 mmol) and HBTU (230 mg, 0.61 mmol) in 4.1 ml dry CH$_{2}$Cl$_{2}$, DIPEA (131 mg, 1.01 mmol) was added. The suspension was stirred at room temperature for 24 h and filtered, washed with hot CH$_{2}$Cl$_{2}$. The filtrate was evaporated to dryness. The residue was treated subsequently with water, an aqueous Na$_{2}$CO$_{3}$ solution, water, diluted HCl and water again. The crude product was crystallized from EtOH to give the product as a white powder (67 mg, 0.21 mmol, 52% yield). $^{1}$H NMR (400 MHz, DMSO-d$_{6}$) δ ppm 11.18 (s, 1H), 8.39 (s, 1H), 8.02 (s, 1H), 7.92 (s, 1H), 7.85 (d, J=8.3 Hz, 1H), 7.15 (s, 1H), 6.85 (d, J=8.3 Hz, 1H), 4.63 (t, J=8.7 Hz, 2H), 3.28 (t, J=8.7 Hz, 2H). M.p.: 192-194° C. LC/MS [M+H]$^{+}$: 313.9.

2-(2,3-Dihydro-1-benzofuran-5-yl)-N-[5-(methoxymethyl)-1,2,4-oxadiazol-3-yl]-1,3-thiazole-4-carboxamide (80)

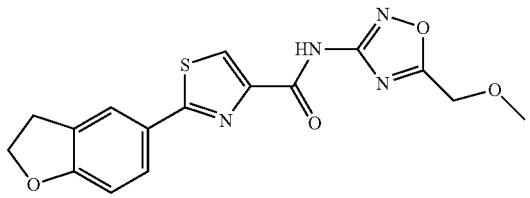 [SMILES: COCc1nc(NC(=O)c2csc(-c3ccc4c(c3)CCO4)n2)no1]

2-(2,3-Dihydro-1-benzofuran-5-yl)-1,3-thiazole-4-carboxylic acid (100 mg, 0.40 mmol) was refluxed in 4.0 ml SOCl$_2$ for 2 h. The excess of SOCl$_2$ was evaporated in vacuo and 3 ml pyridine was added to the residue. The mixture was stirred for 10 minutes, 5-(methoxymethyl)-1,2,4-oxadiazol-3-amine (63 mg, 0.49 mmol) was added and stirring continued overnight. The mixture was poured into ice water, no precipitate was obtained. The solution was diluted with ethyl acetate. The biphasic mixture was separated and the organic layer was washed twice with an aqueous 5% NaHCO$_3$ solution and an aqueous 5% citric acid solution. The organic layer was dried over magnesium sulfate and concentrated in vacuo. The crude product was purified by preparative TLC (PLC silica gel 60 F254, 2 mm, DCM:MeOH 95:5). The product spot was isolated and concentrated in vacuo. The crude product was purified again by preparative TLC (PLC silica gel 60 F254, 0.5 mm, DCM:MeOH 95:5). The main spot was isolated. The product was obtained as a pale yellow solid (5 mg, 0.01 mmol, 4% yield). $^1$H NMR (400 MHz, DMSO-d$_6$) δ ppm 3.22-3.34 (m, 2H), 3.43 (s, 3H), 4.64 (t, J=8.8 Hz, 2H), 4.77 (s, 2H), 6.90 (d, J=8.4 Hz, 1H), 7.91 (dd, J=8.4, 1.51 Hz, 1H), 8.08 (d, J=1.5 Hz, 1H), 8.48 (s, 1H), 11.28 (s, 1H). LC/MS [M+H]$^+$: 359.0.

Ethyl 2-[2-(2,3-dihydro-1-benzofuran-5-yl)-1,3-thiazole-4-amido]-1,3-oxazole-4-carboxylate (81)

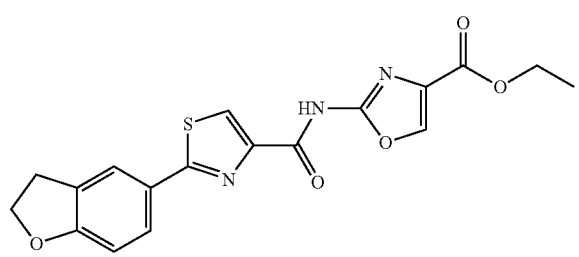 [SMILES: CCOC(=O)c1coc(NC(=O)c2csc(-c3ccc4c(c3)CCO4)n2)n1]

2-(2,3-Dihydro-1-benzofuran-5-yl)-1,3-thiazole-4-carboxylic acid (100 mg, 0.40 mmol) was refluxed in 4 ml SOCl$_2$ for 2 h. The excess of SOCl$_2$ was evaporated in vacuo and 3 ml pyridine was added to the residue. The mixture was stirred for 10 minutes, 2-amino-oxazole-4-carboxylic acid ethyl ester (156 mg, 0.40 mmol) was added and stirring continued for 18 h. The mixture was poured into iced water, no precipitate was obtained. The solution was diluted with ethyl acetate. The biphasic mixture was separated and the organic layer was washed twice with an aqueous 5% NaHCO$_3$ solution and an aqueous 5% citric acid solution. The organic layer was dried over magnesium sulfate and concentrated in vacuo. The crude product was purified by preparative TLC (PLC silica gel 60 F254, 2 mm, DCM:MeOH 95:5). The crude product was dissolved in a mixture of dichloromethane and methanol. The product was filtered off and dried. The product was obtained as a pale pink solid (2 mg, 0.005 mmol, 1% yield). $^1$H NMR (400 MHz, DMSO-d$_6$) δ ppm 1.30 (t, J=7.1 Hz, 3H), 3.20-3.35 (m, 2H), 4.30 (q, J=7.1 Hz, 2H), 4.64 (t, J=8.8 Hz, 2H), 6.90 (d, J=8.3 Hz, 1H), 7.90 (dd, J=8.4, 2.0 Hz, 1H), 8.07 (d, J=1.5 Hz, 1H), 8.48 (s, 1H), 8.71 (s, 1H), 11.69 (bs, 1H). LC/MS [M+H]$^+$: 386.0.

Ethyl 2-[2-(2,3-dihydro-1-benzofuran-5-yl)-1,3-thiazole-4-amido]-1,3-thiazole-5-carboxylate (82)

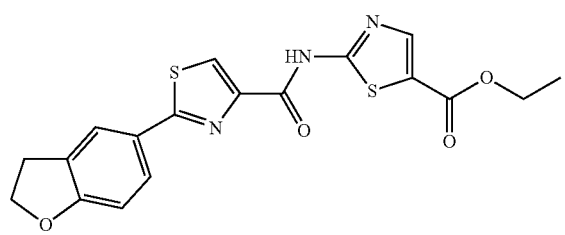 [SMILES: CCOC(=O)c1cnc(NC(=O)c2csc(-c3ccc4c(c3)CCO4)n2)s1]

To a mixture of 2-(2,3-dihydro-1-benzofuran-5-yl)-1,3-thiazole-4-carboxylic acid (80 mg, 0.32 mmol), ethyl 2-amino-1,3-thiazole-5-carboxylate (56 mg, 0.32 mmol) and HBTU (120 mg, 0.32 mmol) under stirring and heating at 90° C. 1 ml of dry pyridine was added. The mixture was heated at 90° C. for 3 h, pyridine was evaporated, and the residue was diluted with an aqueous Na$_2$CO$_3$ solution. The resulting precipitate was filtered off and purified by flash column chromatography on silica gel (CHCl$_3$ as eluent). The product was obtained as a white solid (68 mg, 0.17 mmol, 53% yield). $^1$H NMR (DMSO-d$_6$, CCl$_4$) δ ppm 1.37 (t, J=7.2 Hz, 3H), 3.30 (t, J=8.6 Hz, 2H), 4.31 (q, J=7.2 Hz, 2H), 4.64 (t, J=8.6 Hz, 2H), 6.81 (d, J=8.4 Hz, 1H), 7.86 (1dd, J=8.4, 1.8 Hz, 1H), 8.03 (d, J=1.2 Hz, 1H), 8.13 (s, 1H), 8.49 (s, 1H), 12.45 (bs, 1H). M.p.: 179-181° C. LC/MS [M+H]$^+$: 401.8.

Synthesis of Intermediates and Starting Materials

(2-Amino-4-(3-methoxyphenyl)-1H-imidazol-1-yl)(2-(2,3-dihydrobenzofuran-5-yl)thiazol-4-yl)methanone (I-48)

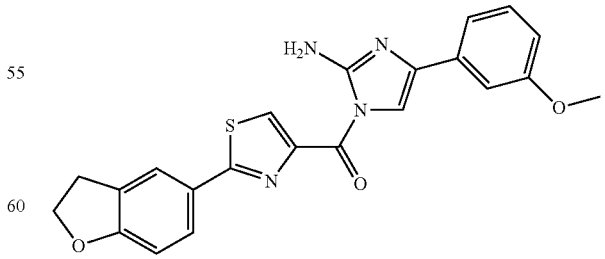

To a solution of 2-(2,3-dihydro-1-benzofuran-5-yl)-1,3-thiazole-4-carboxylic acid (150 mg, 0.61 mmol) in 2 ml N,N-dimethylformamide, were added 5-(3-Methoxyphenyl)-1H-imidazol-2-amine (126 mg, 0.67 mmol), 2-(1H- benzotriazole-1-yl)-1,1,3,3-tetramethyluronium hexafluorophosphate (HBTU) (230 mg, 0.61 mmol), 4-dimethylaminopyridine (7 mg, 0.06 mmol) and N,N-diisopropylethylamine (0.26 ml, 1.52 mmol). The reaction mixture was stirred overnight at room temperature. It was poured into ice water. The formed yellow precipitate was filtered off and washed with water and diisopropylether. The product was obtained as a light yellow solid (206 mg, 0.49 mmol, 81% yield).

$^1$H NMR (400 MHz, DMSO-$d_6$) δ ppm 3.17-3.44 (m, 2H), 3.79 (s, 3H), 4.64 (t, J=8.66 Hz, 2H), 6.83 (br. d, J=7.17 Hz, 1H), 6.94 (br. d, J=8.13 Hz, 1H), 7.06 (bs, 1H), 7.18-7.42 (m, 3H), 7.82 (br. d, J=7.65 Hz, 1H), 7.93 (bs, 1H), 8.28 (bs, 1H), 8.70 (bs, 1H). LC/MS [M+H]$^+$: 418.8

(3,4-dinitrophenyl) [4-(tetrahydrofuran-2-ylmethyl)piperazin-1-yl]methanone (I-49)

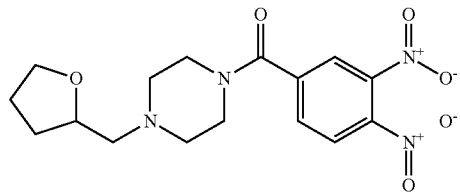

A mixture of 3,4-dinitrobenzoic acid (420 mg, 2.0 mmol) and PCl$_5$ (400 mg, 1.9 mmol) was heated at 60-65° C. for 1 h. After cooling 20 ml hexane was added and the mixture was stirred at room temperature until solidifying of the residue. Solids were filtered off, washed with 10 ml hexane and dissolved in 20 ml CH$_2$Cl$_2$. 2.5 ml Acetic acid and 1-(tetrahydrofuran-2-ylmethyl)piperazine (0.34 g, 2.3 mmol) were added to this solution and the mixture was stirred at room temperature for 1 day. The solvent was evaporated in vacuum, the residue was treated with 15 ml of an aqueous 10% Na$_2$CO$_3$ solution, the precipitate was filtered off, washed with 3% ammonia and dried on air to give the product as pale yellow crystals (600 mg, 1.65 mmol, 82%, yield).

(2-amino-1H-benzimidazol-5-yl)[4-(tetrahydrofuran-2-ylmethyl)piperazin-1-yl]methanone hydrobromide (I-50)

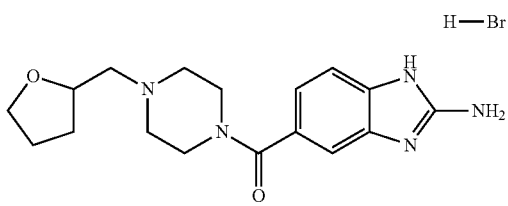 [SMILES: Br ; Nc1nc2cc(C(=O)N3CCN(CC4CCCO4)CC3)ccc2[nH]1]

A mixture of (3,4-dinitrophenyl)[4-(tetrahydrofuran-2-ylmethyl)piperazin-1-yl]methanone (I-49) (60 mg, 1.65 mmol), 20 ml ethanol and Pd/C catalyst (0.08 g, 10% Pd) was stirred in an autoclave under hydrogen pressure 10 kg/cm$^2$ and room temperature for 3 h. Catalyst was filtered off and cyanogen bromide (230 mg, 2.14 mmol) was added to the filtrate. After stirring at room temperature for 1 day the solvent was evaporated in vacuum, the residue suspended in 20 ml ethyl acetate and stirred for 30 min. Slightly rosy precipitate was filtered off, washed with ethyl acetate and dried on air to give the product (0.64 g, 1.55 mmol, 94%, yield).

3,4-dinitro-N-(tetrahydrofuran-2-ylmethyl)benzamide (I-51)

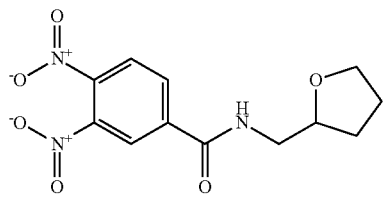

A mixture of 3,4-dinitrobenzoic acid (420 mg, 2.0 mmol) and PCl$_5$ (0.4 g, 1.9 mmol) was heated at 60-65° C. for 1 h. After cooling 20 ml hexane was added and the mixture was stirred at room temperature until solidifying of the residue. Solids were filtered off, washed with 10 ml hexane and dissolved in 20 ml CH$_2$Cl$_2$. 2.5 ml Acetic acid and 1-(tetrahydrofuran-2-yl)methanamine (250 mg, 2.5 mmol) were added to this solution and the mixture was stirred at room temperature for 1 day. The solvent was evaporated in vacuum, the residue was treated with 15 ml of an aqueous 10% Na$_2$CO$_3$ solution, the precipitate was filtered off, washed with 3% ammonia and dried on air to give the as pale yellow crystals (400 mg, 1.4 mmol, 68%, yield).

N-(2-methoxyethyl)-3,4-dinitrobenzamide (I-52)

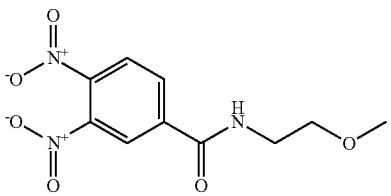

A mixture of 3,4-dinitrobenzoic acid (420 mg, 2.0 mmol) and PCl$_5$ (400 mg, 1.9 mmol) was heated at 60-65° C. for 1 h. After cooling 20 ml hexane was added and the mixture was stirred at room temperature until solidifying of the residue. Solids were filtered off, washed with 10 ml hexane and dissolved in 20 ml CH$_2$Cl$_2$. 2.5 ml Acetic acid and 2-methoxyethanamine (0.20 g, 2.7 mmol) were added to this solution and the mixture was stirred at room temperature for 1 day. The solvent was evaporated in vacuum, the residue was treated with 15 ml of an aqueous 10% Na$_2$CO$_3$ solution, the precipitate was filtered off, washed with 3% ammonia and dried on air to give the product as pale yellow crystals (390 mg, 1.5 mmol, 73%, yield).

(3,4-dinitrophenyl)(4-ethylpiperazin-1-yl)methanone
(I-53)

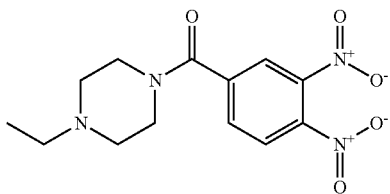 [SMILES: CCN1CCN(C(=O)c2ccc([N+](=O)[O-])c([N+](=O)[O-])c2)CC1]

A mixture of 3.4-dinitrobenzoic acid (420 mg, 2.0 mmol) and PCl$_5$ (400 mg, 1.9 mmol) was heated at 60-65° C. for 1 h. After cooling 20 hexane was added and the mixture was stirred at room temperature until solidifying of the residue. Solids were filtered off, washed with 10 ml hexane and dissolved in 20 ml CH$_2$Cl$_2$. 2.5 ml Acetic acid and N-ethylpiperazine (280 mg, 2.5 mmol) were added to this solution and the mixture was stirred at room temperature for 1 day. The solvent was evaporated in vacuum, the residue was treated with 15 ml of an aqueous 10% Na$_2$CO$_3$ solution, the precipitate was filtered off, washed with 3% ammonia and dried on air to give the product as pale yellow crystals (340 mg, 1.1 mmol, 55%). $^1$H NMR (400 MHz, DMSO-d$_6$) δ ppm 1.05 (t, J=7.15 Hz, 3H), 2.26-2.49 (m, 6H), 3.34 (bs, 2H), 3.66 (bs, 2H), 7.93 (dd, J=8.28, J=1.51 Hz, 1H), 8.18 (d, J=1.51 Hz, 1H), 8.23 (d, J=8.28 Hz, 1H).

(2-amino-1H-benzimidazol-5-yl)(4-ethylpiperazin-1-yl)methanone hydrobromide (I-54)

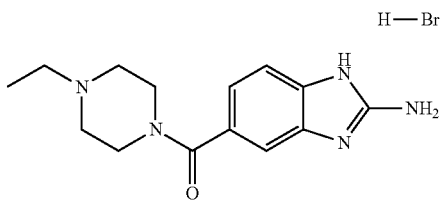 [SMILES: Br ; CCN1CCN(C(=O)c2ccc3[nH]c(N)nc3c2)CC1]

A mixture of (3,4-dinitrophenyl)(4-ethylpiperazin-1-yl)methanone (I-53) (330 mg, 1.07 mmol), 20 ml ethanol and Pd/C catalyst (0.05 g, 10% Pd) was stirred in an autoclave under hydrogen pressure 10 kg/cm$^2$ and room temperature for 3 h. Catalyst was filtered off and cyanogen bromide (150 mg, 1.38 mmol) was added to the filtrate. After stirring at room temperature for 1 day the solvent was evaporated in vacuum, the residue suspended in 20 ml ethyl acetate and stirred for 30 min. Slightly rosy precipitate was filtered off, washed with ethyl acetate and dried on air to give the product (350 mg, 0.99 mmol, 92%, yield).

DYRK1B Kinase Assay

The assay was carried out by Reaction Biology Corp., Malverne, Pa., USA according to specifications by Reaction Biology Corp., as detailed herein below and further described in Anastassiadis et al., Nature Biotechnology, 29 (2011) 1039-1045.

The substrate DYRKtide (synthetic peptide RRRFRPAS-PLRGPPK) was dissolved in freshly prepared Base Reaction Buffer (20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO) at a concentration of 20 μM. DYRK1B was added to the substrate solution in a concentration of 0.3 nM and gently mixed. Dilution series of the compounds according to the present invention in DMSO were prepared. Each dilution was added to a batch of the above reaction mix, followed 20 min later by addition of a mixture of ATP and $^{33}$P ATP (specific activity 0.01 μCi/μl final) to a final concentration of 10 μM. Reactions were carried out at 25° C. for 120 min, followed by spotting the reactions onto P81 ion exchange filter paper. Unbound phosphate was removed by extensive washing of the filters in 0.75% phosphoric acid. After subtraction of background derived from control reactions containing inactive enzyme, kinase activity data were expressed as the percent remaining kinase activity in test samples compared to vehicle (DMSO) reactions. IC$_{50}$ values and curve fits were obtained using Prism (Graph Pad Software).

DYRK1B used in the above assays are further described in the below table:

| | Genbank Accession # | Protein Accession # | Clone | Expression | Tag |
| --- | --- | --- | --- | --- | --- |
| DYRK1B | NP_004705 | Q9Y463 | full-length | Insect | N-terminal GST |

Exemplary compound dilution series, final concentrations of compound in the assay vessel; the individual concentrations and the range of concentrations covered by the dilution series may differ for each compound, as long as enough data points are obtained to determine the compound's IC$_{50}$: DYRK 1B: 1,00E-05 M, 3,33E-06 M, 1,11E-06 M, 3,70E-07 M, 1,23E-07 M, 4,12E-08 M, 1,37E-08 M, 4,57E-09 M, 1,52E-09 M, 5,08E-10 M.

The Following Tables Show Specific Compounds of the Present Invention and their Activity in the Above Kinase Assay:

| No. | Structure | DYRK1B IC$_{50}$ [nM] |
| --- | --- | --- |
| 1 | 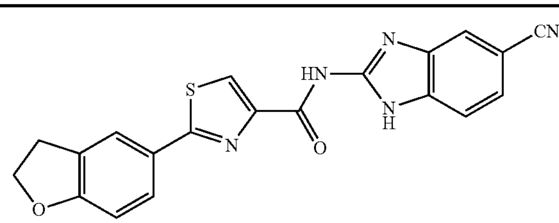 | 1.38 |

-continued

| No. | Structure | DYRK1B IC$_{50}$ [nM] |
|---|---|---|
| 2 | 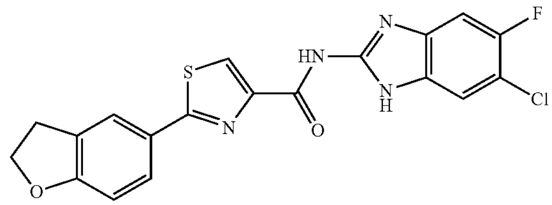 [SMILES: O=C(Nc1nc2cc(F)c(Cl)cc2[nH]1)c1csc(-c2ccc3c(c2)CCO3)n1] | 48.2 |
| 3 | 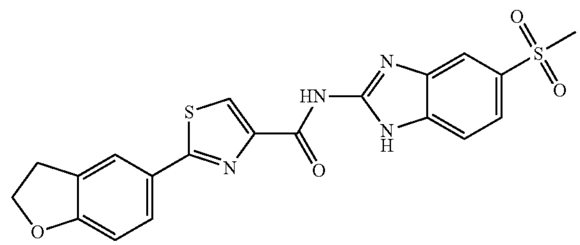 [SMILES: CS(=O)(=O)c1ccc2[nH]c(NC(=O)c3csc(-c4ccc5c(c4)CCO5)n3)nc2c1] | 1.49 |
| 4 | 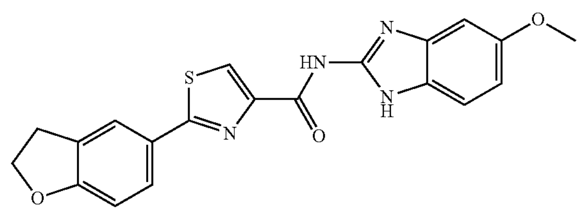 [SMILES: COc1ccc2[nH]c(NC(=O)c3csc(-c4ccc5c(c4)CCO5)n3)nc2c1] | 13.9 |
| 5 | 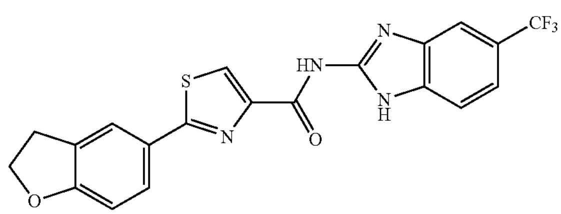 [SMILES: O=C(Nc1nc2cc(C(F)(F)F)ccc2[nH]1)c1csc(-c2ccc3c(c2)CCO3)n1] | 90.88 |
| 6 | 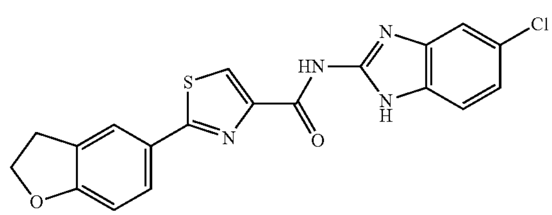 [SMILES: O=C(Nc1nc2cc(Cl)ccc2[nH]1)c1csc(-c2ccc3c(c2)CCO3)n1] | 1.9 |
| 7 | 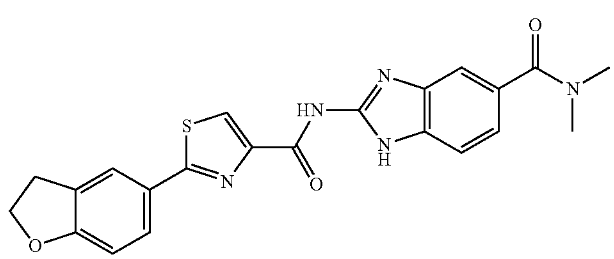 [SMILES: CN(C)C(=O)c1ccc2[nH]c(NC(=O)c3csc(-c4ccc5c(c4)CCO5)n3)nc2c1] | 1.74 |

-continued

| No. | Structure | DYRK1B IC$_{50}$ [nM] |
|---|---|---|
| 8 | 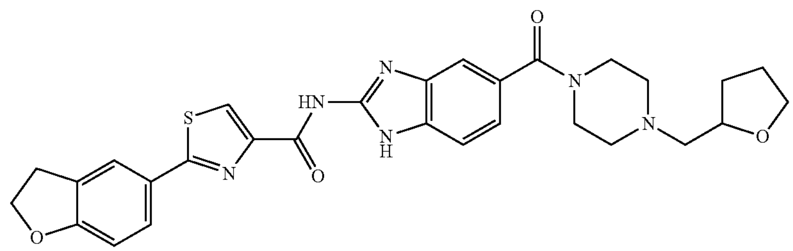 [SMILES: O=C(Nc1nc2cc(C(=O)N3CCN(CC4CCCO4)CC3)ccc2[nH]1)c1csc(-c2ccc3c(c2)CCO3)n1] | 3.11 |
| 9 | 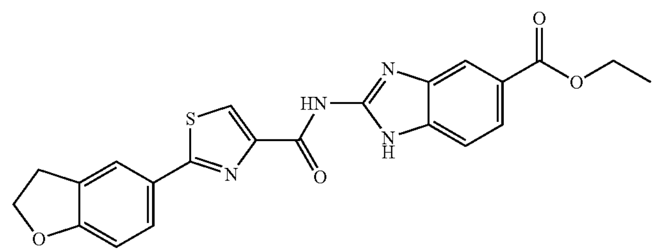 [SMILES: CCOC(=O)c1ccc2[nH]c(NC(=O)c3csc(-c4ccc5c(c4)CCO5)n3)nc2c1] | 3.63 |
| 10 | 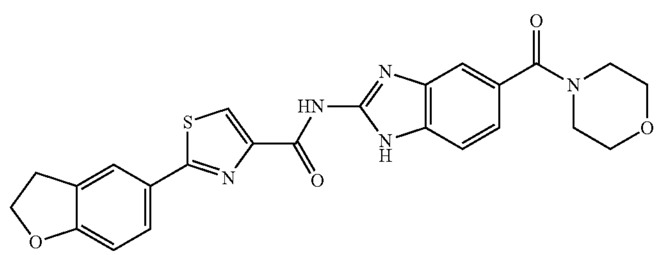 [SMILES: O=C(Nc1nc2cc(C(=O)N3CCOCC3)ccc2[nH]1)c1csc(-c2ccc3c(c2)CCO3)n1] | 3.72 |
| 11 | 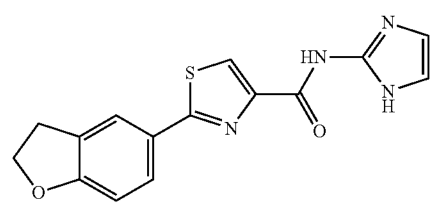 [SMILES: O=C(Nc1ncc[nH]1)c1csc(-c2ccc3c(c2)CCO3)n1] | 66.8 |
| 12 | 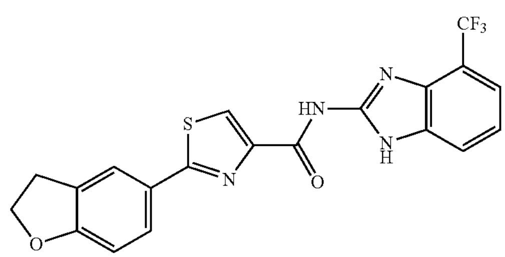 [SMILES: O=C(Nc1nc2c(C(F)(F)F)cccc2[nH]1)c1csc(-c2ccc3c(c2)CCO3)n1] | 156 |
| 13 | 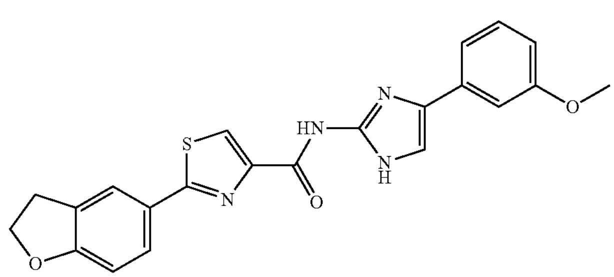 [SMILES: COc1cccc(-c2c[nH]c(NC(=O)c3csc(-c4ccc5c(c4)CCO5)n3)n2)c1] | 111 |

-continued

| No. | Structure | DYRK1B IC$_{50}$ [nM] |
|---|---|---|
| 14 | 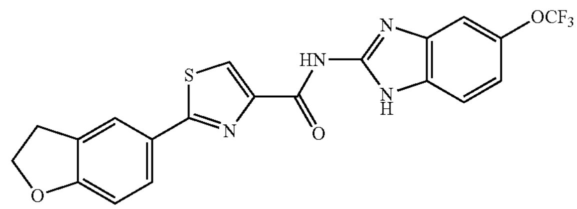 [SMILES: O=C(Nc1nc2cc(OC(F)(F)F)ccc2[nH]1)c1csc(-c2ccc3c(c2)CCO3)n1] | 29.4 |
| 15 | 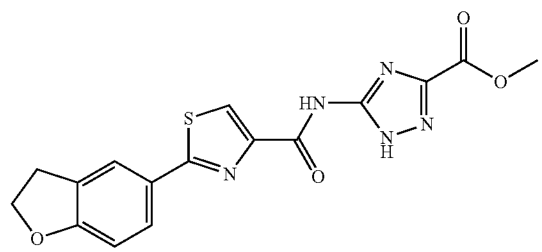 [SMILES: COC(=O)c1n[nH]c(NC(=O)c2csc(-c3ccc4c(c3)CCO4)n2)n1] | 152 |
| 16 | 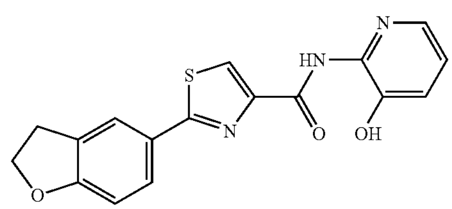 [SMILES: O=C(Nc1ncccc1O)c1csc(-c2ccc3c(c2)CCO3)n1] | 177 |
| 17 | 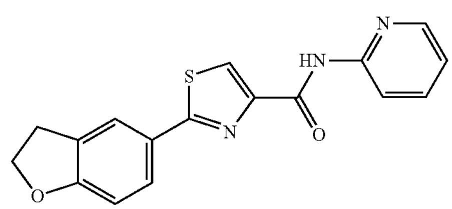 [SMILES: O=C(Nc1ccccn1)c1csc(-c2ccc3c(c2)CCO3)n1] | 29.4 |
| 18 | 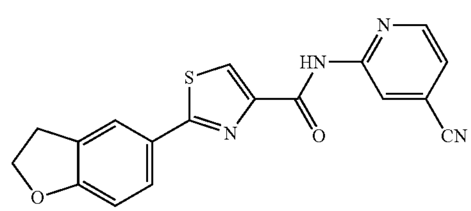 [SMILES: N#Cc1ccnc(NC(=O)c2csc(-c3ccc4c(c3)CCO4)n2)c1] | 19.5 |
| 19 | 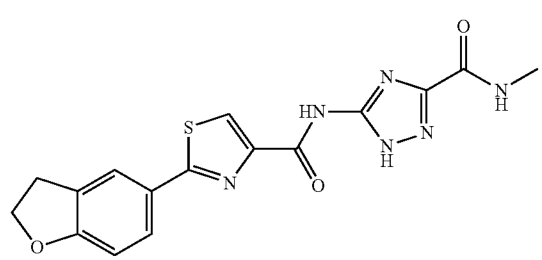 [SMILES: CNC(=O)c1n[nH]c(NC(=O)c2csc(-c3ccc4c(c3)CCO4)n2)n1] | 9.68 |

-continued

| No. | Structure | DYRK1B IC$_{50}$ [nM] |
|---|---|---|
| 20 | 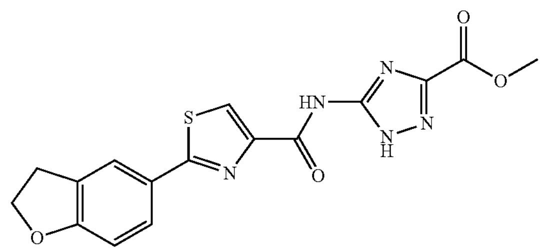 [SMILES: COC(=O)c1n[nH]c(NC(=O)c2csc(-c3ccc4c(c3)CCO4)n2)n1] | 109 |
| 21 | 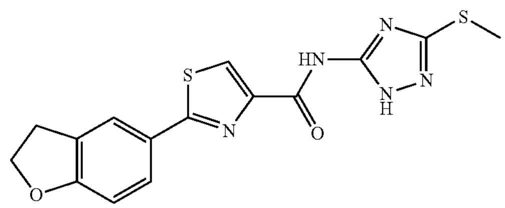 [SMILES: CSc1n[nH]c(NC(=O)c2csc(-c3ccc4c(c3)CCO4)n2)n1] | 18.3 |
| 22 | 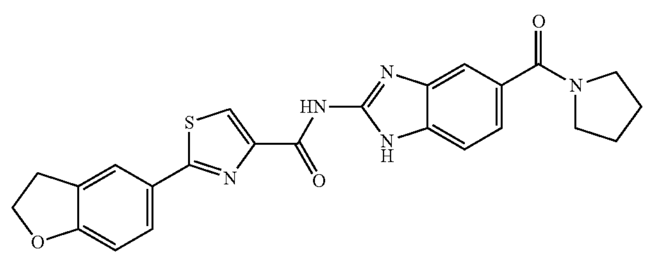 [SMILES: O=C(Nc1nc2cc(C(=O)N3CCCC3)ccc2[nH]1)c1csc(-c2ccc3c(c2)CCO3)n1] | 0.852 |
| 23 | 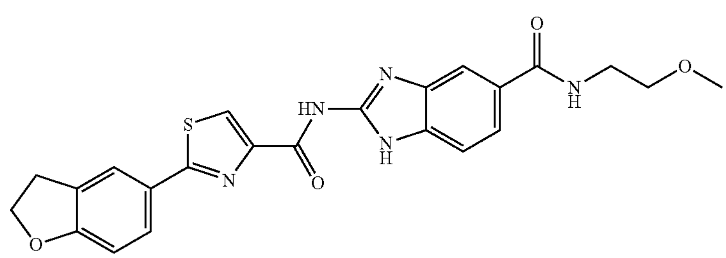 [SMILES: COCCNC(=O)c1ccc2[nH]c(NC(=O)c3csc(-c4ccc5c(c4)CCO5)n3)nc2c1] | 0.699 |
| 24 | 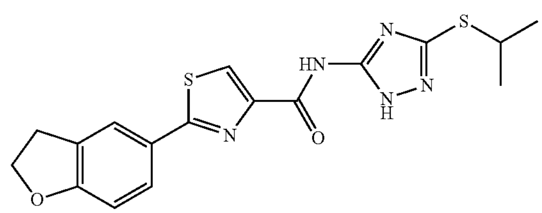 [SMILES: CC(C)Sc1n[nH]c(NC(=O)c2csc(-c3ccc4c(c3)CCO4)n2)n1] | 17.8 |
| 25 | 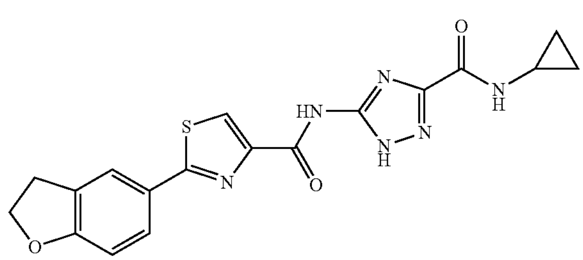 [SMILES: O=C(Nc1nc(C(=O)NC2CC2)n[nH]1)c1csc(-c2ccc3c(c2)CCO3)n1] | 3.51 |

-continued
| No. | Structure | DYRK1B IC$_{50}$ [nM] |
|---|---|---|
| 26 | 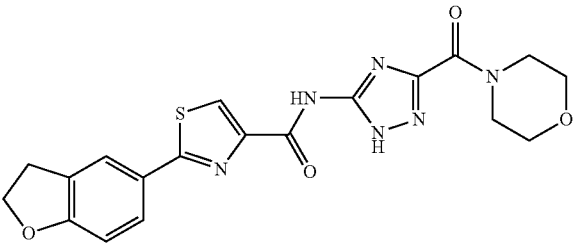 [SMILES: O=C(Nc1nc(C(=O)N2CCOCC2)n[nH]1)c1csc(-c2ccc3c(c2)CCO3)n1] | 85 |
| 27 | 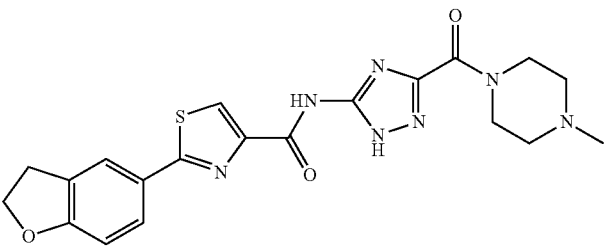 [SMILES: CN1CCN(C(=O)c2n[nH]c(NC(=O)c3csc(-c4ccc5c(c4)CCO5)n3)n2)CC1] | 49.8 |
| 28 | 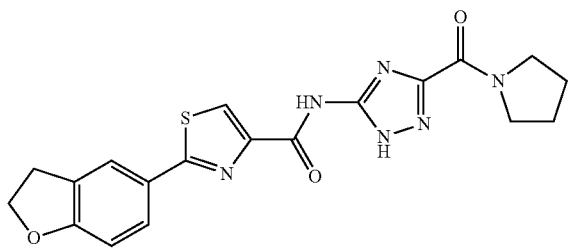 [SMILES: O=C(Nc1nc(C(=O)N2CCCC2)n[nH]1)c1csc(-c2ccc3c(c2)CCO3)n1] | 47.1 |
| 29 | 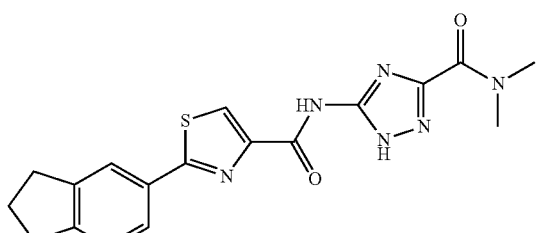 | 72 |
| 30 | 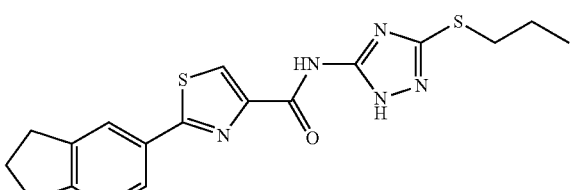 | 7.97 |
| 31 | 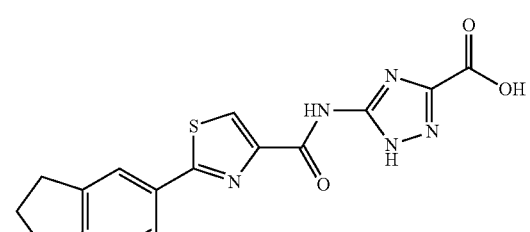 | 68.1 |

-continued
| No. | Structure | DYRK1B IC$_{50}$ [nM] |
|---|---|---|
| 32 | 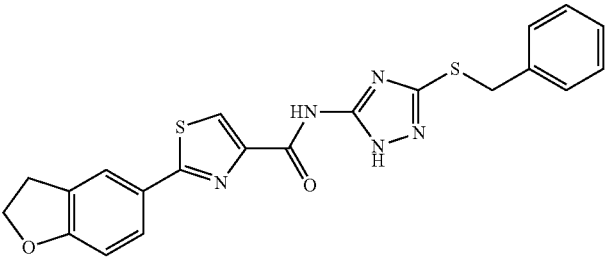 [SMILES: O=C(Nc1nc(SCc2ccccc2)n[nH]1)c1csc(-c2ccc3c(c2)CCO3)n1] | 1350 |
| 33 | 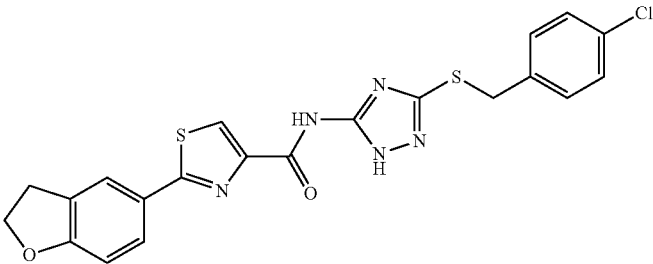 [SMILES: O=C(Nc1nc(SCc2ccc(Cl)cc2)n[nH]1)c1csc(-c2ccc3c(c2)CCO3)n1] | 337 |
| 34 | 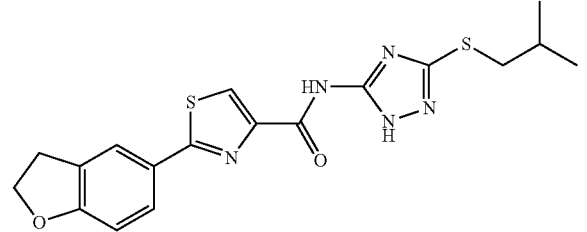 [SMILES: CC(C)CSc1n[nH]c(NC(=O)c2csc(-c3ccc4c(c3)CCO4)n2)n1] | 38.1 |
| 35 | 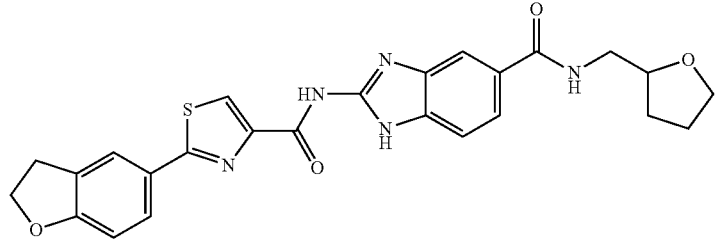 [SMILES: O=C(NCC1CCCO1)c1ccc2[nH]c(NC(=O)c3csc(-c4ccc5c(c4)CCO5)n3)nc2c1] | <0.5 |
| 36 | 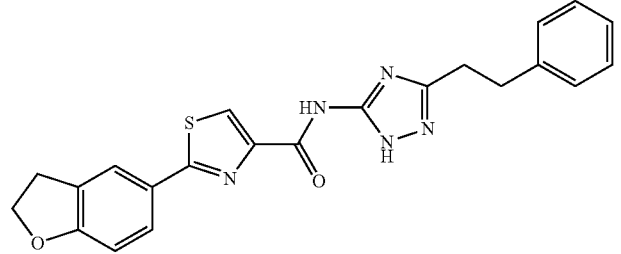 [SMILES: O=C(Nc1nc(CCc2ccccc2)n[nH]1)c1csc(-c2ccc3c(c2)CCO3)n1] | 112 |
| 37 | 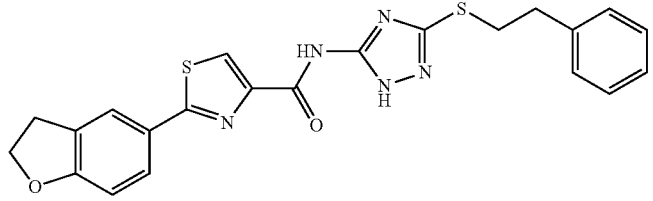 [SMILES: O=C(Nc1nc(SCCc2ccccc2)n[nH]1)c1csc(-c2ccc3c(c2)CCO3)n1] | 56 |

| No. | Structure | DYRK1B IC$_{50}$ [nM] |
|---|---|---|
| 38 | 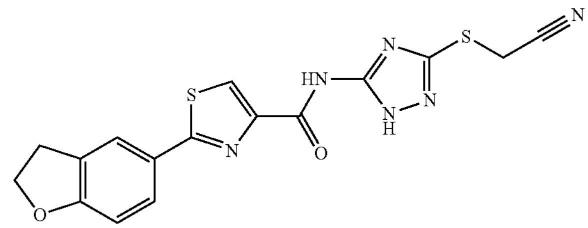 [SMILES: N#CCSc1n[nH]c(NC(=O)c2csc(-c3ccc4c(c3)CCO4)n2)n1] | 3.97 |
| 39 | 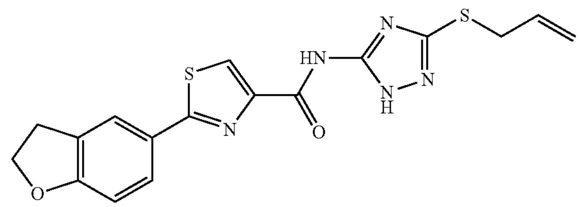 [SMILES: C=CCSc1n[nH]c(NC(=O)c2csc(-c3ccc4c(c3)CCO4)n2)n1] | 11.9 |
| 40 | 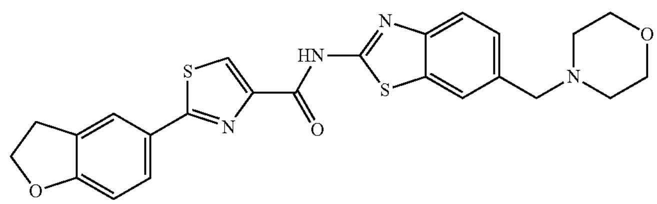 [SMILES: O=C(Nc1nc2ccc(CN3CCOCC3)cc2s1)c1csc(-c2ccc3c(c2)CCO3)n1] | 15.7 |
| 41 | 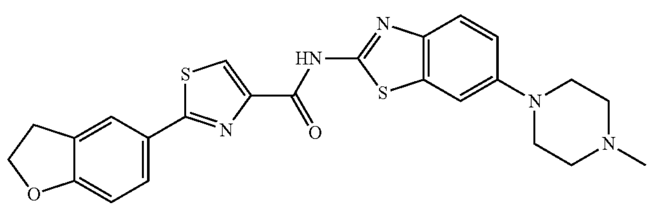 [SMILES: CN1CCN(c2ccc3nc(NC(=O)c4csc(-c5ccc6c(c5)CCO6)n4)sc3c2)CC1] | 19.5 |
| 42 | 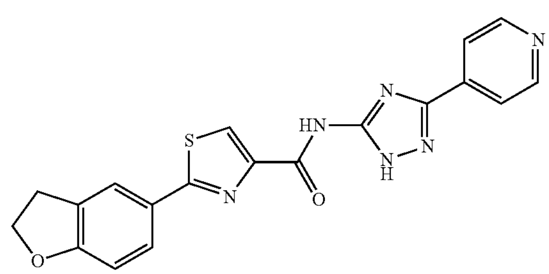 [SMILES: O=C(Nc1nc(-c2ccncc2)n[nH]1)c1csc(-c2ccc3c(c2)CCO3)n1] | 2.06 |
| 43 | 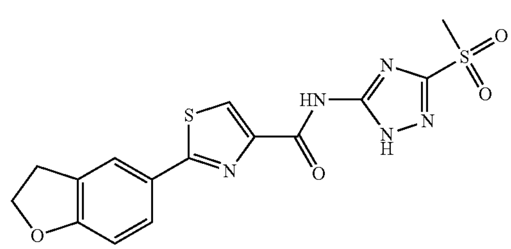 [SMILES: CS(=O)(=O)c1n[nH]c(NC(=O)c2csc(-c3ccc4c(c3)CCO4)n2)n1] | 535 |
| 44 | 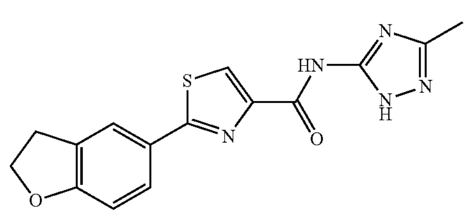 [SMILES: Cc1n[nH]c(NC(=O)c2csc(-c3ccc4c(c3)CCO4)n2)n1] | 60.1 |

-continued

| No. | Structure | DYRK1B IC$_{50}$ [nM] |
|---|---|---|
| 45 | 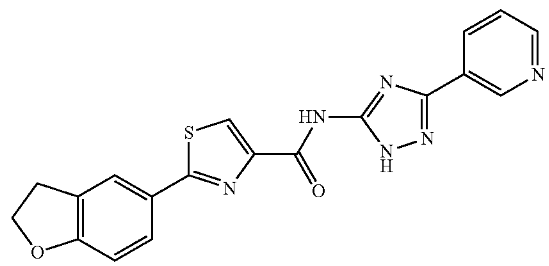 [SMILES: O=C(Nc1nc(-c2cccnc2)n[nH]1)c1csc(-c2ccc3c(c2)CCO3)n1] | 2.81 |
| 46 | 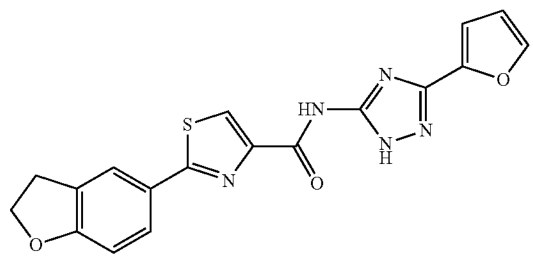 [SMILES: O=C(Nc1nc(-c2ccco2)n[nH]1)c1csc(-c2ccc3c(c2)CCO3)n1] | 15.3 |
| 47 | 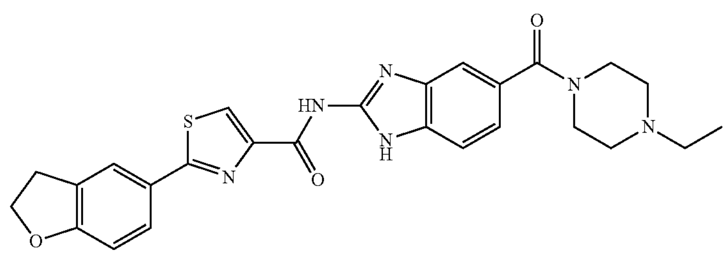 [SMILES: CCN1CCN(C(=O)c2ccc3[nH]c(NC(=O)c4csc(-c5ccc6c(c5)CCO6)n4)nc3c2)CC1] | 2.17 |
| 48 | 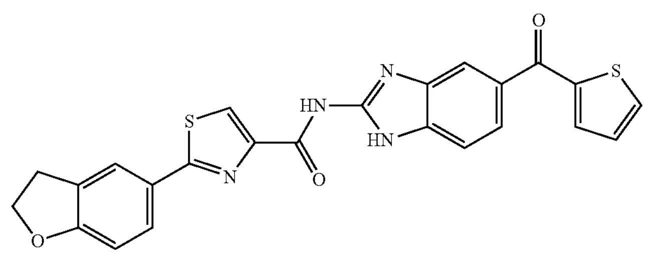 [SMILES: O=C(Nc1nc2cc(C(=O)c3cccs3)ccc2[nH]1)c1csc(-c2ccc3c(c2)CCO3)n1] | 5.57 |
| 49 | 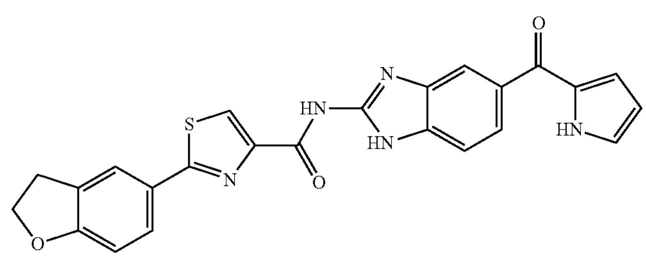 [SMILES: O=C(Nc1nc2cc(C(=O)c3ccc[nH]3)ccc2[nH]1)c1csc(-c2ccc3c(c2)CCO3)n1] | 6.63 |
| 50 | 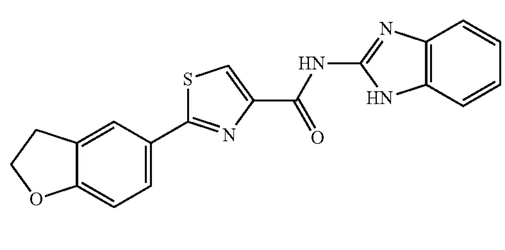 | 6.73 |

-continued
| No. | Structure | DYRK1B IC$_{50}$ [nM] |
|---|---|---|
| 51 | 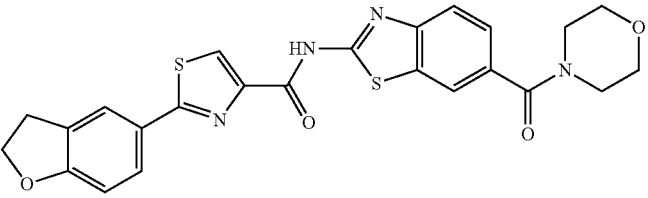 [SMILES: O=C(Nc1nc2ccc(C(=O)N3CCOCC3)cc2s1)c1csc(-c2ccc3c(c2)CCO3)n1] | 9.17 |
| 52 | 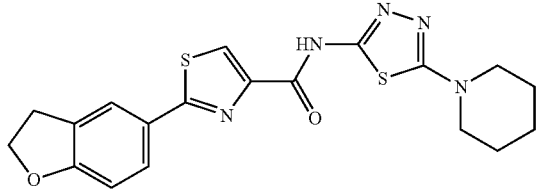 [SMILES: O=C(Nc1nnc(N2CCCCC2)s1)c1csc(-c2ccc3c(c2)CCO3)n1] | 12.6 |
| 53 | 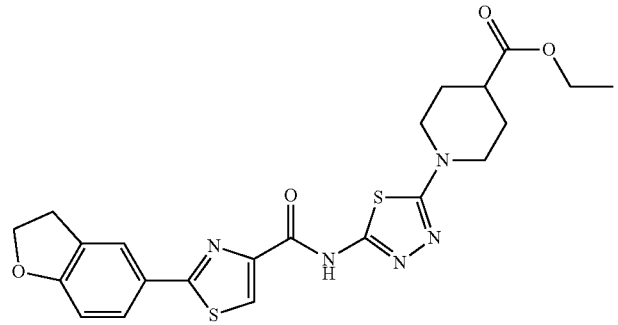 [SMILES: CCOC(=O)C1CCN(c2nnc(NC(=O)c3csc(-c4ccc5c(c4)CCO5)n3)s2)CC1] | 14.4 |
| 54 | 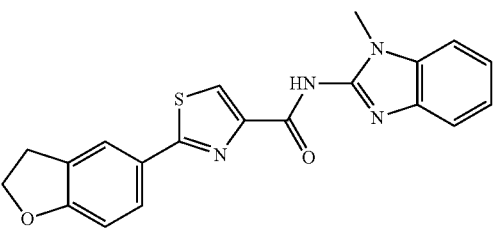 [SMILES: Cn1c(NC(=O)c2csc(-c3ccc4c(c3)CCO4)n2)nc2ccccc21] | 17.6 |
| 55 | 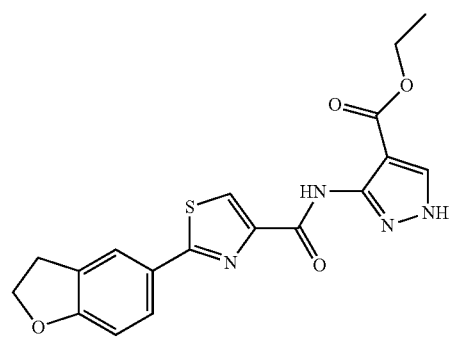 [SMILES: CCOC(=O)c1c[nH]nc1NC(=O)c1csc(-c2ccc3c(c2)CCO3)n1] | 20.6 |
| 56 | 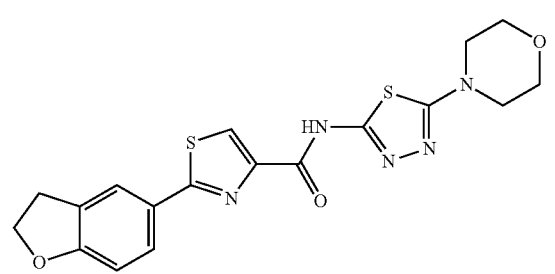 [SMILES: O=C(Nc1nnc(N2CCOCC2)s1)c1csc(-c2ccc3c(c2)CCO3)n1] | 21.7 |

| No. | Structure | DYRK1B IC$_{50}$ [nM] |
|---|---|---|
| 57 | 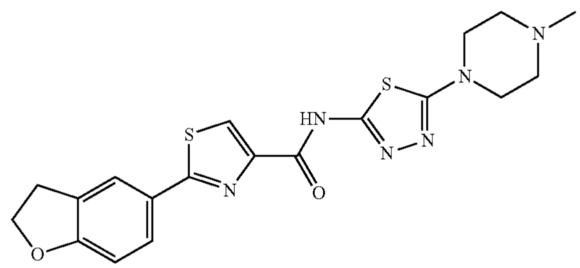 [SMILES: CN1CCN(c2nnc(NC(=O)c3csc(-c4ccc5c(c4)CCO5)n3)s2)CC1] | 26.4 |
| 58 | 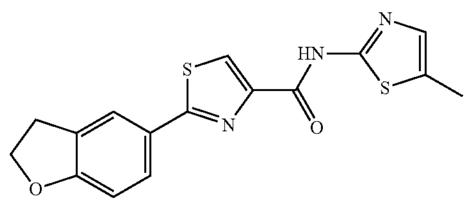 [SMILES: Cc1cnc(NC(=O)c2csc(-c3ccc4c(c3)CCO4)n2)s1] | 27.6 |
| 59 | 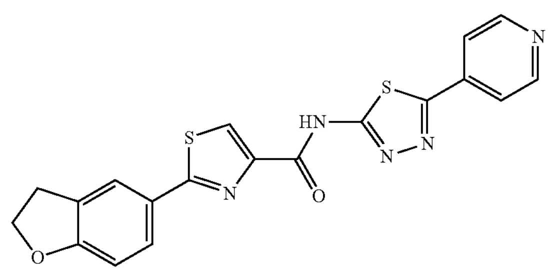 [SMILES: O=C(Nc1nnc(-c2ccncc2)s1)c1csc(-c2ccc3c(c2)CCO3)n1] | 31.5 |
| 60 | 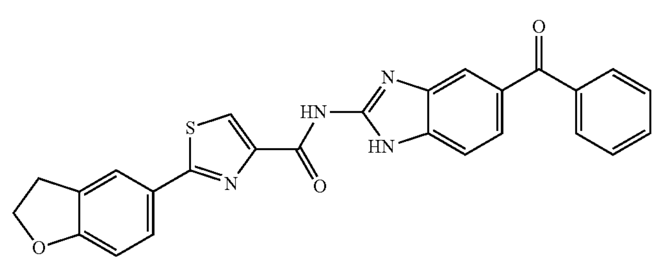 [SMILES: O=C(c1ccccc1)c1ccc2[nH]c(NC(=O)c3csc(-c4ccc5c(c4)CCO5)n3)nc2c1] | 38.3 |
| 61 | 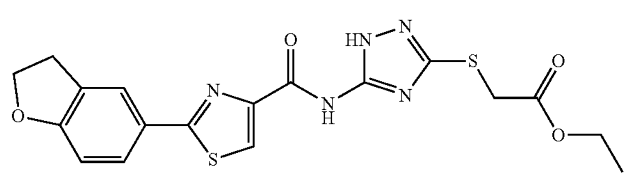 [SMILES: CCOC(=O)CSc1n[nH]c(NC(=O)c2csc(-c3ccc4c(c3)CCO4)n2)n1] | 39.1 |
| 62 | 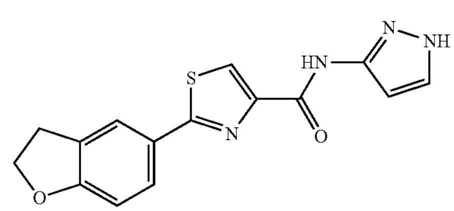 [SMILES: O=C(Nc1cc[nH]n1)c1csc(-c2ccc3c(c2)CCO3)n1] | 42.4 |

| No. | Structure | DYRK1B IC$_{50}$ [nM] |
| --- | --- | --- |
| 63 | 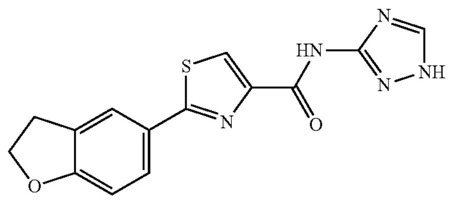 [SMILES: O=C(Nc1nc[nH]n1)c1csc(-c2ccc3c(c2)CCO3)n1] | 47.1 |
| 64 | 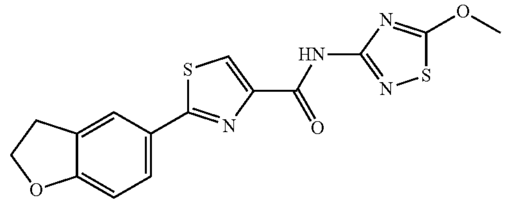 [SMILES: COc1nc(NC(=O)c2csc(-c3ccc4c(c3)CCO4)n2)ns1] | 48.3 |
| 65 | 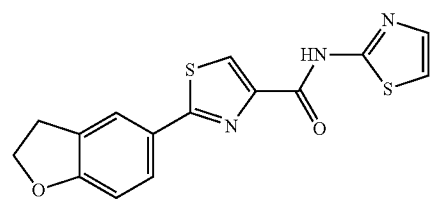 | 48.7 |
| 66 | 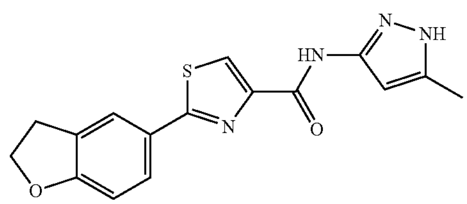 [SMILES: Cc1cc(NC(=O)c2csc(-c3ccc4c(c3)CCO4)n2)n[nH]1] | 50.5 |
| 67 | 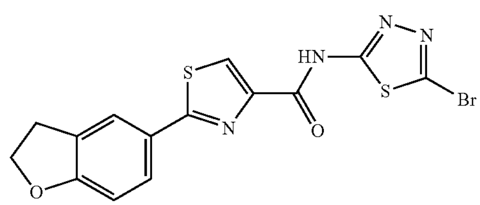 [SMILES: O=C(Nc1nnc(Br)s1)c1csc(-c2ccc3c(c2)CCO3)n1] | 65.9 |
| 68 | 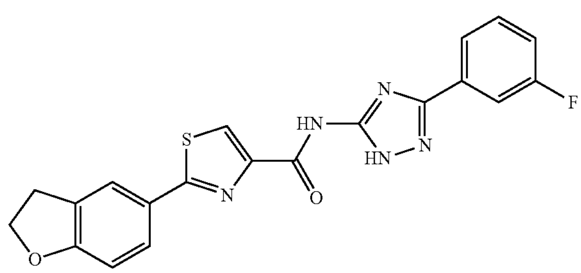 [SMILES: O=C(Nc1nc(-c2cccc(F)c2)n[nH]1)c1csc(-c2ccc3c(c2)CCO3)n1] | 67.1 |
| 69 | 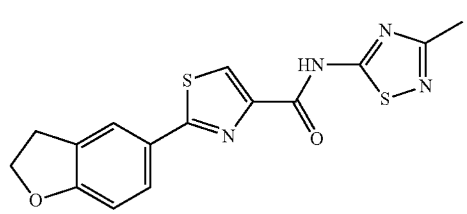 [SMILES: Cc1nsc(NC(=O)c2csc(-c3ccc4c(c3)CCO4)n2)n1] | 72.6 |

| No. | Structure | DYRK1B IC$_{50}$ [nM] |
|---|---|---|
| 70 | 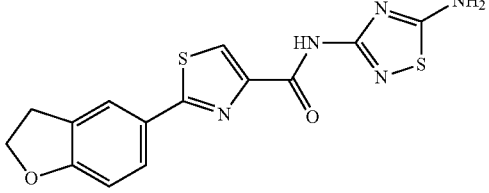 | 73.4 |
| 71 | 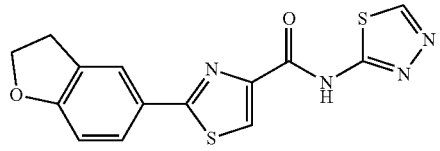 | 76.6 |
| 72 | 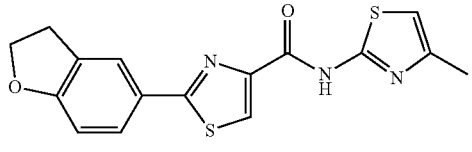 [SMILES: Cc1csc(NC(=O)c2csc(-c3ccc4c(c3)CCO4)n2)n1] | 111 |
| 73 | 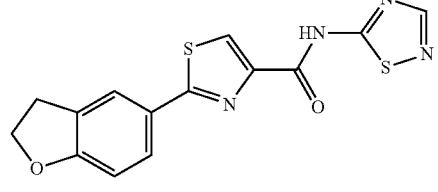 | 114 |
| 74 | 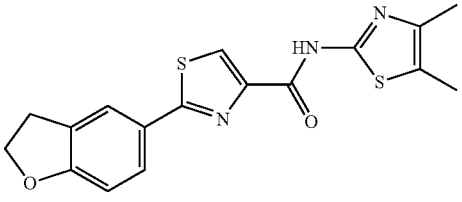 [SMILES: Cc1nc(NC(=O)c2csc(-c3ccc4c(c3)CCO4)n2)sc1C] | 125 |
| 75 | 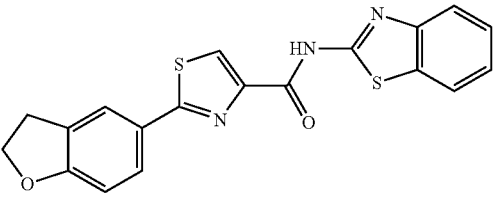 [SMILES: O=C(Nc1nc2ccccc2s1)c1csc(-c2ccc3c(c2)CCO3)n1] | 135 |
| 76 | 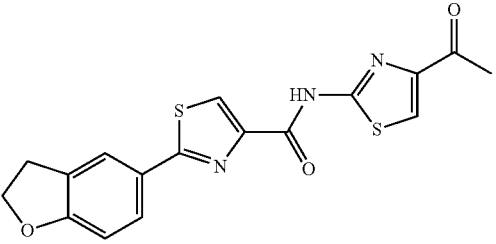 [SMILES: CC(=O)c1csc(NC(=O)c2csc(-c3ccc4c(c3)CCO4)n2)n1] | 185 |

| No. | Structure | DYRK1B IC$_{50}$ [nM] |
|---|---|---|
| 77 | 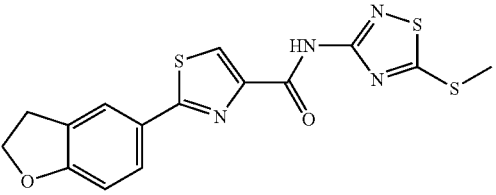 [SMILES: CSc1nc(NC(=O)c2csc(-c3ccc4c(c3)CCO4)n2)ns1] | 420 |
| 78 | 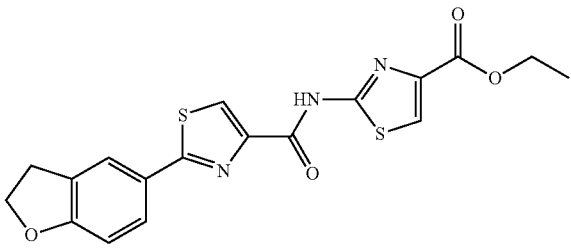 [SMILES: CCOC(=O)c1csc(NC(=O)c2csc(-c3ccc4c(c3)CCO4)n2)n1] | 410 |
| 79 | 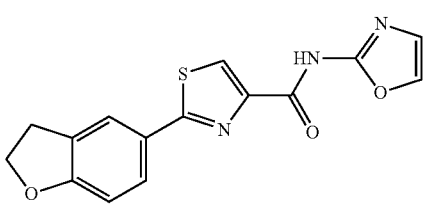 | 766 |
| 80 | 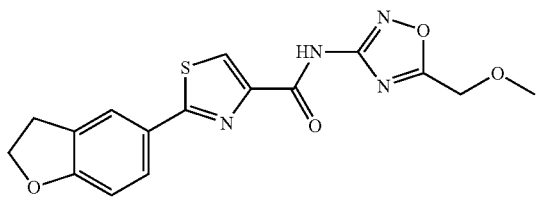 [SMILES: COCc1nc(NC(=O)c2csc(-c3ccc4c(c3)CCO4)n2)no1] | |
| 81 | 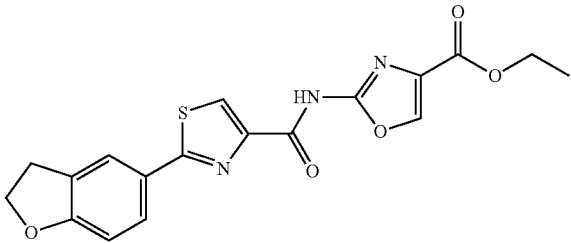 [SMILES: CCOC(=O)c1coc(NC(=O)c2csc(-c3ccc4c(c3)CCO4)n2)n1] | |
| 82 | 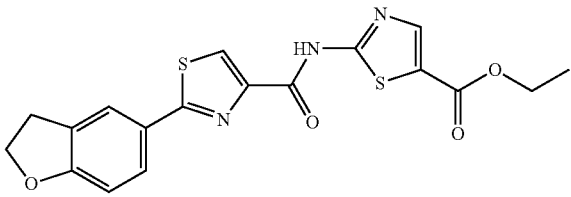 [SMILES: CCOC(=O)c1cnc(NC(=O)c2csc(-c3ccc4c(c3)CCO4)n2)s1] | |

Hedgehog Reporter Assay

In order to investigate the potency of test compounds to inhibit the Hedgehog signaling pathway, a Gli-Reporter assay was performed. The "Gli Reporter—NIH3T3" cell line contains the firefly luciferase gene under the control of Gli responsive elements stably integrated into murine NIH3T3 cells (cells purchased from AMS Biotechnology ltd., 184 Milton Park, Abingdon OX14 4SE, U.K.). The luciferase expression correlates with activation of the hedgehog signaling pathway. This cell line is validated for its response to stimulation with murine Sonic Hedgehog and to treatment with inhibitors of the hedgehog signaling pathway. A multiplexed viability assay was used to discriminate inhibition on the pathway activity from cell toxicity.

Growth Medium: DMEM (Dulbecco's Modified Eagle Medium); 10% Fetal Calf Serum; 1% Penicillin/Streptomycin; 500 µg/ml Geneticin (G418 Stock 50 mg/ml).

Assay Medium: Opti-MEM® Reduced Serum Medium; 0.5% Calf Serum; 1% non-essential amino acids; 1 mM Na-pyruvate; 10 mM HEPES; 1% Penicillin/Streptomycin.

25,000 cells per well were seeded into a white 96 well plate in 100 µl growth medium and incubated over night at 37° C. and 5% $CO_2$. After removing the supernatant the test compounds and controls were added in different concentrations in a final volume of 45 µl and incubated for 1 h at 37° C. and 5% $CO_2$. For the stimulation of the Hedgehog pathway 5 µl of 10 µg/ml concentrated murine SHH (or mSHH; murine sonic hedgehog protein) was added to the cells. A final concentration of 1 µg/ml mSHH and 0.1% DMSO was reached per well. After incubation for 24 h at 37° C. the cells were investigated for viability and reporter activity.

Viability: For the determination of the viability of the treated cells the CellTiter-Fluor™ Kit from Promega comprising the fluorogenic, cell-permeant peptide substrate (glycylphenylalanyl-aminofluorocoumarin GF-AFC was used. Roughly, only proteases of viable cells are able to cleave the GF-AFC. By this cleavage the fluorescent AFC is set free and can be detected in a fluorescence reader. For this assay 10 µl of GF-AFC substrate (CellTiter-Fluor™, Promega #G6082) was diluted in 2 ml assay buffer from the CellTiter-Fluor™ Kit and 10 µl of this dilution was added per well to the cells and incubated for 30 min at 37° C. The fluorescence was measured with an excitation of 380-400 nm and an emission of 505 nm.

Reporter activity: The firefly luciferase reporter activity was detected with the ONE-Glo™ Luciferase Assay System from Promega. For this assay 50 µl ONE-Glo luciferase reagent (Promega #E6120, contains cell lysis buffer and luciferin) was added to each well and incubated at room temperature for 5 min. Luminescence was detected in a plate reader and served as a measure for reporter activity.

In the above hedgehog assay, compounds 4, 12, 17, 26, 27, 28, 29, 32, 41, 44, and 46 show an $IC_{50}$ of 3-10 µM, compounds 1, 2, 5, 6, 11, 13, 14, 19, 25 and 45 show an $IC_{50}$ of 1-3 µM and compounds 3, 7, 8, 9, 10, 22, 23, 35 and 47 show an $IC_{50}$ of less than 1 µM.

Xenograft Assay

A xenograft assay with L3.6pl cancer cells was prepared as follows: $1 \times 10^5$ L3.6pl (Bruns et al., 1999) human metastatic pancreatic adenocarcinoma cells in 25% Matrigel (BD Biosciences, NJ, USA) were injected subcutaneously into the lower flanks of Foxn1nu/nu nude mice (Charles River Laboratories, USA). The compound of example 5 was administered p.o. daily with 100 mg/kg/day, dissolved in a mixture of 20% Glycofurol 75, 20% Oleic acid and 60% Olive oil; administration was started at the same day of injection of tumor cells. As a negative control, separate aminals were administered solvent vehicle without active compound. The tumor volume was measured with a caliper and calculated according to the formula $[4/3 \times \pi \times (length/2) \times (width/2) \times (height/2)]$. Results are shown in FIG. 1, the p value was <0.01. The animals' weight was essentially unchanged over the course of the experiment.

The invention claimed is:

1. A compound of formula (I) or a pharmaceutically acceptable derivative, solvate or salt thereof,

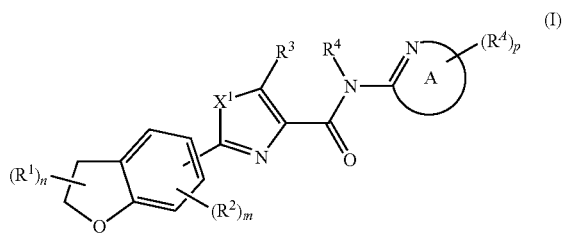

wherein
the $X^1$-azol moiety is attached at the 5- or 6-position of the 2,3-dihydrobenzofuran moiety;
n is an integer from 0 to 2;
m is an integer from 0 to 3;
p is an integer from 0 to 2;
$R^1$ is independently selected from H, halogen, alkyl, aralkyl, haloalkyl, haloalkoxy, OH, alkoxy, —CN, aryl, heteroaryl, cycloalkyl, heterocycloalkyl, —S—R', —SO—R', nitro, —NH$_2$, —N(R')$_2$, —NH(R'), —NHCO(R'), —CONH$_2$, —CONH(R'), —CO(R'), —COH, —COO(R'), —COOH, —SO$_2$NH$_2$, —SO$_2$NH(R'), —SO$_2$(R'), —NH—SO$_2$(R') and —NHCOOR';
$R^2$ is independently selected from H, halogen, alkyl, aralkyl, haloalkyl, haloalkoxy, OH, alkoxy, —CN, aryl, heteroaryl, cycloalkyl, heterocycloalkyl, —S—R', —SO—R', nitro, —NH$_2$, —N(R')$_2$, —NH(R'), —NHCO(R'), —CONH$_2$, —CONH(R'), —CO(R'), —COH, —COO(R'), —COOH, —SO$_2$NH$_2$, —SO$_2$NH(R'), —SO$_2$(R'), —NH—SO$_2$(R') and —NHCOOR';
$R^3$ is independently selected from H, halogen, alkyl, aralkyl, haloalkyl, haloalkoxy, OH, alkoxy, —CN, aryl, heteroaryl, cycloalkyl, heterocycloalkyl, —S—R', —SO—R', nitro, —NH$_2$, —N(R')$_2$, —NH(R'), —NHCO(R'), —CONH$_2$, —CONH(R'), —CO(R'), —COH, —COO(R'), —COOH, —SO$_2$NH$_2$, —SO$_2$NH(R'), —SO$_2$(R'), —NH—SO$_2$(R') and —NHCOOR';
$R^4$ is independently selected from H, alkyl, aralkyl, haloalkyl, haloalkoxy, OH, alkoxy, aryl, heteroaryl, cycloalkyl, heterocycloalkyl, —CONH$_2$, —CONH(R'), —CO(R'), —COO(R'), and —SO$_2$(R');
$X^1$ is independently selected from NR'', O and S;
R'' is independently selected from H, alkyl, aralkyl, haloalkyl, haloalkoxy, OH, alkoxy, aryl, heteroaryl, cycloalkyl, heterocycloalkyl, —CONH$_2$, —CONH(R'), —CO(R'), —COO(R'), and —SO$_2$(R');
A is a monocyclic or bicyclic heteroaromatic ring system having 5 to 10 ring atoms, at least one of which is an N atom, wherein optionally one to three further ring atoms are heteroatoms independently selected from O, S and N, and wherein the remaining ring atoms are carbon atoms;
$R^A$ is independently selected from H, halogen, CN, NO$_2$, alkyl, haloalkyl, aryl, heteroaryl, cycloalkyl, heterocycloalkyl, —OR', —CO—R', —COO—R', —CONH—R', —NHCO—R', —CON(R')$_2$, —NR'CO—R', —NR'—CONR', —NR'—COOR', —S—R', —SO—

R', —SO₂—R', —NHSO₂—R', —SO₂NH—R', —O—CO—NHR', —O—CO—R', —R'''—O—R', —R'''—CO—R', —R'''—NH—R', —R'''—CONH—R', —R'''—NHCO—R', R', —CONH-alkyl-O—R', —CONH-alkyl-R', —NHCO-alkyl-O—R', —NHCO-alkyl-R', CO—R'''-alkyl-R', —CO—R'''-alkyl, N(R')₂, —NHR', NH₂, —S-alkyl-R' and alkyl-R';

—R' is independently selected from H, alkyl, haloalkyl, aryl, heteroaryl, cycloalkyl and heterocycloalkyl;

—R'''— is independently selected from alkylene, haloalkylene, arylene, heteroarylene, cycloalkylene and heterocycloalkylene;

wherein any of the aforementioned alkyl, aryl, heteroaryl, cycloalkyl and heterocycloalkyl may independently be substituted with one or more substituents R'', wherein R'' is in each case independently selected from $C_{1-4}$-alkyl, halogen, $C_{1-4}$-haloalkyl, OH, $C_{1-4}$-alkoxy, $C_{1-4}$-haloalkoxy, nitro, —NH₂, —N($C_{1-4}$-alkyl)₂, —NH($C_{1-4}$-alkyl), —NHCO($C_{1-4}$-alkyl), —CONH₂, —CONH($C_{1-4}$-alkyl), —CO($C_{1-4}$-alkyl), —COH, —COO($C_{1-4}$-alkyl), —COOH and —CN, and wherein A is not pyridine substituted by heterocycloalkyl and A is not a pyrazole substituted with —CONH₂, and wherein said pharmaceutically acceptable derivative is a compound of formula I wherein a carboxylic acid group is derivatized into an ester, a hydroxyl group is derivatized into an ester, a carboxylic acid is derivatized into an amide, an amine is derivatized into an amide, or a hydroxyl group is derivatized into a phosphate ester.

2. A compound according to claim 1, wherein $R^1$ is independently selected from H, fluorine, chlorine, methyl, ethyl, isopropyl, trifluoromethyl, trifluoromethoxy, OH, methoxy, ethoxy, —CN, nitro, —NH₂, —N(methyl)₂, —NH-methyl, —NHCO-methyl, —CONH₂, —CONH-methyl, acetyl, —COO-methyl, and —COOH; and $R^2$ is independently selected from H, fluorine, chlorine, methyl, ethyl, isopropyl, trifluoromethyl, trifluoromethoxy, OH, methoxy, ethoxy, —CN, nitro, —NH₂, —N(methyl)₂, —NH-methyl, —NHCO-methyl, —CONH₂, —CONH-methyl, acetyl, —COO-methyl, and —COOH, or a pharmaceutically acceptable derivative, solvate or salt thereof.

3. A compound according to claim 1, wherein n is 0 and m is 0, or a pharmaceutically acceptable solvate or salt thereof.

4. A compound according to claim 1, wherein $R^3$ is independently selected from H, fluorine, chlorine, methyl, ethyl, isopropyl, trifluoromethyl, trifluoromethoxy, OH, methoxy, ethoxy, —CN, nitro, —NH₂, —N(methyl)₂, —NH-methyl, —NHCO-methyl, —CONH₂, —CONH-methyl, acetyl, —COO-methyl, and —COOH, or a pharmaceutically acceptable derivative, solvate or salt thereof.

5. A compound according to claim 1, wherein $R^3$ is H, or a pharmaceutically acceptable derivative, solvate or salt thereof.

6. A compound according to claim 1, wherein $R^4$ is independently selected from H, $C_{1-3}$-alkyl, $C_{1-4}$-haloalkyl, OH, —CONH₂, —CONH—$C_{1-3}$-alkyl, —CO—$C_{1-3}$-alkyl, and —COO—$C_{1-3}$-alkyl, or a pharmaceutically acceptable derivative, solvate or salt thereof.

7. A compound according to claim 1, wherein $R^4$ is H, or a pharmaceutically acceptable derivative, solvate or salt thereof.

8. A compound according to claim 1, wherein

A is a monocyclic heteroaromatic ring system having 5 or 6 ring atoms, or a bicyclic heteroaromatic ring system having 9 ring atoms, wherein at least one of the ring atoms is an N atom, wherein optionally one or two further ring atoms are N atoms or one further ring atom is an O or S atom, or one further ring atom is an N atom and one ring atom is an O or S atom, and wherein the remaining ring atoms are carbon atoms, and wherein A is optionally substituted with one or two substituents $R^A$ selected from H, CN, NO₂, NH₂, N(alkyl)₂, halogen, OH, alkoxy, haloalkyl, alkyl, haloalkoxy, alkoxyalkyl, heterocycloalkyl, -heterocycloalkyl-alkyl, -heterocycloalkyl-COO-alkyl, heteroaryl, —COOH, —COO-alkyl, aralkyl, aryl, -aryl-halogen, —CO—N(alkyl)₂, —CONH-(alkyl), —CONH-alkyl-alkoxy, —CONH-cycloalkyl, —CONH-alkyl-heterocycloalkyl, —CO-heterocycloalkyl-alkyl-heterocycloalkyl, —CO-heterocycloalkyl, —CO-heteroaryl, —CO-aryl, —CO-alkyl, —SO₂-alkyl, —S-alkyl, —S-alkyl-COO—$C_{1-4}$-alkyl and —S-aralkyl, or a pharmaceutically acceptable derivative, solvate or salt thereof.

9. A compound according to claim 1, wherein A is selected from thiazole, oxazole, pyrazole, pyrrole, benzoxazole, benzothiazole, benzimidazole, imidazole, triazole, pyrazine, triazine, pyrimidine, pyridine, thiadiazole, and oxadiazole, wherein A is optionally substituted with a substituent $R^A$ selected from H, CN, F, Cl, Br, OH, $C_{1-2}$-alkyl, $C_{1-2}$-alkoxy, CF₃, OCF₃, —COOH, —COO—($C_{1-2}$-alkyl), benzyl, phenethyl, phenyl, fluorophenyl, —CO—N($C_{1-2}$-alkyl)₂, —CONH—($C_{1-2}$-alkyl), —CONH—($C_{1-2}$-alkyl)-O($C_{1-2}$-alkyl), —CONH—($C_{3-5}$-cycloalkyl), —CONH—($C_{1-2}$-alkyl-tetrahydrofuryl), —CO-piperazinyl-($C_{1-2}$-alkyl)-tetrahydrofuranyl, —CO-morpholinyl, —CO-pyrrolidinyl, —CO-(methyl-piperazinyl)-, —SO₂($C_{1-2}$-alkyl), —S—($C_{1-4}$-alkyl), —S-benzyl, —S-(chlorophenylmethyl), —S-phenethyl, —CO-thienyl, —CO— pyrrolyl, —CO-piperidinyl, —CO-piperidinyl-COO—($C_{1-2}$-alkyl), morpholinyl, $C_{1-2}$-alkylpiperazinyl, $C_{1-2}$-alkylthiazolyl, pyridyl, —CO-phenyl, —S—($C_{1-2}$-alkyl)-COO—($C_{1-2}$-alkyl), NH₂, N($C_{1-2}$-alkyl)₂, —CO—$C_{1-2}$-alkyl, and —($C_{1-2}$-alkyl)-O($C_{1-2}$-alkyl), wherein, when A is benzoxazole, benzothiazole or benzimidazole, A may optionally further be substituted with a halogen atom, and wherein, when A is thiazole, A may optionally further be substituted with a methyl group, or a pharmaceutically acceptable derivative, solvate or salt thereof.

10. A compound according to claim 1, wherein the $X^1$-azol moiety is attached at the 5-position of the 2,3-dihydrobenzofuran moiety.

11. A compound according to claim 1, wherein the $X^1$-azol moiety is attached at the 5-position of the 2,3-dihydrobenzofuran moiety;

n is 0 or 1;

m is 0 or 1;

$X^1$ is independently selected from NR'', O and S;

R'' is independently selected from H, methyl, ethyl, OH, —CONH₂, —CONH-methyl, and —COO— methyl;

$R^1$ is independently selected from H, fluorine, chlorine, methyl, ethyl, isopropyl, trifluoromethyl, trifluoromethoxy, OH, methoxy, ethoxy, —CN, nitro, —NH₂, —N(methyl)$_2$, —NH-methyl, —NHCO-methyl, —CONH$_2$, —CONH-methyl, acetyl, —COO-methyl, and —COOH;

R$^2$ is independently selected from H, fluorine, chlorine, methyl, ethyl, isopropyl, trifluoromethyl, trifluoromethoxy, OH, methoxy, ethoxy, —CN, nitro, —NH$_2$, —N(methyl)$_2$, —NH-methyl, —NHCO-methyl, —CONH$_2$, —CONH-methyl, acetyl, —COO-methyl, and —COOH;

R$^3$ is independently selected from H, fluorine, chlorine, methyl, ethyl, isopropyl, trifluoromethyl, trifluoromethoxy, OH, methoxy, ethoxy, —CN, nitro, —NH$_2$, —N(methyl)$_2$, —NH-methyl, —NHCO-methyl, —CONH$_2$, —CONH-methyl, acetyl, —COO-methyl, and —COOH;

R$^4$ is independently selected from H, C$_{1-3}$-alkyl, C$_{1-4}$-haloalkyl, OH, —CONH$_2$, —CONH—C$_{1-3}$-alkyl, —CO—C$_{1-3}$-alkyl, and —COO—C$_{1-3}$-alkyl;

A is independently selected from thiazole, oxazole, pyrazole, pyrrole, benzoxazole, benzothiazole, benzimidazole, imidazole, triazole, pyrazine, triazine, pyrimidine, pyridine, thiadiazole, and oxadiazole;

wherein A is optionally substituted with a substituent R$^A$ selected from H, CN, F, Cl, Br, OH, C$_{1-2}$-alkyl, C$_{1-2}$-alkoxy, CF$_3$, OCF$_3$, —COOH, —COO—(C$_{1-2}$-alkyl), benzyl, phenethyl, phenyl, fluorophenyl, —CO—N(C$_{1-2}$-alkyl)$_2$, —CONH—(C$_{1-2}$-alkyl), —CONH—(C$_{1-2}$-alkyl)-O(C$_{1-2}$-alkyl), —CONH—(C$_{3-5}$-cycloalkyl), —CONH—(C$_{1-2}$-alkyl-tetrahydrofuryl), —CO-piperazinyl-(C$_{1-2}$-alkyl)-tetrahydrofuranyl, —CO-morpholinyl, —CO-pyrrolidinyl, —CO-(methyl-piperazinyl)-, —SO$_2$(C$_{1-2}$-alkyl), —S—(C$_{1-4}$-alkyl), —S-benzyl, —S-(chlorophenylmethyl), —S—phenethyl, —CO-thienyl, —CO-pyrrolyl, —CO-piperidinyl, —CO-piperidinyl-COO—(C$_{1-2}$-alkyl), morpholinyl, C$_{1-2}$-alkylpiperazinyl, C$_{1-2}$-alkylthiazolyl, pyridyl, —CO-phenyl, —S—(C$_{1-2}$-alkyl)-COO—(C$_{1-2}$-alkyl), NH$_2$, N(C$_{1-2}$-alkyl)$_2$, —CO—C$_{1-2}$-alkyl, and —(C$_{1-2}$-alkyl)-O(C$_{1-2}$-alkyl);

wherein, when A is benzoxazole, benzothiazole or benzimidazole, A may optionally further be substituted with a halogen atom, and wherein, when A is thiazole, A may optionally further be substituted with a methyl group;

or a pharmaceutically acceptable derivative, solvate or salt thereof.

12. A compound according to claim 1, wherein the X$^1$-azol moiety is attached at the 5-position of the 2,3-dihydrobenzofuran moiety;

n is 0;
m is 0;
X$^1$ is S,
R$^3$ is H;
R$^4$ is H;

A is a monocyclic or bicyclic heteroaromatic ring system selected from 1H-imidazol-2-yl, 1H-1,2,4-triazol-5-yl, 1H-benzo[d]imidazol-2-yl, pyridin-2-yl, 1,3,4-thiadiazol-2-yl, 1H-pyrazol-3-yl, 1,3-thiazol-2-yl, and 1,2,4-thiadiazol-3-yl;

wherein A is optionally substituted with a substituent R$^A$ selected from F, Cl, Br, CN, methyl, —SO$_2$-Me, OMe, CF$_3$, —CO—N(Me)$_2$, 5-(4-((tetrahydrofuran-2-yl)methyl)piperazine-1-carbonyl, —COO-Et, morpholine-4-carbonyl, OCF$_3$, —COO-Me, OH, —CO—NHMe, —S-Me, pyrrolidin-1-carbonyl, —CO—NH—C$_2$H$_4$—OMe, —S-iPr, cyclopropylcarbamoyl, 4-methylpiperazine-1-carbonyl, —S-nPr, COOH, —S-benzyl, —S-(4-chlorobenzyl), —S-iBu, ((tetrahydrofuran-2-yl)methyl)carbamoyl, phenethyl, —S-phenethyl, —CO-thien-2-yl, —CO-pyrrol-2-yl, —CO-piperidin-1-yl, —CO-(4-ethoxy-carbonyl-piperidin-1-yl), morpholin-4-yl, 4-methyl-piperazin-1-yl, 5-methyl-thiazol-2-yl, pyridin-4-yl, —CO— phenyl, —S—(CH$_2$)—COOMe, NH$_2$, —CO—C$_{1-2}$-alkyl, 3-fluorophenyl, acetyl, -methylthio, and methoxymethyl;

wherein, when A is 1H-benzo[d]imidazol-2-yl, A may optionally further be substituted with a chlorine atom, and when A is 1,3-thiazol-2-yl, A may optionally further be substituted with a methyl group;

or a pharmaceutically acceptable derivative, solvate or salt thereof.

13. A compound according to claim 1, wherein said compound is selected from the following compounds:

| No. | Structure |
|---|---|
| 1 | 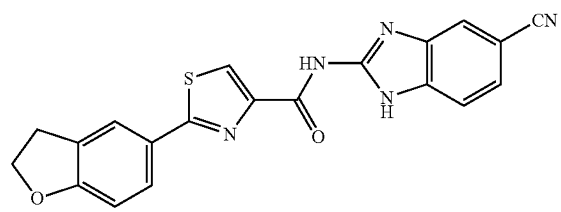 [SMILES: N#Cc1ccc2[nH]c(NC(=O)c3csc(-c4ccc5c(c4)CCO5)n3)nc2c1] |
| 2 | 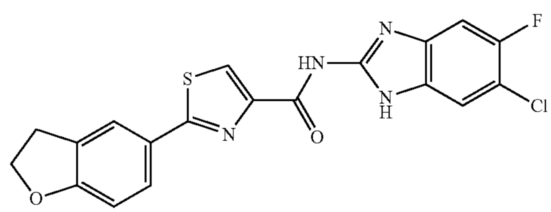 [SMILES: O=C(Nc1nc2cc(F)c(Cl)cc2[nH]1)c1csc(-c2ccc3c(c2)CCO3)n1] |

| No. | Structure |
|---|---|
| 3 | 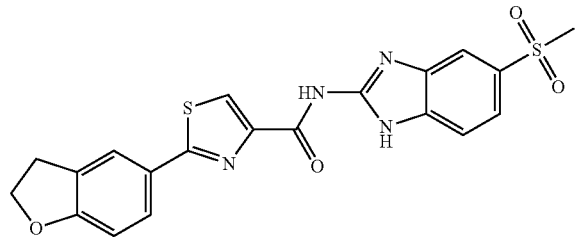 [SMILES: CS(=O)(=O)c1ccc2[nH]c(NC(=O)c3csc(-c4ccc5c(c4)CCO5)n3)nc2c1] |
| 4 | 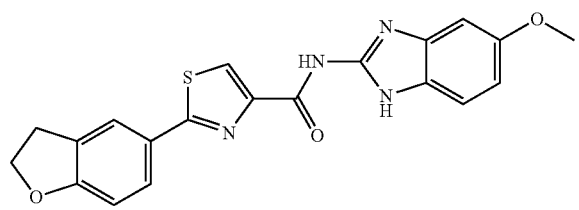 [SMILES: COc1ccc2[nH]c(NC(=O)c3csc(-c4ccc5c(c4)CCO5)n3)nc2c1] |
| 5 | 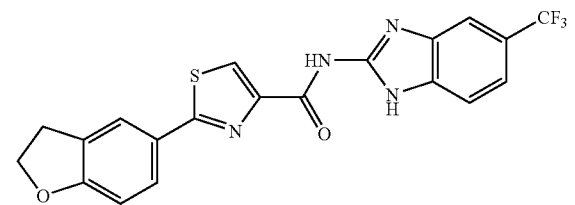 [SMILES: O=C(Nc1nc2cc(C(F)(F)F)ccc2[nH]1)c1csc(-c2ccc3c(c2)CCO3)n1] |
| 6 | 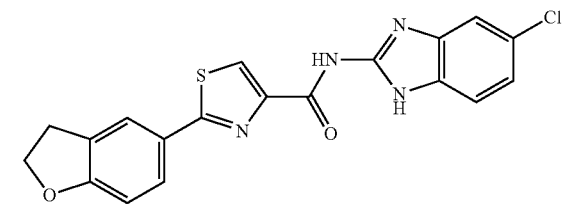 [SMILES: O=C(Nc1nc2cc(Cl)ccc2[nH]1)c1csc(-c2ccc3c(c2)CCO3)n1] |
| 7 | 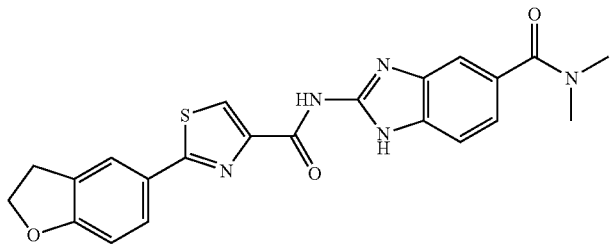 [SMILES: CN(C)C(=O)c1ccc2[nH]c(NC(=O)c3csc(-c4ccc5c(c4)CCO5)n3)nc2c1] |
| 8 | 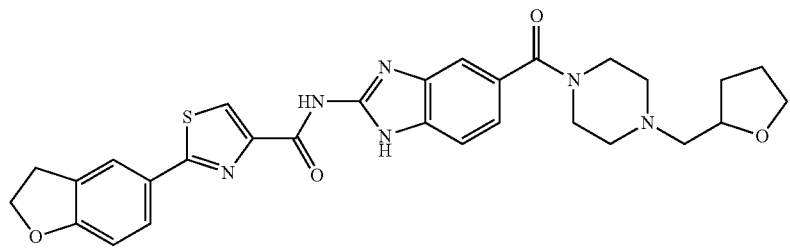 [SMILES: O=C(Nc1nc2cc(C(=O)N3CCN(CC4CCCO4)CC3)ccc2[nH]1)c1csc(-c2ccc3c(c2)CCO3)n1] |

-continued
| No. | Structure |
|---|---|
| 9 | 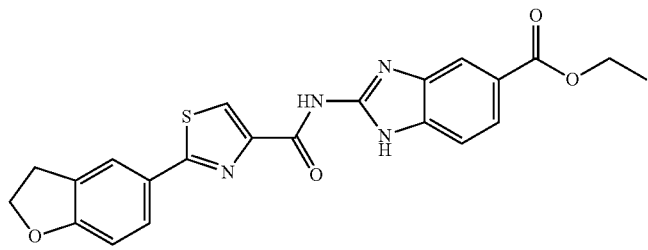 [SMILES: CCOC(=O)c1ccc2[nH]c(NC(=O)c3csc(-c4ccc5c(c4)CCO5)n3)nc2c1] |
| 10 | 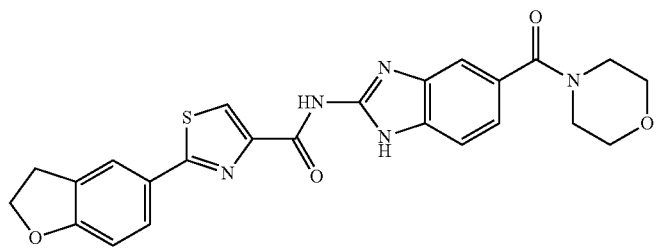 [SMILES: O=C(Nc1nc2cc(C(=O)N3CCOCC3)ccc2[nH]1)c1csc(-c2ccc3c(c2)CCO3)n1] |
| 11 | 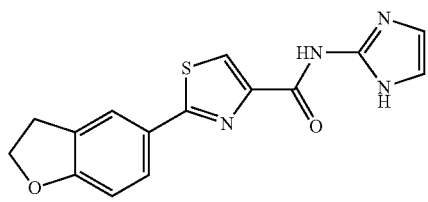 [SMILES: O=C(Nc1ncc[nH]1)c1csc(-c2ccc3c(c2)CCO3)n1] |
| 12 | 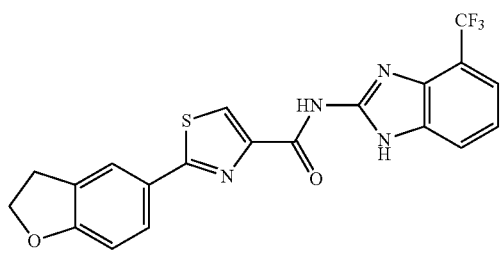 [SMILES: O=C(Nc1nc2c(C(F)(F)F)cccc2[nH]1)c1csc(-c2ccc3c(c2)CCO3)n1] |
| 13 | 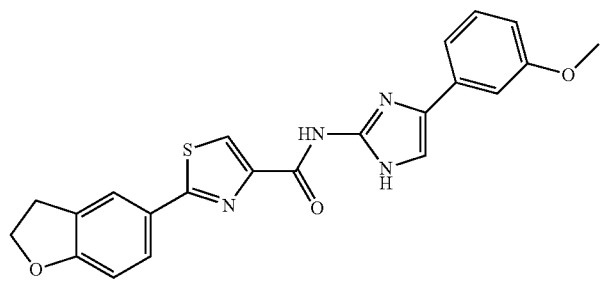 |
| 14 | 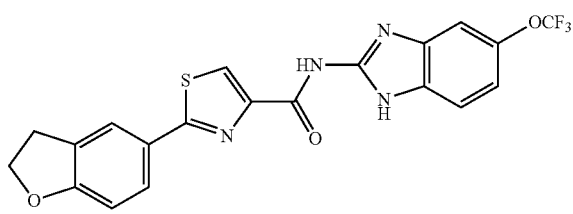 [SMILES: O=C(Nc1nc2cc(OC(F)(F)F)ccc2[nH]1)c1csc(-c2ccc3c(c2)CCO3)n1] |

| No. | Structure |
|---|---|
| 15 | 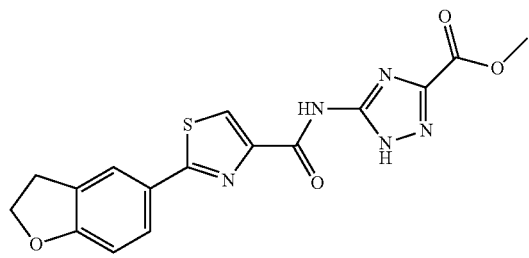 [SMILES: COC(=O)c1n[nH]c(NC(=O)c2csc(-c3ccc4c(c3)CCO4)n2)n1] |
| 16 | 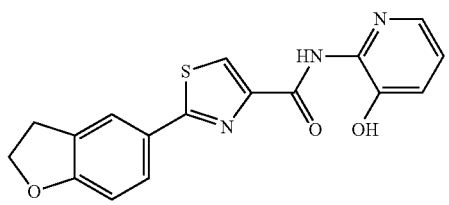 [SMILES: O=C(Nc1ncccc1O)c1csc(-c2ccc3c(c2)CCO3)n1] |
| 17 | 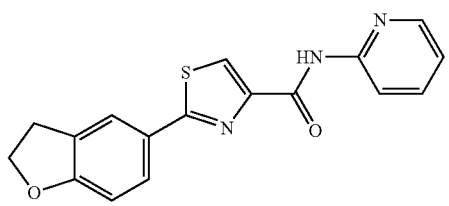 [SMILES: O=C(Nc1ccccn1)c1csc(-c2ccc3c(c2)CCO3)n1] |
| 18 | 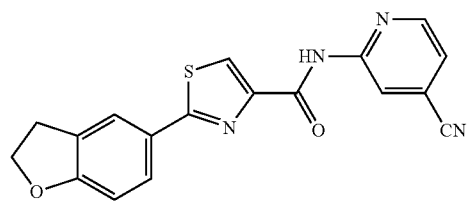 [SMILES: N#Cc1ccnc(NC(=O)c2csc(-c3ccc4c(c3)CCO4)n2)c1] |
| 19 | 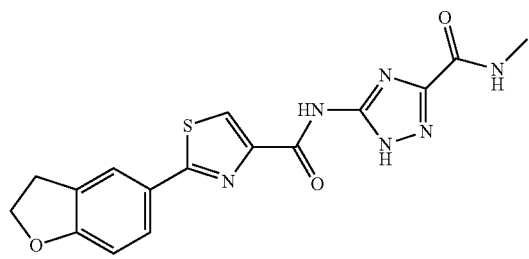 |
| 20 | 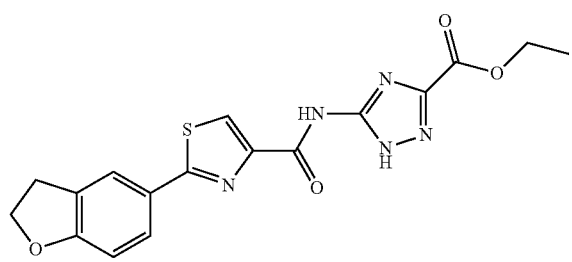 [SMILES: CCOC(=O)c1n[nH]c(NC(=O)c2csc(-c3ccc4c(c3)CCO4)n2)n1] |

| No. | Structure |
|---|---|
| 21 | 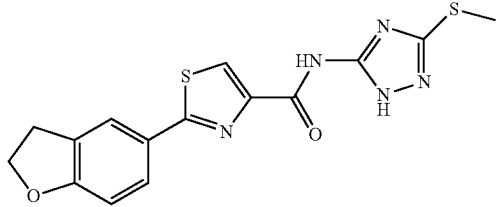 [SMILES: CSc1n[nH]c(NC(=O)c2csc(-c3ccc4c(c3)CCO4)n2)n1] |
| 22 | 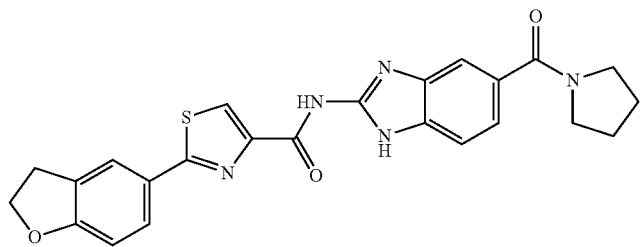 [SMILES: O=C(Nc1nc2cc(C(=O)N3CCCC3)ccc2[nH]1)c1csc(-c2ccc3c(c2)CCO3)n1] |
| 23 | 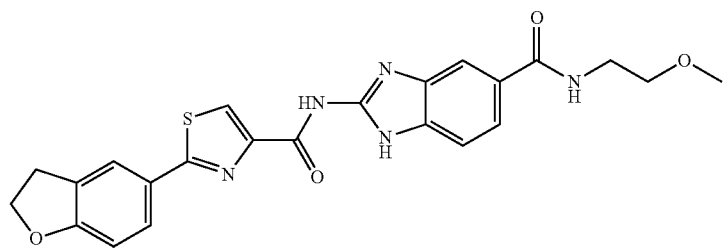 [SMILES: COCCNC(=O)c1ccc2[nH]c(NC(=O)c3csc(-c4ccc5c(c4)CCO5)n3)nc2c1] |
| 24 | 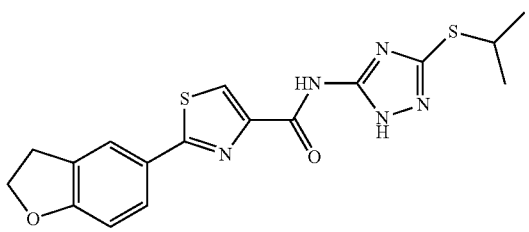 [SMILES: CC(C)Sc1n[nH]c(NC(=O)c2csc(-c3ccc4c(c3)CCO4)n2)n1] |
| 25 | 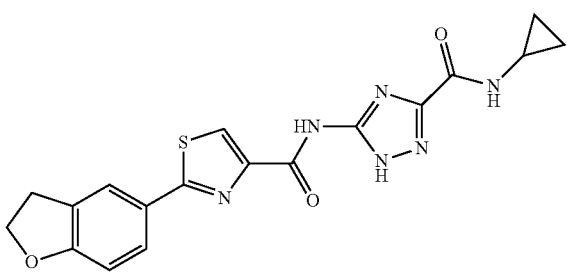 [SMILES: O=C(Nc1nc(C(=O)NC2CC2)n[nH]1)c1csc(-c2ccc3c(c2)CCO3)n1] |
| 26 | 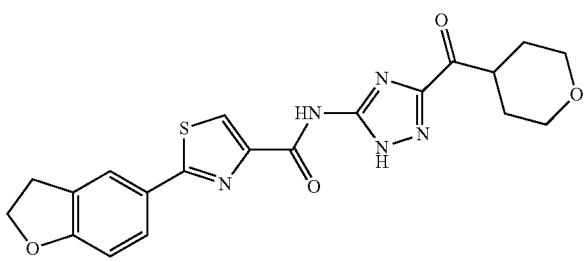 [SMILES: O=C(Nc1nc(C(=O)C2CCOCC2)n[nH]1)c1csc(-c2ccc3c(c2)CCO3)n1] |

-continued
| No. | Structure |
|---|---|
| 27 | 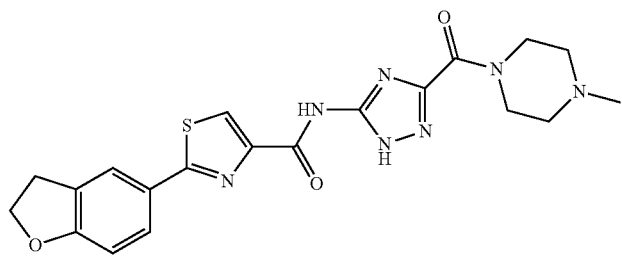 [SMILES: CN1CCN(C(=O)c2n[nH]c(NC(=O)c3csc(-c4ccc5c(c4)CCO5)n3)n2)CC1] |
| 28 | 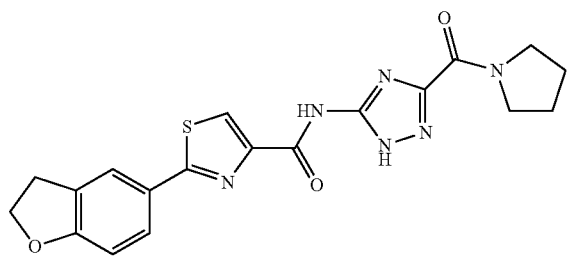 [SMILES: O=C(Nc1nc(C(=O)N2CCCC2)n[nH]1)c1csc(-c2ccc3c(c2)CCO3)n1] |
| 29 | 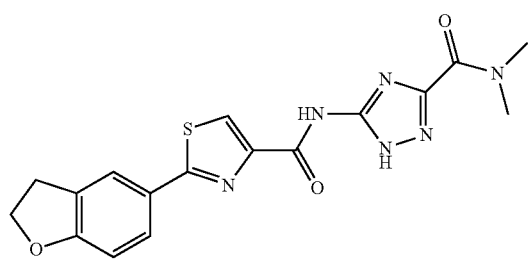 [SMILES: CN(C)C(=O)c1n[nH]c(NC(=O)c2csc(-c3ccc4c(c3)CCO4)n2)n1] |
| 30 | 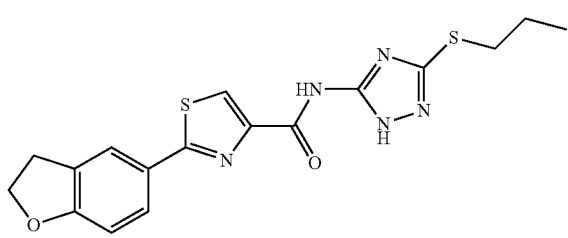 [SMILES: CCCSc1n[nH]c(NC(=O)c2csc(-c3ccc4c(c3)CCO4)n2)n1] |
| 31 | 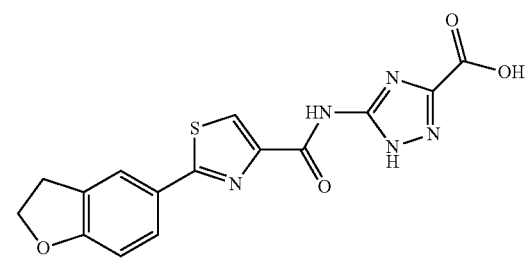 [SMILES: O=C(Nc1nc(C(=O)O)n[nH]1)c1csc(-c2ccc3c(c2)CCO3)n1] |
| 32 | 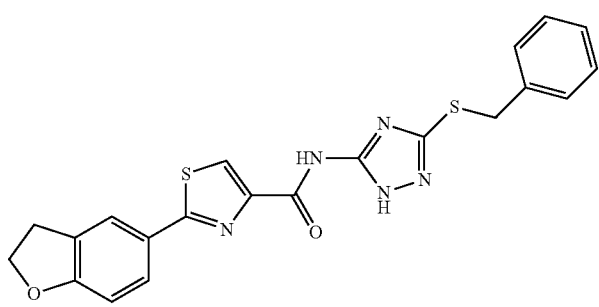 [SMILES: O=C(Nc1nc(SCc2ccccc2)n[nH]1)c1csc(-c2ccc3c(c2)CCO3)n1] |

| No. | Structure |
|---|---|
| 33 | 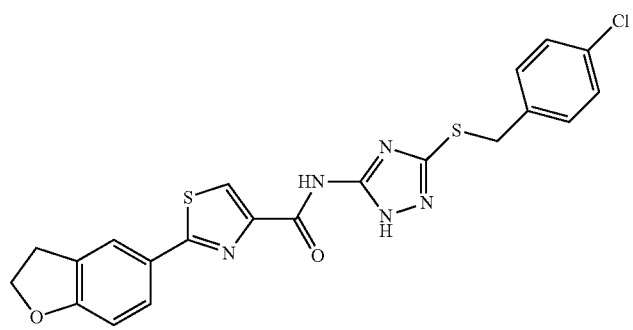 [SMILES: O=C(Nc1nc(SCc2ccc(Cl)cc2)n[nH]1)c1csc(-c2ccc3c(c2)CCO3)n1] |
| 34 | 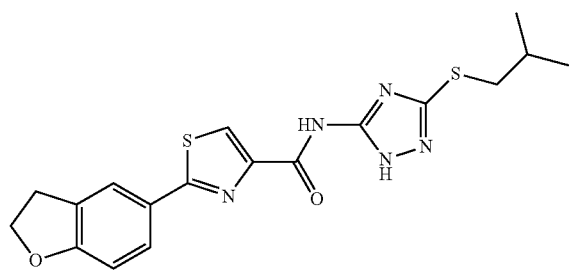 [SMILES: CC(C)CSc1n[nH]c(NC(=O)c2csc(-c3ccc4c(c3)CCO4)n2)n1] |
| 35 | 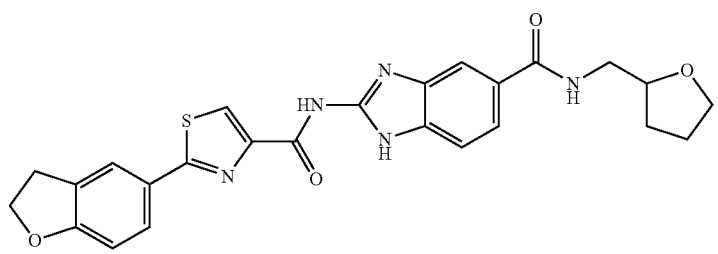 [SMILES: O=C(NCC1CCCO1)c1ccc2[nH]c(NC(=O)c3csc(-c4ccc5c(c4)CCO5)n3)nc2c1] |
| 36 | 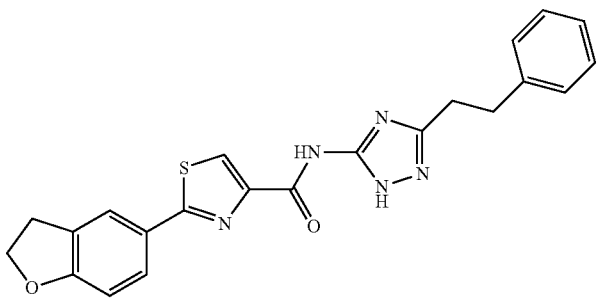 [SMILES: O=C(Nc1nc(CCc2ccccc2)n[nH]1)c1csc(-c2ccc3c(c2)CCO3)n1] |
| 37 | 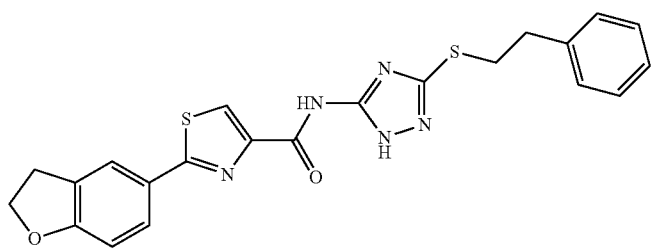 [SMILES: O=C(Nc1nc(SCCc2ccccc2)n[nH]1)c1csc(-c2ccc3c(c2)CCO3)n1] |

| No. | Structure |
|---|---|
| 38 | 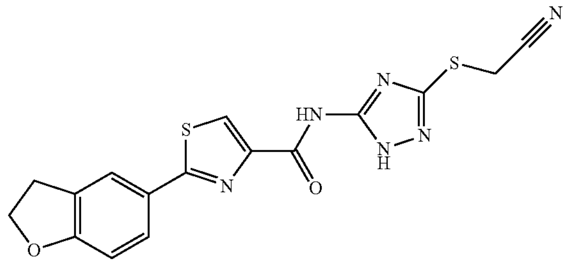 [SMILES: N#CCSc1n[nH]c(NC(=O)c2csc(-c3ccc4c(c3)CCO4)n2)n1] |
| 39 | 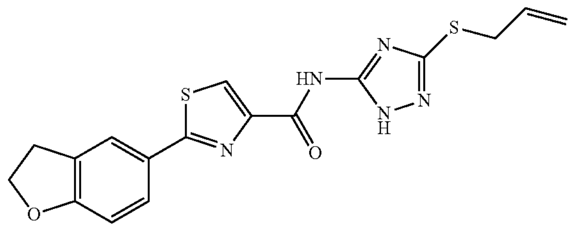 [SMILES: C=CCSc1n[nH]c(NC(=O)c2csc(-c3ccc4c(c3)CCO4)n2)n1] |
| 40 | 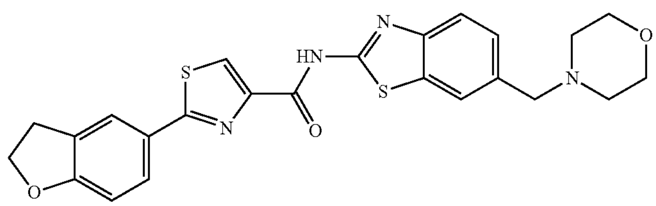 [SMILES: O=C(Nc1nc2ccc(CN3CCOCC3)cc2s1)c1csc(-c2ccc3c(c2)CCO3)n1] |
| 41 | 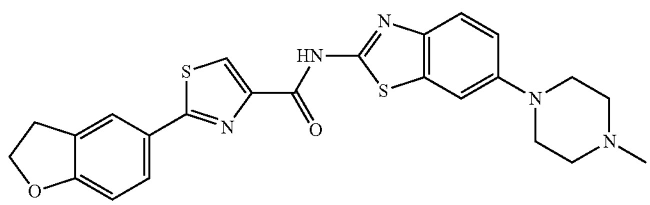 [SMILES: CN1CCN(c2ccc3nc(NC(=O)c4csc(-c5ccc6c(c5)CCO6)n4)sc3c2)CC1] |
| 42 | 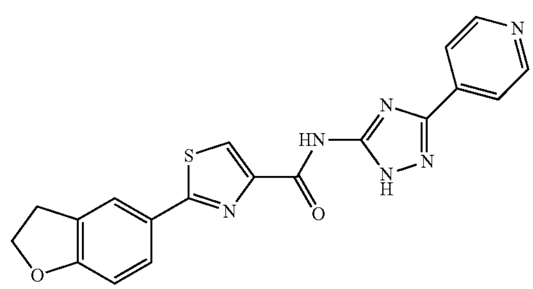 [SMILES: O=C(Nc1nc(-c2ccncc2)n[nH]1)c1csc(-c2ccc3c(c2)CCO3)n1] |
| 43 | 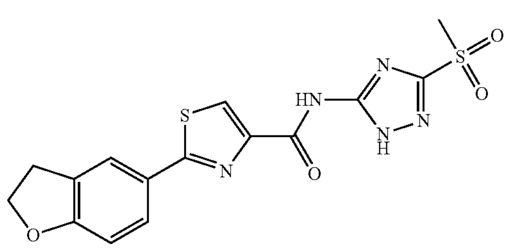 [SMILES: CS(=O)(=O)c1n[nH]c(NC(=O)c2csc(-c3ccc4c(c3)CCO4)n2)n1] |

| No. | Structure |
|---|---|
| 44 | 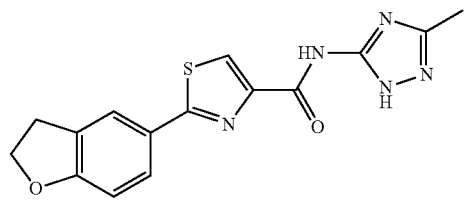 [SMILES: Cc1n[nH]c(NC(=O)c2csc(-c3ccc4c(c3)CCO4)n2)n1] |
| 45 | 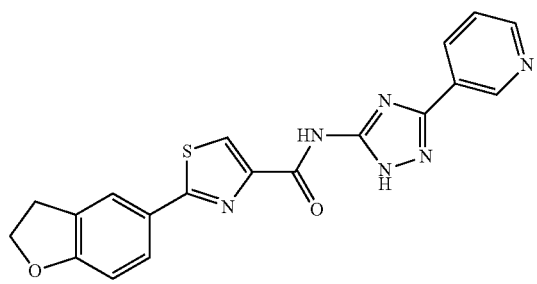 [SMILES: O=C(Nc1nc(-c2cccnc2)n[nH]1)c1csc(-c2ccc3c(c2)CCO3)n1] |
| 46 | 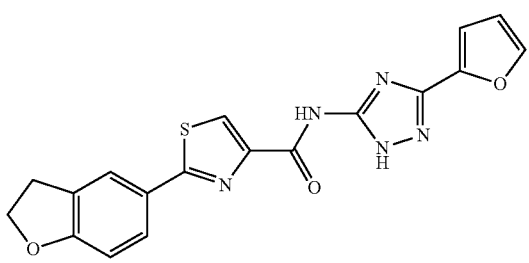 [SMILES: O=C(Nc1nc(-c2ccco2)n[nH]1)c1csc(-c2ccc3c(c2)CCO3)n1] |
| 47 | 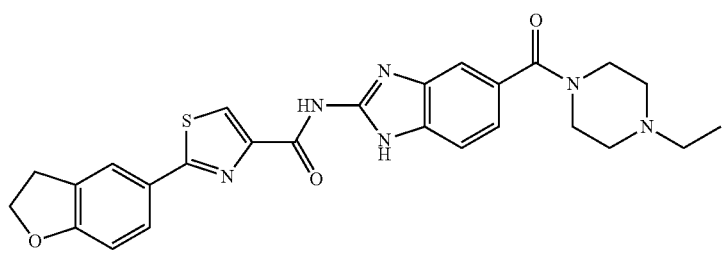 [SMILES: CCN1CCN(C(=O)c2ccc3[nH]c(NC(=O)c4csc(-c5ccc6c(c5)CCO6)n4)nc3c2)CC1] |
| 48 | 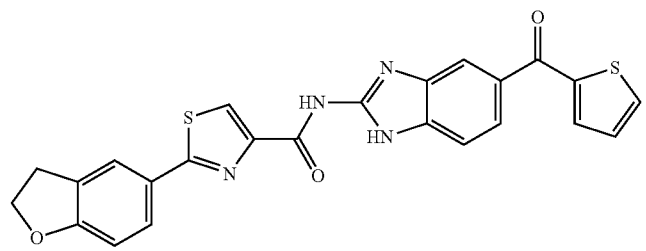 [SMILES: O=C(Nc1nc2cc(C(=O)c3cccs3)ccc2[nH]1)c1csc(-c2ccc3c(c2)CCO3)n1] |
| 49 | 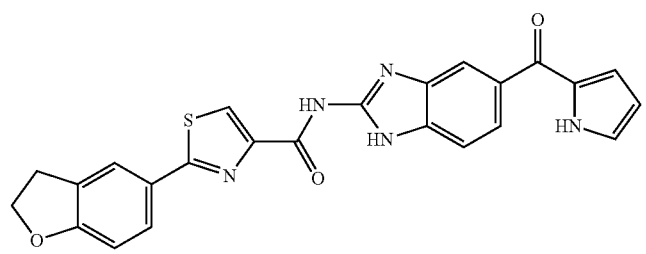 [SMILES: O=C(Nc1nc2cc(C(=O)c3ccc[nH]3)ccc2[nH]1)c1csc(-c2ccc3c(c2)CCO3)n1] |

-continued
| No. | Structure |
|---|---|
| 50 | 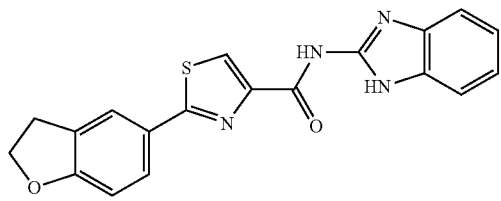 [SMILES: O=C(Nc1nc2ccccc2[nH]1)c1csc(-c2ccc3c(c2)CCO3)n1] |
| 51 | 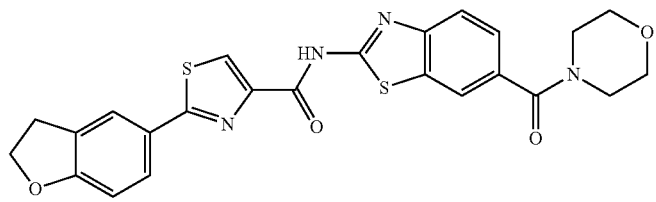 [SMILES: O=C(Nc1nc2ccc(C(=O)N3CCOCC3)cc2s1)c1csc(-c2ccc3c(c2)CCO3)n1] |
| 52 | 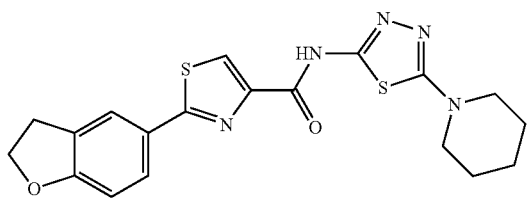 [SMILES: O=C(Nc1nnc(N2CCCCC2)s1)c1csc(-c2ccc3c(c2)CCO3)n1] |
| 53 | 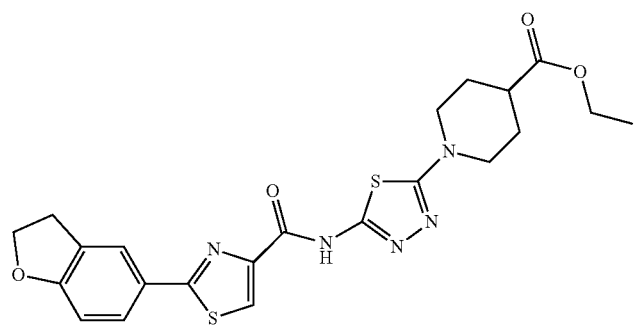 [SMILES: CCOC(=O)C1CCN(c2nnc(NC(=O)c3csc(-c4ccc5c(c4)CCO5)n3)s2)CC1] |
| 54 | 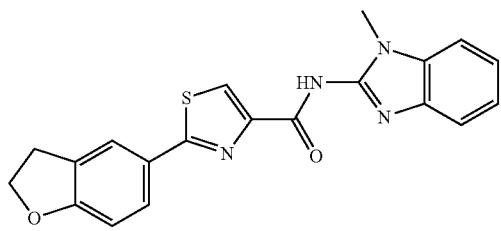 [SMILES: Cn1c(NC(=O)c2csc(-c3ccc4c(c3)CCO4)n2)nc2ccccc21] |
| 55 | 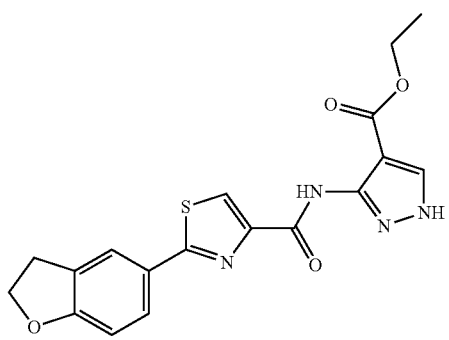 [SMILES: CCOC(=O)c1c[nH]nc1NC(=O)c1csc(-c2ccc3c(c2)CCO3)n1] |

| No. | Structure |
|---|---|
| 56 | 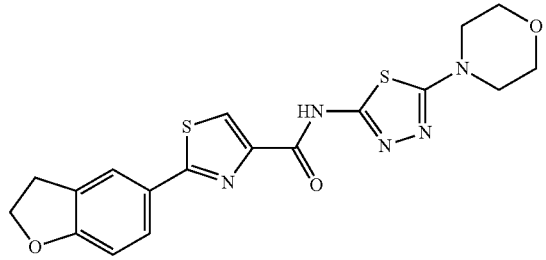 [SMILES: O=C(Nc1nnc(N2CCOCC2)s1)c1csc(-c2ccc3c(c2)CCO3)n1] |
| 57 | 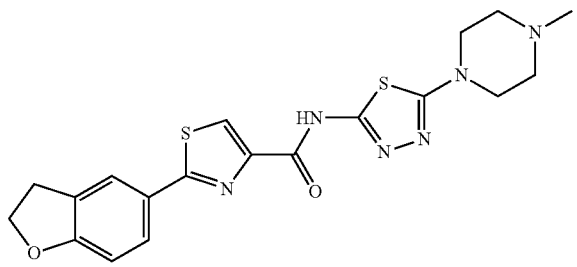 [SMILES: CN1CCN(c2nnc(NC(=O)c3csc(-c4ccc5c(c4)CCO5)n3)s2)CC1] |
| 58 | 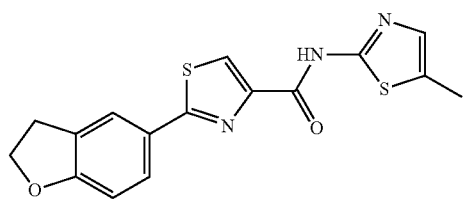 [SMILES: Cc1cnc(NC(=O)c2csc(-c3ccc4c(c3)CCO4)n2)s1] |
| 59 | 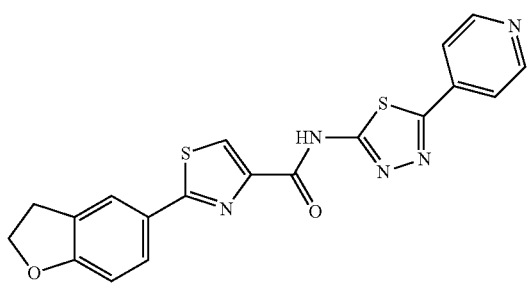 [SMILES: O=C(Nc1nnc(-c2ccncc2)s1)c1csc(-c2ccc3c(c2)CCO3)n1] |
| 60 | 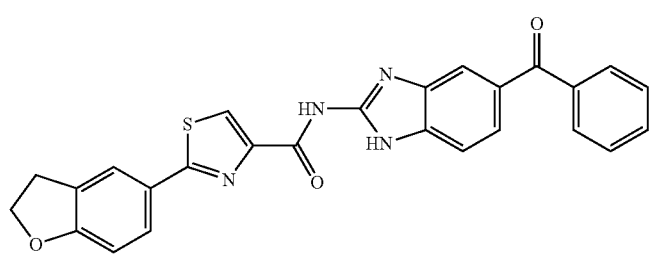 [SMILES: O=C(c1ccccc1)c1ccc2[nH]c(NC(=O)c3csc(-c4ccc5c(c4)CCO5)n3)nc2c1] |
| 61 | 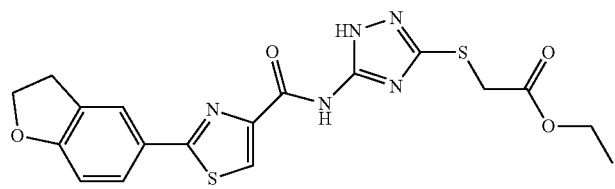 [SMILES: CCOC(=O)CSc1n[nH]c(NC(=O)c2csc(-c3ccc4c(c3)CCO4)n2)n1] |

| No. | Structure |
|---|---|
| 62 | 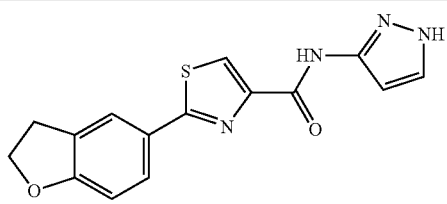 [SMILES: O=C(Nc1cc[nH]n1)c1csc(-c2ccc3c(c2)CCO3)n1] |
| 63 | 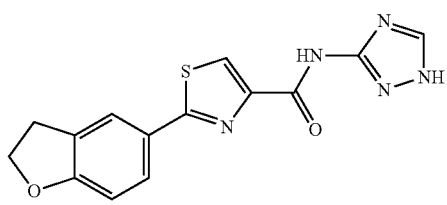 [SMILES: O=C(Nc1nc[nH]n1)c1csc(-c2ccc3c(c2)CCO3)n1] |
| 64 | 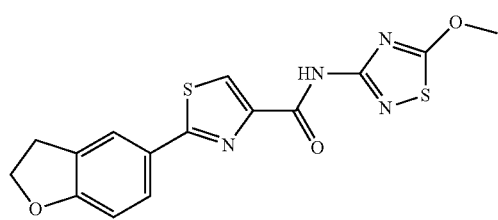 [SMILES: COc1nc(NC(=O)c2csc(-c3ccc4c(c3)CCO4)n2)ns1] |
| 65 | 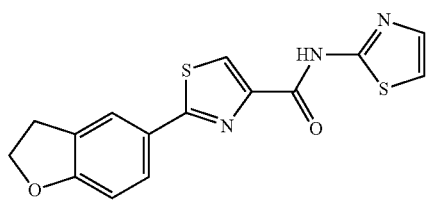 |
| 66 | 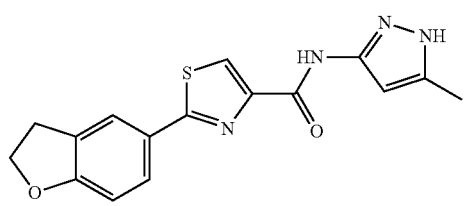 [SMILES: Cc1cc(NC(=O)c2csc(-c3ccc4c(c3)CCO4)n2)n[nH]1] |
| 67 | 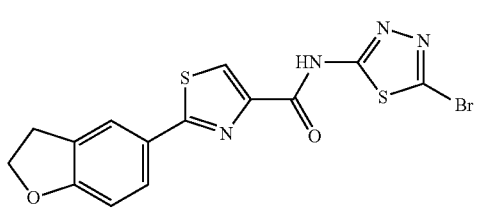 [SMILES: O=C(Nc1nnc(Br)s1)c1csc(-c2ccc3c(c2)CCO3)n1] |
| 68 | 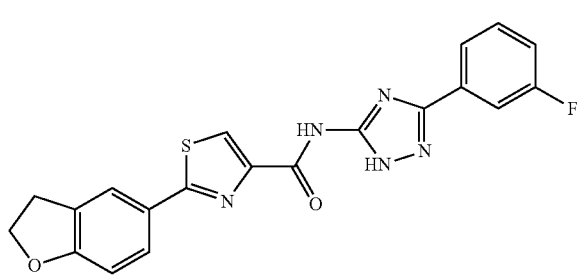 [SMILES: O=C(Nc1nc(-c2cccc(F)c2)n[nH]1)c1csc(-c2ccc3c(c2)CCO3)n1] |

| No. | Structure |
|---|---|
| 69 | 2-(2,3-dihydrobenzofuran-5-yl)-N-(3-methyl-1,2,4-thiadiazol-5-yl)thiazole-4-carboxamide |
| 70 | N-(5-amino-1,2,4-thiadiazol-3-yl)-2-(2,3-dihydrobenzofuran-5-yl)thiazole-4-carboxamide |
| 71 | 2-(2,3-dihydrobenzofuran-5-yl)-N-(1,3,4-thiadiazol-2-yl)thiazole-4-carboxamide |
| 72 | 2-(2,3-dihydrobenzofuran-5-yl)-N-(4-methylthiazol-2-yl)thiazole-4-carboxamide |
| 73 | 2-(2,3-dihydrobenzofuran-5-yl)-N-(1,2,4-thiadiazol-5-yl)thiazole-4-carboxamide |
| 74 | 2-(2,3-dihydrobenzofuran-5-yl)-N-(4,5-dimethylthiazol-2-yl)thiazole-4-carboxamide |
| 75 | N-(benzo[d]thiazol-2-yl)-2-(2,3-dihydrobenzofuran-5-yl)thiazole-4-carboxamide |

| No. | Structure |
|---|---|
| 76 | 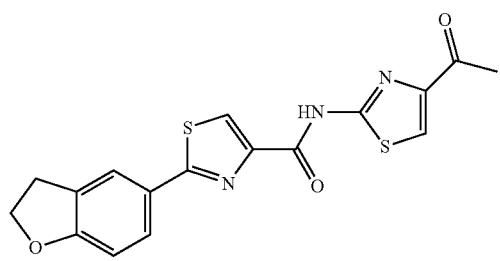 [SMILES: CC(=O)c1csc(NC(=O)c2csc(-c3ccc4c(c3)CCO4)n2)n1] |
| 77 | 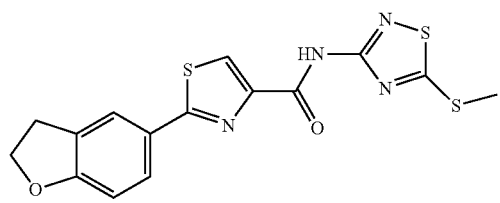 [SMILES: CSc1nc(NC(=O)c2csc(-c3ccc4c(c3)CCO4)n2)ns1] |
| 78 | 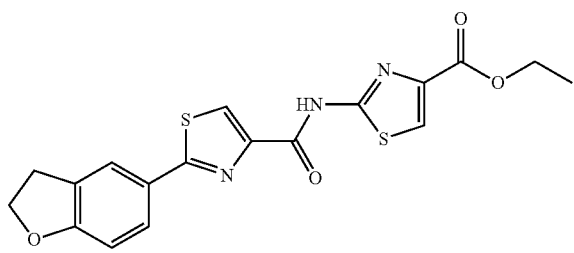 [SMILES: CCOC(=O)c1csc(NC(=O)c2csc(-c3ccc4c(c3)CCO4)n2)n1] |
| 79 | 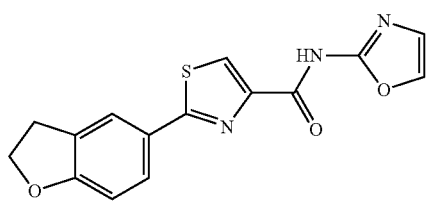 |
| 80 | 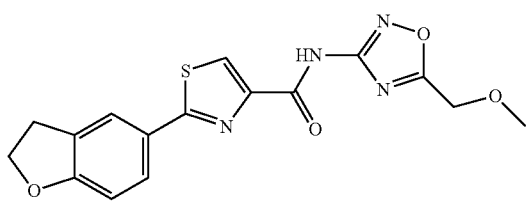 [SMILES: COCc1nc(NC(=O)c2csc(-c3ccc4c(c3)CCO4)n2)no1] |
| 81 | 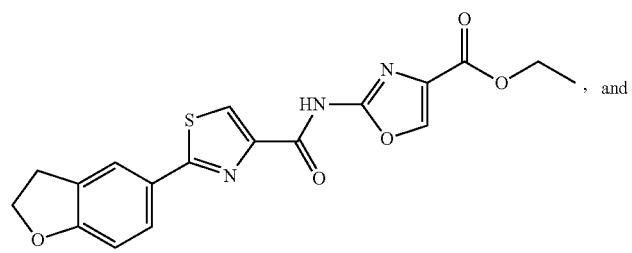 [SMILES: CCOC(=O)c1coc(NC(=O)c2csc(-c3ccc4c(c3)CCO4)n2)n1], and |
| 82 | 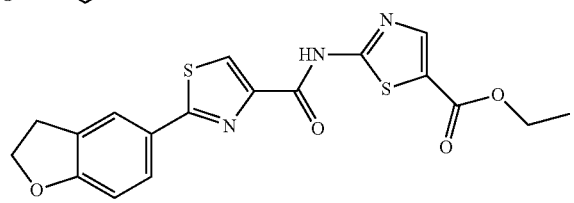 | and pharmaceutically acceptable derivatives, solvates and salts thereof.

14. A method of treatment of a medical condition selected from cancer of the breast, esophagus, gastrointestinal tract, gastro-intestinal stromal tumors, pancreas, prostate, biliary tract, bladder, basal cell carcinoma, medulloblastoma, rhabdomyosarcoma, glioma, small-cell lung cancer, oral squamous cell carcinoma, melanoma, colorectal cancer, non-small cell lung cancer, osteosarcoma, glioblastoma, chronic lymphocytic leukemia, chronic myeloid leukemia, multiple myeloma, acute myeloid leukemia, ovarian cancer, meningioma, and liver cancer, said method comprising:
administering an effective amount of a compound according to claim 13 to a subject in need thereof and wherein said treatment involves alleviation of said condition, stop of progression of said condition, or partial healing of said condition.

15. A pharmaceutical composition comprising a compound according to claim 1 and one or more pharmaceutically acceptable excipients.

16. A method of treatment of a medical condition selected from cancer of the breast, esophagus, gastrointestinal tract, gastro-intestinal stromal tumors, pancreas, prostate, biliary tract, bladder, basal cell carcinoma, medulloblastoma, rhabdomyosarcoma, glioma, small-cell lung cancer, oral squamous cell carcinoma, melanoma, colorectal cancer, non-small cell lung cancer, osteosarcoma, glioblastoma, chronic lymphocytic leukemia, chronic myeloid leukemia, multiple myeloma, acute myeloid leukemia, ovarian cancer, meningioma, and liver cancer, said method comprising:
administering an effective amount of a compound according to claim 1 to a subject in need thereof and wherein said treatment involves alleviation of said condition, stop of progression of said condition, or partial healing of said condition.

17. A method according to claim 16, wherein said medical condition is pancreatic cancer.

18. A compound according to claim 1, wherein $X^1$ is S, $R^3$ is H, $R^4$ is H.

19. A compound according to claim 1, wherein $X^1$ is $NR''$.

20. A compound according to claim 1, wherein $X^1$ is O.

21. A compound according to claim 1, wherein $X^1$ is S.

22. A compound according to claim 1, wherein A is thiazole, oxazole, pyrazole, pyrrole, benzoxazole, benzothiazole, benzimidazole, imidazole, triazole, pyrazine, triazine, pyrimidine, thiadiazole, oxadiazole, or pyridine.

23. A compound according to claim 22, wherein A is thiazol-2-yl, oxazol-2-yl, pyrazol-2-yl, pyrrol-2-yl, benzoxazol-2-yl, benzothiazol-2-yl, benzimidazol-2-yl, imidazol-2-yl, triazol-5-yl, pyrazin-2-yl, triazin-2-yl, pyrimidin-2-yl, thiadiazol-2-yl, thiadiazol-3-yl, thiadiazol-5-yl, oxadiazol-2-yl, oxadiazol-3-yl, oxadiazol-5-yl, or pyridin-2-yl.

24. A compound according to claim 22, wherein A is 1H-imidazol-2-yl, 1H-1,2,4-triazol-5-yl, 1H-benzo[d]imidazol-2-yl, pyridin-2-yl, 1,3,4-thiadiazol-2-yl, 1H-pyrazol-3-yl, 1,3-thiazol-2-yl, 1,2,4-thiadiazol-3-yl, 1,3,4-thiadiazol-2-yl, 1,2,4-thiadiazol-5-yl, 1,3-oxazol-2-yl or 1,2,4-oxadiazol-3-yl.

25. A compound according to claim 22, wherein A is thiazole, oxazole, pyrazole, pyrrole, benzoxazole, benzothiazole, benzimidazole, triazole, pyrazine, triazine, pyrimidine, thiadiazole, oxadiazole, or pyridine.

26. A compound according to claim 25, wherein A is oxazol-2-yl, pyrazol-2-yl, pyrrol-2-yl, benzoxazol-2-yl, benzothiazol-2-yl, benzimidazol-2-yl, triazol-5-yl, pyrazin-2-yl, triazin-2-yl, pyrimidin-2-yl, thiadiazol-2-yl, thiadiazol-3-yl, thiadiazol-5-yl, oxadiazol-2-yl, oxadiazol-3-yl, oxadiazol-5-yl, or pyridin-2-yl.

27. A compound according to claim 25, wherein A is 1H-1,2,4-triazol-5-yl, 1H-benzo[d]imidazol-2-yl, pyridin-2-yl, 1,3,4-thiadiazol-2-yl, 1,3-thiazol-2-yl, 1,2,4-thiadiazol-3-yl, 1,3,4-thiadiazol-2-yl, 1,2,4-thiadiazol-5-yl, 1,3-oxazol-2-yl or 1,2,4-oxadiazol-3-yl.

28. A compound according to claim 1, wherein
$R^1$ is, in each case independently, H, fluorine, chlorine, methyl, ethyl, isopropyl, trifluoromethyl, trifluoromethoxy, OH, methoxy, ethoxy, —CN, nitro, —NH$_2$, —N(methyl)$_2$, —NH-methyl, —NHCO-methyl, —CONH$_2$, —CONH-methyl, acetyl, —COO-methyl, or —COOH;
$R^2$ is, in each case independently, H, fluorine, chlorine, methyl, ethyl, isopropyl, trifluoromethyl, trifluoromethoxy, OH, methoxy, ethoxy, —CN, nitro, —NH$_2$, —N(methyl)$_2$, —NH-methyl, —NHCO-methyl, —CONH$_2$, —CONH-methyl, acetyl, —COO-methyl, or —COOH;
$R^3$ is, in each case independently, H, fluorine, chlorine, methyl, ethyl, isopropyl, trifluoromethyl, —OCF$_3$, OH, methoxy, ethoxy, —CN, nitro, —NH$_2$, —N(methyl)$_2$, —NH-methyl, —NHCO— methyl, —CONH$_2$, —CONH-methyl, acetyl, —COO-methyl, or —COOH; and
$R^4$ is, in each case independently, H, $C_{1-3}$-alkyl, $C_{1-4}$-haloalkyl, OH, —CONH$_2$, —CONH—$C_{1-3}$-alkyl, —CO—$C_{1-3}$-alkyl, or —COO—$C_{1-3}$-alkyl.

29. A compound according to claim 28, wherein
$R^4$ is, in each case independently, H, CN, F, Cl, Br, OH, $C_{1-2}$-alkyl, $C_{1-2}$-alkoxy, CF$_3$, OCF$_3$, —COOH, —COO—($C_{1-2}$-alkyl), benzyl, phenethyl, phenyl, fluorophenyl, —CO—N($C_{1-2}$-alkyl)$_2$, —CONH—($C_{1-2}$-alkyl), —CONH—($C_{1-2}$-alkyl)-O($C_{1-2}$-alkyl), —CONH—($C_{3-5}$-cycloalkyl), —CONH—($C_{1-2}$-alkyl-tetrahydrofuryl), —CO-piperazinyl-($C_{1-2}$-alkyl)-tetrahydrofuranyl, —CO— morpholinyl, —CO-pyrrolidinyl, —CO-(methyl-piperazinyl)-, —SO$_2$($C_{1-2}$-alkyl), —S—($C_{1-4}$-alkyl), —S-benzyl, —S-(chlorophenylmethyl), —S-phenethyl, —CO-thienyl, —CO-pyrrolyl, —CO-piperidinyl, —CO-piperidinyl-COO—($C_{1-2}$-alkyl), morpholinyl, $C_{1-2}$-alkylpiperazinyl, $C_{1-2}$-alkylthiazolyl, pyridyl, —CO-phenyl, —S—($C_{1-2}$-alkyl)-COO—($C_{1-2}$-alkyl), NH$_2$, N($C_{1-2}$-alkyl)$_2$, —CO—$C_{1-2}$-alkyl, or —($C_{1-2}$-alkyl)-O($C_{1-2}$-alkyl).

30. A compound according to claim 29, wherein A is thiazole, oxazole, pyrazole, pyrrole, benzoxazole, benzothiazole, benzimidazole, imidazole, triazole, pyrazine, triazine, pyrimidine, thiadiazole, oxadiazole, or pyridine.

31. A compound according to claim 30, wherein A is oxazole, pyrazole, pyrrole, benzoxazole, benzothiazole, benzimidazole, triazole, pyrazine, triazine, pyrimidine, thiadiazole, oxadiazole, or pyridine.

32. A compound according to claim 28, wherein $R^1$, $R^2$, $R^3$, and $R^4$ are each H.

33. A compound according to claim 29, wherein $R^1$, $R^2$, $R^3$, and $R^4$ are each H.

34. A compound according to claim 32, wherein $X^1$ is S.

35. A compound according to claim 33, wherein $X^1$ is S.

36. A compound of formula (I) or a pharmaceutically acceptable derivative, solvate or salt thereof,

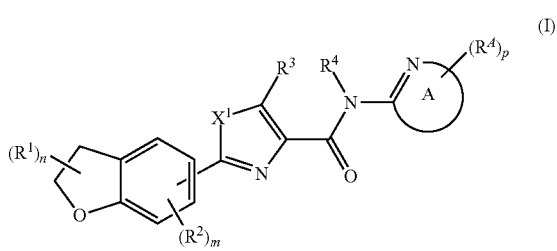

wherein
the $X^1$-azol moiety is attached at the 5- or 6-position of the 2,3-dihydrobenzofuran moiety;
n is an integer from 0 to 2;
m is an integer from 0 to 3;
p is an integer from 0 to 2;
$R^1$ is independently selected from H, halogen, alkyl, aralkyl, haloalkyl, haloalkoxy, OH, alkoxy, —CN, aryl, heteroaryl, cycloalkyl, heterocycloalkyl, —S—R', —SO—R', nitro, —NH$_2$, —N(R')$_2$, —NH(R'), —NHCO(R'), —CONH$_2$, —CONH(R'), —CO(R'), —COH, —COO(R'), —COOH, —SO$_2$NH$_2$, —SO$_2$NH(R'), —SO$_2$(R'), —NH—SO$_2$(R') and —NHCOOR';
$R^2$ is independently selected from H, halogen, alkyl, aralkyl, haloalkyl, haloalkoxy, OH, alkoxy, —CN, aryl, heteroaryl, cycloalkyl, heterocycloalkyl, —S—R', —SO—R', nitro, —NH$_2$, —N(R')$_2$, —NH(R'), —NHCO(R'), —CONH$_2$, —CONH(R'), —CO(R'), —COH, —COO(R'), —COOH, —SO$_2$NH$_2$, —SO$_2$NH(R'), —SO$_2$(R'), —NH—SO$_2$(R') and —NHCOOR';
$R^3$ is independently selected from H, halogen, alkyl, aralkyl, haloalkyl, haloalkoxy, OH, alkoxy, —CN, aryl, heteroaryl, cycloalkyl, heterocycloalkyl, —S—R', —SO—R', nitro, —NH$_2$, —N(R')$_2$, —NH(R'), —NHCO(R'), —CONH$_2$, —CONH(R'), —CO(R'), —COH, —COO(R'), —COOH, —SO$_2$NH$_2$, —SO$_2$NH(R'), —SO$_2$(R'), —NH—SO$_2$(R') and —NHCOOR';
$R^4$ is independently selected from H, alkyl, aralkyl, haloalkyl, haloalkoxy, OH, alkoxy, aryl, heteroaryl, cycloalkyl, heterocycloalkyl, —CONH$_2$, —CONH(R'), —CO(R'), —COO(R'), and —SO$_2$(R');
$X^1$ is independently selected from NR", O and S;
R" is independently selected from H, alkyl, aralkyl, haloalkyl, haloalkoxy, OH, alkoxy, aryl, heteroaryl, cycloalkyl, heterocycloalkyl, —CONH$_2$, —CONH(R'), —CO(R'), —COO(R'), and —SO$_2$(R');
A is a monocyclic or bicyclic heteroaromatic ring system having 5 to 10 ring atoms, at least one of which is an N atom, wherein optionally one to three further ring atoms are heteroatoms independently selected from O, S and N, and wherein the remaining ring atoms are carbon atoms;
$R^A$ is independently selected from H, halogen, CN, NO$_2$, alkyl, haloalkyl, aryl, heteroaryl, cycloalkyl, heterocycloalkyl, —OR', —CO—R', —COO—R', —CONH—R', —NHCO—R', —CON(R')$_2$, —NR'CO—R', —NR'—CONR', —NR'—COOR', —S—R', —SO—R', —SO$_2$—R', —NHSO$_2$—R', —SO$_2$NH—R', —O—CO—NHR', —O—CO—R', —R'''—O—R', —R'''—CO—R', —R'''—NH—R', —R'''—CONH—R', —R'''—NHCO—R', —CONH-alkyl-O—R', —CONH-alkyl-R', —NHCO-alkyl-O—R', —NHCO-alkyl-R', CO—R'''-alkyl-R', —CO—R'''-alkyl-R', N(R')$_2$, —NHR', NH$_2$, —S-alkyl-R' and alkyl-R';

—R' is independently selected from H, alkyl, haloalkyl, aryl, heteroaryl, cycloalkyl and heterocycloalkyl;
—R'''— is independently selected from alkylene, haloalkylene, arylene, heteroarylene, cycloalkylene and heterocycloalkylene;
wherein any of the aforementioned alkyl, aryl, heteroaryl, cycloalkyl and heterocycloalkyl may independently be substituted with one or more substituents R", wherein R" is in each case independently selected from $C_{1-4}$-alkyl, halogen, $C_{1-4}$-haloalkyl, OH, $C_{1-4}$-alkoxy, $C_{1-4}$-haloalkoxy, nitro, —NH$_2$, —N($C_{1-4}$-alkyl)$_2$, —NH($C_{1-4}$-alkyl), —NHCO($C_{1-4}$-alkyl), —CONH$_2$, —CONH($C_{1-4}$-alkyl), —CO($C_{1-4}$-alkyl), —COH, —COO($C_{1-4}$-alkyl), —COOH and —CN, and
wherein A is not pyridine substituted by heterocycloalkyl and A is not pyrazole, and
wherein said pharmaceutically acceptable derivative is a compound of formula I wherein a carboxylic acid group is derivatized into an ester, a hydroxyl group is derivatized into an ester, a carboxylic acid is derivatized into an amide, an amine is derivatized into an amide, or a hydroxyl group is derivatized into a phosphate ester.

37. A compound of formula (I) or a pharmaceutically acceptable derivative, solvate or salt thereof,

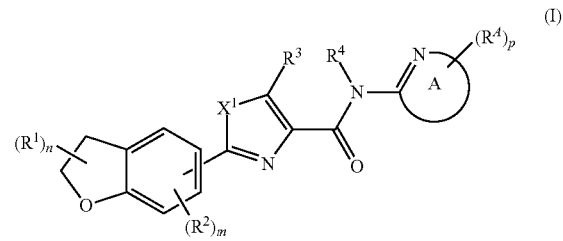

wherein
the $X^1$-azol moiety is attached at the 5- or 6-position of the 2,3-dihydrobenzofuran moiety;
n is an integer from 0 to 2;
m is an integer from 0 to 3;
p is an integer from 0 to 2;
$R^1$ is independently selected from H, halogen, alkyl, aralkyl, haloalkyl, haloalkoxy, OH, alkoxy, —CN, aryl, heteroaryl, cycloalkyl, heterocycloalkyl, —S—R', —SO—R', nitro, —NH$_2$, —N(R')$_2$, —NH(R'), —NHCO(R'), —CONH$_2$, —CONH(R'), —CO(R'), —COH, —COO(R'), —COOH, —SO$_2$NH$_2$, —SO$_2$NH(R'), —SO$_2$(R'), —NH—SO$_2$(R') and —NHCOOR';
$R^2$ is independently selected from H, halogen, alkyl, aralkyl, haloalkyl, haloalkoxy, OH, alkoxy, —CN, aryl, heteroaryl, cycloalkyl, heterocycloalkyl, —S—R', —SO—R', nitro, —NH$_2$, —N(R')$_2$, —NH(R'), —NHCO(R'), —CONH$_2$, —CONH(R'), —CO(R'), —COH, —COO(R'), —COOH, —SO$_2$NH$_2$, —SO$_2$NH(R'), —SO$_2$(R'), —NH—SO$_2$(R') and —NHCOOR';
$R^3$ is independently selected from H, halogen, alkyl, aralkyl, haloalkyl, haloalkoxy, OH, alkoxy, —CN, aryl, heteroaryl, cycloalkyl, heterocycloalkyl, —S—R', —SO—R', nitro, —NH$_2$, —N(R')$_2$, —NH(R'), —NHCO(R'), —CONH$_2$, —CONH(R'), —CO(R'), —COH, —COO(R'), —COOH, —SO$_2$NH$_2$, —SO$_2$NH(R'), —SO$_2$(R'), —NH—SO$_2$(R') and —NHCOOR';
$R^4$ is independently selected from H, alkyl, aralkyl, haloalkyl, haloalkoxy, OH, alkoxy, aryl, heteroaryl, cycloalkyl, heterocycloalkyl, —CONH$_2$, —CONH(R'), —CO(R'), —COO(R'), and —SO$_2$(R');

$X^1$ is independently selected from NR", O and S;

R" is independently selected from H, alkyl, aralkyl, haloalkyl, haloalkoxy, OH, alkoxy, aryl, heteroaryl, cycloalkyl, heterocycloalkyl, —CONH$_2$, —CONH(R'), —CO(R'), —COO(R'), and —SO$_2$(R');

A is a monocyclic or bicyclic heteroaromatic ring system having 5 to 10 ring atoms, at least one of which is an N atom, wherein optionally one to three further ring atoms are heteroatoms independently selected from O, S and N, and wherein the remaining ring atoms are carbon atoms;

$R^4$ is independently selected from H, halogen, CN, NO$_2$, alkyl, haloalkyl, aryl, heteroaryl, cycloalkyl, heterocycloalkyl, —OR', —CO—R', —COO—R', —NHCO—R', —CON(R')$_2$, —NR'CO—R', —NR'—CONR', —NR'—COOR', —S—R', —SO—R', —SO$_2$—R', —NHSO$_2$—R', —SO$_2$NH—R', —O—CO—NHR', —O—CO—R', —R'''—O—R', —R'''—CO—R', —R'''—NH—R', —R'''—CONH—R', —R'''—NHCO—R', —CONH-alkyl-O—R', —CONH-alkyl-R', —NHCO-alkyl-O—R', —NHCO-alkyl-R', CO—R'''-alkyl-R', —CO—R'''-alkyl, N(R')$_2$, —NHR', NH$_2$, —S-alkyl-R' and alkyl-R';

—R' is independently selected from H, alkyl, haloalkyl, aryl, heteroaryl, cycloalkyl and heterocycloalkyl;

—R'''— is independently selected from alkylene, haloalkylene, arylene, heteroarylene, cycloalkylene and heterocycloalkylene;

wherein any of the aforementioned alkyl, aryl, heteroaryl, cycloalkyl and heterocycloalkyl may independently be substituted with one or more substituents R", wherein R" is in each case independently selected from $C_{1-4}$-alkyl, halogen, $C_{1-4}$-haloalkyl, OH, $C_{1-4}$-alkoxy, $C_{1-4}$-haloalkoxy, nitro, —NH$_2$, —N($C_{1-4}$-alkyl)$_2$, —NH($C_{1-4}$-alkyl), —NHCO($C_{1-4}$-alkyl), —CONH$_2$, —CONH($C_{1-4}$-alkyl), —CO($C_{1-4}$-alkyl), —COH, —COO($C_{1-4}$-alkyl), —COOH and —CN, and wherein A is not pyridine substituted by heterocycloalkyl and A is not a pyrazole substituted with —CONH$_2$, and wherein said pharmaceutically acceptable derivative is a compound of formula I wherein a carboxylic acid group is derivatized into an ester, a hydroxyl group is derivatized into an ester, a carboxylic acid is derivatized into an amide, an amine is derivatized into an amide, or a hydroxyl group is derivatized into a phosphate ester.

38. A method of treatment of a medical condition selected from cancer of the breast, esophagus, gastrointestinal tract, gastro-intestinal stromal tumors, pancreas, prostate, biliary tract, bladder, basal cell carcinoma, medulloblastoma, rhabdomyosarcoma, glioma, small-cell lung cancer, oral squamous cell carcinoma, melanoma, colorectal cancer, non-small cell lung cancer, osteosarcoma, glioblastoma, chronic lymphocytic leukemia, chronic myeloid leukemia, multiple myeloma, acute myeloid leukemia, ovarian cancer, meningioma, and liver cancer, said method comprising:

administering an effective amount of a compound according to claim 36 to a subject in need thereof and wherein said treatment involves alleviation of said condition, stop of progression of said condition, or partial healing of said condition.

39. A method of treatment of a medical condition selected from cancer of the breast, esophagus, gastrointestinal tract, gastro-intestinal stromal tumors, pancreas, prostate, biliary tract, bladder, basal cell carcinoma, medulloblastoma, rhabdomyosarcoma, glioma, small-cell lung cancer, oral squamous cell carcinoma, melanoma, colorectal cancer, non-small cell lung cancer, osteosarcoma, glioblastoma, chronic lymphocytic leukemia, chronic myeloid leukemia, multiple myeloma, acute myeloid leukemia, ovarian cancer, meningioma, and liver cancer, said method comprising:

administering an effective amount of a compound according to claim 37 to a subject in need thereof and wherein said treatment involves alleviation of said condition, stop of progression of said condition, or partial healing of said condition.

\* \* \* \* \*